US012668589B2

(12) United States Patent
Cheng et al.

(10) Patent No.: US 12,668,589 B2
(45) Date of Patent: Jun. 30, 2026

(54) N-FORMAMIDOPYRAZOLINE DERIVATIVE AS P2X3 RECEPTOR ANTAGONIST AND USE THEREOF

(71) Applicant: HANGZHOU WESTAN PHARMACEUTICAL TECHNOLOGY CO., LTD, Zhejiang (CN)

(72) Inventors: Yunfeng Cheng, Hangzhou (CN); Xinqiang Zhu, Hangzhou (CN)

(73) Assignee: HANGZHOU WESTAN PHARMACEUTICAL TECHNOLOGY CO., LTD, Hangzhou (CN)

( * ) Notice: Subject to any disclaimer, the term of this patent is extended or adjusted under 35 U.S.C. 154(b) by 830 days.

(21) Appl. No.: 17/909,429

(22) PCT Filed: Jun. 30, 2021

(86) PCT No.: PCT/CN2021/103402
§ 371 (c)(1),
(2) Date: Sep. 5, 2022

(87) PCT Pub. No.: WO2022/028154
PCT Pub. Date: Feb. 10, 2022

(65) Prior Publication Data

US 2023/0357218 A1 Nov. 9, 2023

(30) Foreign Application Priority Data

Aug. 5, 2020 (CN) ......................... 202010777545.9
Jun. 23, 2021 (CN) ......................... 202110695453.0

(51) Int. Cl.

| | |
|---|---|
| *C07D 413/14* | (2006.01) |
| *C07D 231/06* | (2006.01) |
| *C07D 401/12* | (2006.01) |
| *C07D 401/14* | (2006.01) |
| *C07D 403/04* | (2006.01) |
| *C07D 403/12* | (2006.01) |
| *C07D 405/14* | (2006.01) |
| *C07D 413/04* | (2006.01) |

(52) U.S. Cl.
CPC ......... *C07D 413/14* (2013.01); *C07D 231/06* (2013.01); *C07D 401/12* (2013.01); *C07D 401/14* (2013.01); *C07D 403/04* (2013.01); *C07D 403/12* (2013.01); *C07D 405/14* (2013.01); *C07D 413/04* (2013.01)

(58) Field of Classification Search
CPC .................................................... C07D 413/14
USPC .......................................................... 514/230
See application file for complete search history.

(56) References Cited

U.S. PATENT DOCUMENTS 5,798,311 A * 8/1998 Jacobson ............ C07F 9/65031
548/371.7

FOREIGN PATENT DOCUMENTS

| | | |
|---|---|---|
| EP | 0466408 | 1/1992 |
| WO | WO2009058298 | 5/2009 |
| WO | WO2010111059 | 9/2010 |
| WO | WO2018111738 | 6/2018 |

* cited by examiner

*Primary Examiner* — Jeffrey H Murray
*Assistant Examiner* — Rilla Marie Samsell
(74) *Attorney, Agent, or Firm* — Jiwen Chen; Joywin IP Law PLLC

(57) ABSTRACT

An N-formamidopyrazoline derivative is a compound having General Formula (I) or an enantiomer, a diastereomer, an epimer and a racemate thereof, or a pharmaceutically acceptable salt thereof. The compound is an antagonist of a ligand-gated non-selective cation channel receptor subtype P2X3, and can be used for treating or preventing various diseases mediated by the receptor P2X3.

(I)

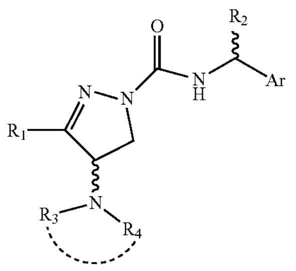

10 Claims, 6 Drawing Sheets

N-FORMAMIDOPYRAZOLINE DERIVATIVE AS P2X3 RECEPTOR ANTAGONIST AND USE THEREOF

This is a U.S. national stage application of PCT Application No. PCT/CN2021/103402 under 35 U.S.C. 371, filed Jun. 30, 2021 in Chinese, claiming priority to Chinese Patent Applications No. 202010777545.9 filed Aug. 5, 2020 and Chinese Patent Applications No. 202110695453.0 filed Jun. 23, 2021, all of which are hereby incorporated by reference.

TECHNICAL FIELD

The present invention belongs to the field of medicine, and relates to an N-formamidopyrazoline derivative as a ligand-gated non-selective cation channel receptor subtype P2X3 inhibitor, and use thereof in preparation of a drug for treating diseases mediated by P2X3.

BACKGROUND TECHNOLOGY

P2X3 is a ligand-gated non-selective cation channel receptor subtype, belonging to an ionic P2X receptor in the P2 class of purinergic receptors, originally cloned in mammals in 1995 (Chen C et al., Nature, 1995, 428; Lewis, C, et al., Nature, 1995, 432), so far, seven P2X receptor subtypes (P2X1 to P2X7) have been cloned in the mammals. Each P2X receptor molecule consists of intracellular N-terminal and C-terminal and two transmembrane structure domains. Although there are differences in subtypes and species of P2X receptors, there is no obvious difference in basic structures constituting the P2X receptors, they are all trimers composed of three homologous or heterologous subunits, for example, P2X3 is a homologous trimer, and P2X1/2 and P2X2/3 are heterologous trimers (Jacobson et al., Neuropharmacology, 2016, 31). The P2X3 receptors are widely distributed in the body, mainly expressed in peripheral sensory neurons related to nociceptive information, and play an important mediating role in the generation and transmission of the nociceptive information. After the body is injured or subjected to nerve damage, a large amount of ATP is released, which binds to the P2X3 receptors and causes a conformational change in the transmembrane domain of the receptors, thereby activating the P2X3 receptors, causing influx of a large number of $Ca^{2+}$, and the increase in the intracellular calcium concentration activates phosphorylation of a protein kinase A, a protein kinase C, etc., promotes the release of glutamic acid and the further activation of NMDA receptors and the like, which eventually leads to sensitization of nervous centralis.

P2X3 is involved in a variety of physiological and pathological responses, including inflammatory pain, neuropathic pain, cancer pain and other pathological pain, cough, hypertension, bladder urination, etc. For example, up-regulation of P2X3 receptor expression can lead to the formation of hyperalgesia, which is involved in pain signaling, and knockout of the P2X3 receptors can alleviate pain-related behaviors in mice (Cockayne D A et al., Nature, 2000, 1011). Inhibition of the P2X3 receptors can improve the reflex function of spontaneous cardiac baroreceptors and help to inhibit sympathetic nerves in rats, thereby exerting antihypertensive effects (Pijacks W et al., Nature Medicine, 2016, 1151). There is a correlation between the P2X3 receptors and the urination frequency of the mice, and the deletion of the P2X3 receptors will reduce the urination frequency of the mice (Gao X F et al., Nature Communication, 2015, 7650). An ATP/P2X3 signal path in human skin is associated with chronic pruritus, so P2X3 receptor inhibitors can also be used for the treatment of chronic pruritus (Chauret, N. et al., 49th Annual ESDR Meeting, 2019).

Another study has showed that P2X3 is expressed in guinea pig C-fibres vagi, and upon activation by its agonist ATP, can stimulate sensory nerves in a respiratory tract and induce cough (Abdulgawi R et al., Eur Respir J, 2013). Studies have found that Cough Hypersensitivity Syndrome, that is, chronic cough, especially refractory chronic cough, is one of the most common diseases of the respiratory system. The causes include various diseases of respiratory system, environment, smoking and drug allergies, etc. These diseases seriously affect the health and quality of life of patients, and are increasing year by year under being affected by factors such as environmental deterioration and population aging. However, there are few treatment options for existing drugs. Therefore, studies on the mechanisms of cough are needed to uncover new therapeutic targets and develop new treatments to improve the quality of life of the patients. Clinical data in recent years have shown that a P2X3 receptor inhibitor AF-219 is significantly effective in reducing the frequency and severity of cough in patients with chronic cough (Abdulgawi R et al., Eur Respir J, 2013, 42; Abdulgawi R et al., Lancet, 2015, 1198; Garceau D et al, Pulmonary Pharmacology & Therapeutics, 2019, 56; Muccino D et al, Pulmonary Pharmacology & Therapeutics, 2019, 75).

AF-219

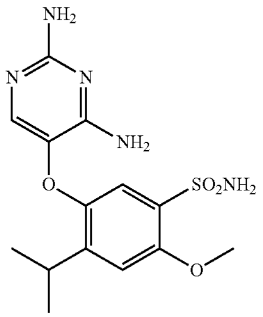

However, at the same time, clinical trials have also shown that the AF-219 can lead to taste disorders in treated subjects by affecting the taste on the tongue (Abdulgawi et al., Lancet 2015). This side effect has been attributed to blockade of P2X2/3 channels (heterologous trimers of P2X2 and P2X3 subtypes) (Cockayne, D. A. et al., J. Physiol. 2005, 621; Pulmonary Pharmacology & Therapeutics, 2019). Therefore, the development of antagonists with P2X3 subtype receptor selectivity can solve the problem of insufficient patient compliance during the treatment of such chronic diseases. The P2X3 inhibitor with a novel compound structure of the present invention has unexpected and favorable properties in terms of selectivity, pharmacokinetics and pharmacodynamics, etc., and can greatly expand the research and development of P2X3 targeted drugs, which constitutes a basis of the present invention.

SUMMARY OF THE INVENTION

The present invention provides a novel N-formamidopyrazoline derivative as a ligand-gated non-selective cation channel receptor subtype P2X3 inhibitor.

The present invention also discloses use of the above N-formamidopyrazoline derivative.

An N-formamidopyrazoline derivative has a compound structure shown in General Formula (I) or is an enantiomer, a diastereomer, an epimer and a racemate thereof, or a pharmaceutically acceptable salt thereof:

(I)

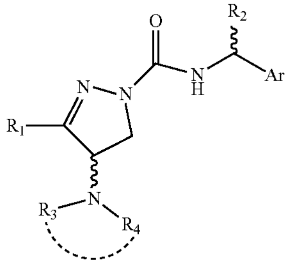

wherein

Ar is selected from a substituted or unsubstituted phenyl, a substituted or unsubstituted five-membered heteroaromatic ring group containing 1 to 3 atoms selected from O, N and S, or a substituted or unsubstituted six-membered heteroaromatic ring group containing 1 to 2 N atoms; and when the Ar is selected from an ortho-disubstituted phenyl, two ortho-substituted groups are independent of each other or form a ring;

$R_1$ is selected from a substituted or unsubstituted phenyl or a substituted or unsubstituted pyridyl; and $R_2$ is selected from a methyl, an ethyl, an isopropyl and a cyclopropyl; and $R_3$ and $R_4$ are each independently selected from H, a C1 to C5 alkyl, a C1 to C5 alkoxycarbonyl, and a substituted or unsubstituted C1 to C5 acyl respectively; or $R_3$ and $R_4$ together with N to which they both are connected form a substituted or unsubstituted C5 to C6 heterocycloalkyl or a C5 to C6 heterocycloalkyl ketone or a C5 to C6 heteroaryl; and a carbon atom on the heterocycloalkyl or a heterocycloalkyl ketone ring can be further substituted by one or more O and N.

The Ar is selected from the following substituted phenyls, substituted five-membered or six-membered heteroaromatic ring groups:

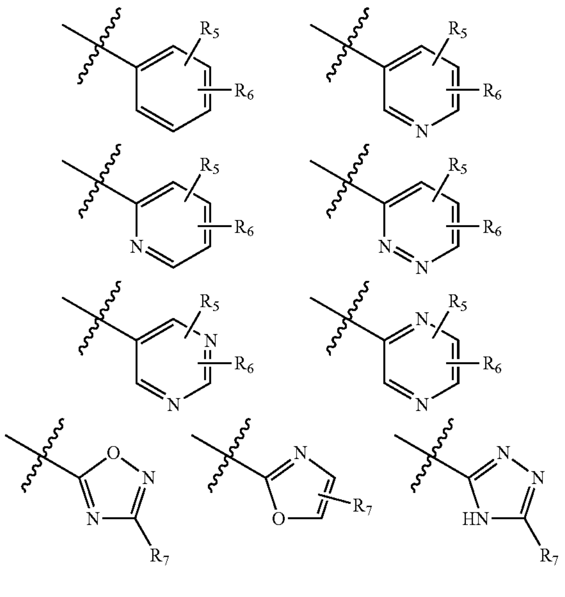

-continued

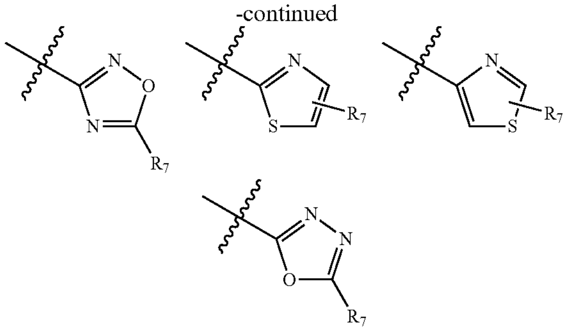

$R_5$ and $R_6$ are the same or different or deleted, independently selected from H, a halogen, a nitryl, a cyano group, a methyl, a trifluoromethyl, a trifluoromethoxy, a methoxy, a dioxymethylene, and a C1 to C3 straight or branched chain alkoxy respectively, and substituted on carbon atoms of any ring; and when the dioxymethylene is selected, the $R_5$ and the $R_6$ are oxygen atoms therein, and form a ring with connected methylenes; and $R_7$ is selected from a methyl, an ethyl, an isopropyl and a cyclopropyl.

The halogen includes F, Cl and Br.

In the present invention, the C1 to C5 alkyl includes a methyl, an ethyl, a propyl, an isopropyl, a butyl, a tert-butyl, etc.; and the C1 to C5 alkoxycarbonyl includes oxycarbonyls connected by a methyl, an ethyl, a propyl, an isopropyl, a butyl, a tert-butyl and the like. The C1 to C5 acyl includes acyls connected by a methyl, an ethyl, a propyl, an isopropyl, a butyl, a tert-butyl and the like. The C1 to C3 straight or branched chain alkoxy includes a methoxy, an ethoxy, a propoxy or an isopropyloxy and the like.

Preferably, in the $R_1$, a substituted group on a phenyl or pyridyl ring is selected from a halogen, a C1 to C3 straight or branched chain alkyl (including a methyl, an ethyl, a propyl, an isopropyl, etc.), a C1 to C3 straight or branched chain alkoxy, a trifluoromethyl and a trifluoromethoxy.

Preferably, the $R_3$ and the $R_4$ are each independently selected from H, a methyl, an ethyl, a methoxycarbonyl, an ethoxycarbonyl, a propoxycarbonyl, an isopropoxycarbonyl, a tert-butoxycarbonyl, a formyl, an acetyl, and an N,N-dialkylacetyl respectively; or the $R_3$ and the $R_4$ together with the N to which they both are connected form a substituted or unsubstituted morpholinone group, a substituted or unsubstituted morpholinyl, a substituted or unsubstituted piperidinyl, a substituted or unsubstituted piperazinyl, a substituted or unsubstituted piperazinone group, a substituted or unsubstituted pyrrolidone group, a substituted or unsubstituted oxazolidinone group, a substituted or unsubstituted imidazolidinone group, a substituted or unsubstituted imidazolyl, a substituted or unsubstituted pyrazolyl, a 1,2,3-triazolyl, and a 1,2,4-triazolyl.

Further preferably, substituted groups on the morpholinone group, the morpholinyl, the piperidinyl, the piperazinyl, the piperazinone group, the pyrrolidone group, the oxazolidinone group, the imidazolidinone group, the imidazolyl and the pyrazolyl are selected from a C1 to C3 straight or branched chain alkyl, a formyl, an acetyl, and a C1 to C5 straight or branched chain alkoxy (including methyl, ethyl, propyl, isopropyl, butyl and tert-butyl connected oxy-substituted groups).

Unless otherwise indicated, optionally substituted components described herein may be substituted at any chemically possible position.

Preferably, the N-formamidopyrazoline derivative has structures shown in General Formulas (Ia), (Ib), (Ic) or (Id) or is an enantiomer, a diastereomer and a racemate thereof, or a pharmaceutically acceptable salt thereof:

(Ia)

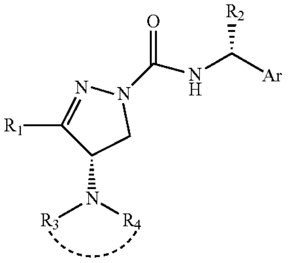

(S,R)

(Ib)

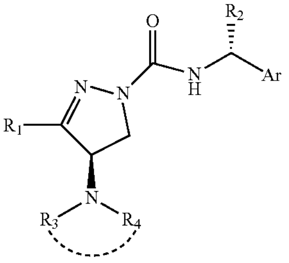

(R,R)

(Ic)

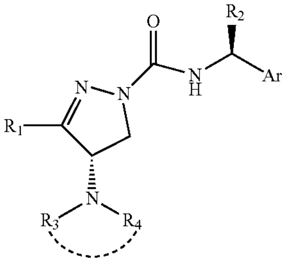

(S,S)

-continued (Id)

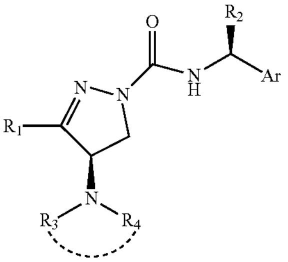

(R,S)

Preferably, the Ar is selected from a phenyl, a p-trifluoromethylphenyl, a dimethoxyphenyl, a dioxolane phenyl, a p-cyanophenyl, a chlorophenyl, a methoxypyridyl, a trifluoromethyl pyridyl, a chloropyridyl, a difluoropyridyl, a trifluoromethyloxypyridyl, a trifluoromethylpyrazinyl, a methylpyrazinyl, a chloropyrazinyl, a methoxypyridazinyl, a trifluoromethylpyridazinyl, a chloropyridazinyl, a trifluoromethylpyrimidinyl, a methylpyrimidinyl, a chloropyrimidinyl, a methyl-1,2,4-oxadiazolyl, and a methyl-1,3,4-oxadiazolyl; the $R_1$ is selected from a p-methylphenyl, a p-methoxyphenyl, a p-fluorophenyl, a p-chlorophenyl, and a methylpyridyl; the $R_2$ is selected from a methyl and an ethyl; the $R_3$ and the $R_4$ are each independently selected from H, a methyl, an ethyl, a methoxycarbonyl, an ethoxycarbonyl, an acetyl, and an N,N-dialkylacetyl respectively; or the $R_3$ and the $R_4$ together with the N to which they both are connected form a morpholinone group, a piperazinone group, an N-methylpiperazinone group, a methylpiperazinone group, a pyrrolidone group, an oxazolidinone group, an imidazolidinone group, an acetyl imidazolidinone group, a morpholinyl, a piperazinyl, an N-acetylpiperazinyl, and a pyrazolyl.

More specifically, among the compounds in General Formula (I) of the present invention, preferred compounds include but are not limited to:

| Serial number | Compound name | Structure |
|---|---|---|
| 1 | (S)-4-(3-oxomorpholin-4-yl)-3-(4-methylphenyl)-N-((R)-1-(6-(trifluoromethyl)pyridin-3-yl)ethyl)-4,5-dihydro-1H-pyrazol-1-carboxamide | 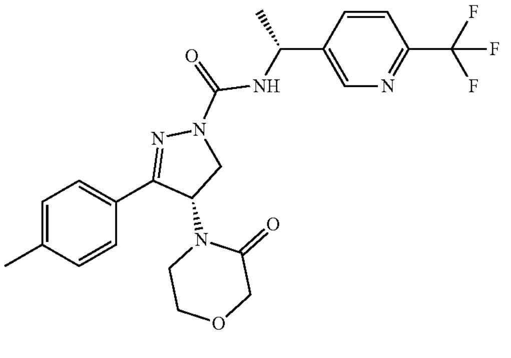 [SMILES: Cc1ccc(C2=NN(C(=O)N[C@H](C)c3ccc(C(F)(F)F)nc3)C[C@@H]2N2CCOCC2=O)cc1] |

-continued

| Serial number | Compound name | Structure |
|---|---|---|
| 1a | (R)-4-(3-oxomorpholin-4-yl)-3-(4-methylphenyl])-N-((R)-1-(6-(trifluoromethyl)pyridin-3-yl)ethyl)-4,5-dihydro-1H-pyrazol-1-carboxamide | 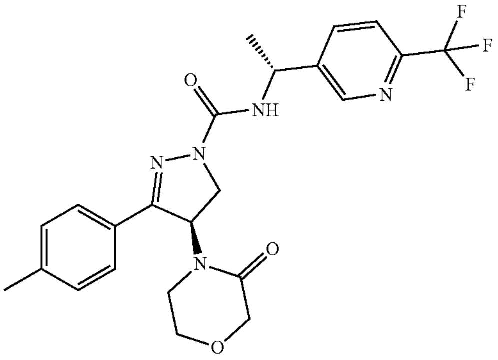 [SMILES: Cc1ccc(C2=NN(C(=O)N[C@H](C)c3ccc(C(F)(F)F)nc3)C[C@H]2N2CCOCC2=O)cc1] |
| 2 | (S)-4-(4-methyl-2-oxopiperazin-1-yl)-3-(4-methylphenyl)-N-((R)-1-(4-chlorophenyl) ethyl)-4,5-dihydro-1H-pyrazol-1-carboxamide | 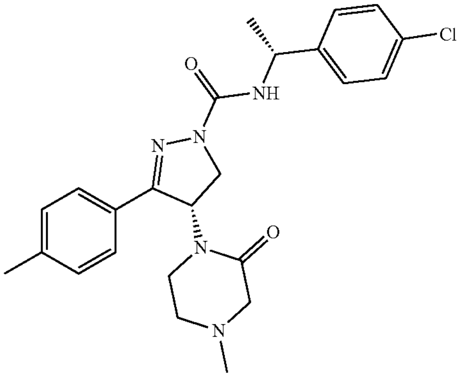 [SMILES: Cc1ccc(C2=NN(C(=O)N[C@H](C)c3ccc(Cl)cc3)C[C@@H]2N2CCN(C)CC2=O)cc1] |
| 2a | (R)-4-(4-methyl-2-oxopiperazin-1-y])-3-(4-methylphenyl)-N-((R)-1-(4-chlorophenyl)) ethyl)-4,5-dihydro-1H-pyrazol-1-carboxamide | 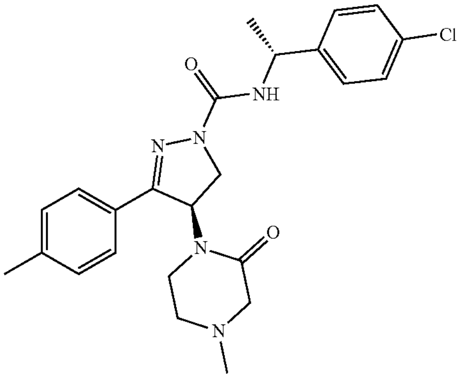 [SMILES: Cc1ccc(C2=NN(C(=O)N[C@H](C)c3ccc(Cl)cc3)C[C@H]2N2CCN(C)CC2=O)cc1] |
| 3 | (S)-4-(3-oxomorpholin-4-yl)-3-(4-methylphenyl])-N-((R)-1-(2-(trifluoromethyl)pyrimidin-5-yl)ethyl)-4,5-dihydro-1H-pyrazol-1-carboxamide | 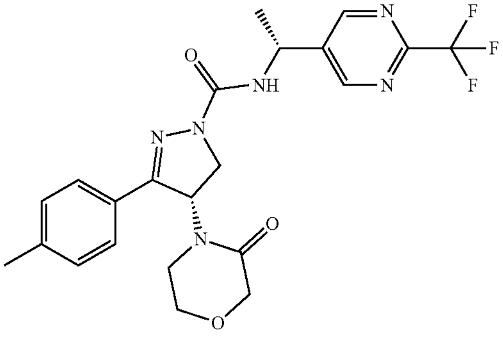 [SMILES: Cc1ccc(C2=NN(C(=O)N[C@H](C)c3cnc(C(F)(F)F)nc3)C[C@@H]2N2CCOCC2=O)cc1] |

-continued

| Serial number | Compound name | Structure |
|---|---|---|
| 3a | (R)-4-(3-oxomorpholin-4-yl)-3-(4-methylphenyl)-N-((R)-1-(2-(trifluoromethyl)pyrimidin-5-yl)ethyl)-4,5-dihydro-1H-pyrazol-1-carboxamide | 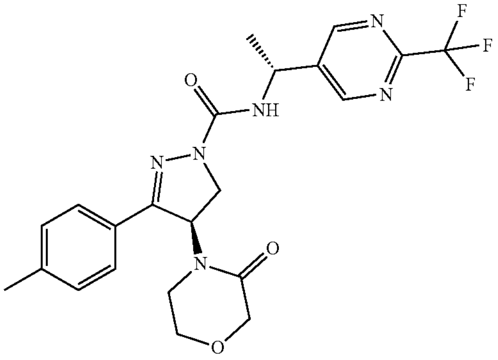 |
| 4 | (S)-4-(N-methyl-N-ethoxycarbonylamino)-3-(4-methylphenyl)-N-((R)-1-(2-(trifluoromethyl) pyrimidin-5-yl)ethyl)-4,5-dihydro-1H-pyrazol-1-carboxamide | 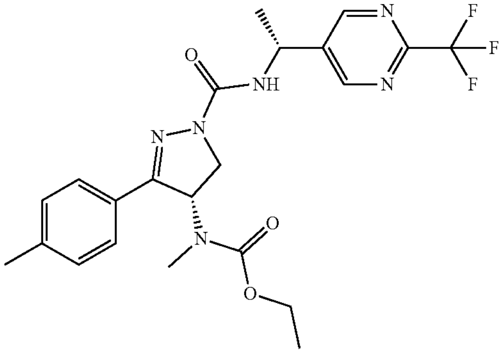 [SMILES: CCOC(=O)N(C)[C@H]1CN(C(=O)N[C@H](C)c2cnc(C(F)(F)F)nc2)N=C1c1ccc(C)cc1] |
| 4c | (R)-4-(N-methyl-N-ethoxycarbonylamino)-3-(4-methylphenyl)-N-((R)-1-(2-(trifluoromethyl) pyrimidin-5-yl)ethyl)-4,5-dihydro-1H-pyrazol-1-carboxamide | 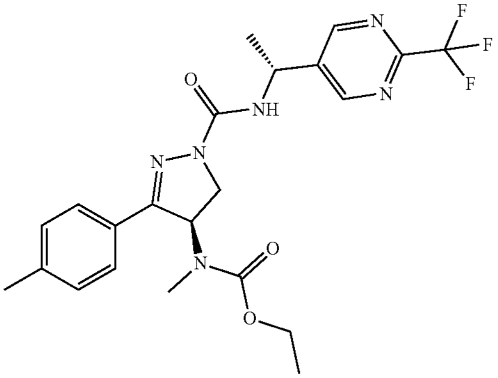 [SMILES: CCOC(=O)N(C)[C@@H]1CN(C(=O)N[C@H](C)c2cnc(C(F)(F)F)nc2)N=C1c1ccc(C)cc1] |
| 5 | (S)-4-(N-methylacetamido)-3-(4-methylphenyl])-N-((R)-1-(4-(trifluoromethyl)phenyl)ethyl)-4,5-dihydro-1H-pyrazol-1-carboxamide | 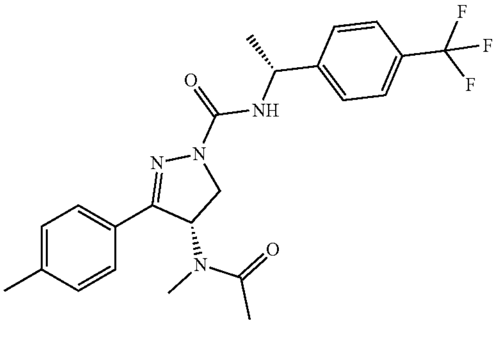 [SMILES: CC(=O)N(C)[C@H]1CN(C(=O)N[C@H](C)c2ccc(C(F)(F)F)cc2)N=C1c1ccc(C)cc1] |

-continued

| Serial number | Compound name | Structure |
|---|---|---|
| 5a | (R)-4-(N-methylacetamido)-3-(4-methylphenyl)-N-((R)-1-(4-(trifluoromethyl)phenyl)ethyl)-4,5-dihydro-1H-pyrazol-1-carboxamide | 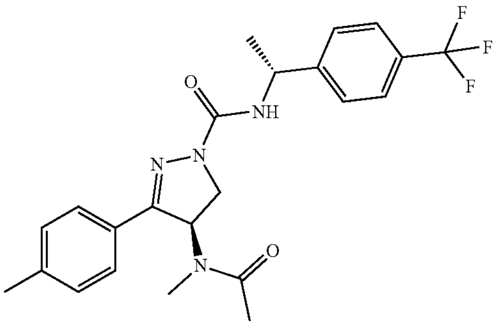 [SMILES: CC(=O)N(C)[C@@H]1CN(C(=O)N[C@H](C)c2ccc(C(F)(F)F)cc2)N=C1c1ccc(C)cc1] |
| 6 | (S)-4-(2-oxooxazolidin-3-yl)-3-(4-methylphenyl])-N-((R)-1-(3,4-dimethoxyphenyl)ethyl)-4,5-dihydro-1H-pyrazol-1-carboxamide | 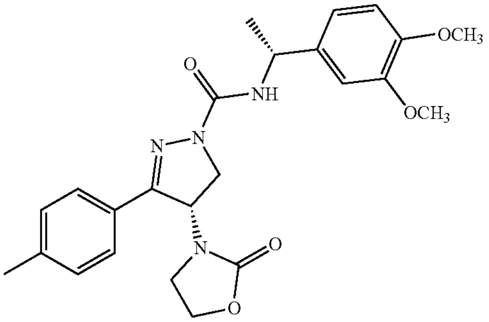 [SMILES: COc1ccc([C@@H](C)NC(=O)N2C[C@H](N3CCOC3=O)C(c3ccc(C)cc3)=N2)cc1OC] |
| 6a | (R)-4-(2-oxooxazolidin-3-yl)-3-(4-methylphenyl)-N-((R)-1-(3,4-dimethoxyphenyl)ethyl)-4,5-dihydro-1H-pyrazol-1-carboxamide | 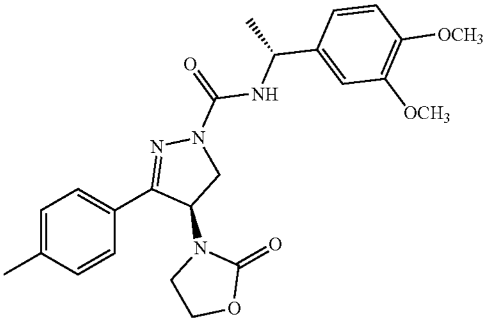 [SMILES: COc1ccc([C@@H](C)NC(=O)N2C[C@@H](N3CCOC3=O)C(c3ccc(C)cc3)=N2)cc1OC] |
| 7 | (S)-4-(2-oxopyrrolidin-1-yl)-3-(4-methylphenyl)-N-((R)-1-(3,4-(methylenedioxy)phenyl)ethyl)-4,5-dihydro-1H-pyrazol-1-carboxamide | 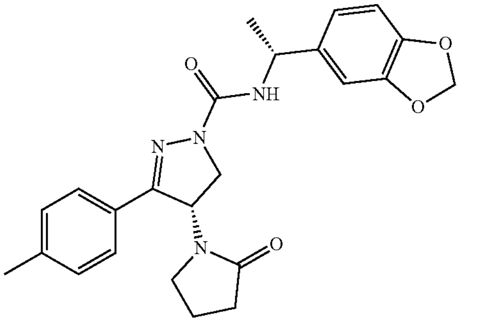 [SMILES: Cc1ccc(C2=NN(C(=O)N[C@H](C)c3ccc4c(c3)OCO4)C[C@@H]2N2CCCC2=O)cc1] |

-continued

| Serial number | Compound name | Structure |
|---|---|---|
| 7a | (R)-4-(2-oxopyrrolidin-1-yl)-3-(4-methylphenyl])-N-((R)-1-(3,4-(methylenedioxy)phenyl)ethyl)-4,5-dihydro-1H-pyrazol-1-carboxamide | 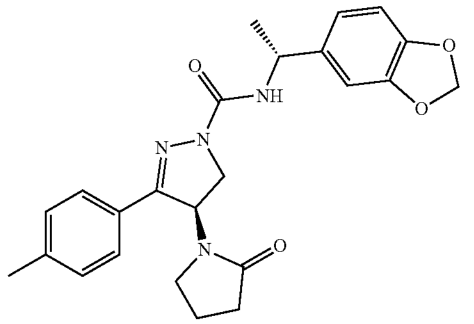 [SMILES: Cc1ccc(C2=NN(C(=O)N[C@H](C)c3ccc4c(c3)OCO4)C[C@H]2N2CCCC2=O)cc1] |
| 8 | (S)-4-(3-acetyl-2-oxoimidazolidin-1-yl)-3-(4-methylphenyl)-N-((R)-1-(4-cyanophenyl)ethyl)-4,5-dihydro-1H-pyrazol-1-carboxamide | 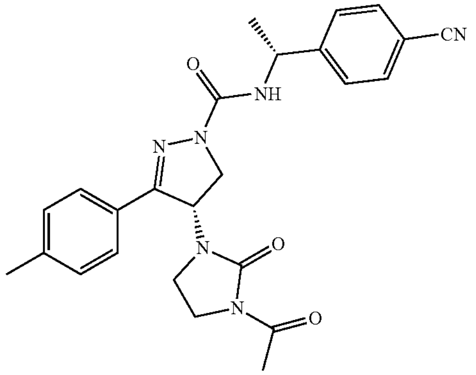 [SMILES: CC(=O)N1CCN([C@H]2CN(C(=O)N[C@H](C)c3ccc(C#N)cc3)N=C2c2ccc(C)cc2)C1=O] |
| 8a | (R)-4-(3-acetyl-2-oxoimidazolidin-1-yl)-3-(4-methylphenyl)-N-((R)-1-(4-cyanophenyl)ethyl)-4,5-dihydro-1H-pyrazol-1-carboxamide | 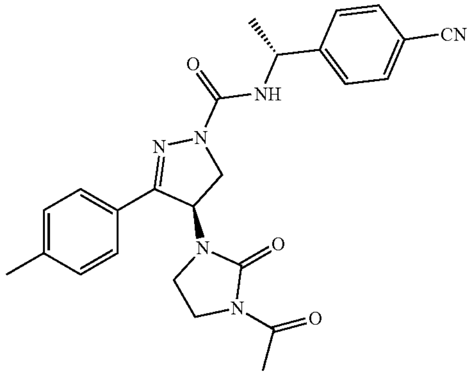 [SMILES: CC(=O)N1CCN([C@@H]2CN(C(=O)N[C@H](C)c3ccc(C#N)cc3)N=C2c2ccc(C)cc2)C1=O] |
| 9 | (S)-4-(2-oxopyrrolidin-1-yl)-3-(4-methylphenyl])-N-((R)-1-(5-methoxypyridin-2-yl)ethyl)-4,5-dihydro-1H-pyrazol-1-carboxamide | 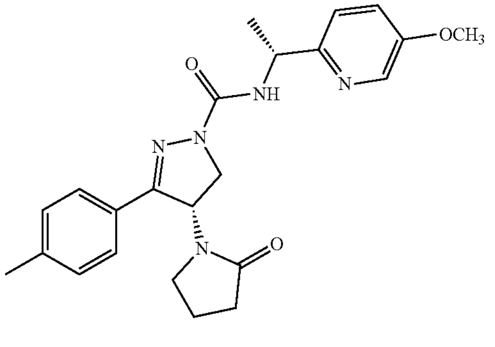 [SMILES: COc1ccc([C@@H](C)NC(=O)N2C[C@H](N3CCCC3=O)C(c3ccc(C)cc3)=N2)nc1] |

-continued

| Serial number | Compound name | Structure |
|---|---|---|
| 9a | (R)-4-(2-oxopyrrolidin-1-yl)-3-(4-methylphenyl])-N-((R)-1-(5-methoxypyridin-2-yl)ethyl)-4,5-dihydro-1H-pyrazol-1-carboxamide | 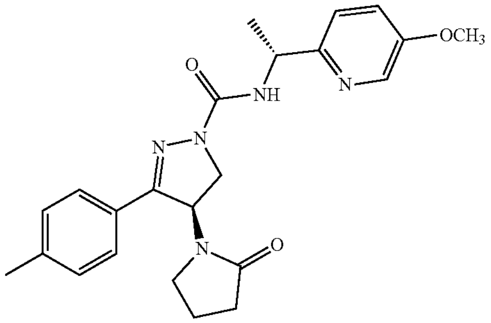 [SMILES: COc1ccc([C@@H](C)NC(=O)N2C[C@@H](N3CCCC3=O)C(c3ccc(C)cc3)=N2)nc1] |
| 10 | (S)-4-(2-oxopyrrolidin-1-y])-3-(4-methylphenyl])-N-((R)-1-(5-(trifluoromethyl)pyridin-2-yl)ethyl)-4,5-dihydro-1H-pyrazol-1-carboxamide | 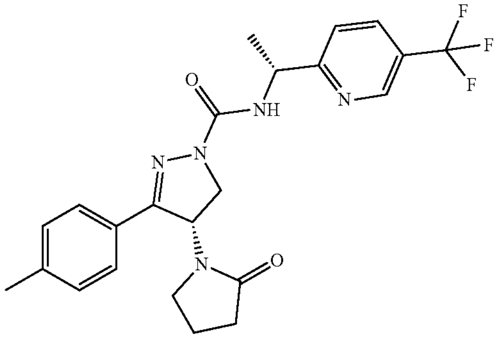 [SMILES: Cc1ccc(C2=NN(C(=O)N[C@H](C)c3ccc(C(F)(F)F)cn3)C[C@@H]2N2CCCC2=O)cc1] |
| 10a | (R)-4-(2-oxopyrrolidin-1-yl)-3-(4-methylphenyl])-N-((R)-1-(5-(trifluoromethyl)pyridin-2-yl)ethyl)-4,5-dihydro-1H-pyrazol-1-carboxamide | 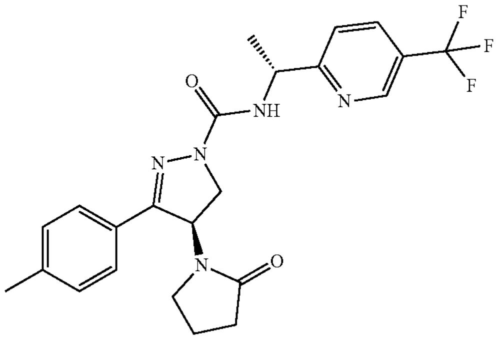 [SMILES: Cc1ccc(C2=NN(C(=O)N[C@H](C)c3ccc(C(F)(F)F)cn3)C[C@H]2N2CCCC2=O)cc1] |
| 11 | (S)-4-(N-methylacetamido)-3-(4-methylphenyl])-N-((R)-1-(6-chloropyridin-3-yl)ethyl)-4,5-dihydro-1H-pyrazol-1-carboxamide | 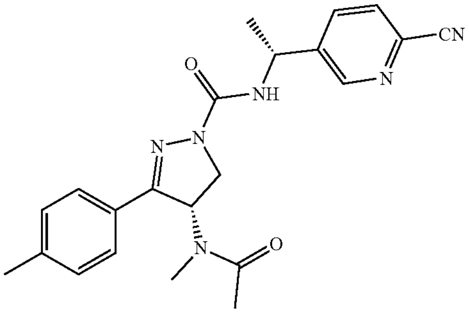 [SMILES: CC(=O)N(C)[C@H]1CN(C(=O)N[C@H](C)c2ccc(C#N)nc2)N=C1c1ccc(C)cc1] |

-continued

| Serial number | Compound name | Structure |
|---|---|---|
| 11a | (R)-4-(N-methylacetamido)-3-(4-methylphenyl])-N-((R)-1-(6-chloropyridin-3-yl)ethyl)-4,5-dihydro-1H-pyrazol-1-carboxamide | 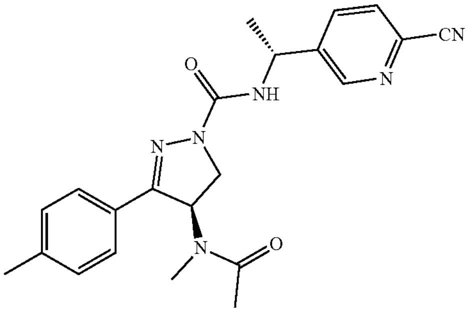 [SMILES: CC(=O)N(C)[C@@H]1CN(C(=O)N[C@H](C)c2ccc(C#N)nc2)N=C1c1ccc(C)cc1] |
| 12 | (S)-4-(2-oxooxazolidin-3-yl)-3-(4-methylphenyl])-N-((R)-1-(5,6-difluoropyridin-3-yl)ethyl)-4,5-dihydro-1H-pyrazol-1-carboxamide | 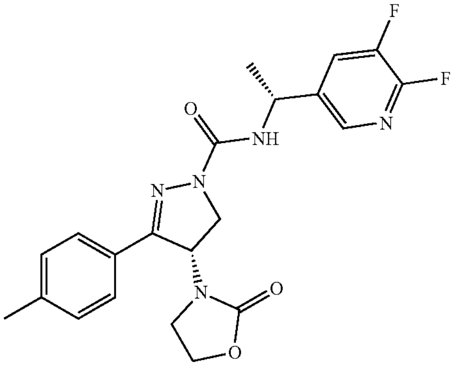 [SMILES: Cc1ccc(C2=NN(C(=O)N[C@H](C)c3cnc(F)c(F)c3)C[C@@H]2N2CCOC2=O)cc1] |
| 12a | (R)-4-(2-oxooxazolidin-3-yl)-3-(4-methylphenyl])-N-((R)-1-(5,6-difluoropyridin-3-yl)ethyl)-4,5-dihydro-1H-pyrazol-1-carboxamide | 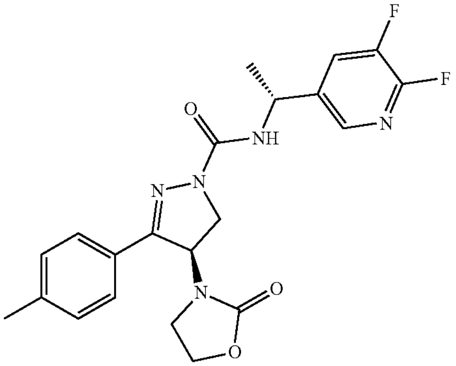 [SMILES: Cc1ccc(C2=NN(C(=O)N[C@H](C)c3cnc(F)c(F)c3)C[C@H]2N2CCOC2=O)cc1] |
| 13 | (S)-4-(2-oxopyrrolidin-1-yl)-3-(4-methylphenyl])-N-((R)-1-(6-(trifluoromethoxy)pyridin)-3-yl)ethyl)-4,5-dihydro-1H-pyrazol-1-carboxamide | 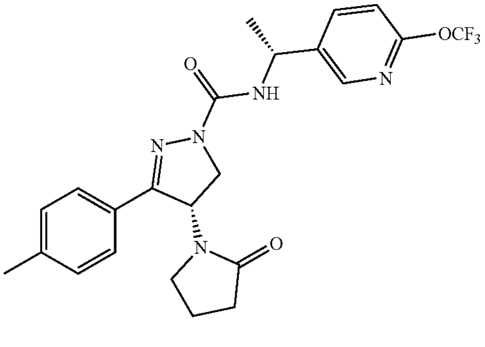 [SMILES: Cc1ccc(C2=NN(C(=O)N[C@H](C)c3ccc(OC(F)(F)F)nc3)C[C@@H]2N2CCCC2=O)cc1] |

-continued

| Serial number | Compound name | Structure |
|---|---|---|
| 13a | (R)-4-(2-oxopyrrolidin-1-yl)-3-(4-methylphenyl)-N-((R)-1-(6-(trifluoromethoxy)pyridin)-3-yl)ethyl)-4,5-dihydro-1H-pyrazol-1-carboxamide | 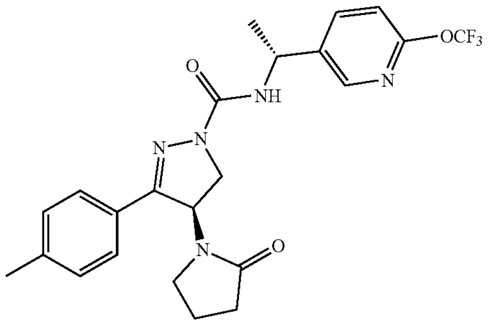 [SMILES: Cc1ccc(C2=NN(C(=O)N[C@H](C)c3ccc(OC(F)(F)F)nc3)C[C@H]2N2CCCC2=O)cc1] |
| 14 | (S)-4-(morpholin-4-yl)-3-(4-fluorophenyl)-N-((R)-1-(6-methoxypyridin-3-yl)ethyl)-4,5-dihydro-1H-pyrazol-1-carboxamide | 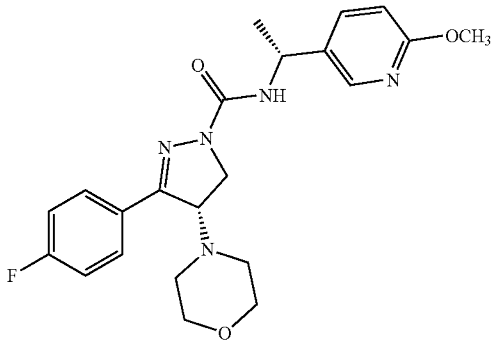 [SMILES: COc1ccc([C@@H](C)NC(=O)N2C[C@H](N3CCOCC3)C(c3ccc(F)cc3)=N2)cn1] |
| 14a | (R)-4-(morpholin-4-yl)-3-(4-fluorophenyl)-N-((R)-1-(6-methoxypyridin-3-yl)ethyl)-4,5-dihydro-1H-pyrazol-1-carboxamide | 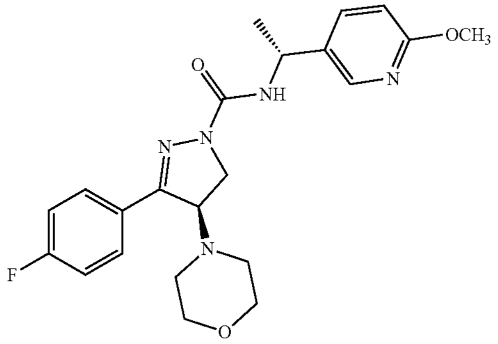 [SMILES: COc1ccc([C@@H](C)NC(=O)N2C[C@@H](N3CCOCC3)C(c3ccc(F)cc3)=N2)cn1] |
| 15 | (S)-4-(2-(dimethylamino)-N-methylacetamido)-3-(4-methylphenyl)-N-((R)-1-(6-(trifluoromethyl) pyridin-3-yl)ethyl)-4,5-dihydro-1H-pyrazol-1-carboxamide | 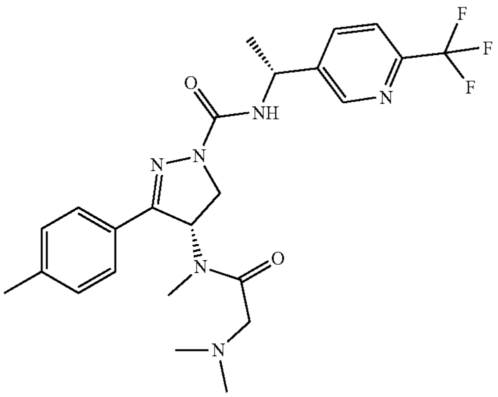 [SMILES: Cc1ccc(C2=NN(C(=O)N[C@H](C)c3ccc(C(F)(F)F)nc3)C[C@@H]2N(C)C(=O)CN(C)C)cc1] |

-continued

| Serial number | Compound name | Structure |
| --- | --- | --- |
| 15a | (R)-4-(2-(dimethylamino)-N-methylacetamido)-3-(4-methylphenyl)-N-((R)-1-(6-(trifluoromethyl) pyridin-3-yl)ethyl)-4,5-dihydro-1H-pyrazol-1-carboxamide | 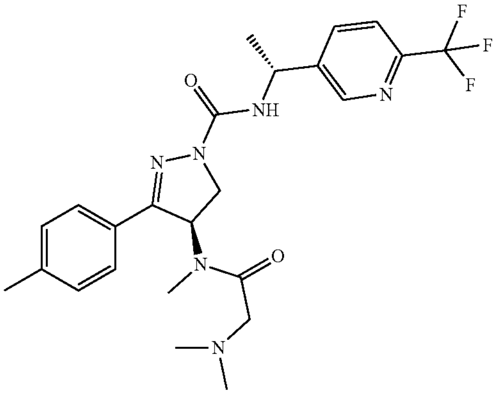 [SMILES: Cc1ccc(C2=NN(C(=O)N[C@H](C)c3ccc(C(F)(F)F)nc3)C[C@H]2N(C)C(=O)CN(C)C)cc1] |
| 16 | (S)-4-(N-methyl-N-methoxycarbonylamino)-3-(4-methoxyphenyl)-N-((R)-1-(6-(trifluoromethyl) pyridin-3-yl)ethyl)-4,5-dihydro-1H-pyrazol-1-carboxamide | 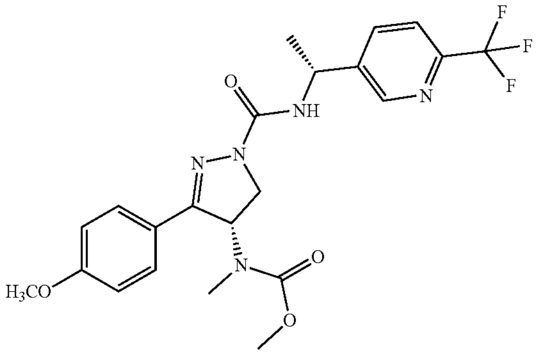 [SMILES: COC(=O)N(C)[C@H]1CN(C(=O)N[C@H](C)c2ccc(C(F)(F)F)nc2)N=C1c1ccc(OC)cc1] |
| 16a | (R)-4-(N-methyl-N-methoxycarbonylamino)-3-(4-methoxyphenyl)-N-((R)-1-(6-(trifluoromethyl) pyridin-3-yl)ethyl)-4,5-dihydro-1H-pyrazol-1-carboxamide | 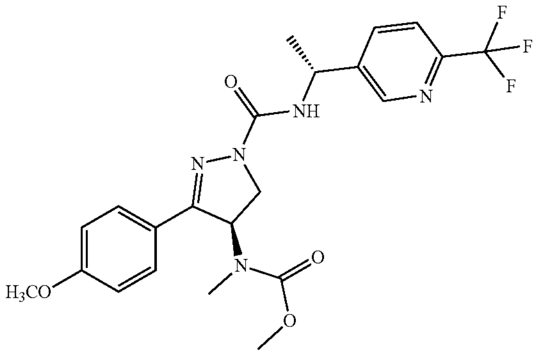 [SMILES: COC(=O)N(C)[C@@H]1CN(C(=O)N[C@H](C)c2ccc(C(F)(F)F)nc2)N=C1c1ccc(OC)cc1] |
| 17 | (S)-4-(4-methyl-2-oxopiperazin-1-yl)-3-(4-methylphenyl)-N-((R)-1-(6-(trifluoromethyl) pyridin-3-yl)ethyl)-4,5-dihydro-1H-pyrazol-1-carboxamide | 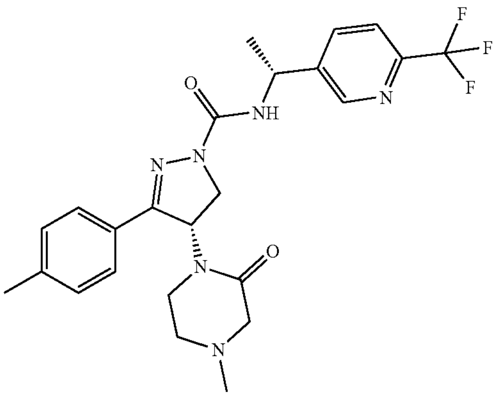 [SMILES: Cc1ccc(C2=NN(C(=O)N[C@H](C)c3ccc(C(F)(F)F)nc3)C[C@@H]2N2CCN(C)CC2=O)cc1] |

-continued

| Serial number | Compound name | Structure |
|---|---|---|
| 17a | (R)-4-(4-methyl-2-oxopiperazin-1-yl)-3-(4-methylphenyl)-N-((R)-1-(6-(trifluoromethyl)pyridin-3-yl)ethyl)-4,5-dihydro-1H-pyrazol-1-carboxamide | 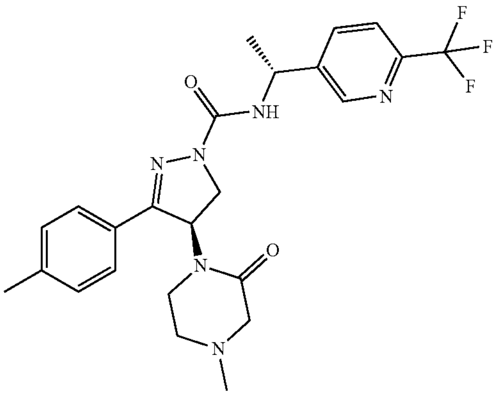 [SMILES: Cc1ccc(C2=NN(C(=O)N[C@H](C)c3ccc(C(F)(F)F)nc3)C[C@H]2N2CCN(C)CC2=O)cc1] |
| 18 | (S)-4-(3-acetyl-2-oxoimidazolidin-1-yl)-3-(4-methylphenyl)-N-((R)-1-(6-(trifluoromethyl)pyridin-3-yl)ethyl)-4,5-dihydro-1H-pyrazol-1-carboxamide | 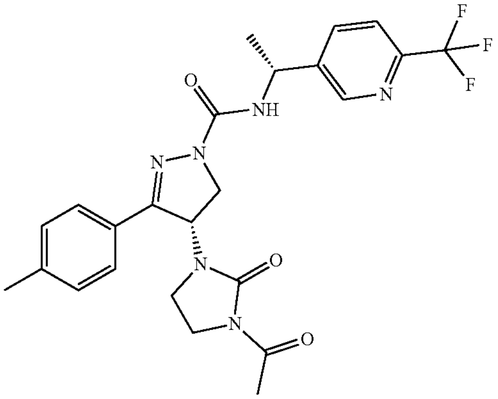 [SMILES: CC(=O)N1CCN([C@H]2CN(C(=O)N[C@H](C)c3ccc(C(F)(F)F)nc3)N=C2c2ccc(C)cc2)C1=O] |
| 18a | (R)-4-(3-acetyl-2-oxoimidazolidin-1-yl)-3-(4-methylphenyl)-N-((R)-1-(6-(trifluoromethyl)pyridin-3-yl)ethyl)-4,5-dihydro-1H-pyrazol-1-carboxamide | 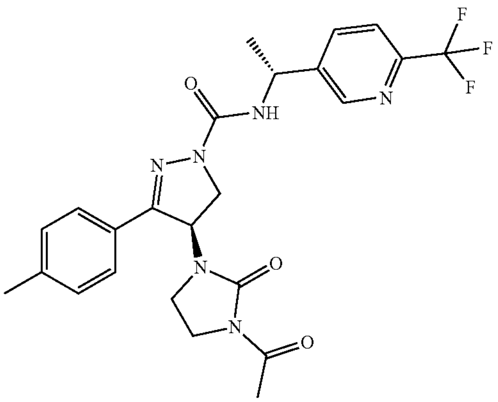 [SMILES: CC(=O)N1CCN([C@@H]2CN(C(=O)N[C@H](C)c3ccc(C(F)(F)F)nc3)N=C2c2ccc(C)cc2)C1=O] |

-continued

| Serial number | Compound name | Structure |
|---|---|---|
| 19 | (S)-4-(4-acetylpiperazin-1-yl)-3-(4-methylphenyl])-N-((R)-1-(6-(trifluoromethyl)pyridin-3-yl)ethyl)-4,5-dihydro-1H-pyrazol-1-carboxamide | 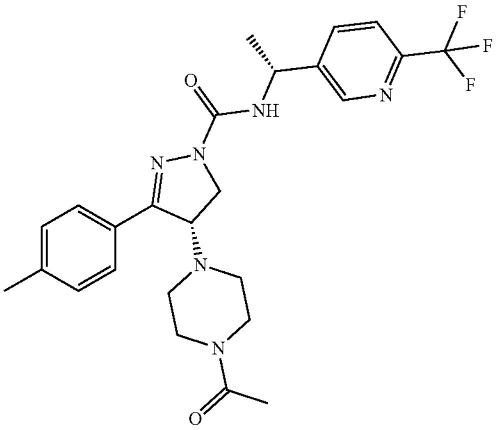 [SMILES: CC(=O)N1CCN([C@H]2CN(C(=O)N[C@H](C)c3ccc(C(F)(F)F)nc3)N=C2c2ccc(C)cc2)CC1] |
| 19a | (R)-4-(4-acetylpiperazin-1-yl)-3-(4-methylphenyl)-N-((R)-1-(6-(trifluoromethyl)pyridin-3-yl)ethyl)-4,5-dihydro-1H-pyrazol-1-carboxamide | 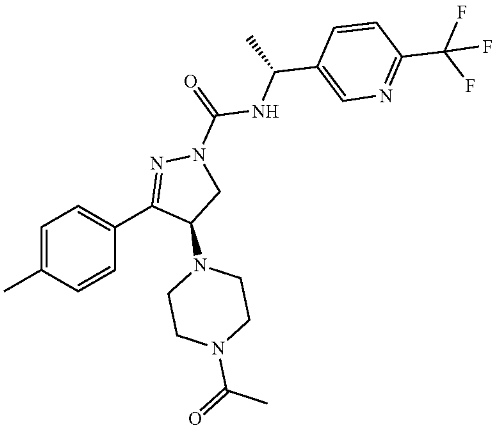 [SMILES: CC(=O)N1CCN([C@@H]2CN(C(=O)N[C@H](C)c3ccc(C(F)(F)F)nc3)N=C2c2ccc(C)cc2)CC1] |
| 20 | (S)-4-(3-oxomorpholin-4-yl)-3-(4-methylphenyl])-N-((R)-1-(4-(trifluoromethyl)phenyl)ethyl)-4,5-dihydro-1H-pyrazol-1-carboxamide | 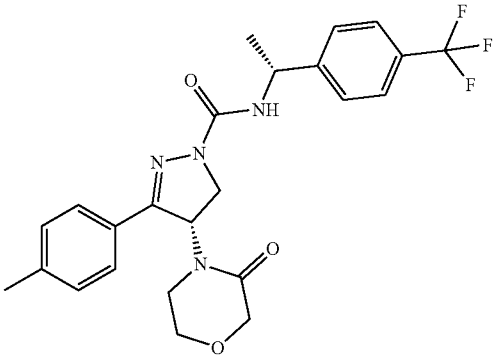 [SMILES: Cc1ccc(C2=NN(C(=O)N[C@H](C)c3ccc(C(F)(F)F)cc3)C[C@@H]2N2CCOCC2=O)cc1] |
| 20a | (R)-4-(3-oxomorpholin-4-yl)-3-(4-methylphenyl)-N-((R)-1-(4-(trifluoromethyl)phenyl)ethyl)-4,5-dihydro-1H-pyrazol-1-carboxamide | 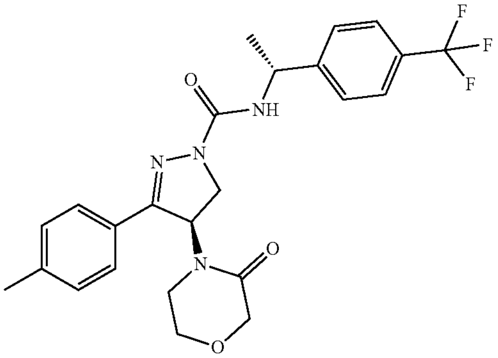 [SMILES: Cc1ccc(C2=NN(C(=O)N[C@H](C)c3ccc(C(F)(F)F)cc3)C[C@H]2N2CCOCC2=O)cc1] |

-continued

| Serial number | Compound name | Structure |
|---|---|---|
| 21 | (S)-4-(2-oxopyrrolidin-1-yl)-3-(4-methylphenyl])-N-((R)-1-(6-(trifluoromethyl)pyridin-3-yl)ethyl)-4,5-dihydro-1H-pyrazol-1-carboxamide | 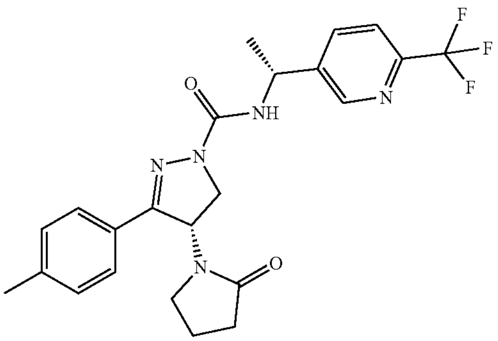 [SMILES: Cc1ccc(C2=NN(C(=O)N[C@H](C)c3ccc(C(F)(F)F)nc3)C[C@@H]2N2CCCC2=O)cc1] |
| 21a | (S)-4-(2-oxopyrrolidin-1-yl)-3-(4-methylphenyl])-N-((R)-1-(6-(trifluoromethyl)pyridin-3-yl)ethyl)-4,5-dihydro-1H-pyrazol-1-carboxamide | 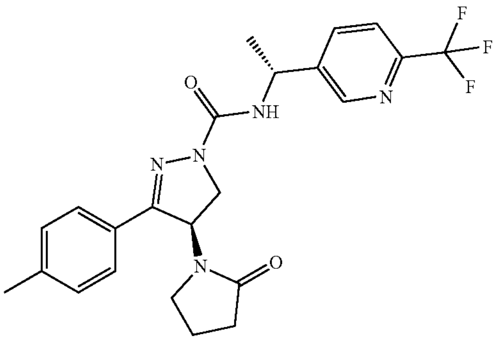 [SMILES: Cc1ccc(C2=NN(C(=O)N[C@H](C)c3ccc(C(F)(F)F)nc3)C[C@H]2N2CCOC2=O)cc1] |
| 22 | (S)-4-(2-oxooxazolidin-3-yl)-3-(4-methylphenyl])-N-((R)-1-(6-(trifluoromethyl)pyridin-3-yl)ethyl)-4,5-dihydro-1H-pyrazol-1-carboxamide | 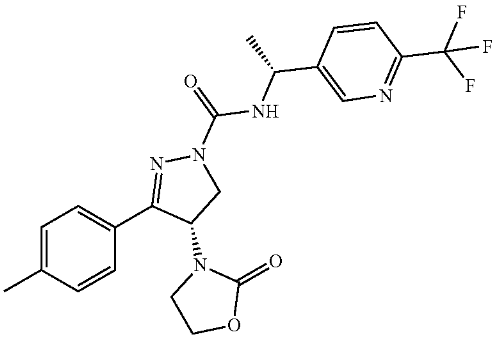 [SMILES: Cc1ccc(C2=NN(C(=O)N[C@H](C)c3ccc(C(F)(F)F)nc3)C[C@@H]2N2CCOC2=O)nc1] |
| 22a | (R)-4-(2-oxooxazolidin-3-yl)-3-(4-methylphenyl)-N-((R)-1-(6-(trifluoromethyl)pyridin-3-yl)ethyl)-4,5-dihydro-1H-pyrazol-1-carboxamide | 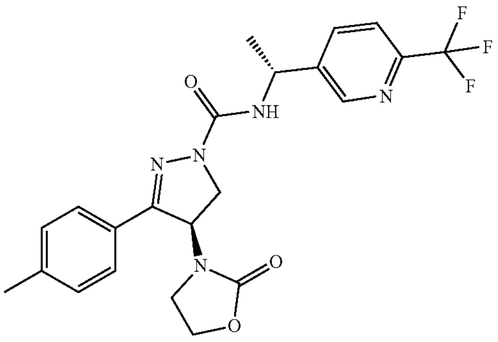 |

-continued

| Serial number | Compound name | Structure |
|---|---|---|
| 23 | (S)-4-(2-oxooxazolidin-3-yl)-3-(5-methylpyridin-2-yl)-N-((R)-1-(6-(trifluoromethyl)pyridin-3-yl) ethyl)-4,5-dihydro-1H-pyrazol-1-carboxamide | 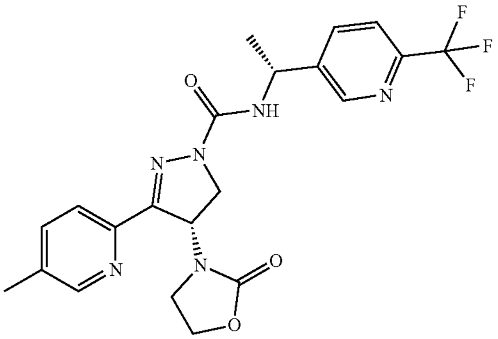 |
| 23a | (R)-4-(2-oxooxazolidin-3-yl)-3-(5-methylpyridin-2-yl)-N-((R)-1-(6-(trifluoromethyl)pyridin-3-yl) ethyl)-4,5-dihydro-1H-pyrazol-1-carboxamide | 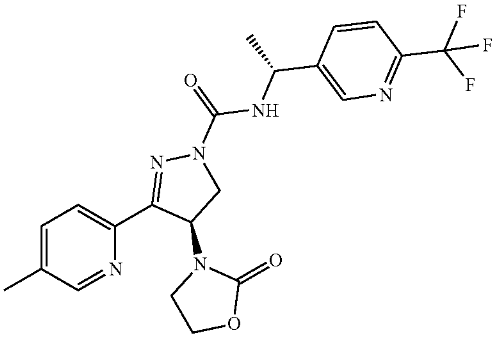 [SMILES: Cc1ccc(C2=NN(C(=O)N[C@H](C)c3ccc(C(F)(F)F)nc3)C[C@H]2N2CCOC2=O)nc1] |
| 24 | (S)-4-(3-oxomorpholin-4-y])-3-(4-fluorophenyl)-N-((R)-1-(2-(6-(trifluoromethyl)pyridin-3-yl)ethyl)-4,5-dihydro-1H-pyrazol-1-carboxamide | 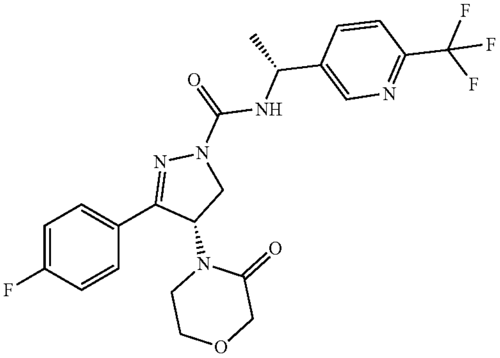 [SMILES: C[C@@H](NC(=O)N1C[C@H](N2CCOCC2=O)C(c2ccc(F)cc2)=N1)c1ccc(C(F)(F)F)nc1] |
| 24a | (R)-4-(3-oxomorpholin-4-yl)-3-(4-fluorophenyl)-N-((R)-1-(2-(6-(trifluoromethyl)pyridin-3-yl)ethyl)-4,5-dihydro-1H-pyrazol-1-carboxamide | 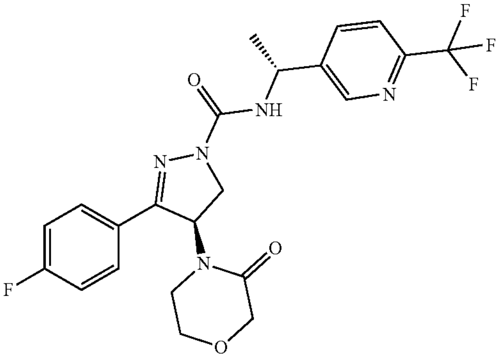 [SMILES: C[C@@H](NC(=O)N1C[C@@H](N2CCOCC2=O)C(c2ccc(F)cc2)=N1)c1ccc(C(F)(F)F)nc1] |

-continued

| Serial number | Compound name | Structure |
|---|---|---|
| 25 | (S)-4-(N-methylacetamido)-3-(4-methylphenyl])-N-((R)-1-(6-(trifluoromethyl)pyridin-3-yl)ethyl)-4,5-dihydro-1H-pyrazol-1-carboxamide | 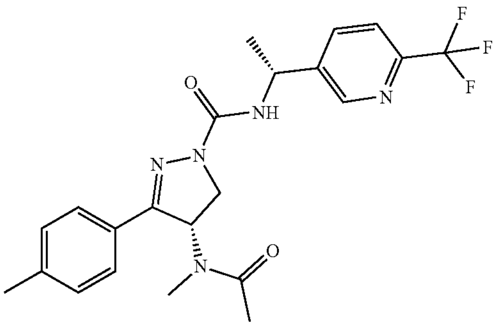 [SMILES: CC(=O)N(C)[C@H]1CN(C(=O)N[C@H](C)c2ccc(C(F)(F)F)nc2)N=C1c1ccc(C)cc1] |
| 25a | (R)-4-(N-methylacetamido)-3-(4-methylphenyl])-N-((R)-1-(6-(trifluoromethyl)pyridin-3-yl)ethyl)-4,5-dihydro-1H-pyrazol-1-carboxamide | 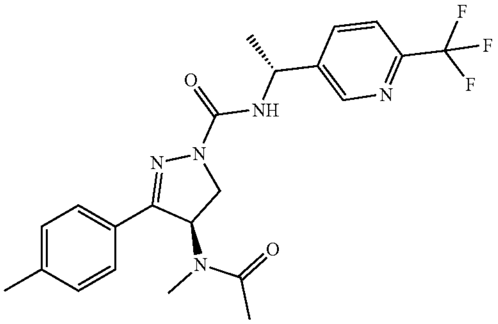 [SMILES: CC(=O)N(C)[C@@H]1CN(C(=O)N[C@H](C)c2ccc(C(F)(F)F)nc2)N=C1c1ccc(C)cc1] |
| 26 | (S)-4-(3-oxomorpholin-4-yl)-3-(4-methylphenyl])-N-((R)-1-(5-(trifluoromethyl)pyrazin)-2-yl)ethyl)-4,5-dihydro-1H-pyrazol-1-carboxamide | 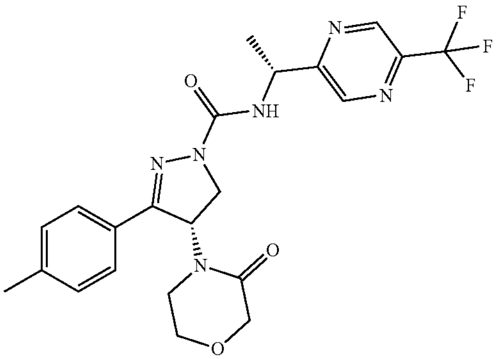 [SMILES: Cc1ccc(C2=NN(C(=O)N[C@H](C)c3cnc(C(F)(F)F)cn3)C[C@@H]2N2CCOCC2=O)cc1] |
| 26a | (R)-4-(3-oxomorpholin-4-yl)-3-(4-methylphenyl])-N-((R)-1-(5-(trifluoromethyl)pyrazin)-2-yl)ethyl)-4,5-dihydro-1H-pyrazol-1-carboxamide | 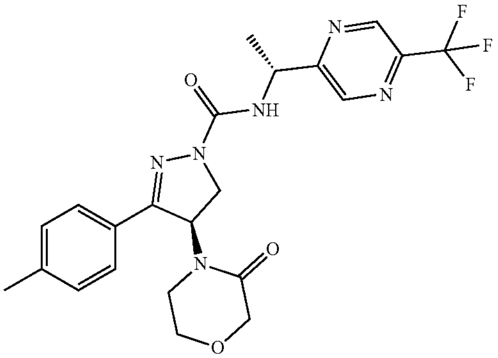 |

-continued

| Serial number | Compound name | Structure |
|---|---|---|
| 27 | (S)-4-(2-oxooxazolidin-3-yl)-3-(4-methylphenyl])-N-((R)-1-(5-methylpyrazin-2-yl)ethyl)-4,5-dihydro-1H-pyrazol-1-carboxamide | 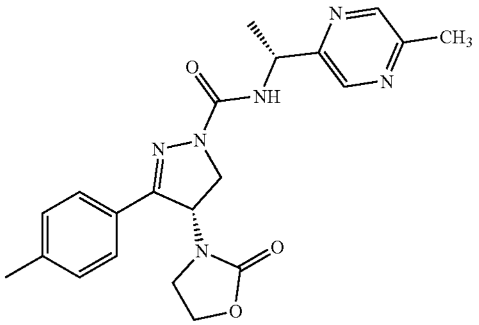 |
| 27a | (R)-4-(2-oxooxazolidin-3-yl)-3-(4-methylphenyl])-N-((R)-1-(5-methylpyrazin-2-yl)ethyl)-4,5-dihydro-1H-pyrazol-1-carboxamide | 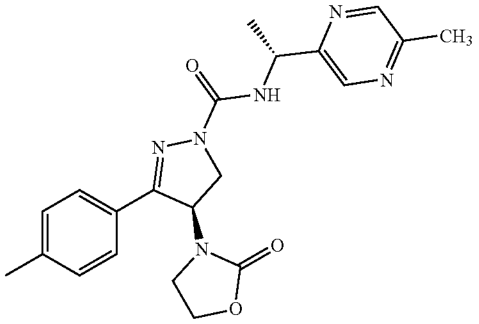 |
| 28 | (S)-4-(2-oxopyrrolidin-1-yl)-3-(4-fluorophenyl)-N-((R)-1-(5-methylpyrazin-2-yl)ethyl)-4,5-dihydro-1H-pyrazol-1-carboxamide | 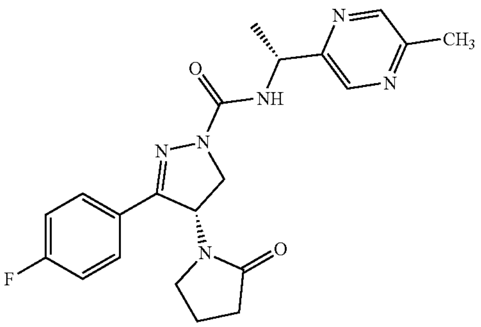 [SMILES: Cc1cnc([C@@H](C)NC(=O)N2C[C@H](N3CCCC3=O)C(c3ccc(F)cc3)=N2)cn1] |
| 28a | (R)-4-(2-oxopyrrolidin-1-yl)-3-(4-fluorophenyl)-N-((R)-1-(5-methylpyrazin-2-yl)ethyl)-4,5-dihydro-1H-pyrazol-1-carboxamide | 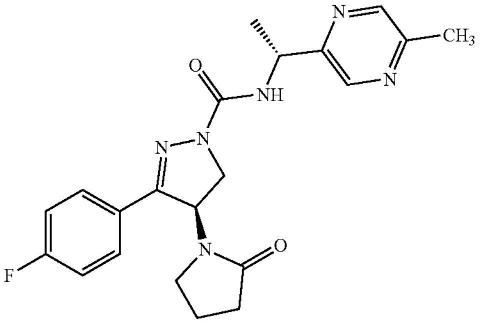 [SMILES: Cc1cnc([C@@H](C)NC(=O)N2C[C@@H](N3CCCC3=O)C(c3ccc(F)cc3)=N2)cn1] |

-continued

| Serial number | Compound name | Structure |
|---|---|---|
| 29 | (S)-4-(2-oxooxazolidin-3-yl)-3-(4-chlorophenyl)-N-((R)-1-(6-(methoxy)pyridazin-3-yl)ethyl)-4,5-dihydro-1H-pyrazol-1-carboxamide | 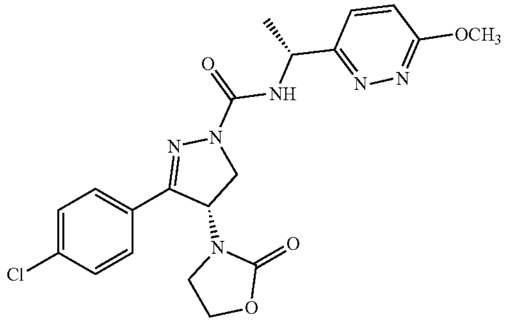 [SMILES: COc1ccc([C@@H](C)NC(=O)N2C[C@H](N3CCOC3=O)C(c3ccc(Cl)cc3)=N2)nn1] |
| 29a | (R)-4-(2-oxooxazolidin-3-yl)-3-(4-chlorophenyl)-N-((R)-1-(6-(methoxy)pyridazin-3-yl)ethyl)-4,5-dihydro-1H-pyrazol-1-carboxamide | 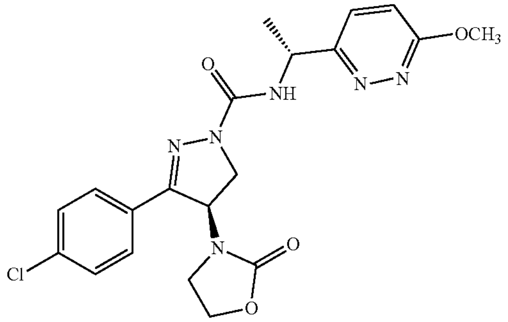 [SMILES: COc1ccc([C@@H](C)NC(=O)N2C[C@@H](N3CCOC3=O)C(c3ccc(Cl)cc3)=N2)nn1] |
| 30 | (S)-4-(3-oxomorpholin-4-yl)-3-(4-methylphenyl)-N-((R)-1-(6-(trifluoromethyl)pyridazin-3-yl)ethyl)-4,5-dihydro-1H-pyrazol-1-carboxamide | 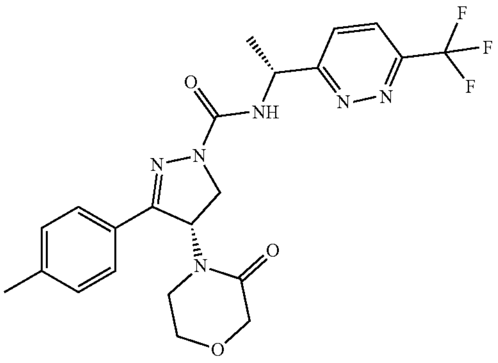 [SMILES: Cc1ccc(C2=NN(C(=O)N[C@H](C)c3ccc(C(F)(F)F)nn3)C[C@@H]2N2CCOCC2=O)cc1] |
| 30a | (R)-4-(3-oxomorpholin-4-y])-3-(4-methylphenyl)-N-((R)-1-(6-(trifluoromethyl)pyridazin-3-yl)ethyl)-4,5-dihydro-1H-pyrazol-1-carboxamide | 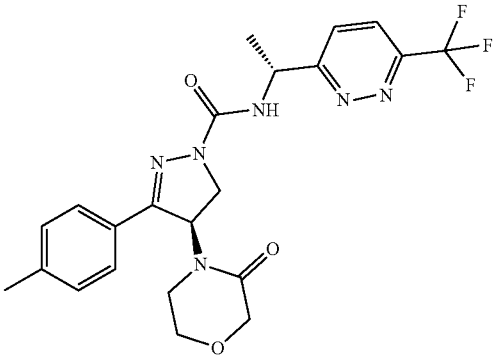 [SMILES: Cc1ccc(C2=NN(C(=O)N[C@H](C)c3ccc(C(F)(F)F)nn3)C[C@H]2N2CCOCC2=O)cc1] |

-continued

| Serial number | Compound name | Structure |
|---|---|---|
| 31 | (S)-4-(2-oxooxazolidin-3-yl)-3-(4-methylphenyl])-N-((R)-1-(6-chloropyridazin-3-yl)ethyl)-4,5-dihydro-1H-pyrazol-1-carboxamide | 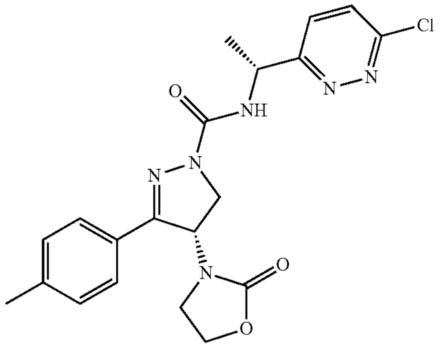 [SMILES: Cc1ccc(C2=NN(C(=O)N[C@H](C)c3ccc(Cl)nn3)C[C@@H]2N2CCOC2=O)cc1] |
| 31a | (R)-4-(2-oxooxazolidin-3-yl)-3-(4-methylphenyl])-N-((R)-1-(6-chloropyridazin-3-yl)ethyl)-4,5-dihydro-1H-pyrazol-1-carboxamide | 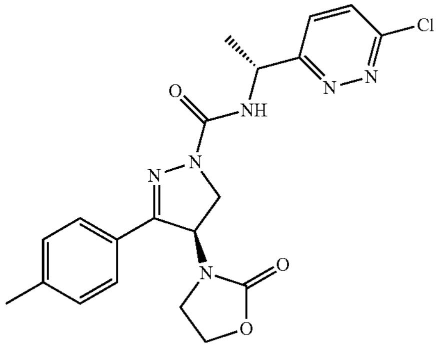 [SMILES: Cc1ccc(C2=NN(C(=O)N[C@H](C)c3ccc(Cl)nn3)C[C@H]2N2CCOC2=O)cc1] |
| 32 | (S)-4-(2-oxopyrrolidin-1-yl)-3-(4-methylphenyl)-N-((R)-1-(2-(trifluoromethyl)pyrimidin-5-yl)ethyl)-4,5-dihydro-1H-pyrazol-1-carboxamide | 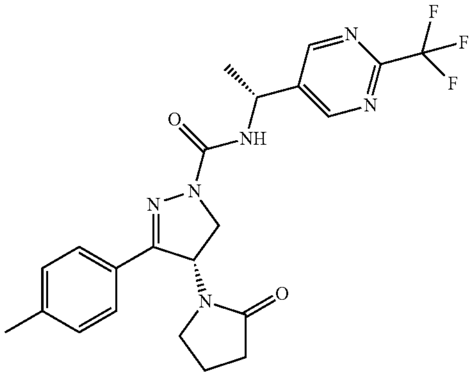 [SMILES: Cc1ccc(C2=NN(C(=O)N[C@H](C)c3cnc(C(F)(F)F)nc3)C[C@@H]2N2CCCC2=O)cc1] |
| 32a | (R)-4-(2-oxopyrrolidin-1-yl)-3-(4-methylphenyl)-N-((R)-1-(2-(trifluoromethyl)pyrimidin-5-yl)ethyl)-4,5-dihydro-1H-pyrazol-1-carboxamide | 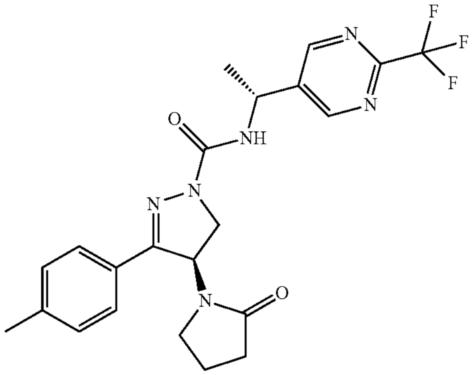 |

-continued

| Serial number | Compound name | Structure |
|---|---|---|
| 33 | (S)-4-(3-oxomorpholin-4-yl)-3-(4-fluorophenyl)-N-((R)-1-(2-(trifluoromethyl)pyrimidin-5-yl)ethyl)-4,5-dihydro-1H-pyrazol-1-carboxamide | 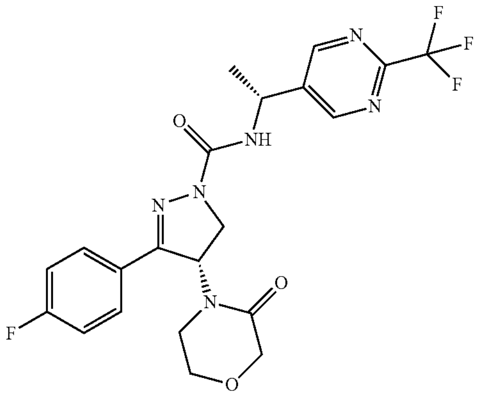 [SMILES: C[C@@H](NC(=O)N1C[C@H](N2CCOCC2=O)C(c2ccc(F)cc2)=N1)c1cnc(C(F)(F)F)nc1] |
| 33a | (R)-4-(3-oxomorpholin-4-yl)-3-(4-fluorophenyl)-N-((R)-1-(2-(trifluoromethyl)pyrimidin-5-yl)ethyl)-4,5-dihydro-1H-pyrazol-1-carboxamide | 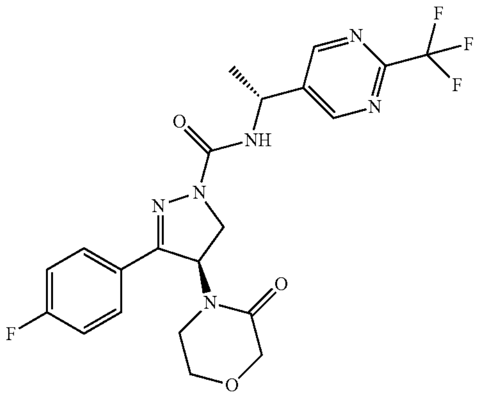 [SMILES: C[C@@H](NC(=O)N1C[C@@H](N2CCOCC2=O)C(c2ccc(F)cc2)=N1)c1cnc(C(F)(F)F)nc1] |
| 34 | (S)-4-(N-methylacetamido)-3-(4-methylphenyl)-N-((R)-1-(2-(trifluoromethyl)pyrimidin-5-yl)ethyl)-4,5-dihydro-1H-pyrazol-1-carboxamide | 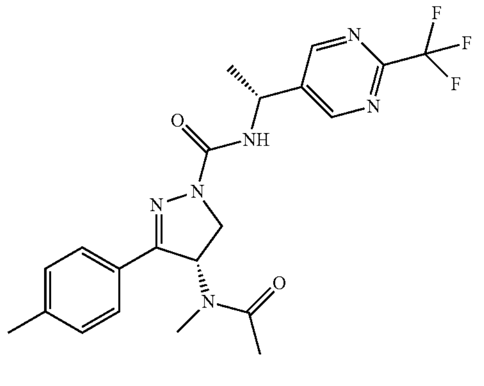 [SMILES: CC(=O)N(C)[C@H]1CN(C(=O)N[C@H](C)c2cnc(C(F)(F)F)nc2)N=C1c1ccc(C)cc1] |
| 34a | (R)-4-(N-methylacetamido)-3-(4-methylphenyl)-N-((R)-1-(2-(trifluoromethyl)pyrimidin-5-yl)ethyl)-4,5-dihydro-1H-pyrazol-1-carboxamide | 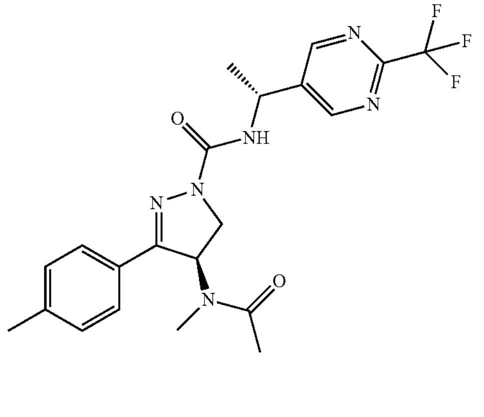 [SMILES: CC(=O)N(C)[C@@H]1CN(C(=O)N[C@H](C)c2cnc(C(F)(F)F)nc2)N=C1c1ccc(C)cc1] |

-continued

| Serial number | Compound name | Structure |
|---|---|---|
| 35 | (S)-4-(3-oxomorpholin-4-yl)-3-(4-chlorophenyl)-N-((R)-1-(2-(trifluoromethyl)pyrimidin-5-yl)ethyl)-4,5-dihydro-1H-pyrazol-1-carboxamide | 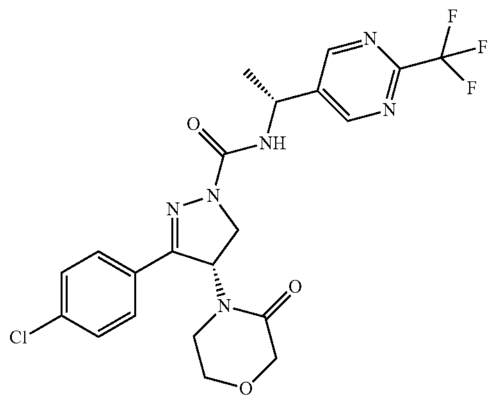 [SMILES: C[C@@H](NC(=O)N1C[C@H](N2CCOCC2=O)C(c2ccc(Cl)cc2)=N1)c1cnc(C(F)(F)F)nc1] |
| 35a | (R)-4-(3-oxomorpholin-4-yl)-3-(4-chlorophenyl)-N-((R)-1-(2-(trifluoromethyl)pyrimidin-5-yl)ethyl)-4,5-dihydro-1H-pyrazol-1-carboxamide | 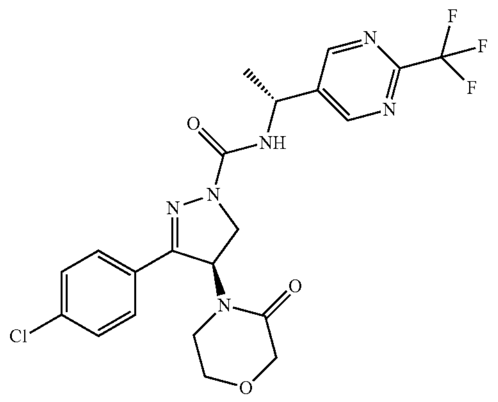 [SMILES: C[C@@H](NC(=O)N1C[C@@H](N2CCOCC2=O)C(c2ccc(Cl)cc2)=N1)c1cnc(C(F)(F)F)nc1] |
| 36 | (S)-4-(3-oxomorpholin-4-yl)-3-(4-methoxyphenyl)-N-((R)-1-(2-(trifluoromethyl)pyrimidin-5-yl)ethyl)-4,5-dihydro-1H-pyrazol-1-carboxamide | 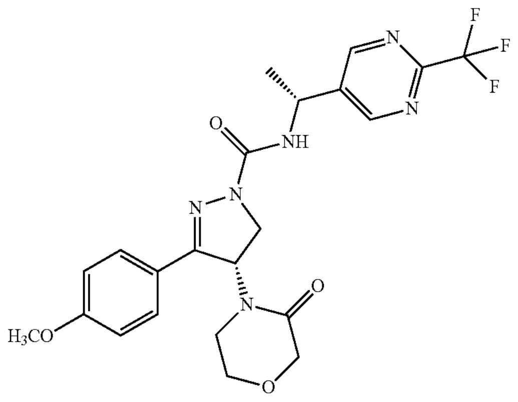 [SMILES: COc1ccc(C2=NN(C(=O)N[C@H](C)c3cnc(C(F)(F)F)nc3)C[C@@H]2N2CCOCC2=O)cc1] |
| 36a | (R)-4-(3-oxomorpholin-4-yl)-3-(4-methoxyphenyl)-N-((R)-1-(2-(trifluoromethyl)pyrimidin-5-yl)ethyl)-4,5-dihydro-1H-pyrazol-1-carboxamide | 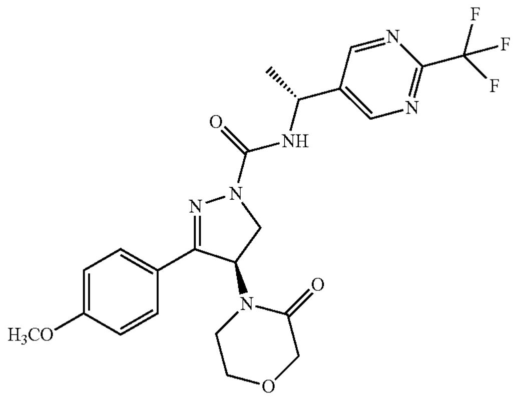 [SMILES: COc1ccc(C2=NN(C(=O)N[C@H](C)c3cnc(C(F)(F)F)nc3)C[C@H]2N2CCOCC2=O)cc1] |

-continued

| Serial number | Compound name | Structure |
|---|---|---|
| 37 | (S)-4-(4-acetylpiperazin-1-yl)-3-(4-methylphenyl)-N-((R)-1-(2-(trifluoromethyl)pyrimidin-5-yl)ethyl)-4,5-dihydro-1H-pyrazol-1-carboxamide | 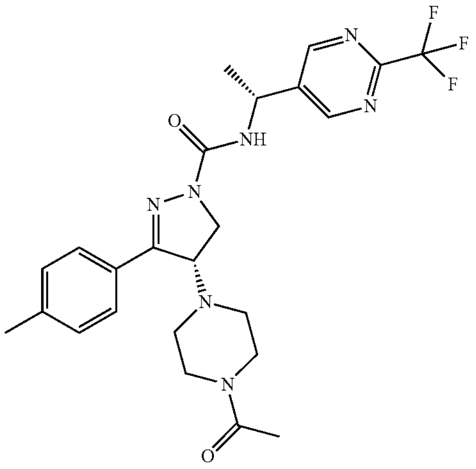 [SMILES: CC(=O)N1CCN([C@H]2CN(C(=O)N[C@H](C)c3cnc(C(F)(F)F)nc3)N=C2c2ccc(C)cc2)CC1] |
| 37a | (R)-4-(4-acetylpiperazin-1-yl)-3-(4-methylphenyl])-N-((R)-1-(2-(trifluoromethyl)pyrimidin-5-yl)ethyl)-4,5-dihydro-1H-pyrazol-1-carboxamide | 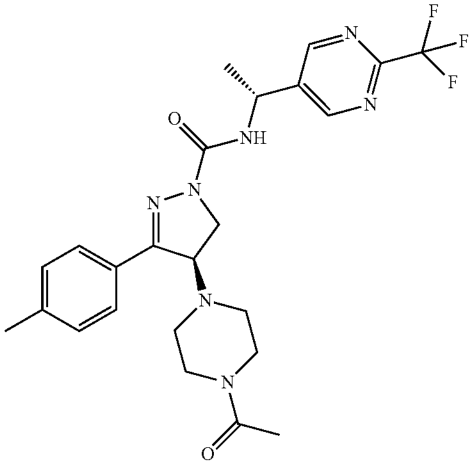 [SMILES: CC(=O)N1CCN([C@@H]2CN(C(=O)N[C@H](C)c3cnc(C(F)(F)F)nc3)N=C2c2ccc(C)cc2)CC1] |
| 38 | (S)-4-(4-methylpiperazin-1-yl)-3-(4-methylphenyl])-N-((R)-1-(2-(trifluoromethyl)pyrimidin-5-yl)ethyl)-4,5-dihydro-1H-pyrazol-1-carboxamide | 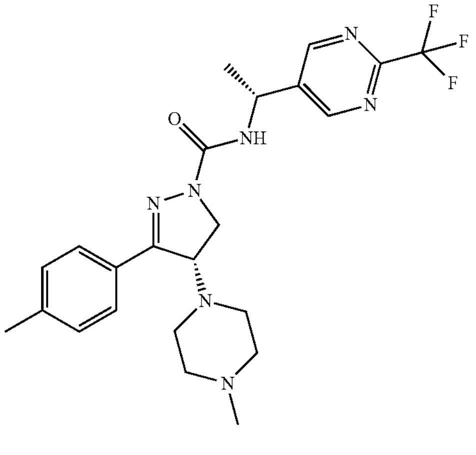 [SMILES: Cc1ccc(C2=NN(C(=O)N[C@H](C)c3cnc(C(F)(F)F)nc3)C[C@@H]2N2CCN(C)CC2)cc1] |

-continued
| Serial number | Compound name | Structure |
|---|---|---|
| 38a | (R)-4-(4-methylpiperazin-1-yl)-3-(4-methylphenyl)-N-((R)-1-(2-(trifluoromethyl)pyrimidin-5-yl)ethyl)-4,5-dihydro-1H-pyrazol-1-carboxamide | 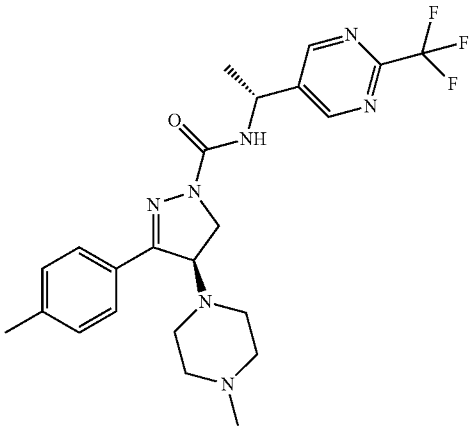 [SMILES: Cc1ccc(C2=NN(C(=O)N[C@H](C)c3cnc(C(F)(F)F)nc3)C[C@H]2N2CCN(C)CC2)cc1] |
| 39 | (S)-4-(morpholin-4-yl)-3-(4-methylphenyl)-N-((R)-1-(2-(trifluoromethyl)pyrimidin-5-yl)ethyl)-4,5-dihydro-1H-pyrazol-1-carboxamide | 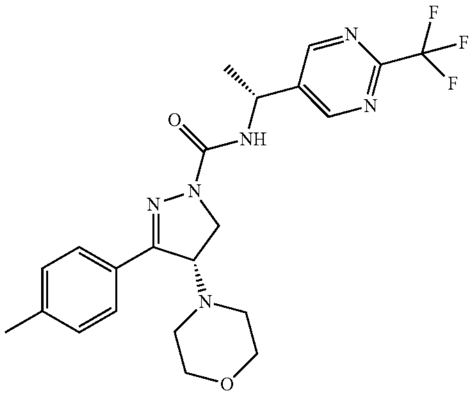 [SMILES: Cc1ccc(C2=NN(C(=O)N[C@H](C)c3cnc(C(F)(F)F)nc3)C[C@@H]2N2CCOCC2)cc1] |
| 39a | (S)-4-(morpholin-4-yl)-3-(4-methylphenyl])-N-((R)-1-(2-(trifluoromethyl)pyrimidin-5-yl)ethyl)-4,5-dihydro-1H-pyrazol-1-carboxamide | 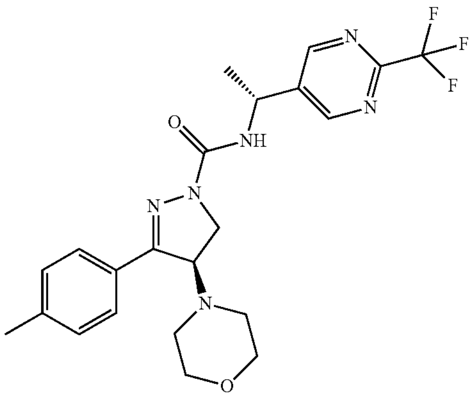 [SMILES: Cc1ccc(C2=NN(C(=O)N[C@H](C)c3cnc(C(F)(F)F)nc3)C[C@H]2N2CCOCC2)cc1] |

-continued

| Serial number | Compound name | Structure |
|---|---|---|
| 40 | (S)-4-(2-oxooxazolidin-3-yl)-3-(4-methylphenyl)-N-((R)-1-(2-(trifluoromethyl)pyrimidin-5-yl)ethyl)-4,5-dihydro-1H-pyrazol-1-carboxamide | 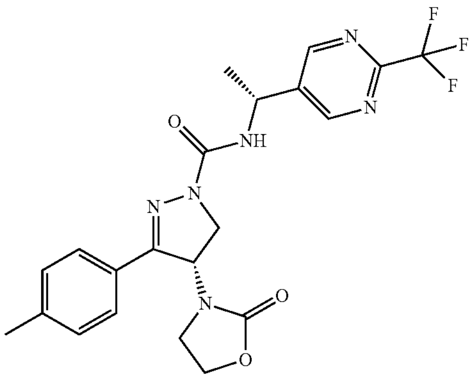 [SMILES: Cc1ccc(C2=NN(C(=O)N[C@H](C)c3cnc(C(F)(F)F)nc3)C[C@@H]2N2CCOC2=O)cc1] |
| 40a | (R)-4-(2-oxooxazolidin-3-yl)-3-(4-methylphenyl])-N-((R)-1-(2-(trifluoromethyl)pyrimidin-5-yl)ethyl)-4,5-dihydro-1H-pyrazol-1-carboxamide | 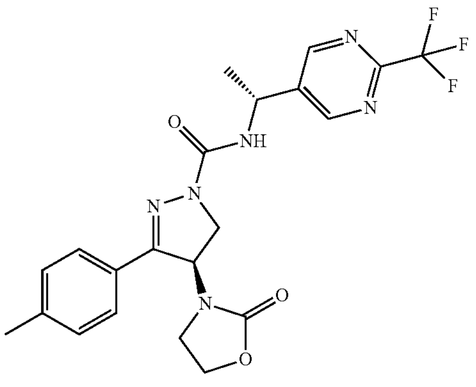 [SMILES: Cc1ccc(C2=NN(C(=O)N[C@H](C)c3cnc(C(F)(F)F)nc3)C[C@H]2N2CCOC2=O)cc1] |
| 41 | (S)-4-(3-methyl-2-oxoimidazolidin-1-yl)-3-(4-methylphenyl)-N-((R)-1-(2-trifluoromethyl)pyrimidin-5-yl)ethyl)-4,5-dihydro-1H-pyrazol-1-carboxamide | 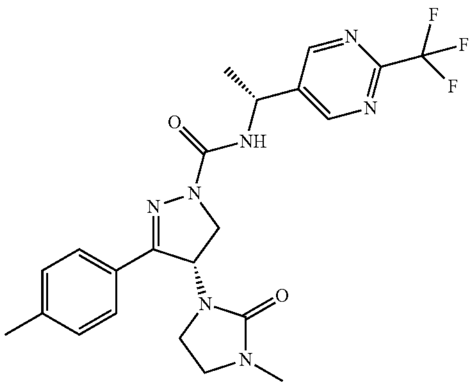 [SMILES: Cc1ccc(C2=NN(C(=O)N[C@H](C)c3cnc(C(F)(F)F)nc3)C[C@@H]2N2CCN(C)C2=O)cc1] |
| 41a | (R)-4-(3-methyl-2-oxoimidazolidin-1-yl)-3-(4-methylphenyl)-N-((R)-1-(2-trifluoromethyl)pyrimidin-5-yl)ethyl)-4,5-dihydro-1H-pyrazol-1-carboxamide | 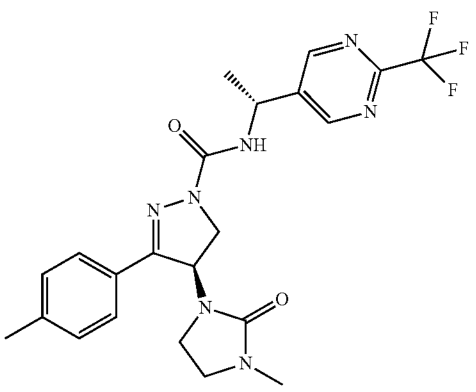 [SMILES: Cc1ccc(C2=NN(C(=O)N[C@H](C)c3cnc(C(F)(F)F)nc3)C[C@H]2N2CCN(C)C2=O)cc1] |

-continued

| Serial number | Compound name | Structure |
|---|---|---|
| 42 | (S)-4-(pyrazol-1-yl)-3-(4-methylphenyl])-N-((R)-1-(2-trifluoromethyl)pyrimidin-5-yl)ethyl)-4,5-dihydro-1H-pyrazol-1-carboxamide | 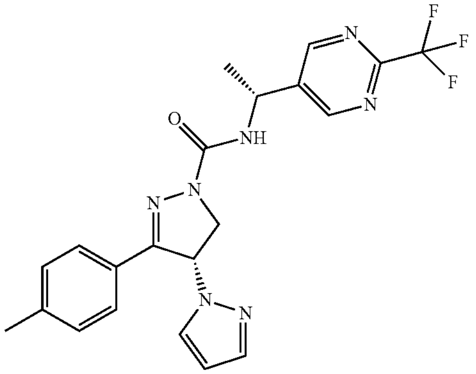 [SMILES: Cc1ccc(C2=NN(C(=O)N[C@H](C)c3cnc(C(F)(F)F)nc3)C[C@@H]2n2cccn2)cc1] |
| 42a | (R)-4-(pyrazol-1-yl)-3-(4-methylphenyl])-N-((R)-1-(2-trifluoromethyl)pyrimidin-5-yl)ethyl)-4,5-dihydro-1H-pyrazol-1-carboxamide | 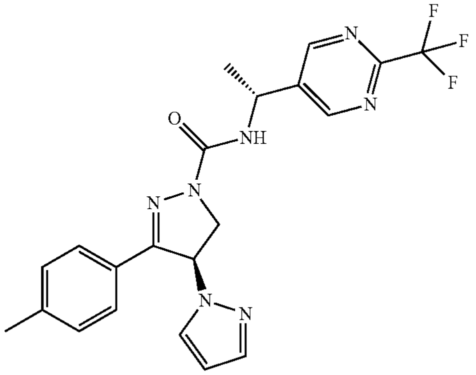 [SMILES: Cc1ccc(C2=NN(C(=O)N[C@H](C)c3cnc(C(F)(F)F)nc3)C[C@H]2n2cccn2)cc1] |
| 43 | (S)-4-(2-oxooxazolidin-3-yl)-3-(4-chlorophenyl)-N-((R)-1-(2-methylpyrimidin-5-yl)ethyl)-4,5-dihydro-1H-pyrazol-1-carboxamide | 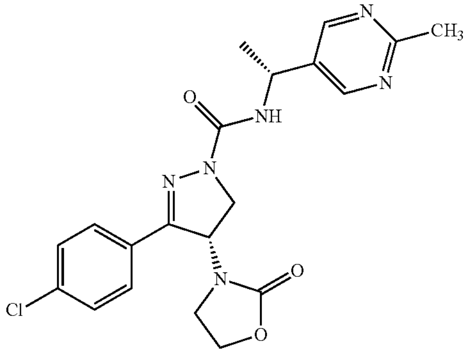 [SMILES: Cc1ncc([C@@H](C)NC(=O)N2C[C@H](N3CCOC3=O)C(c3ccc(Cl)cc3)=N2)cn1] |
| 43a | (R)-4-(2-oxooxazolidin-3-yl)-3-(4-chlorophenyl)-N-((R)-1-(2-methylpyrimidin-5-yl)ethyl)-4,5-dihydro-1H-pyrazol-1-carboxamide | 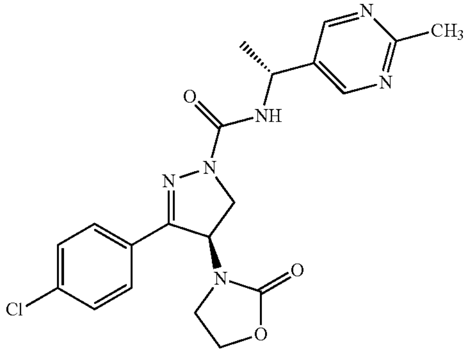 [SMILES: Cc1ncc([C@@H](C)NC(=O)N2C[C@@H](N3CCOC3=O)C(c3ccc(Cl)cc3)=N2)cn1] |

-continued

| Serial number | Compound name | Structure |
|---|---|---|
| 44 | (S)-4-(2-oxopyrrolidin-1-yl)-3-(4-fluorophenyl)-N-((R)-1-(2-chloropyrimidin-5-yl)ethyl)-4,5-dihydro-1 H-pyrazol-1-carboxamide | 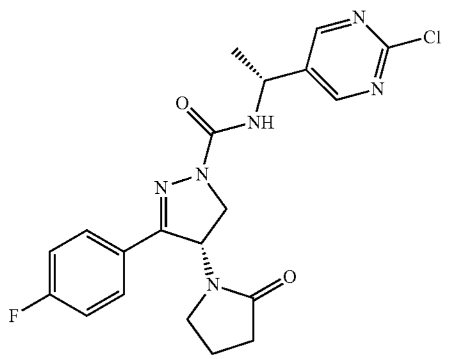 [SMILES: C[C@@H](NC(=O)N1C[C@H](N2CCCC2=O)C(c2ccc(F)cc2)=N1)c1cnc(Cl)nc1] |
| 44a | (R)-4-(2-oxopyrrolidin-1-yl)-3-(4-fluorophenyl)-N-((R)-1-(2-chloropyrimidin-5-yl)ethyl)-4,5-dihydro-1H-pyrazol-1-carboxamide | 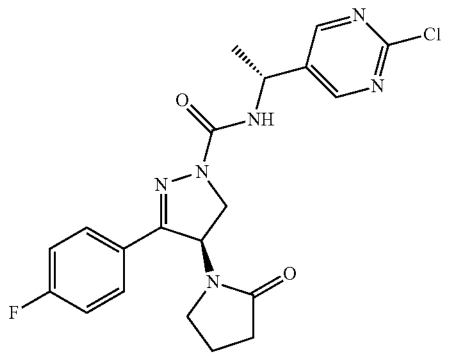 [SMILES: C[C@@H](NC(=O)N1C[C@@H](N2CCCC2=O)C(c2ccc(F)cc2)=N1)c1cnc(Cl)nc1] |
| 45 | (S)-4-(2-oxopyrrolidin-1-yl)-3-(4-methylphenyl])-N-((R)-1-(3-methyl-1,2,4-oxadiazol-5-yl)ethyl)-4,5-dihydro-1H-pyrazol-1-carboxamide | 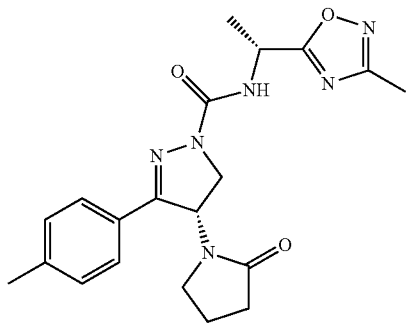 |
| 45a | (R)-4-(2-oxopyrrolidin-1-yl)-3-(4-methylphenyl)-N-((R)-1-(3-methyl-1,2,4-oxadiazol-5-yl)ethyl)-4,5-dihydro-1H-pyrazol-1-carboxamide | 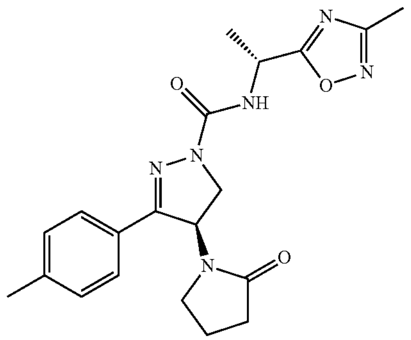 |

-continued

| Serial number | Compound name | Structure |
|---|---|---|
| 46 | (S)-4-(3-oxomorpholin-4-yl)-3-(4-methylphenyl])-N-((R)-1-(3-methyl-1,2,4-oxadiazol-5-yl)ethyl)-4,5-dihydro-1H-pyrazol-1-carboxamide | 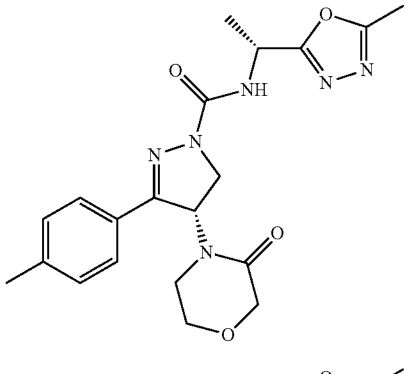 |
| 46a | (R)-4-(3-oxomorpholin-4-yl)-3-(4-methylphenyl])-N-((R)-1-(3-methyl-1,2,4-oxadiazol-5-yl)ethyl)-4,5-dihydro-1H-pyrazol-1-carboxamide | 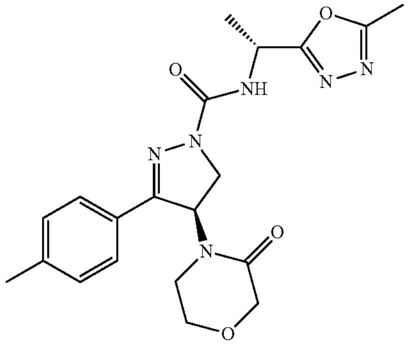 |
| 47 | (S)-4-(N-methylacetamido)-3-(4-methylphenyl])-N-((S)-1-(6-(trifluoromethyl)pyridin-3-yl)ethyl)-4,5-dihydro-1H-pyrazol-1-carboxamide | 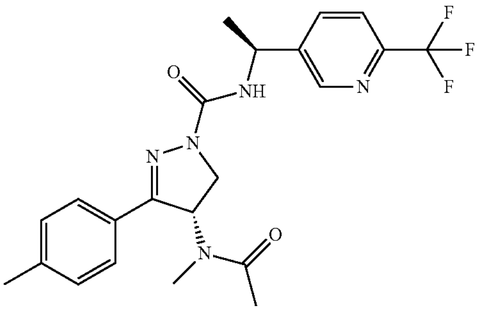 [SMILES: CC(=O)N(C)[C@H]1CN(C(=O)N[C@@H](C)c2ccc(C(F)(F)F)nc2)N=C1c1ccc(C)cc1] |
| 47a | (R)-4-(N-methylacetamido)-3-(4-methylphenyl)-N-((S)-1-(6-(trifluoromethyl)pyridin-3-yl)ethyl)-4,5-dihydro-1H-pyrazol-1-carboxamide | 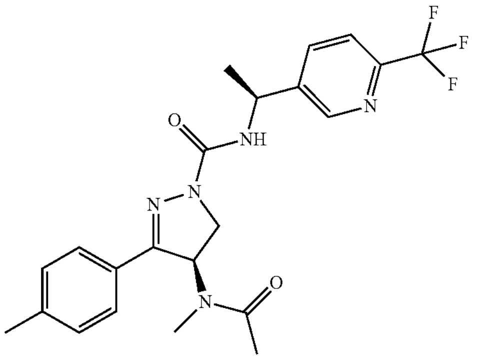 [SMILES: CC(=O)N(C)[C@@H]1CN(C(=O)N[C@@H](C)c2ccc(C(F)(F)F)nc2)N=C1c1ccc(C)cc1] |

Another objective of the present invention is to provide a pharmaceutical composition. The pharmaceutical composition includes at least one active component and one or more pharmaceutically acceptable carriers or excipients. The active component may be any one or more of the N-formamidopyrazoline derivative of the present invention and a pharmaceutically acceptable salt thereof, and an isomer, an enantiomer, a diastereomer and a racemate of the compound. The salt is selected from pharmaceutically acceptable inorganic acid salts and organic acid salts. The inorganic acid salts include salts formed with a haloid acid, a nitric acid, a carbonic acid, a sulfuric acid and a phosphoric acid. The organic acid salts include salts formed with a malic acid, an L-malic acid, a D-malic acid, a citric acid, a fumaric acid, an oxalic acid, a lactic acid, a camphorsulfonic acid, an L-camphorsulfonic acid, a D-camphorsulfonic acid, a p-toluenesulfonic acid, a methanesulfonic acid and a benzoic acid. The haloid acid is selected from a hydrofluoric acid, a hydrobromic acid, a hydroiodic acid and a hydrochloric acid.

The carriers or excipients include conventional fillers in the pharmaceutical field, a diluent, a wetting agent, a lubricant, a binder, a disintegrant, an absorption enhancer, a surfactant, an adsorption carrier, an antioxidant, an emulsifier, a metal chelating agent, a pH conditioning agent and the like. A flavouring agent, a sweetening agent and the like can also be added if necessary. A drug of the present invention can be made into various forms such as tablets, capsules, inhalants, emulsions, suspensions, gels, powders, granules, oral liquids and injections. The drug in each of the above dosage forms can be prepared according to conventional methods in the pharmaceutical field.

tuted arylmethylamine or substituted heteroarylmethylamine under an alkaline condition. In particular, when a chiral molecule R-substituted arylmethylamine or R-substituted heteroarylmethylamine is selected as a synthon, an obtained target molecule is a mixture of epimers, which can be subjected to gradient separation by column chromatography to obtain an S,R-isomer and an R,R-isomer, and an eluent used is petroleum ether:ethyl acetate=3:1 to 1:3 (v/v) or methanol:ethyl acetate=1:3 to 1:6 (v/v); when a chiral molecule S-substituted arylmethylamine or S-substituted heteroarylmethylamine is used as a synthon, an obtained target molecule can be subjected to gradient separation by column chromatography to obtain an S,S-isomer and an R,S-isomer, and an eluent used is petroleum ether:ethyl acetate=4:1 to 1:3 (v/v) or methanol:ethyl acetate=1:3 to 1:6 (v/v); and a spatial configuration of a title compound is confirmed by correlation spectroscopy COSY and NOSEY spectrums, respectively.

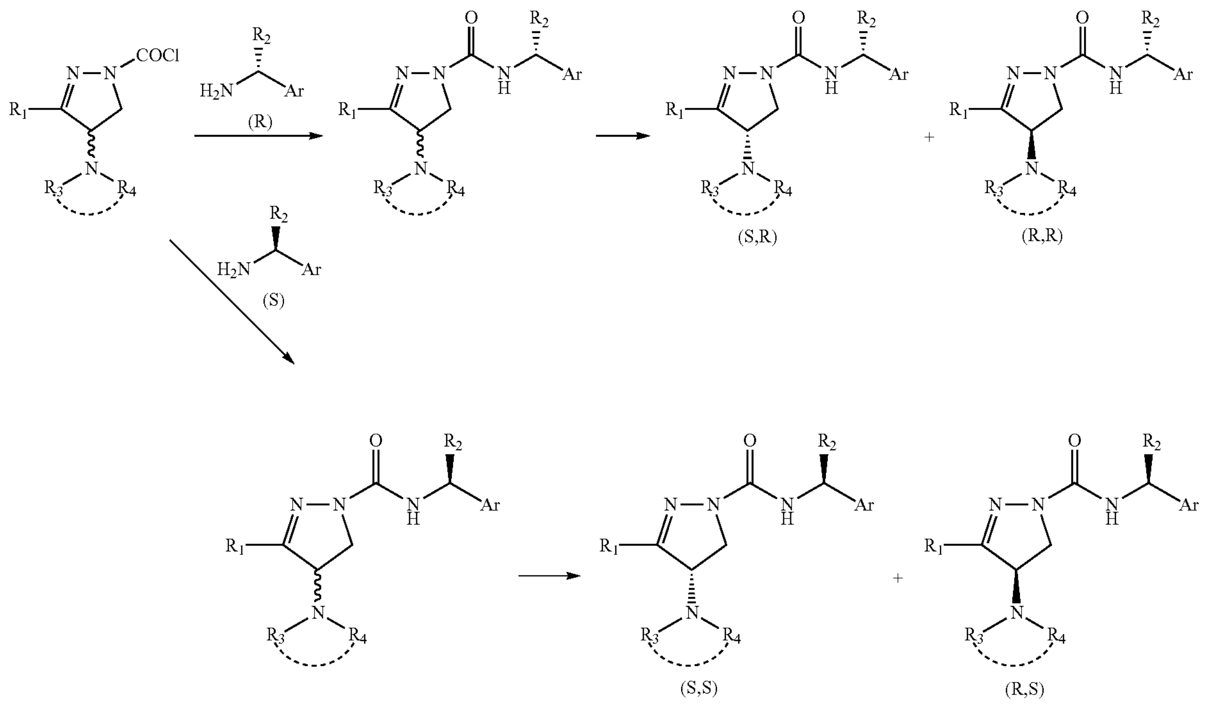

The present invention further provides use of any one of the compounds in General Formula (I) and a pharmaceutically acceptable salt thereof alone and/or in combination with other drugs in preparation of a P2X3 inhibitor, particularly use in preparation of a drug for treating diseases mediated by P2X3. The diseases mediated by the P2X3 include diseases of respiratory system such as chronic obstructive pulmonary disease, asthma, acute, subacute and chronic cough, and bronchospasm; pain caused by various reasons such as surgical pain, inflammatory pain, cancer pain, bladder pain, endometriosis pain, diabetic neuralgia, traumatic pain, dental pain, migraine, and pain associated with irritable bowel syndrom; and skin diseases such as chronic itching.

The compound having General Formula (I) of the present invention can be prepared by the following steps.

A title molecule is prepared by condensation of corresponding substituted N-formchloropyrazoline with substiwherein for the preparation of an intermediate substituted N-formchloropyrazoline, a corresponding aminoketone can be taken as a raw material, which reacts with formaldehyde under an alkaline condition to generate a ketene, and then reacts with hydrazine to obtain a cyclic compound pyrazoline, which further reacts with triphosgene to prepare substituted N-formchloropyrazoline; and

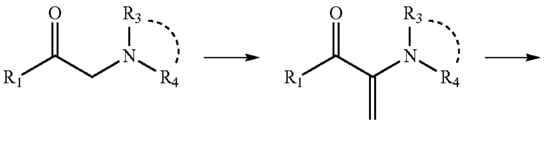

-continued

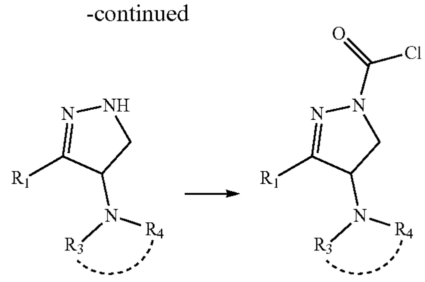

for the preparation of intermediates R-substituted arylmethylamine and R-substituted heteroarylmethylamine, or S-substituted arylmethylamine and S-substituted heteroarylmethylamine, a corresponding aromatic aldehyde can be taken as a raw material, which reacts with S-tert-butanesulfinamide or R-tert-butanesulfinamide to obtain an imine, which is then subjected to addition and hydrolysis with a corresponding Grignard reagent or lithium alkylide under a low temperature condition to prepare the R-substituted arylmethylamine or the S-substituted heteroarylmethylamine.

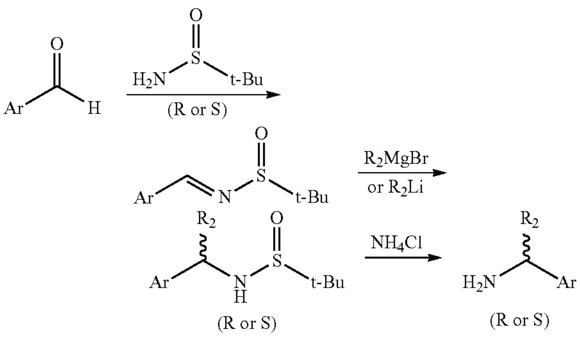

The present invention confirms through experiments that the compounds of the present invention can selectively inhibit the activity of P2X3 channels, and can be used in a drug for treating diseases mediated by P2X3. The inhibitor provided by the present invention further include the pharmaceutical composition of the compounds.

BRIEF DESCRIPTION OF DRAWINGS

FIG. 3 shows a chemical structure (A), a 3D simulation diagram (B) and $^1$HNMR(C) of a compound 1a.

FIG. 4 shows an NOESY spectrum (D) of the compound 1a.

DETAILED DESCRIPTION OF EMBODIMENTS

Figure 1:
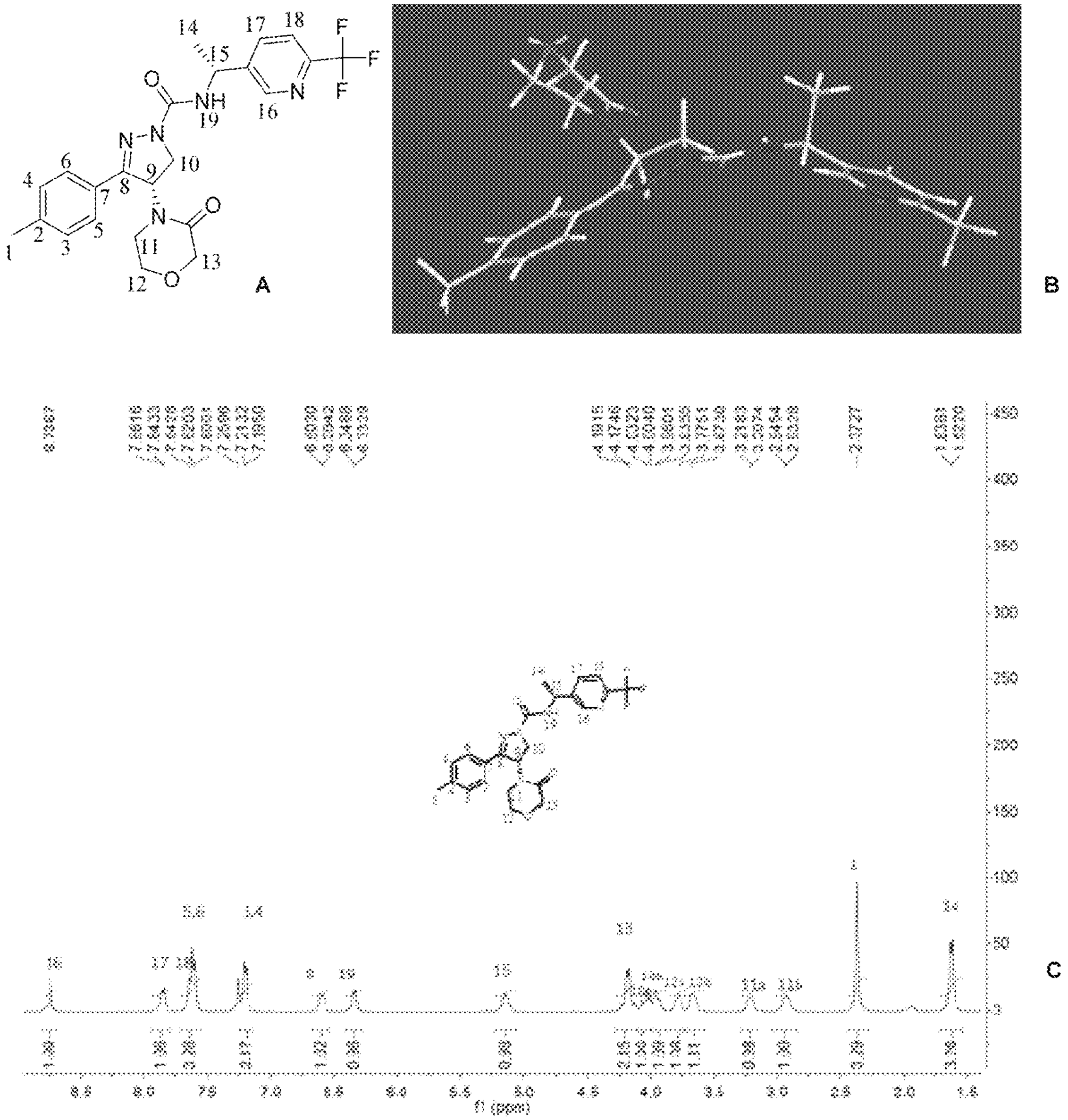
FIG. 1 shows a chemical structure (A), a 3D simulation diagram (B) and $^1$HNMR(C) of a title compound 1.

The present invention will be further described with reference to embodiments. The following embodiments are only to specifically illustrate the present invention, rather than limit the present invention in any way. In addition, the raw materials, intermediates, reagents, etc. used in the present embodiment, unless otherwise specified, are prepared according to methods commonly practiced in the art, or may be commercially available.

I. Preparation Method of Main Intermediates

1. Preparation of an Intermediate N-formchloropyrazoline Derivative (A)

1). Synthesis of 4-(N-methylacetamido)-3-(4-methylphenyl)-4,5-dihydro-1H-pyrazol-1-carbonyl chloride (A-1)

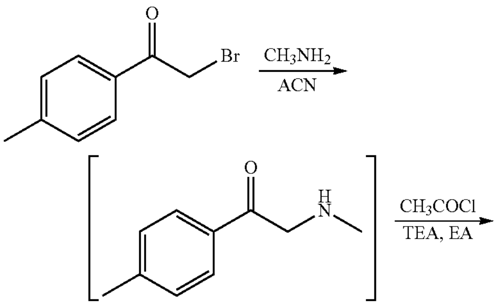

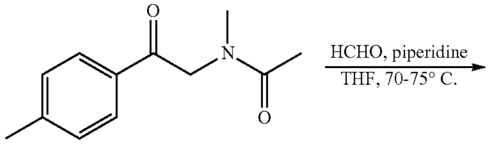

A-1a

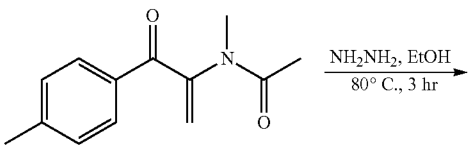

A-1b

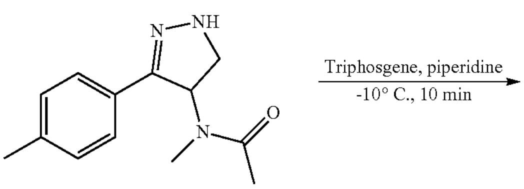

A-1c

-continued

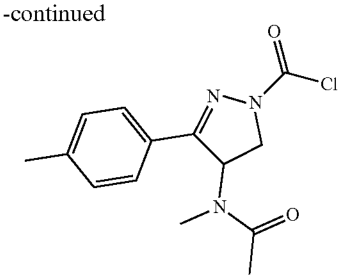

A-1

Step 1. Synthesis of N-methyl-N-(2-oxo-2-(4-methylphenyl)ethyl)acetamide (A-1a)

A 30% methylamine alcohol solution (7.29 g, 70.41 mmol) was added into acetonitrile (20 mL), and under protection of $N_2$, cooled to −15° C. to −10° C. An acetonitrile (40 mL) solution of 4-methyl-α-bromoacetophenone (5 g, 23.47 mmol) was slowly added dropwise. After dropwise adding was completed, stirring was conducted for 20 minutes under a temperature maintained at −15° C. to −10° C. A reaction solution was heated to −5° C. to 0° C. Ice water (60 mL) was added dropwise. Stirring was conducted for 5 minutes. Ethyl acetate (30 mL) was added. Stirring was conducted for 5 minutes. Still standing for stratification was conducted. An aqueous phase was extracted with ethyl acetate (20 mL×2). Organic phases were combined, washed twice with water and dried with anhydrous $Na_2SO_4$, and filtered. Triethylamine (3.5 g, 35.2 mmol) was added into a filtrate, and under protection of $N_2$, cooled to −10° C. to −5° C. Acetyl chloride (3.68 g, 46.94 mmol) was added dropwise. Stirring continued for 10 to 20 minutes. Water (80 mL) was added. Stirring was conducted for 10 minutes at a room temperature. An aqueous phase was extracted with ethyl acetate (30 mL×2). Organic phases were combined, dried with anhydrous $Na_2SO_4$, and filtered. A filtrate was subjected to decompression concentration to dryness. A residue was separated by silica gel column chromatography (PE: EA=3:1, v/v) to obtain a compound A-1a, which was a pale yellow solid with a yield of 41.5%; ESI-MS: m/z=206[M+1]$^+$.

Step 2. Synthesis of N-methyl-N-(3-oxo-3-(4-methylphenyl)propyl-1-ene-2-yl)acetamide (A-1b)

The compound A-1a (2.0 g, 9.76 mmol), a 37% formaldehyde solution (2.38 g, 29.28 mmol) and piperidine (0.41 g, 4.88 mmol) were added into THF (10 mL). After heating to 70° C. to 75° C. and stirring for 5 hours, a 37% formaldehyde solution (2.38 g, 29.28 mmol) and piperidine (0.41 g, 4.88 mmol) were added. Stirring was conducted overnight. Monitoring was conducted by TLC until there was no raw material. Cooling was conducted to a room temperature. Filtering was conducted. A filtrate was subjected to decompression concentration to dryness. A residue was separated by silica gel column chromatography (PE: EA=2:1, v/v) to obtain a compound A-1b with a yield of 67.0%; $^1$H NMR (500 MHz, DMSO-$d_6$): δ 7.77 (d, J=7.3 Hz, 2H), 7.35 (d, J=7.4 Hz, 2H), 5.70 (d, J=2.3 Hz, 1H), 5.28 (d, J=2.2 Hz, 1H), 3.22 (s, 3H), 2.42 (s, 3H), 1.95 (s, 3H); ESI-MS: m/z=218[M+1]$^+$.

Step 3. Synthesis of 4-(N-methylacetamido)-3-(4-methylphenyl)-4,5-dihydro-1H-pyrazol-1-carbonyl chloride (A-1)

The compound A-1b (3.0 g, 13.8 mmol), hydrazine hydrate (1.38 g, 27.6 mmol), and EtOH (15 mL) were added into a reaction flask, and under protection of $N_2$, heated to 80° C. and stirred for 3 hours. A reaction solution was cooled to a room temperature. Ethanol was evaporated under reduced pressure. Water (10 mL) was added. Stirring was conducted. Extracting was conducted with ethyl acetate (15 mL×2). An organic phase was dried with anhydrous $Na_2SO_4$, and filtered. A filtrate was subjected to decompression concentration to dryness to obtain a crude product of a compound A-1c, which was used directly in a next reaction without being further purified.

Triphosgene (1.30 g, 4.32 mmol) and dichloromethane (20 mL) were added into a dry reaction flask, and under protection of $N_2$, cooled to −10° C. Moreover, the compound A-1c (2.0 g, 8.64 mmol), pyridine (2.04 g, 25.80 mmol) and dichloromethane (20 mL) were mixed. A mixed solution was added dropwise into the reaction flask at −10° C. After addition was completed, stirring was conducted for 10 minutes at a room temperature. A diluted hydrochloric acid was added for a quenching reaction. Organic phases were separated. An aqueous phase was extracted with dichloromethane (10 mL×2). The organic phases were combined, washed with saturated brine, dried with anhydrous $Na_2SO_4$, and filtered. A filtrate was subjected to decompression concentration to dryness. A residue was separated by silica gel column chromatography (PE:EA=3:1 to 1:3, v/v), to obtain a compound A-1, which was a pale yellow solid with a second-step yield of 46%; $^1$H NMR (500 MHz, $CDCl_3$): δ 7.86 (d, J=8.0 Hz, 2H), 7.26 (d, J=8.0 Hz, 2H), 5.20-5.11 (m, 1H), 4.02-3.87 (m, 2H), 3.27 (s, 3H), 2.42 (s, 3H), 2.32 (s, 3H); ESI-MS: m/z=294[M+1]$^+$.

An intermediate A-6 listed in Table 1.1 was obtained by synthesis by using 4-fluoro-α-bromoacetophenone instead of 4-methyl-α-bromoacetophenone as a raw material in the same way as preparing the compound A-1.

2). Synthesis of 4-(3-oxomorpholin-4-yl)-3-(4-methylphenyl)-4,5-dihydro-1H-pyrazol-1-carbonyl chloride (A-2)

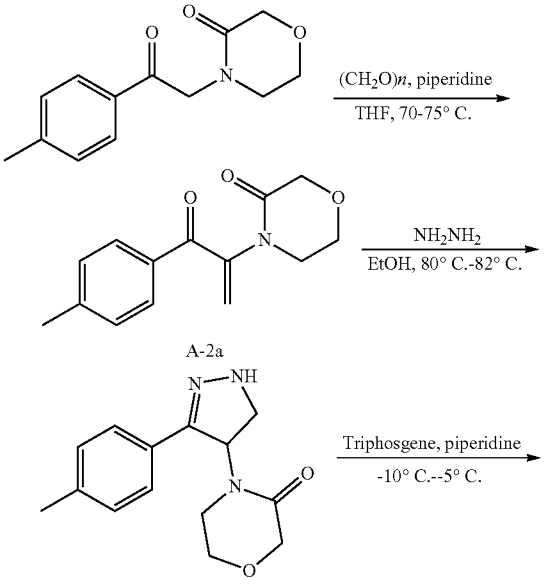

A-2b

-continued

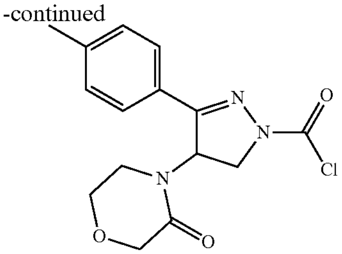

A-2

Step 1. Synthesis of 4-(3-oxo-3-(4-methylphenyl) propyl-1-ene-2-yl)morpholin-3-one (A-2a)

4-(2-Oxo-2-(4-methylphenyl)ethyl)morpholin-3-one (10.0 g, 42.9 mmol), paraformaldehyde (3.8 g, 128.7 mmol) and piperidine (1.8 g, 21.5 mmol) were added into THF (100 mL). After stirring for 5 hours at 70° C. to 75° C., paraformaldehyde (3.8 g, 128.7 mmol) and piperidine (1.8 g, 21.5 mmol) were added. Stirring was conducted overnight. Monitoring was conducted by TLC until there was no raw material. Cooling was conducted to a room temperature. Filtering was conducted. A filtrate was subjected to decompression concentration to dryness. A residue was separated by silica gel column chromatography (PE:EA=3:1, v/v) to obtain a compound A-2a with a yield of 88.0%; $^1$HNMR (500 MHz, DMSO-$d_6$): δ 7.67 (d, J=7.5 Hz, 2H), 7.55 (d, J=7.5 Hz, 2H), 5.70 (d, J=2.1 Hz, 1H), 5.24 (d, J=2.1 Hz, 1H), 4.21 (s, 2H), 3.56 (m, 2H), 3.37 (m, 2H), 2.41 (s, 3H); ESI-MS: m/z=246[M+1]$^+$.

Step 2. Synthesis of 4-(3-oxomorpholin-4-yl)-3-(4-methylphenyl)-4,5-dihydro-1H-pyrazol-1-carbonyl chloride (A-2)

The compound A-2a (5.0 g, 20.4 mmol) and hydrazine hydrate (2.05 g, 40.75 mmol) were added into EtOH (25 mL). Under protection of $N_2$, stirring was conducted for 3 hours at 80° C. to 82° C. Monitoring was conducted by TLC until there was no raw material. Cooling was conducted to a room temperature. Ethanol in a system was evaporated under reduced pressure. Water was added. Stirring was conducted. Extracting was conducted with ethyl acetate. An organic phase was dried with anhydrous $Na_2SO_4$, and filtered. A filtrate was subjected to decompression concentration to dryness to obtain a crude product of a compound A-2b, which was used directly in a next reaction without further purification.

Triphosgene (1.71 g, 5.76 mmol) and dichloromethane (30 mL) were added into a dry reaction flask, and under protection of $N_2$, cooled to −10° C. to −5° C. The compound A-2b (3.0 g, 11.55 mmol) and pyridine (2.7 g, 34.2 mmol) were added into dichloromethane (30 mL), which were added dropwise into the reaction flask at −10° C. to −5° C. After dropwise addition was completed, stirring was conducted for 10 minutes at a room temperature. A diluted hydrochloric acid was added for a quenching reaction. An organic layer was separated. An aqueous phase was extracted with dichloromethane (10 mL×2). Organic phases were combined, washed with saturated brine, dried with anhydrous $Na_2SO_4$, and filtered. A filtrate was subjected to decompression concentration to dryness. Separating was conducted by silica gel column chromatography (PE: EA=4:1 to 1:1, v/v), to obtain an intermediate compound A-2, which was a pale yellow solid with a second-step yield of 56%; $^1$H NMR (500 MHz, $CDCl_3$): δ 7.72 (d, J=8.0 Hz, 2H), 7.25 (d, J=8.0 Hz, 2H), 6.61-6.57 (m, 1H), 4.29-4.17 (m, 2H), 4.03-3.94 (m, 2H), 3.78-3.67 (m, 2H), 3.21-2.93 (m, 2H), 2.39 (s, 3H); ESI-MS: m/z=322[M+1]$^+$.

Compounds A-7 to A-14 listed in Table 1.1 were obtained by synthesis by using corresponding substituted morpholinone or substituted morpholine or substituted piperazine or substituted piperazinone (A-7:4-(2-oxo-2-(4-fluorophenyl) ethyl)morpholin-3-one; A-8: 4-(2-oxo-2-(4-chlorophenyl) ethyl)morpholin-3-one; A-9: 4-(2-oxo-2-(4-methoxyphenyl) ethyl)morpholin-3-one; A-10:4-(2-oxo-2-(4-fluorophenyl) ethyl)morpholine; A-11:4-acetyl-1-(2-oxo-2-(4-methylphenyl)ethyl)piperazine; A-12:4-methyl-1-(2-oxo-2-(4-methylphenyl)ethyl)piperazine; A-13:4-methyl-1-(2-oxo-2-(4-methylphenyl)ethyl)piperazin-2-one; A-14:4-(2-oxo-2-(4-methylphenyl)ethyl)morpholine) instead of 4-(2-oxo-2-(4-methylphenyl)ethyl)morpholin-3-one as raw materials in the same way as preparing the compound A-2.

3). Synthesis of 4-(2-oxopyrrolidin-1-yl)-3-(4-methylphenyl)-4,5-dihydro-1H-pyrazol-1-carbonyl chloride (A-3)

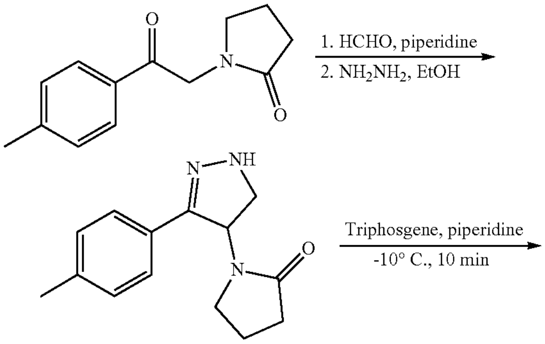

A-3a

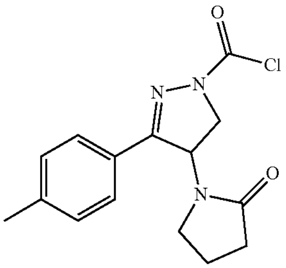

A-3

Step 1. Synthesis of 1-(3-(4-methylphenyl)-4,5-dihydro-1H-pyrazol-4-yl)pyrrolidin-2-one (A-3a)

1-(2-Oxo-2-(4-methylphenyl)ethyl)pyrrolidin-2-one (5.0 g, 23.01 mmol) and a 37% formaldehyde solution (2.70 mL, 33.2 mmol) were dissolved into dioxane (50 mL). Piperidine (2.83 g, 33.2 mmol) was added dropwise. After addition was completed, stirring was conducted for 6 hours at 105° C. Cooling was conducted to a room temperature. The dioxane was evaporated under reduced pressure. 45 mL of Ethyl acetate and 50 mL of saturated brine were added into a system, and stirred for 5 minutes. Still standing for stratification was conducted. An aqueous phase was extracted with ethyl acetate (20 mL). Organic phases were combined, dried with anhydrous $Na_2SO_4$, and filtered. A filtrate was subjected to decompression concentration to dryness to obtain a yellow oily matter. The above yellow oily matter was dissolved into ethanol (120 mL). Hydrazine hydrate (4.16 g, 66.5 mmol) was added. A mixture was subjected to a heating and stirring reaction for 3 hours at 70° C. to 80° C., and cooled to a room temperature. A solvent was evaporated under reduced pressure. THF (30 mL) and water (10 mL) were added into a residue, stirred at the room temperature, and filtered. A filter cake was washed twice with a small amount of THF. A solid matter was dried in vacuum to obtain a compound A-3a with a yield of 65%; $^1$H NMR (500 MHz, DMSO-$d_6$): δ9.15 (brs, 1H), 7.70 (d, J=7.4 Hz, 2H), 7.30 (d, J=7.4 Hz, 2H), 4.51 (m, 1H), 3.30-3.04 (m, 4H), 2.42 (s, 3H), 2.24 (m, 2H), 1.95 (m, 2H); ESI-MS: m/z=244 $[M+1]^+$.

Step 2. Synthesis of 4-(2-oxopyrrolidin-1-yl)-3-(4-methylphenyl)-4,5-dihydro-1H-pyrazol-1-carbonyl chloride (A-3)

Triphosgene (1.55 g, 5.14 mmol) and anhydrous dichloromethane (25 mL) were added into a dry reaction flask, and under protection of $N_2$, cooled to −8° C. to −10° C. Moreover, the compound A-3a (2.5 g, 10.28 mmol) and pyridine (2.65 g, 22.54 mmol) were dissolved into dichloromethane (25 mL), which were added dropwise into the reaction flask at −10° C. After dropwise addition was completed, stirring was conducted for 10 minutes at a room temperature. A diluted hydrochloric acid was added for a quenching reaction. Organic phases were separated. An aqueous phase was extracted with dichloromethane (10 mL×2). The organic phases were combined, washed with saturated brine, dried with anhydrous $Na_2SO_4$, and filtered. A filtrate was subjected to decompression concentration to dryness. A residue was separated by silica gel column chromatography (PE: EA=4:1 to 1:2, v/v), to obtain a compound A-3, which was a pale yellow solid with a yield of 66%; $^1$HNMR (500 MHz, $CDCl_3$): δ 7.78 (d, J=8.0 Hz, 2H), 7.21 (d, J=8.0 Hz, 2H), 5.10-4.86 (m, 1H), 3.65-3.54 (m, 2H), 3.29-3.20 (m, 2H), 2.42 (s, 3H), 2.35-2.27 (m, 2H), 1.99-1.91 (m, 2H); ESI-MS: m/z=306$[M+1]^+$.

Compounds A-15, A-16, A-18 to A-21 listed in Table 1.1 were obtained by synthesis by using corresponding raw materials (A-15:1-(2-oxo-2-(4-fluorophenyl)ethyl)pyrrolidin-2-one; A-16: 3-(2-oxo-2-(4-methylphenyl)ethyl)oxazolidin-2-one; A-18: 3-(2-oxo-2-(4-chlorophenyl)ethyl)oxazolidin-2-one; A-19: 1-(2-oxo-2-(4-methylphenyl)ethyl)-3-methylimidazolidin-2-one; A-20: 1-(2-oxo-2-(4-methylphenyl)ethyl)-3-acetylimidazolidin-2-one; A-21:1-(2-oxo-2-(5-methylpyridin-2-yl)ethyl)pyrrolidin-2-one) instead of 1-(2-oxo-2-(4-methylphenyl)ethylpyrrolidin-2-one in the same way as preparing the compound A-3.

4). Synthesis of 4-(N-methyl-N-tert-butoxycarbonylamino)-3-(4-methylphenyl)-4,5-dihydro-1H-pyrazol-1-carbonyl chloride (A-4)

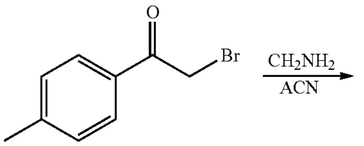

-continued

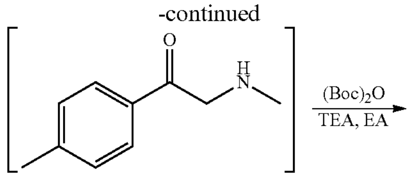

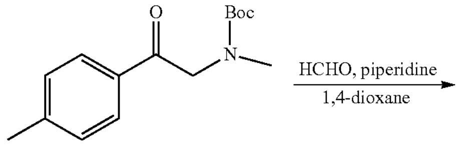

A-4a

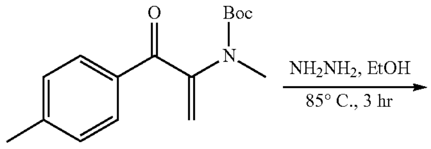

A-4b

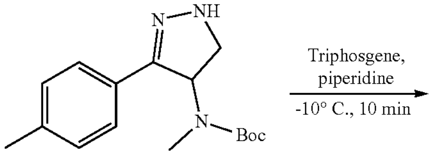

A-4c

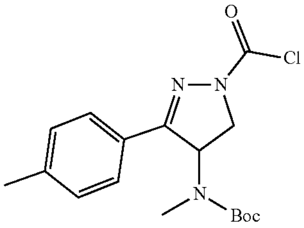

A-4

Step 1. Synthesis of tert-butyl N-methyl-N-(2-oxo-2-(4-methylphenyl)ethyl)carbamate (A-4a)

A 30% methylamine alcohol solution (11.5 mL, 70.41 mmol) and acetonitrile (20 mL) were added into a reaction flask, and under protection of $N_2$, cooled to −15° C. to −10° C. An acetonitrile (40 mL) solution of 4-methyl-α-bromo-acetophenone (5 g, 23.47 mmol) was slowly added dropwise. After dropwise addition was completed, stirring was conducted for 20 minutes under temperature keeping. A reaction system was heated to −5° C. to 0° C. Ice water (60 mL) was added dropwise. Stirring was conducted for 5 minutes. Ethyl acetate (30 mL) was added. Stirring was conducted for 5 minutes. Still standing for stratification was conducted. An aqueous phase was extracted with ethyl acetate (20 mL×2). Organic phases were combined, washed twice with water and dried with anhydrous $Na_2SO_4$, and filtered. Triethylamine (4.8 mL, 35.2 mmol) was added into a filtrate, and under protection of $N_2$, cooled to −10° C. to −5° C. $(Boc)_2O$ (7.68 g, 35.21 mmol) was added dropwise. After addition was completed, stirring was conducted for 30 minutes at a room temperature. Water (80 mL) was added. Stirring continued for 10 minutes at the room temperature. Still standing for stratification was conducted. An aqueous phase was extracted with ethyl acetate (20 mL×2). Organic phases were combined, dried with anhydrous $Na_2SO_4$, and filtered. A filtrate was subjected to decompression concentration to dryness. A residue was separated by silica gel column chromatography (PE:EA=3:1 to 1:1, v/v) to obtain a compound A-4a, which was a pale yellow solid with a yield of 63.9%; ESI-MS: m/z=264[M+1]$^+$.

Step 2. Synthesis of tert-butyl N-methyl-N-(3-oxo-3-(4-methylphenyl)propyl-1-ene-2-yl)carbamate (A-4b)

The compound A-4a (3.5 g, 13.29 mmol), a 37% formaldehyde solution (3.0 mL, 39.87 mmol) and piperidine (0.6 mL, 6.65 mmol) were added into dioxane (30 mL). Stirring was conducted for 6 hours at 105° C. Monitoring was conducted by TLC until there was no raw material. Cooling was conducted to a room temperature. The dioxane was evaporated under reduced pressure. 15 mL of Ethyl acetate and 30 mL of saturated brine were added into a system, and stirred for 5 minutes. Still standing for stratification was conducted. An aqueous phase was extracted once with ethyl acetate (15 mL). Organic phases were combined, dried with anhydrous $Na_2SO_4$, and filtered. A filtrate was subjected to decompression concentration to dryness to obtain a compound A-4b, which was yellow oily, with a yield of 65%, and could be directly used in a next reaction without further refinement.

Step 3. Synthesis of 4-(N-methyl-N-tert-butoxycarbonylamino)-3-(4-methylphenyl)-4,5-dihydro-1H-pyrazole (A-4c)

The compound A-4b (5.12 g, 18.6 mmol), hydrazine hydrate (1.0 mL, 19.98 mmol) were added into ethanol (40 mL), and under protection of $N_2$, heated to 85° C. and stirred for 3 hours. Cooling was conducted to a room temperature. The ethanol was evaporated under reduced pressure. Water (10 mL) was added into a residue. Stirring was conducted. Extracting was conducted with ethyl acetate (2×20 mL). Organic phases were combined, dried with anhydrous $Na_2SO_4$, and filtered. A filtrate was subjected to decompression concentration to dryness to obtain a crude product of a compound A-4c, which was a yellow oily matter with a yield of 68%, and could be directly used in a next reaction without further refinement.

Step 4. Synthesis of 4-(N-methyl-N-tert-butoxycarbonylamino)-3-(4-methylphenyl)-4,5-dihydro-1H-pyrazol-1-carbonyl chloride (A-4)

Triphosgene (1.97 g, 6.65 mmol) and dried dichloromethane (30 mL) were added into a three-necked flask, and under protection of $N_2$, cooled to −10° C. Dichloromethane (30 mL) containing the compound A-4c (6.07 g, 21.0 mmol) and pyridine (3.4 mL, 39.87 mmol) was slowly added dropwise into the above three-necked flask. After addition was completed, stirring was conducted for 10 minutes at a room temperature. A water was added for a quenching reaction. An organic layer was separated. An aqueous phase was extracted with dichloromethane (2×20 mL). Organic phases were combined, washed with saturated brine, dried with anhydrous $Na_2SO_4$, and filtered. A filtrate was subjected to decompression concentration to dryness. A residue was separated by silica gel column chromatography (PE:EA=3:1 to 1:1, v/v), to obtain an intermediate A-4, which was a pale yellow solid with a yield of 76%; $^1$HNMR (500 MHz, $CDCl_3$): δ 7.82 (d, J=7.8 Hz, 2H), 7.31 (d, J=8.0 Hz, 2H), 4.68 (m, 1H), 3.60=3.47 (m, 2H), 3.27 (s, 3H), 2.41 (s, 3H), 1.41 (s, 9H); ESI-MS: m/z=352[M+1]$^+$.

An intermediate A-17 listed in Table 1.1 was obtained by synthesis by using 4-methoxy-α-bromoacetophenone instead of 4-methyl-α-bromoacetophenone as a raw material in the same way as preparing the compound A-4.

5). Synthesis of 4-(pyrazol-1-yl)-3-(4-methylphenyl)-4,5-dihydro-1H-pyrazol-1-carbonyl chloride (A-5)

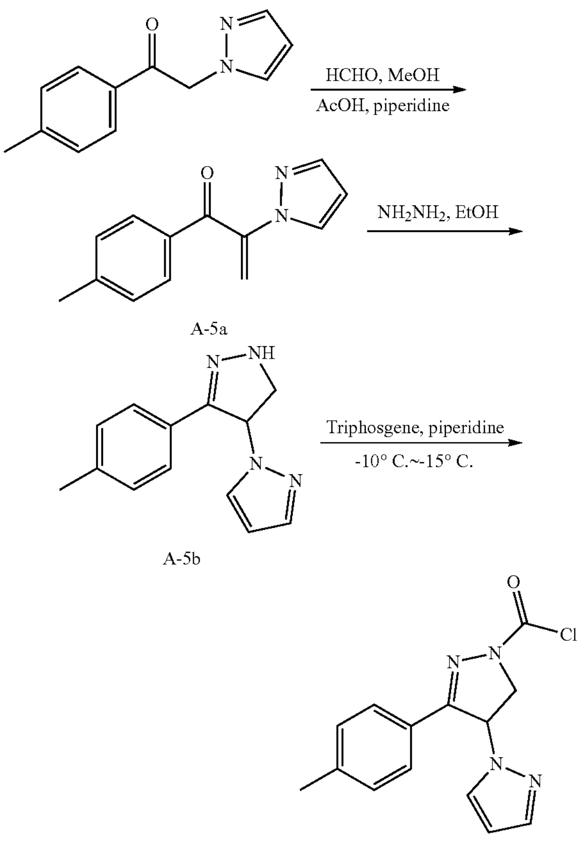

A-5a
A-5b
A-5

Step 1. Synthesis of 2-(1H-pyrazol-1-yl)-1-(4-methylphenyl)propyl-2-ene-1-one (A-5a)

2-(Pyrazol-1-yl)-1-(4-methylphenyl)ethyl-1-one (10.02 g, 50 mmol) and 20 mL of methanol were respectively added into a reaction flask. A 37% aqueous formaldehyde solution (20 mL, 250 mmol), piperidine (2.5 g, 30 mmol) and 2.8 mL of a glacial acetic acid were added under stirring. A stirring reaction was conducted for about 5 hours at a room temperature. A reaction end point was detected by TLC. After the reaction was completed, extracting was conducted with ethyl acetate (100 mL×2). An ethyl acetate layer was washed with saturated brine, dried with anhydrous $Na_2SO_4$, and filtered. The ethyl acetate was recovered from a filtrate under reduced pressure to obtain a compound A-5a, which was a pale yellow oily matter with a yield of 66%, and was directly used in a next reaction without further purification.

Step 2. Synthesis of 4-(pyrazol-1-yl)-3-(4-methylphenyl)-4,5-dihydro-1H-pyrazole (A-5b)

The compound A-5a (6.5 g, 30 mmol) was dissolved into 70 mL of ethanol. Hydrazine hydrate (3 g, 60 mmol) was added under stirring. Heating was conducted to 45° C. to 50° C. for reaction for 40 minutes. The ethanol was evaporated under reduced pressure. A residue was extracted with dichloromethane (50 mL×2), washed with saturated brine, dried with anhydrous $Na_2SO_4$, and filtered. A residue was recrystallized with ethyl acetate/petroleum ether to obtain a compound A-5b, which was an off-white solid with a yield of 62%; ESI-MS: m/z=227[M+1]$^+$.

Step 3. Synthesis of 4-(pyrazol-1-yl)-3-(4-methylphenyl)-4,5-dihydro-1H-pyrazole-1-carbonyl chloride (A-5)

Triphosgene (2.75 g, 9.09 mmol) and anhydrous dichloromethane (45 mL) were added into a dry reaction flask, and under protection of $N_2$, cooled to −15° C. to −10° C. Moreover, the compound A-5b (4.0 g, 18.2 mmol) and pyridine (4.7 g, 39.9 mmol) were dissolved into dichloromethane (45 mL), which were added dropwise into the reaction flask at −15° C. to −10° C. After dropwise addition was completed, stirring was conducted for 10 minutes at a room temperature. A diluted hydrochloric acid was added for a quenching reaction. Organic phases were separated. An aqueous phase was extracted with dichloromethane (20 mL×2). The organic phases were combined, washed with saturated brine, dried with anhydrous $Na_2SO_4$, and filtered. A filtrate was subjected to decompression concentration to dryness. A residue was separated by silica gel column chromatography (PE:EA=3:1 to 1.5:1, v/v), to obtain a compound A-5, which was a pale yellow solid with a yield of 56%; $^1$HNMR (500 MHz, $CDCl_3$): δ 7.83 (d, J=7.5 Hz, 1H), 7.68 (d, J=8.0 Hz, 2H), 7.30 (d, J=7.5 Hz, 1H), 7.21 (d, J=8.0 Hz, 2H), 6.40-6.33 (m, 1H), 6.25-6.22 (m, 1H), 3.81-3.56 (m, 2H), 2.43 (s, 3H); ESI-MS: m/z=289[M+1]$^+$.

TABLE 1.1

Structures and Mass Spectrometric Data of Intermediates A-6 to A-21

| Serial number | Structure | MS(ESI) [M + 1]$^+$ | Serial number | Structure | MS(ESI) [M + 1]$^+$ |
|---|---|---|---|---|---|
| A-6 | 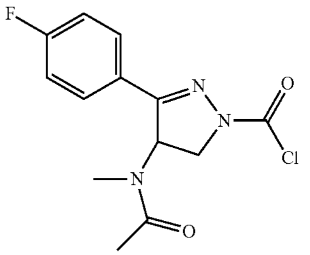 [SMILES: CC(=O)N(C)C1CN(C(=O)Cl)N=C1c1ccc(F)cc1] | 298 | A-14 | 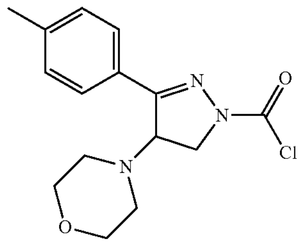 [SMILES: Cc1ccc(C2=NN(C(=O)Cl)CC2N2CCOCC2)cc1] | 308 |
| A-7 | 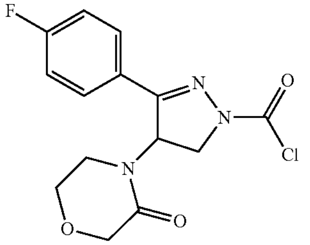 [SMILES: O=C(Cl)N1CC(N2CCOCC2=O)C(c2ccc(F)cc2)=N1] | 326 | A-15 | 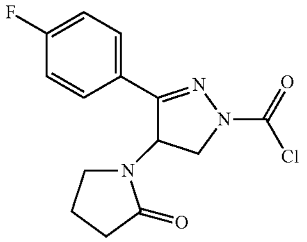 [SMILES: O=C(Cl)N1CC(N2CCCC2=O)C(c2ccc(F)cc2)=N1] | 310 |
| A-8 | 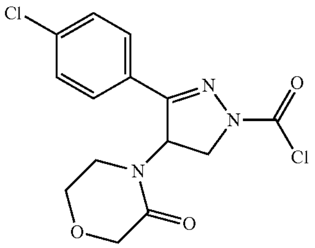 [SMILES: O=C(Cl)N1CC(N2CCOCC2=O)C(c2ccc(Cl)cc2)=N1] | 343 | A-16 | 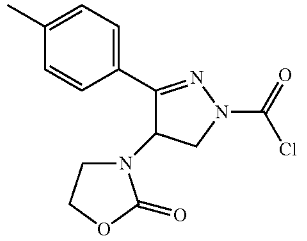 [SMILES: Cc1ccc(C2=NN(C(=O)Cl)CC2N2CCOC2=O)cc1] | 308 |
| A-9 | 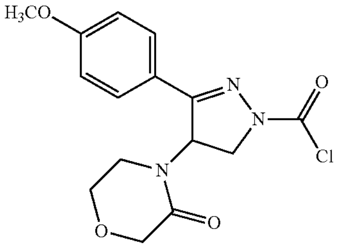 [SMILES: COc1ccc(C2=NN(C(=O)Cl)CC2N2CCOCC2=O)cc1] | 338 | A-17 | 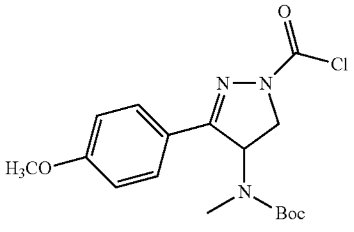 [SMILES: COc1ccc(C2=NN(C(=O)Cl)CC2N(C)C(=O)OC(C)(C)C)cc1] | 368 |

TABLE 1.1-continued
Structures and Mass Spectrometric Data of Intermediates A-6 to A-21
| Serial number | Structure | MS(ESI) $[M + 1]^+$ | Serial number | Structure | MS(ESI) $[M + 1]^+$ |
|---|---|---|---|---|---|
| A-10 | 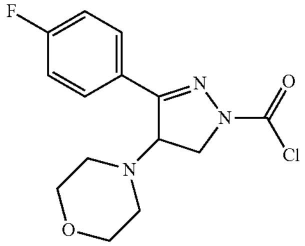 [SMILES: O=C(Cl)N1CC(N2CCOCC2)C(c2ccc(F)cc2)=N1] | 312 | A-18 | 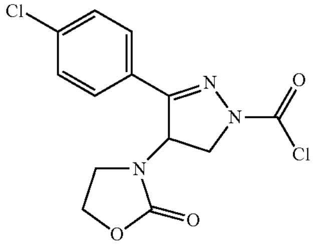 [SMILES: O=C(Cl)N1CC(N2CCOC2=O)C(c2ccc(Cl)cc2)=N1] | 329 |
| A-11 | 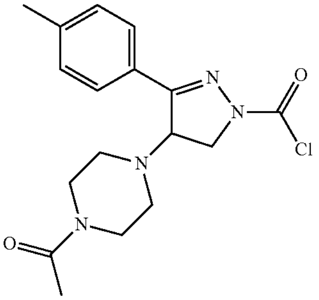 [SMILES: CC(=O)N1CCN(C2CN(C(=O)Cl)N=C2c2ccc(C)cc2)CC1] | 349 | A-19 | 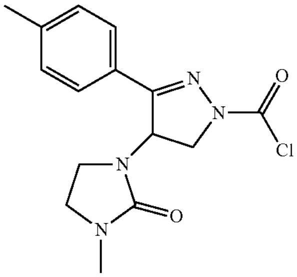 [SMILES: Cc1ccc(C2=NN(C(=O)Cl)CC2N2CCN(C)C2=O)cc1] | 321 |
| A-12 | 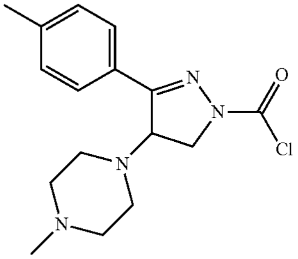 [SMILES: Cc1ccc(C2=NN(C(=O)Cl)CC2N2CCN(C)CC2)cc1] | 321 | A-20 | 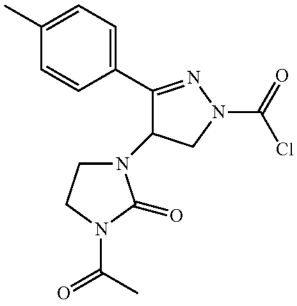 [SMILES: CC(=O)N1CCN(C2CN(C(=O)Cl)N=C2c2ccc(C)cc2)C1=O] | 349 |
| A-13 | 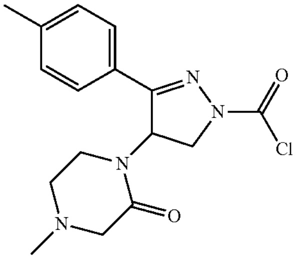 [SMILES: Cc1ccc(C2=NN(C(=O)Cl)CC2N2CCN(C)CC2=O)cc1] | 335 | A-21 | 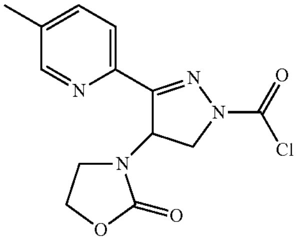 [SMILES: Cc1ccc(C2=NN(C(=O)Cl)CC2N2CCOC2=O)nc1] | 309 |

2. Preparation of an Intermediate Chiral-α-Substituted-Aryl/Heteroarylmethylamine Derivative (B)

1). Synthesis of (R)-1-(4-(trifluoromethyl)phenyl) ethyl-1-amine (B-1)

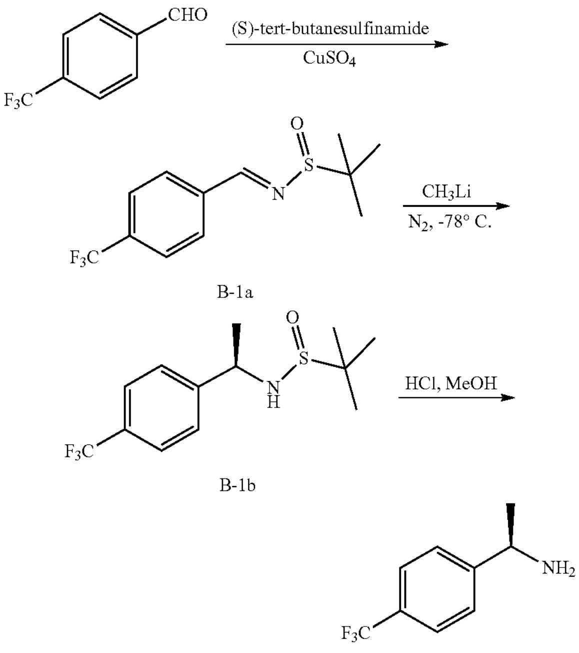

B-1a

B-1b

B-1

Step 1. Synthesis of (E)-2-methyl-N-(4-(trifluoromethyl)benzylidene)propyl-2-sulfinamide (B-1a)

4-Trifluoromethylbenzaldehyde (5.0 g, 28.7 mmol), S-tert-butanesulfinamide (3.80 g, 31.7 mmol) and anhydrous copper sulfate (9.16 g, 57.4 mmol) were added into dichloromethane (70 mL), and stirred for 18 to 20 hours at 50° C. under temperature keeping. Monitoring was conducted by TLC until there was no raw material. Cooling was conducted to a room temperature. Filtering was conducted. A filtrate was subjected to decompression concentration. A residue was separated by silica gel column chromatography (PE: EA=5:1 to 1:1, v/v) to obtain a compound B-1a, which was a white solid with a yield of 76.6%. ESI-MS: m/z=278[M+1]$^+$.

Step 2. Synthesis of N—((R)-1-(4-(trifluoromethyl) phenyl)ethyl)-2-methyl-propyl-2-sulfinamide (B-1b)

The compound B-1a (5.0 g, 18.03 mmol) and toluene (80 mL) were added into a three-necked flask, and under protection of $N_2$, cooled to −70° C. Lithium methide (10.2 mL of a 1.6 M ether solution, 16.3 mmol) was slowly added dropwise into the three-necked flask. A stirring reaction was conducted for 1 hour under a temperature maintained at −78° C. Saturated ammonium chloride (50 mL) was added for a quenching reaction and stirring was conducted for 10 minutes at a room temperature. Still standing for stratification was conducted. An aqueous phase was extracted three times with dichloromethane. Organic phases were combined, dried with anhydrous $Na_2SO_4$, and filtered. A filtrate was subjected to decompression concentration to dryness. A residue was separated by silica gel column chromatography (PE:EA=3:1 to 1:3, v/v) to obtain a compound B-1b, which was a white solid with a yield of 52.2%. ESI-MS: m/z=294 [M+1]$^+$.

Step 3. Synthesis of (R)-1-(4-(trifluoromethyl)phenyl)ethyl-1-amine (B-1)

The compound B-1b (2.0 g, 6.8 mmol) and methanol (30 mL) were added into a 100 mL reaction flask. 6 mL (24 mmol) of a dioxane solution of 4.0 M HCl was added dropwise at a room temperature. Stirring continued for 1 hour at the room temperature. A solvent was recovered under reduced pressure. 10 ml of an aqueous potassium carbonate solution was added into a residue. After stirring for 10 minutes, extracting was conducted four times with a dichloromethane-methanol mixed solution (10:1). A solvent was recovered under reduced pressure to obtain a compound B-1, which was a pale yellow oily matter with a yield of 71.3%. ee Value: 99% (HPLC, Chiralpak AD-3 Column, Detection Conditions: hexane/isopropanol=93/7, Flow Rate=0.8 mL/min, uv-vis Detector); $^1$HNMR (400 MHz, $CDCl_3$): δ 8.77 (brs, 2H), 7.54 (m, 2H), 7.21 (m, 2H), 4.01 (m, 1H), 1.27 (d, J=6.8 Hz, 3H); ESI-MS: m/z=190[M+1]$^+$.

Intermediates B-2 to B-5 listed in Table 1.2 were obtained by synthesis by using corresponding substituted aromatic aldehydes (B-2:4-chlorobenzaldehyde; B-3:3,4-dimethoxybenzaldehyde; B-4:4-cyanobenzaldehyde; B-5:3,4-methylenedioxybenzaldehyde) instead of 4-trifluoromethylbenzaldehyde as raw materials in the same way as preparing the compound B-1.

2). Synthesis of (R)-1-(2-(trifluoromethyl)pyrimidin-5-yl)ethyl-1-amine (B-6)

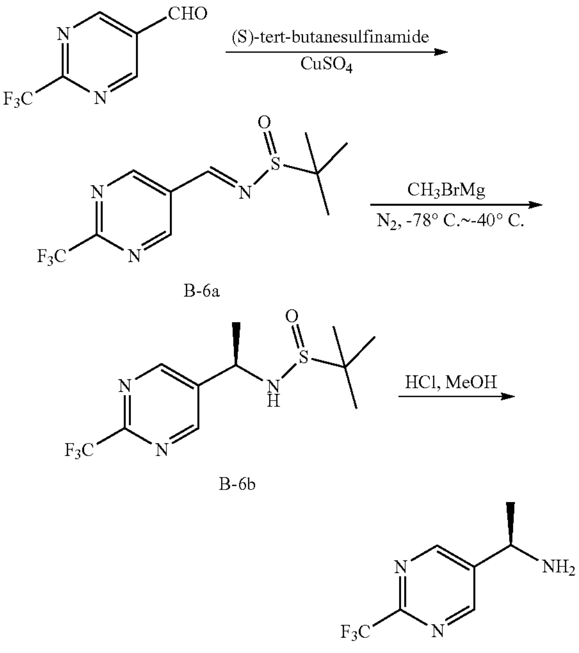

B-6a

B-6b

B-6

Step 1. Synthesis of (E)-2-methyl-N-((2-(trifluoromethyl)pyrimidin-5-yl)methylene)propyl-2-sulfinamide (B-6a)

2-Trifluoromethylpyrimidin-5-carbaldehyde (5 g, 28.4 mmol), S-tert-butanesulfinamide (3.79 g, 31.3 mmol) and anhydrous copper sulfate (9.06 g, 56.8 mmol) were added into dichloromethane (70 mL), and stirred for 18 to 20 hours at 50° C. under temperature keeping. Monitoring was conducted by TLC until there was no raw material. Cooling was conducted to a room temperature. Filtering was conducted. A filtrate was subjected to decompression concentration. A residue was separated by silica gel column chromatography (PE:EA=5:1 to 1:1, v/v) to obtain a compound B-6a, which was a white solid with a yield of 70%. ESI-MS: m/z=280 $[M+1]^+$.

Step 2. Synthesis of N—((R)-1-(2-(trifluoromethyl)pyrimidin-5-yl)ethyl)-2-methyl-propyl-2-sulfinamide (B-6b)

The compound B-6a (4.0 g, 14.3 mmol) and dried dichloromethane (80 mL) were added into a three-necked flask, and under protection of $N_2$, cooled to −78° C. Methyl magnesium bromide (10.5 mL of a 3.0 M tetrahydrofuran solution, 31.5 mmol) was slowly added dropwise into the three-necked flask. A stirring reaction was conducted for 2.5 hours under a temperature maintained at −78° C. to −70° C. Then, heating was conducted to −40° C. After a stirring reaction continued for 2 hours, saturated ammonium chloride (50 mL) was added for a quenching reaction and stirring was conducted for 10 minutes at a room temperature. Still standing for stratification was conducted. An aqueous phase was extracted three times with dichloromethane. Organic phases were combined, dried with anhydrous $Na_2SO_4$, and filtered. A filtrate was subjected to decompression concentration to dryness. A residue was separated by silica gel column chromatography (PE:EA=3:1 to 1:3, v/v) to obtain a compound B-16b, which was a white solid with a yield of 45%. ESI-MS: m/z=296$[M+1]^+$.

Step 3. Synthesis of (R)-1-(2-(trifluoromethyl)pyrimidin-5-yl)ethyl-1-amine (B-6)

The compound B-6b (1.2 g, 4.06 mmol) and methanol (20 mL) were added into a 100 mL reaction flask. HCl (a 4.0 M dioxane solution; 5 mL, 20 mmol) was added dropwise into the reaction flask at a room temperature. Stirring was conducted for 1 hour at a room temperature. The disappearance of raw materials was detected by TLC. A solvent was recovered under reduced pressure. 10 ml of an aqueous potassium carbonate solution was added. After stirring for 10 minutes, extracting was conducted four times with a dichloromethane:MeOH (10:1). A solvent was recovered under reduced pressure to obtain a compound B-6, which was a pale yellow oily matter with a yield of 80%. ee Value: 99% (HPLC, Chiralpak AD-3 Column, Detection Conditions: hexane/isopropanol=93/7, Flow Rate=0.8 mL/min, uv-vis Detector); $^1$HNMR (500 MHz, $CDCl_3$): δ 8.85 (s, 2H), 8.77 (brs, 1H), 4.91-4.85 (m, 1H), 1.67 (d, J=7.0 Hz, 3H); ESI-MS: m/z=192$[M+1]^+$.

Intermediates B-7 to B-22 listed in Table 1.2 were obtained by synthesis by using corresponding substituted heteroaromatic aldehydes (B-7:2-methylpyrimidin-5-carbaldehyde; B-8: 2-chloropyrimidin-5-carbaldehyde; B-9, B-21: 6-trifluoromethylpyridin-3-carbaldehyde; B-10:6-methoxypyridin-3-carbaldehyde; B-11:6-trifluoromethoxypyridin-3-carbaldehyde; B-12:5,6-difluoropyridin-3-carbaldehyde; B-13:6-chloropyridin-3-carbaldehyde; B-14:5-trifluoromethylpyridin-2-carbaldehyde; B-15:5-methoxypyridin-2-carbaldehyde; B-16: 5-trifluoromethylpiperazin-2-carbaldehyde; B-17:5-methylpiperazin-2-carbaldehyde; B-18: 6-trifluoromethylpyridazin-3-carbaldehyde; B-19: 6-chloropyridazin-3-carbaldehyde; B-20: 2-trifluoromethylpyrimidin-5-carbaldehyde; B-22:6-methoxypyridazin-3-carbaldehyde) instead of 2-trifluoromethylpyrimidin-5-carbaldehyde as raw materials in the same way as preparing the compound B-6. In particular, preparation of the intermediates B-20 and B-21 uses R-tert-butanesulfinamide as a chiral source reagent.

TABLE 1.2

Structures and Mass Spectrometric Data of Intermediates B-2 to B-22

| Serial number | Structure | MS(ESI) $[M + 1]^+$ | Serial number | Structure | MS(ESI) $[M + 1]^+$ |
|---|---|---|---|---|---|
| B-2 | 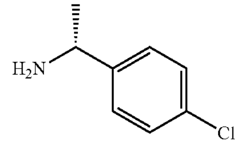 | 156 | B-13 | 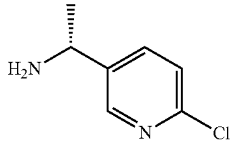 | 157 |
| B-3 | 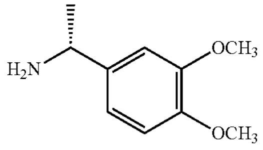 | 182 | B-14 | 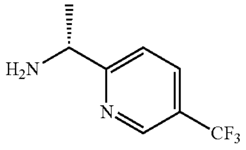 | 190 |
| B-4 | 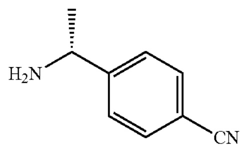 | 147 | B-15 | 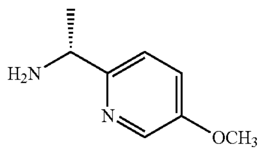 | 153 |

TABLE 1.2-continued
Structures and Mass Spectrometric Data of Intermediates B-2 to B-22
| Serial number | Structure | MS(ESI) [M + 1]+ | Serial number | Structure | MS(ESI) [M + 1]+ |
|---|---|---|---|---|---|
| B-5 | 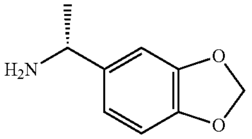 | 166 | B-16 | 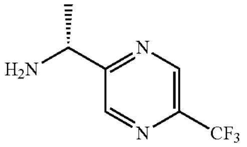 | 192 |
| B-7 | 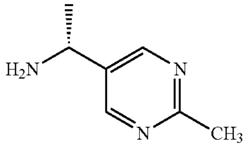 | 138 | B-17 | 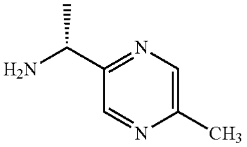 | 138 |
| B-8 | 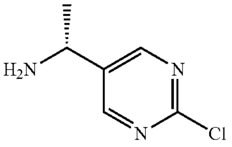 | 158 | B-18 | 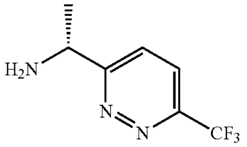 | 192 |
| B-9 | 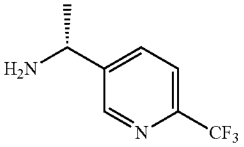 | 190 | B-19 | 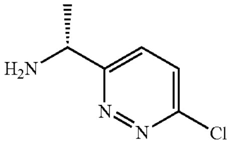 | 158 |
| B-10 | 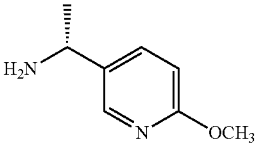 | 153 | B-20 | 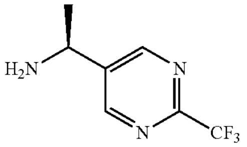 | 192 |
| B-11 | 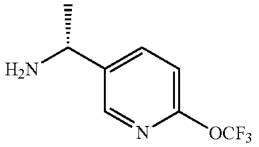 | 207 | B-21 | 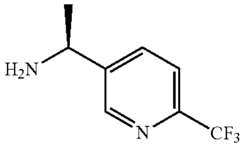 | 191 |
| B-12 | 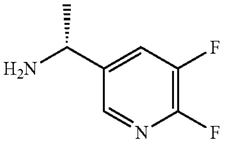 | 159 | B-22 | 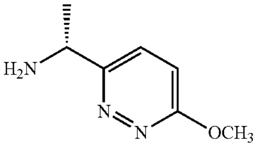 | 154 |

II. Preparation Embodiments of Title Compounds

Preparation Embodiment 1. Synthesis of (S)-4-(3-oxomorpholin-4-yl)-3-(4-methylphenyl)-N—((R)-1-(6-(trifluoromethyl)pyridin-3-yl)ethyl)-4,5-dihydro-1H-pyrazol-1-carboxamide (Compound 1) and Epimer 1a

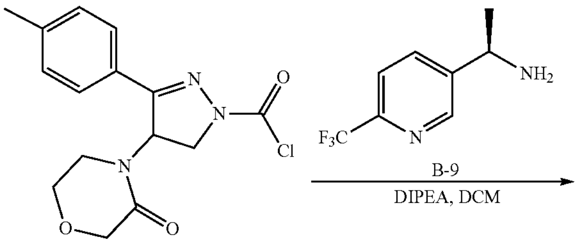

A-2

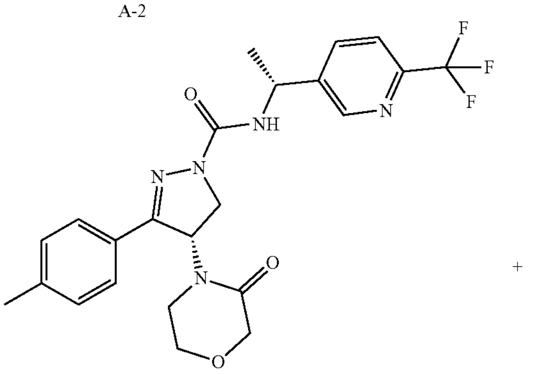

S,R
1

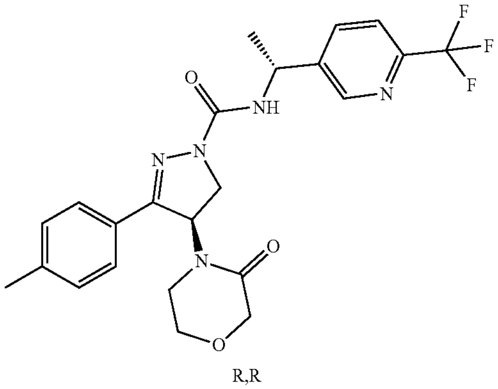

R,R
1a

Synthesis steps: a compound A-2 (1.05 g, 3.26 mmol) and a compound B-9 (0.62 g, 3.26 mmol) were added into dichloromethane (10 mL). Then, N,N-diisopropylethylamine (DIPEA, 1.26 g, 9.75 mmol) was added. Stirring was conducted at a room temperature overnight. A 0.5 N hydrochloric acid (10 mL) was added. Stirring was conducted for 10 minutes. Still standing for stratification was conducted. Organic phases were separated. An aqueous phase was extracted with dichloromethane (10 mL×3). The organic phases were combined, dried with anhydrous $Na_2SO_4$, and filtered. A filtrate was subjected to decompression concentration to dryness. A residue was subjected to gradient separation by silica gel column chromatography (PE: EA=3:1 to 1:3, v/v) to obtain a title compound 1 with a yield of 32%, and an R,R-epimer 1a thereof with a yield of 29%.

Figure 2:
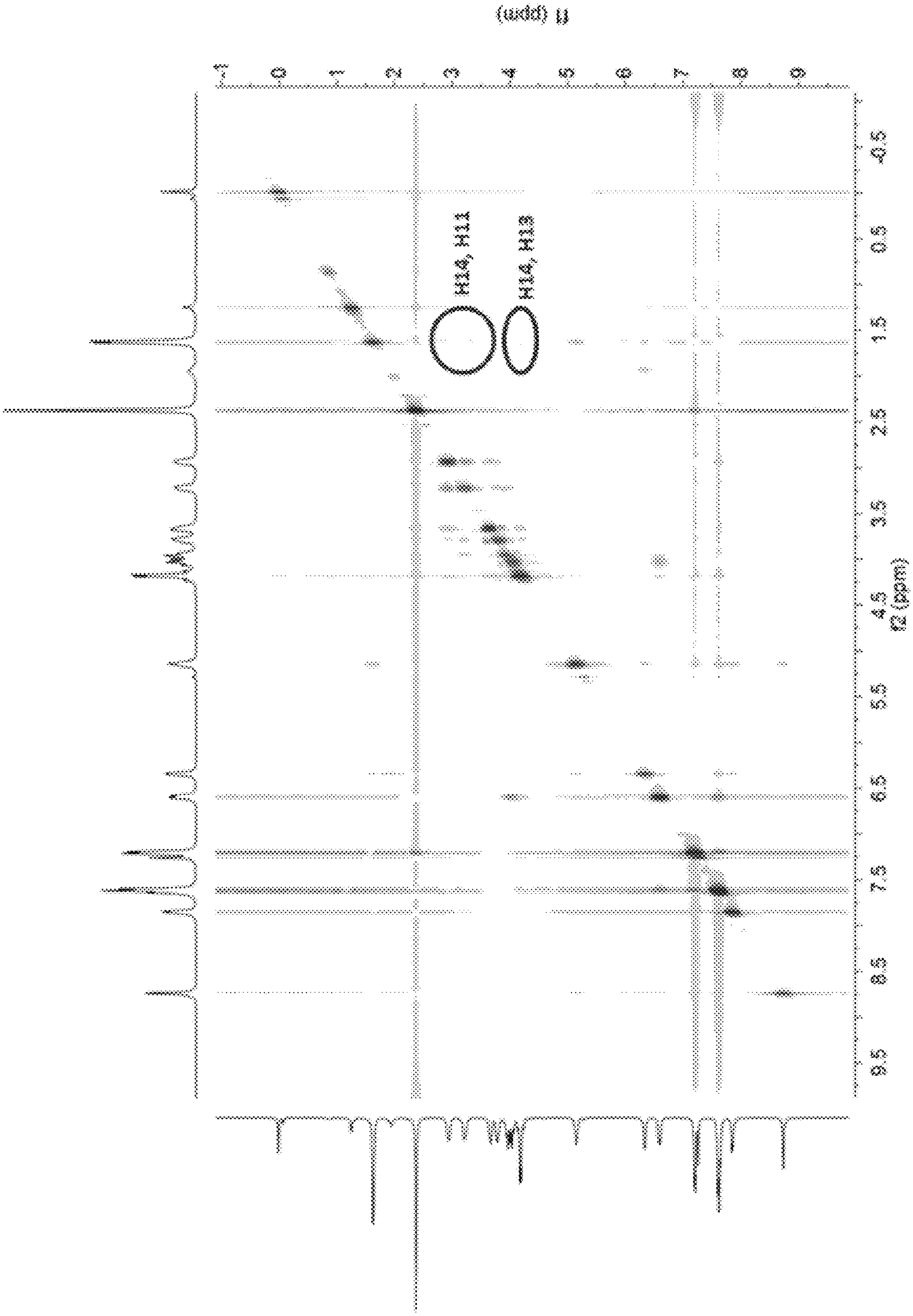
FIG. 2 shows an NOESY spectrum of the title compound 1.
Figure 3:
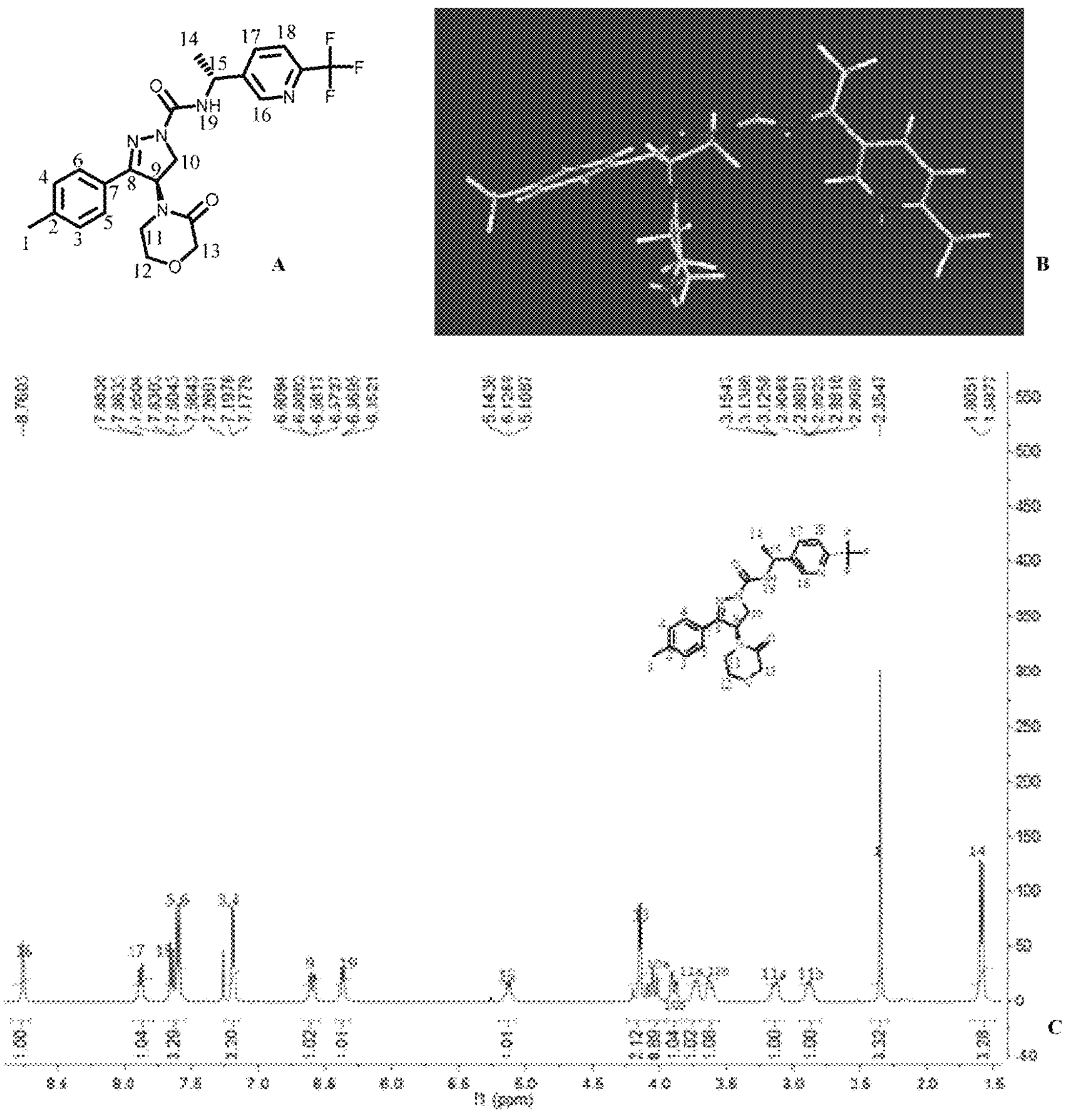
Figure 4:
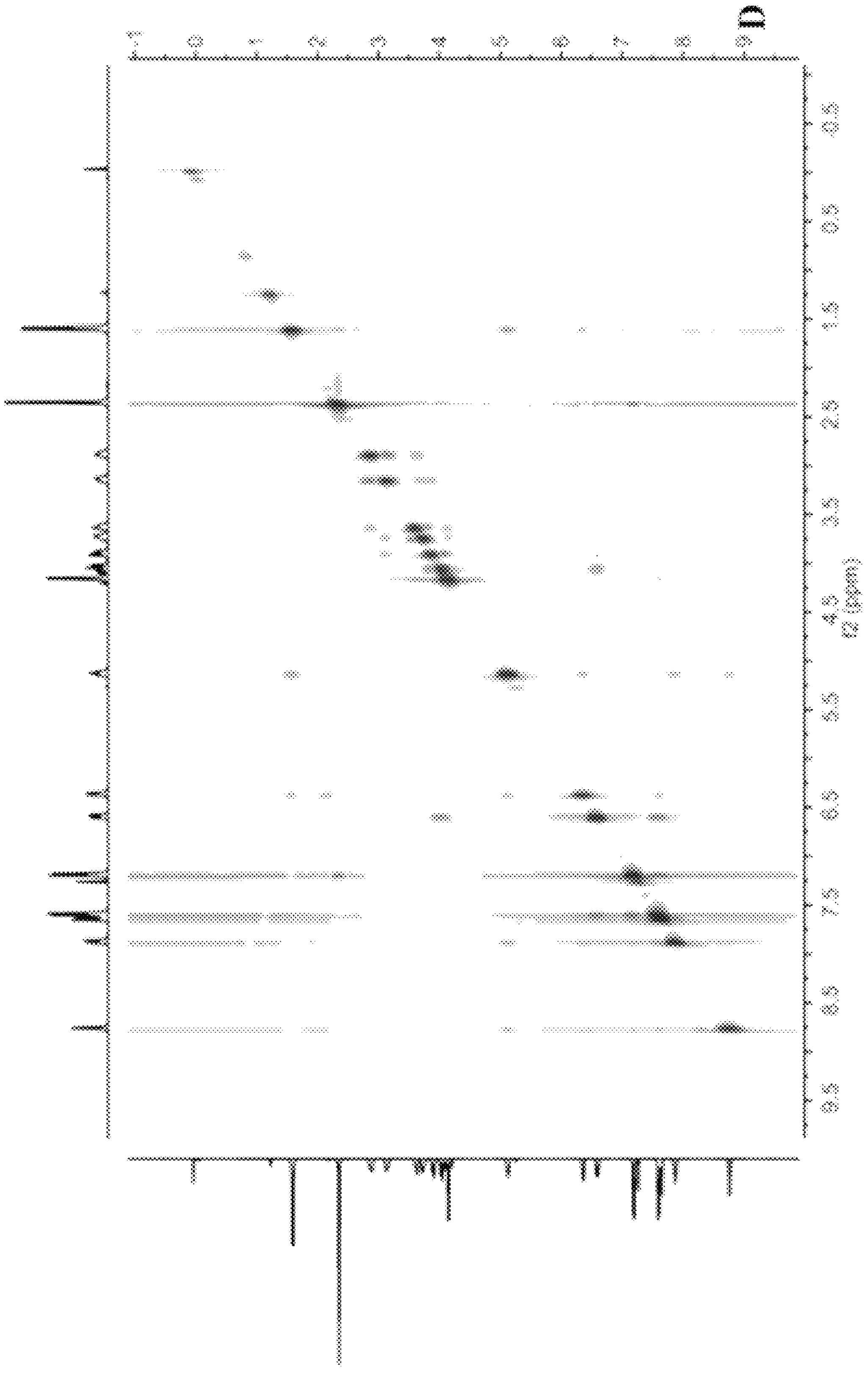

Structures and $^1$H-NMR spectrums of the title compound 1 and the epimer 1a thereof were shown in FIGS. 1 and 3, and three-dimensional structure analysis of the title compound 1 and the epimer 1a thereof (FIGS. 2 and 4) was as follows.

1) Considering that in the synthesis of the title compound 1, the intermediate B-9 was an R-type chiral synthon, while another synthon A-2 was a racemate, and mass spectrometric data of the title compounds 1 and 1a were both ESI-MS: m/z=476[M+H]$^+$, meanwhile, the two have the same number of hydrogen protons, so they are epimers of each other;

2) hydrogen proton signals of the title compound 1 were assigned according to chemical shifts of the hydrogen protons of the title compound 1 $^1$H-NMR (400 MHz, $CDCl_3$) and a $^1$H-$^1$HCOSY spectrum:

δ8.74 (s, 1H, H-16), 7.86 (d, J=7.9 Hz, 1H, H-17), 7.64 (d, J=8.0 Hz, 1H, H-18), 7.62 (d, J=8.0 Hz, 2H, H-5H-6), 7.21 (d, J=7.9 Hz, 2H, H-3H-4), 6.60 (dd, J=11.0, 3.7 Hz, 1H, H-9), 6.34 (d, J=7.0 Hz, 1H, H-19), 5.14 (brs, 1H, H-15), 4.23-4.13 (m, 2H, H-13), 4.00 (t, J=12.0 Hz, 1H, H-10a), 3.96 (dd, J=12.9, 3.7 Hz, 1H, H-10b), 3.78 (m, 1H, H-12a), 3.67 (m, 1H, H-12b), 3.22 (m, 1H, H-11a), 2.95 (m, 1H, H-11b), 2.37 (s, 3H, H-1), 1.64 (d, J=7.0 Hz, 3H, H-14);

An assignment order of hydrogen spectroscopy signals of the compound 1a from a low field to a high field was consistent with that of the title compound 1.

3) According to chemical structures of the compounds 1 and 1a, in combination with three-dimensional simulation diagrams, it could be seen that three parts of a methylbenzene ring/a pyrazoline ring/carbamide were all basically in the same plane structure, respectively. When a C-9 configuration was S, a morpholinone ring was on the same side as a C-14 methyl, and an NOSEY spectrum shown that C-14 methyl hydrogen protons were related to 11 and 13 hydrogen protons, thus it was confirmed that the C-9 configuration in the structure of the title compound 1 was S-type. On the contrary, when the C-9 configuration was R-type, the morpholinone ring was on the different side from the C-14 methyl, and an NOSEY spectrum shown that the C-14 methyl hydrogen protons were irrelated to C-11, C-12 and C-13 hydrogen protons, thus it was confirmed that the C-9 configuration in the structure of the compound 1a was R-type.

Preparation Embodiment 2. Synthesis of (S)-4-(4-methyl-2-oxopiperazin-1-yl)-3-(4-methylphenyl)-N—((R)-1-(4-chlorophenyl))ethyl)-4,5-dihydro-1H-pyrazol-1-carboxamide (Compound 2) and Epimer 2a

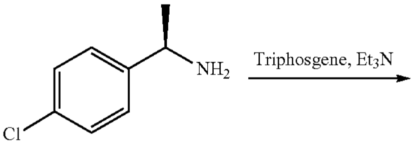

B-2

-continued

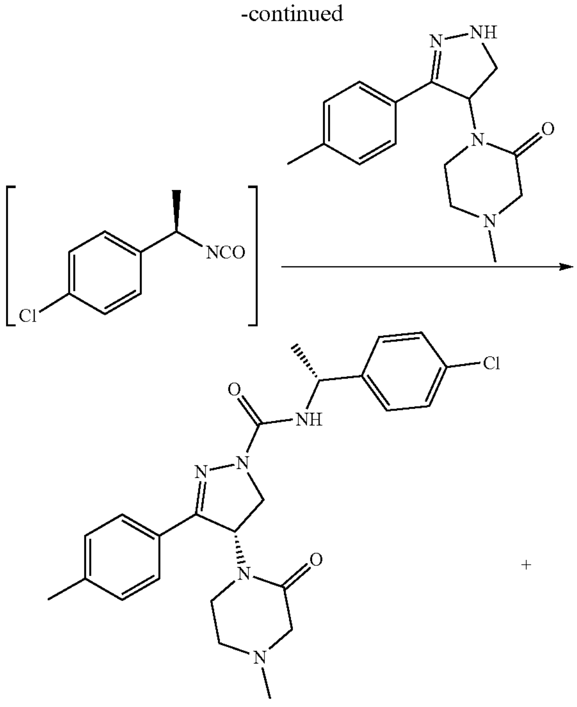

S,R
2

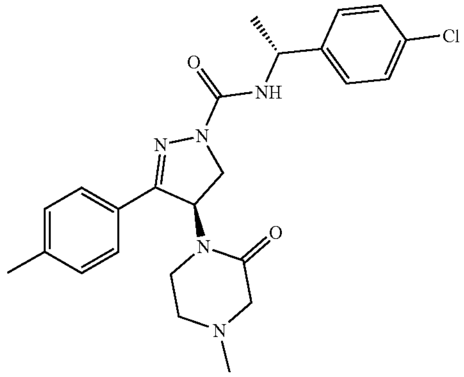

R,R
2a

Synthesis steps: a compound B-2 (500 mg, 2.63 mmol) was added into dichloromethane (5 mL), and cooled to 0° C. Under protection of $N_2$, triphosgene (370 mg, 1.25 mmol) and $Et_3N$ (660 mg, 6.55 mmol) were added. Heating was conducted to a room temperature for stirring for 1 hour. A reaction solution was poured into water, and extracted with dichloromethane (10 mL×2). Organic phases were dried with anhydrous $Na_2SO_4$, and filtered. A solvent was recovered under reduced pressure to obtain crude isocyanate, which was directly used in a next reaction without further purification.

A compound 1-(3-(4-methylphenyl)-4,5-dihydro-1H-pyrazol-4-yl)-4-methylpiperazin-2-one (500 mg, 1.80 mmol), the crude isocyanate (410 mg, 2.27 mmol), and $K_2CO_3$ were added into acetone (10 mL), and under protection of $N_2$, stirred for 2 hours at a room temperature. The disappearance of raw materials was showed by TLC. A reaction solution was poured into dichloromethane, washed with water, and washed with saturated brine. Organic phases were dried with anhydrous $Na_2SO_4$, and filtered. A solvent was recovered from a filtrate under reduced pressure. A residue was subjected to gradient separation by silica gel column chromatography (MeOH:EA=1:4, v/v) to obtain a title compound 2, which was a white solid with a yield of 35%, and an R,R-epimer 2a thereof with a yield of 25%.

Title Compound 2: $^1$H NMR (400 MHz, $CDCl_3$): δ 7.65 (d, J=7.4 Hz, 2H), 7.36-7.28 (m, 4H), 7.24 (d, J=7.8 Hz, 2H), 6.68-6.60 (m, 1H), 6.29 (d, J=8.0 Hz, 1H), 5.08 (dd, J=14.3, 7.4 Hz, 1H), 4.12-3.95 (m, 2H), 3.27-3.01 (m, 4H), 2.83-2.47 (m, 2H), 2.41 (s, 3H), 2.26 (s, 3H), 1.60 (d, J=6.9 Hz, 3H); ESI-MS: m/z=454[M+H]$^+$.

Epimer 2a: $^1$H NMR (400 MHz, $CDCl_3$): δ 7.70 (d, J=7.8 Hz, 2H), 7.46-7.42 (m, 4H), 7.22 (d, J=7.8 Hz, 2H), 6.66-6.58 (m, 1H), 6.32 (d, J=8.0 Hz, 1H), 5.06 (dd, J=14.0, 7.0 Hz, 1H), 4.11-3.94 (m, 2H), 3.30-3.05 (m, 4H), 2.86-2.42 (m, 2H), 2.42 (s, 3H), 2.28 (s, 3H), 1.62 (d, J=7.2 Hz, 3H); ESI-MS: m/z=454[M+H]$^+$.

Preparation Embodiment 3. Synthesis of (S)-4-(3-oxomorpholin-4-yl)-3-(4-fluorophenyl)-N—((R)-1-(2-(trifluoromethyl)pyrimidin-5-yl)ethyl)-4, 5-dihydro-1H-pyrazol-1-carboxamide (Compound 3) and Epimer 3a

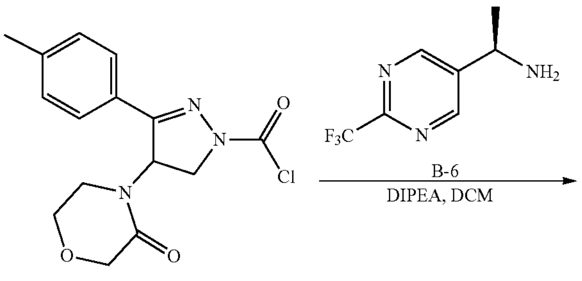

A-2

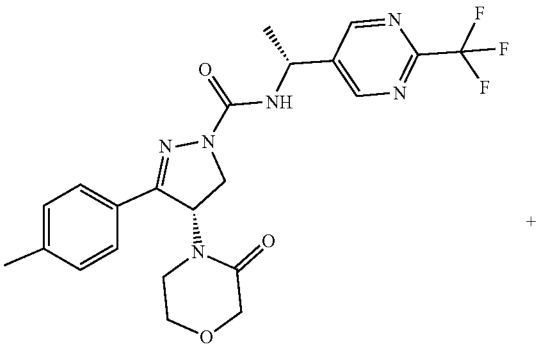

S,R
3

-continued

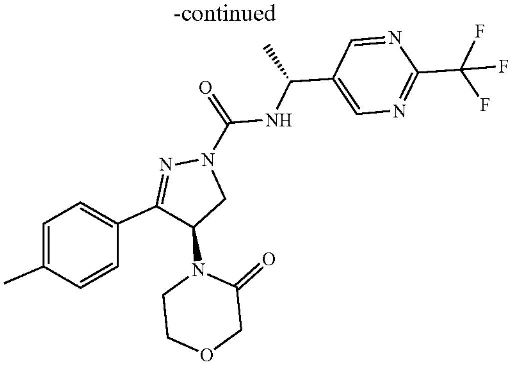

R,R
3a

Synthesis steps: a compound A-2 (1.05 g, 3.26 mmol) and a compound B-6 (0.62 g, 3.25 mmol) were added into dichloromethane (10 mL). Then, N,N-diisopropylethylamine (DIPEA, 1.26 g, 9.75 mmol) was added. Stirring was conducted at a room temperature overnight. A 0.5 N hydrochloric acid (10 mL) was added. Stirring was conducted for 10 minutes. Still standing for stratification was conducted. Organic phases were separated. An aqueous phase was extracted with dichloromethane (10 mL×3). The organic phases were combined, dried with anhydrous $Na_2SO_4$, and filtered. A filtrate was subjected to decompression concentration to dryness. A residue was subjected to gradient separation by silica gel column chromatography (PE: EA=2:1 to 1:3, v/v) to obtain a title compound 3 with a yield of 37%, and an R,R-epimer 3a thereof with a yield of 30%.

Title Compound 3: $^1H$ NMR (500 MHz, $CDCl_3$): δ 8.91 (s, 2H), 7.62 (d, J=8.2 Hz, 2H), 7.23 (d, J=8.0 Hz, 2H), 6.62 (dd, J=11.1, 4.1 Hz, 1H), 6.34 (d, J=7.0 Hz, 1H), 5.20-5.12 (m, 1H), 4.20 (m, 2H), 4.05 (dd, J=13.0, 11.1 Hz, 1H), 3.96 (dd, J=13.0, 4.1 Hz, 1H), 3.80 (m, 1H), 3.68 (m, 1H), 3.23 (m, 1H), 2.94 (m, 1H), 2.39 (s, 3H), 1.69 (d, J=7.1 Hz, 3H); ESI-MS: m/z=477[M+1]$^+$.

Epimer 3a: $^1H$ NMR (500 MHz, $CDCl_3$): δ 8.88 (s, 2H), 7.70 (d, J=8.0 Hz, 2H), 7.25 (d, J=8.0 Hz, 2H), 6.60 (dd, J=11.0, 4.0 Hz, 1H), 6.40 (brs, 1H), 5.22-5.13 (m, 1H), 4.22 (m, 2H), 4.02 (dd, J=12.2, 11.0 Hz, 1H), 3.94 (dd, J=12.0, 4.0 Hz, 1H), 3.78 (m, 1H), 3.65 (m, 1H), 3.21 (m, 1H), 2.92 (m, 1H), 2.36 (s, 3H), 1.65 (d, J=7.5 Hz, 3H); ESI-MS: m/z=477[M+1]$^+$.

Preparation Embodiment 4. Synthesis of (S)-4-(N-methyl-N-ethoxycarbonylamino)-3-(4-methylphenyl)-N—((R)-1-(2-(trifluoromethyl)pyrimidin-5-yl)ethyl)-4,5-dihydro-1H-pyrazol-1-carboxamide (Compound 4)

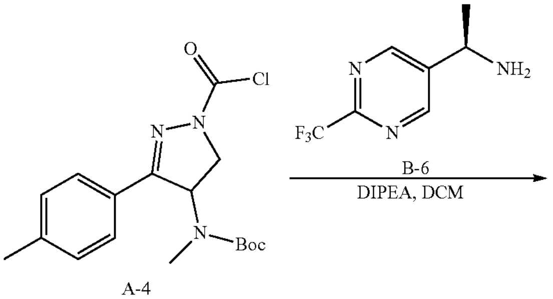

A-4

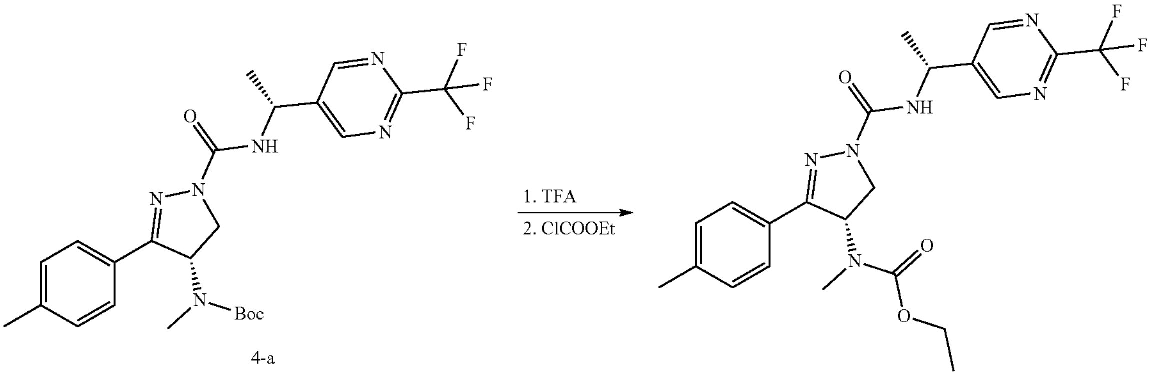

4-a

S,R
4

+

-continued

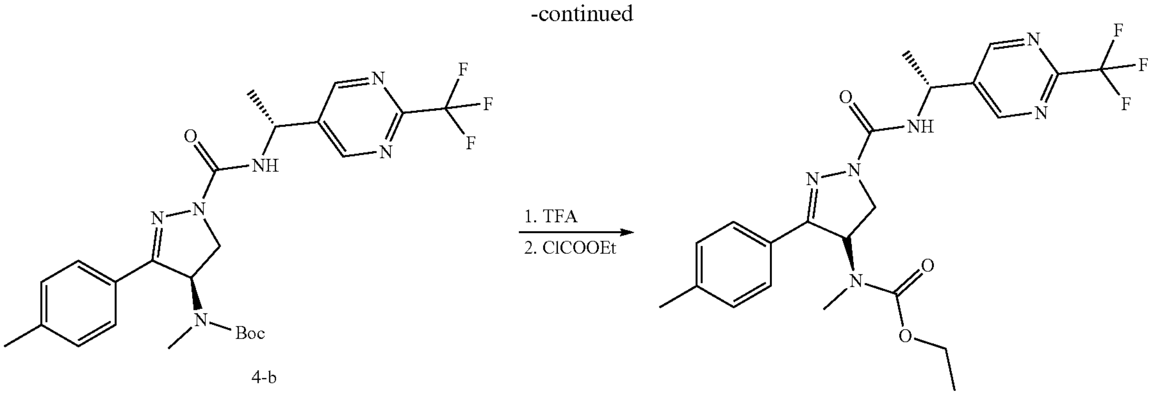

4-b

R,R
4c

Step 1. Synthesis of (S)-4-(N-methyl-N-tert-butoxycarbonylamino)-3-(4-methylphenyl)-N—((R)-1-(2-(trifluoromethyl))pyrimidin-5-yl)ethyl)-4,5-dihydro-1H-pyrazol-1-carboxamide (4-a) and Epimer 4c A compound A-4 (1.0 g, 2.84 mmol) and a compound B-6 (0.52 g, 2.70 mmol) were added into dichloromethane (10 mL). Then, N,N-diisopropylethylamine (DIPEA, 1.0 g, 7.75 mmol) was added. Stirring was conducted at a room temperature overnight. Hydrochloric acid (0.5 N, 10 mL) was added and stirring was conducted for 10 minutes. Still standing for stratification was conducted. An aqueous phase was extracted with dichloromethane (10 mL×3). Organic phases were combined, dried with anhydrous $Na_2SO_4$, and filtered. A filtrate was subjected to decompression concentration to dryness. A residue was subjected to gradient separation by silica gel column chromatography (PE:EA=2:1 to 1:3, v/v) to obtain a compound 4-a with a yield of 40.7%; ESI-MS: m/z=507[M+1]$^+$. Meanwhile, a compound 4-b was obtained with a yield of 35%; ESI-MS: m/z=507[M+1]$^+$.

Step 2. Synthesis of (S)-4-(N-methyl-N-ethoxycarbonylamino)-3-(4-methylphenyl)-N—((R)-1-(2-(trifluoromethyl)pyrimidin-5-yl)ethyl)-4,5-dihydro-1H-pyrazol-1-carboxamide (Compound 4) and Epimer 4c The compound 4-a (0.73 g, 1.44 mmol) was added into dichloromethane (10 mL). Trifluoroacetic acid (0.3 mL, 4.32 mmol) was added. Stirring was conducted for 1 hour at a room temperature. Excess trifluoroacetic acid was evaporated under reduced pressure. Dichloromethane (10 mL) and triethylamine (0.8 mL, 5.76 mmol) were added into a reaction flask. A reaction system was cooled to −10° C. to −5° C., and ethyl chloroformate (0.2 mL, 1.73 mmol) was added dropwise into a reaction under this temperature. After addition was completed, heating was conducted to the room temperature and stirring was conducted for 1 hour. Water was added for a quenching reaction. Organic layers were separated. An aqueous layer was extracted with ethyl acetate (10 mL×3). Organic phases were combined, dried with anhydrous $Na_2SO_4$, and filtered. A filtrate was subjected to decompression concentration to dryness. A residue was subjected to gradient separation by silica gel column chromatography (PE:EA=2:1 to 1:3, v/v) to obtain the title compound 4 with a yield of 56%; $^1$H NMR (400 MHz, $CDCl_3$): δ 8.97 (d, J=1.7 Hz, 2H), 7.71 (d, J=7.4 Hz, 2H), 7.26 (d, J=7.9 Hz, 2H), 6.39 (d, J=6.3 Hz, 1H), 5.24-5.15 (m, 1H), 4.22 (q, J=7.0 Hz, 2H), 4.11-4.02 (m, 1H), 3.94 (td, J=12.6, 4.6 Hz, 1H), 2.64 (d, J=16.1 Hz, 1H), 2.43 (s, 3H), 1.72 (d, J=7.5 Hz, 3H), 1.65 (s, 3H), 1.30 (t, J=6.7 Hz, 3H); ESI-MS: m/z=479[M+1]$^+$.

The epimer 4c was obtained by synthesis by using a compound 4b as a raw material in the same 5 way as preparing the title compound 4, with a yield of 470%; $^1$H NMR (400 MHz, $CDCl_3$): δ 8.92 (s, 2H), 7.73 (d, J=7.6 Hz, 2H), 7.28 (d, J=7.4 Hz, 2H), 6.44 (br, 1H), 5.20-5.08 (m, 1H), 4.58-4.51 (m, 1H), 4.25 (q, J=7.8 Hz, 2H), 3.88 (td, J=12.8, 5.0 Hz, 1H), 2.64 (d, J=16.1 Hz, 1H), 2.43 (s, 3H), 1.74 (d, J=7.6 Hz, 3H), 1.67 (s, 3H), 1.35 (t, J=7.6 Hz, 3H); ESI-MS: m/z=479[M+1]$^+$.

Preparation Embodiments 5 to 13, 18, 20 to 25

Title compounds 5 to 13, 18, 20 to 25 and R,R-epimers thereof in Preparation Embodiments 5 to 13, 18, 20 to 25 were obtained by synthesis by using corresponding intermediates A and B as raw materials in the same way as preparing the title compound 1 (Table 2)

| Embodiments | Intermediate A | Intermediate B | Yield S,R | Yield R,R |
|---|---|---|---|---|
| Embodiment 5 | A-1 | B-1 | 33% | 31% |
| Embodiment 6 | A-16 | B-3 | 26% | 28% |
| Embodiment 7 | A-3 | B-5 | 31% | 32% |
| Embodiment 8 | A-20 | B-4 | 30% | 33% |
| Embodiment 9 | A-3 | B-15 | 37% | 40% |
| Embodiment 10 | A-3 | B-14 | 32% | 31% |
| Embodiment 11 | A-1 | B-13 | 35% | 34% |
| Embodiment 12 | A-16 | B-12 | 28% | 27% |
| Embodiment 13 | A-3 | B-11 | 37% | 39% |
| Embodiment 18 | A-20 | B-9 | 29% | 30% |
| Embodiment 20 | A-2 | B-1 | 40% | 38% |
| Embodiment 21 | A-3 | B-9 | 33% | 32% |
| Embodiment 22 | A-16 | B-9 | 35% | 33% |
| Embodiment 23 | A-21 | B-9 | 23% | 22% |
| Embodiment 24 | A-7 | B-9 | 31% | 32% |
| Embodiment 25 | A-1 | B-9 | 39% | 36% |

Preparation Embodiments 14, 17, 19, 37 to 39

Title compounds 14, 17, 19, 37 to 39 and R,R-epimers thereof in Preparation Embodiments 14, 17, 19, 37 to 39 were obtained by synthesis by using corresponding intermediates A and B as raw materials in the same way as preparing the title compound 2 (Table 2).

| Embodiments | Intermediate A | Intermediate B | Yield S,R | Yield R,R |
|---|---|---|---|---|
| Embodiment 14 | A-10 | B-10 | 31% | 32% |
| Embodiment 17 | A-13 | B-9 | 28% | 29% |
| Embodiment 19 | A-11 | B-9 | 33% | 32% |
| Embodiment 37 | A-11 | B-6 | 38% | 37% |
| Embodiment 38 | A-12 | B-6 | 31% | 29% |
| Embodiment 39 | A-14 | B-6 | 27% | 28% |

Preparation Embodiments 26 to 36, 40 to 44

Title compounds 26 to 36, 40 to 44 and R,R-epimers thereof in Preparation Embodiments 26 to 36, 40 to 44 were obtained by synthesis by using corresponding intermediates A and B as raw materials in the same way as preparing the title compound 3 (Table 2).

| Embodiments | Intermediate A | Intermediate B | Yield S,R | Yield R,R |
|---|---|---|---|---|
| Embodiment 26 | A-2 | B-16 | 39% | 40% |
| Embodiment 27 | A-16 | B-17 | 36% | 34% |
| Embodiment 28 | A-15 | B-17 | 38% | 36% |
| Embodiment 29 | A-18 | B-22 | 29% | 30% |
| Embodiment 30 | A-2 | B-18 | 35% | 33% |
| Embodiment 31 | A-16 | B-19 | 38% | 35% |
| Embodiment 32 | A-3 | B-6 | 41% | 38% |
| Embodiment 33 | A-7 | B-6 | 33% | 34% |

-continued

| Embodiments | Intermediate A | Intermediate B | Yield S,R | Yield R,R |
|---|---|---|---|---|
| Embodiment 34 | A-1 | B-6 | 43% | 40% |
| Embodiment 35 | A-8 | B-6 | 31% | 29% |
| Embodiment 36 | A-9 | B-6 | 28% | 30% |
| Embodiment 40 | A-16 | B-6 | 41% | 38% |
| Embodiment 41 | A-19 | B-6 | 33% | 31% |
| Embodiment 42 | A-5 | B-6 | 38% | 37% |
| Embodiment 43 | A-18 | B-7 | 30% | 27% |
| Embodiment 44 | A-15 | B-8 | 42% | 40% |

Preparation Embodiments 15 and 16

Title compounds 15 and 16 and R,R-epimers thereof in Preparation Embodiments 15 and 16 were obtained by synthesis by using corresponding intermediate A (meanwhile, during preparation of the compound 15: using $ClCOCH_2N(CH_3)_2$ instead of ClCOOEt in Embodiment 4; during preparation of the compound 16: using ClCOOMe instead of ClCOOEt in Embodiment 4) and intermediate B as raw materials in the same way as preparing the title compound 4 (Table 2)

| Embodiments | Intermediate A | Intermediate B | Yield S,R | Yield R,R |
|---|---|---|---|---|
| Embodiment 15 | A-4 | B-9 | 56% | 61% |
| Embodiment 16 | A-17 | B-9 | 62% | 67% |

TABLE 2

Nuclear Magnetic and Mass Spectrometric Data of Title Compounds 5 to 44

| Serial numbers of preparation embodiments | Names and structures of title compounds | Nuclear magnetic and mass spectrometric data |
|---|---|---|
| 5 | (S)-4-(N-methylacetamido)-3-(4-methylphenyl)-N-((R)-1-(4-(trifluoromethyl)phenyl)ethyl)-4,5-dihydro-1H-pyrazol-1-carboxamide 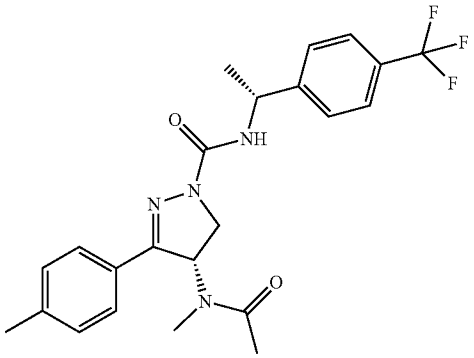 [SMILES: CC(=O)N(C)[C@H]1CN(C(=O)N[C@H](C)c2ccc(C(F)(F)F)cc2)N=C1c1ccc(C)cc1] | $^1H$ NMR (400 MHz, $CDCl_3$) δ 7.60 (d, J = 8.2 Hz, 2H), 7.53 (d, J = 8.0 Hz, 2H), 7.47 (d, J = 8.1 Hz, 2H), 7.20 (d, J = 8.1 Hz, 2H), 6.59 (dd, J = 11.3, 4.2 Hz, 1H), 6.32 (d, J = 7.7 Hz, 1H), 5.11 (q, J = 7.1 Hz, 1H), 4.04-4.01 (m, 1H), 3.92-3.80 (m, 1H), 2.69 (s, 3H), 2.37 (s, 3H), 2.07 (s, 3H), 1.59 (d, J = 7.0 Hz, 3H); ESI-MS: m/z = 447 $[M + H]^+$. |

TABLE 2-continued

| Nuclear Magnetic and Mass Spectrometric Data of Title Compounds 5 to 44 | | |
|---|---|---|
| Serial numbers of preparation embodiments | Names and structures of title compounds | Nuclear magnetic and mass spectrometric data |
| 5a | (R)-4-(N-methylacetamido)-3-(4-methylphenyl)-N-((R)-1-(4-(trifluoromethyl)phenyl)ethyl)-4,5-dihydro-1H-pyrazol-1-carboxamide 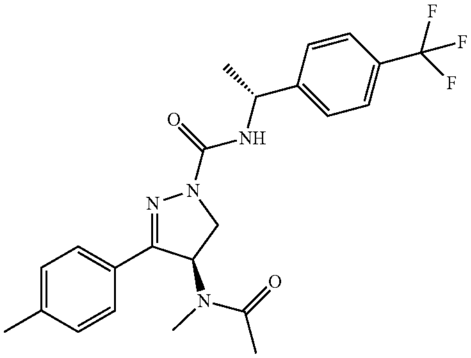 [SMILES: CC(=O)N(C)[C@@H]1CN(C(=O)N[C@H](C)c2ccc(C(F)(F)F)cc2)N=C1c1ccc(C)cc1] | $^1H$ NMR (400 MHz, $CDCl_3$) δ 7.71 (d, J = 7.8 Hz, 2H), 7.57 (d, J = 8.0 Hz, 2H), 7.28 (d, J = 7.6 Hz, 2H), 7.22(d, J = 7.8 Hz, 2H), 6.51 (m, 1H), 6.32 (br, 1H), 5.14 (q, J = 7.6 Hz, 1H), 4.42-4.31 (m, 1H), 4.00-3.50 (m, 1H), 2.70 (s,3H), 2.35 (s,3H), 2.15 (s, 3H), 1.60 (d, J = 7.2 Hz, 3H); ESI-MS: m/z = 447 $[M + H]^+$. |
| 6 | (S)-4-(2-oxooxazolidin-3-yl)-3-(4-methylphenyl)-N-((R)-1-(3,4-dimethoxyphenyl)ethyl)-4,5-dihydro-1H-pyrazol-1-carboxamide 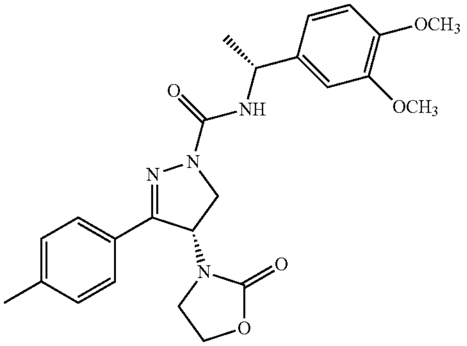 [SMILES: COc1ccc([C@@H](C)NC(=O)N2C[C@H](N3CCOC3=O)C(c3ccc(C)cc3)=N2)cc1OC] | $^1$HNMR (500 MHz, $CDCl_3$) δ 7.71 (d, J = 7.5 Hz, 2H), 7.25 (d, J = 7.5 Hz, 2H), 6.97 (s, 1H), 6.90 (d, J = 7.5 Hz, 1H), 6.86 (d, J = 7.5 Hz, 1H), 6.49 (brs, 1H), 6.15 (dd, J = 11.0, 4.0 Hz, 1H), 5.18-5.12 (m, 1H), 4.39-4.26 (m, 1H), 3.99 (dd, J = 12.0, 11.0 Hz, 1H), 3.87 (dd, J = 12.0, 4.0 Hz, 1H), 3.83 (s, 3H), 3.75 (s, 3H), 3.24-3.13 (m, 2H), 2.40 (s, 3H), 1.58 (d, J = 7.2 Hz, 3H); ESI-MS: m/z = 453 $[M + H]^+$. |
| 6a | (R)-4-(2-oxooxazolidin-3-yl)-3-(4-methylphenyl)-N-((R)-1-(3,4-dimethoxyphenyl)ethyl)-4,5-dihydro-1H-pyrazol-1-carboxamide 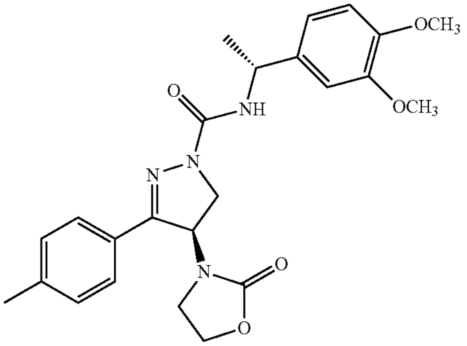 [SMILES: COc1ccc([C@@H](C)NC(=O)N2C[C@@H](N3CCOC3=O)C(c3ccc(C)cc3)=N2)cc1OC] | $^1$HNMR (400 MHz, $CDCl_3$) δ 7.72 (d, J = 7.8 Hz, 2H), 7.28 (d, J = 7.6 Hz, 2H), 7.00 (s, 1H), 6.92 (d, J = 7.8 Hz, 1H), 6.87 (d, J = 7.5 Hz, 1H), 6.52 (brs, 1H), 6.20 (dd, J = 11.2, 3.8 Hz, 1H), 5.16-5.10 (m, 1H), 4.40-4.27 (m, 1H), 4.00 (dd, J = 12.2, 11.0 Hz, 1H), 3.86 (dd, J = 12.0, 4.2 Hz, 1H), 3.83 (s, 6H), 3.26-3.14 (m, 2H), 2.42 (s, 3H), 1.60 (d, J = 7.5 Hz, 3H); ESI-MS: m/z = 453 $[M + H]^+$. |

TABLE 2-continued

Nuclear Magnetic and Mass Spectrometric Data of Title Compounds 5 to 44

| Serial numbers of preparation embodiments | Names and structures of title compounds | Nuclear magnetic and mass spectrometric data |
| --- | --- | --- |
| 7 | (S)-4-(2-oxopyrrolidin-1-yl)-3-(4-methylphenyl)-N-((R)-1-(3,4-(methylenedioxy) phenyl)ethyl)-4,5-dihydro-1H-pyrazol-1-carboxamide 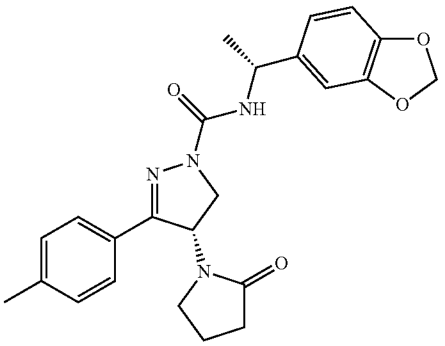 [SMILES: Cc1ccc(C2=NN(C(=O)N[C@H](C)c3ccc4c(c3)OCO4)C[C@@H]2N2CCCC2=O)cc1] | $^1$HNMR (500 MHz, $CDCl_3$) δ 7.65 (d, J = 7.6 Hz, 2H), 7.23 (d, J = 7.6 Hz, 2H), 6.95 (s, 1H), 6.90 (d, J = 7.5 Hz, 1H), 6.84 (d, J = 7.5 Hz, 1H), 6.36 (brs, 1H),6.10 (dd, J = 11.0, 4.0 Hz, 1H), 5.96 (s, 2H), 5.18-5.13 (m, 1H), 4.00 (dd, J = 12.0, 11.0 Hz, 1H), 3.86 (dd, J = 12.0, 4.0 Hz, 1H), 3.20-2.92 (m, 2H), 2.38 (s, 3H),2.29-2.22 (m, 2H), 1.93-1.82 (m, 2H), 1.67 (d, J = 7.1 Hz, 3H); ESI-MS: m/z = 435 $[M + H]^+$. |
| 7a | (R)-4-(2-oxopyrrolidin-1-yl)-3-(4-methylphenyl)-N-((R)-1-(3,4-(methylenedioxy) phenyl)ethyl)-4,5-dihydro-1H-pyrazol-1-carboxamide 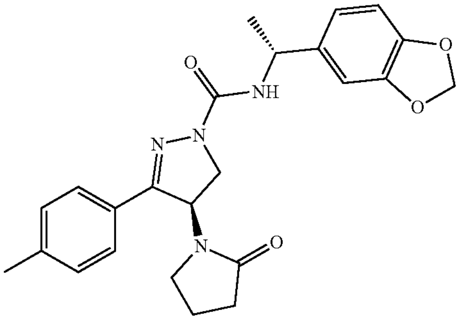 [SMILES: Cc1ccc(C2=NN(C(=O)N[C@H](C)c3ccc4c(c3)OCO4)C[C@H]2N2CCCC2=O)cc1] | $^1$HNMR (400 MHz, $CDCl_3$) δ 7.70 (d, J = 7.8 Hz, 2H), 7.28 (d, J = 7.8 Hz, 2H), 6.96 (s, 1H), 6.82 (d, J = 7.5Hz, 1H), 6.78 (d, J = 7.5 Hz, 1H), 6.48 (brs, 1H), 6.12 (dd, J = 11.5, 4.0 Hz, 1H), 6.08 (s, 2H), 5.16-5.11 (m, 1H), 3.96 (dd, J = 12.2, 11.0 Hz, 1H), 3.86 (m, 1H), 3.29-3.01 (m, 2H), 2.34 (s, 3H), 2.30-2.21 (m, 2H), 1.91-1.80 (m, 2H), 1.64 (d, J = 7.2 Hz, 3H); ESI-MS: m/z = 435 $[M + H]^+$. |
| 8 | (S)-4-(3-acetyl-2-oxoimidazolidin-1-yl)-3-(4-methylphenyl])-N-((R)-1-(4-cyanophenyl) ethyl)-4,5-dihydro-1H-pyrazol-1-carboxamide 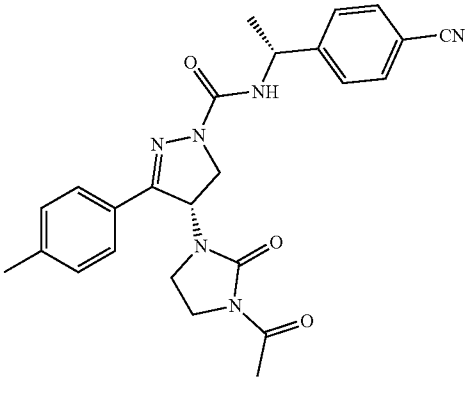 [SMILES: CC(=O)N1CCN([C@H]2CN(C(=O)N[C@H](C)c3ccc(C#N)cc3)N=C2c2ccc(C)cc2)C1=O] | $^1$HNMR (500 MHz, $CDCl_3$) δ 7.76 (d, J = 8.0 Hz, 2H), 7.65 (d, J = 8.0 Hz, 2H), 7.42 (d, J = 8.0 Hz, 2H), 7.22 (d, J = 8.0 Hz, 2H), 6.34 (brs, 1H), 6.15 (dd, J = 11.0, 3.8 Hz, 1H), 5.17-5.14 (m, 1H), 4.01 (dd, J = 12.0, 11.2 Hz, 1H), 3.84 (dd, J = 12.0, 3.8 Hz, 1H), 3.42 (m, 4H), 2.39 (s, 3H), 2.29 (s, 3H), 1.58 (d, J = 7.1 Hz, 3H); ESI-MS: m/z = 459 $[M + H]^+$. |

TABLE 2-continued

| Nuclear Magnetic and Mass Spectrometric Data of Title Compounds 5 to 44 | | |
|---|---|---|
| Serial numbers of preparation embodiments | Names and structures of title compounds | Nuclear magnetic and mass spectrometric data |
| 8a | (R)-4-(3-acetyl-2-oxoimidazolidin-1-yl)-3-(4-methylphenyl])-N-((R)-1-(4-cyanophenyl) ethyl)-4,5-dihydro-1H-pyrazol-1-carboxamide 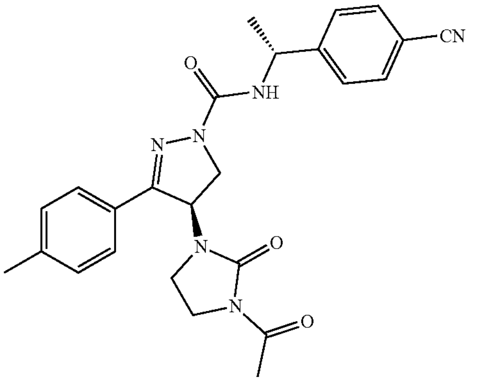 [SMILES: CC(=O)N1CCN([C@@H]2CN(C(=O)N[C@H](C)c3ccc(C#N)cc3)N=C2c2ccc(C)cc2)C1=O] | $^1$HNMR (400 MHz, $CDCl_3$) δ 7.72 (d, J = 7.8 Hz, 2H), 7.60 (d, J = 7.6 Hz, 2H), 7.47 (d, J = 7.8 Hz, 2H), 7.26 (d, J = 7.8 Hz, 2H), 6.45 (brs, 1H), 6.28 (dd, J = 11.0, 4.0 Hz, 1H), 5.18-5.15 (m, 1H), 4.00 (dd, J = 12.0, 11.0 Hz, 1H), 3.84 (m, 1H), 3.42-3.38 (m, 4H), 2.43 (s, 3H), 2.39 (s, 3H), 1.60 (d, J = 7.0 Hz, 3H); ESI-MS: m/z = 459 $[M + H]^+$. |
| 9 | (S)-4-(2-oxopyrrolidin-1-yl)-3-(4-methylphenyl)-N-((R)-1-(5-methoxypyridin-2-yl)ethyl)-4,5-dihydro-1H-pyrazol-1-carboxamide 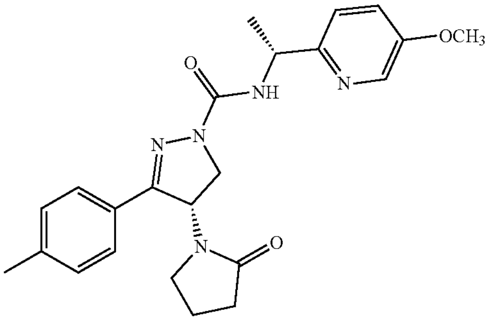 [SMILES: COc1ccc([C@@H](C)NC(=O)N2C[C@H](N3CCCC3=O)C(c3ccc(C)cc3)=N2)nc1] | $^1$HNMR (500 MHz, $CDCl_3$) δ 8.38 (s, 1H), 7.70 (d, J = 8.1 Hz, 2H), 7.61 (d, J = 8.0 Hz, 1H), 7.36 (d, J = 8.0 Hz, 1H), 7.26 (d, J = 8.0 Hz, 2H), 6.62 (dd, J = 11.0, 4.0 Hz, 1H), 6.35 (brs, 1H), 5.16-5.11(m, 1H), 3.98 (dd, J = 12.2, 11.0 Hz, 1H), 3.85 (dd, J = 12.0, 4.0 Hz, 1H), 3.81 (s, 3H), 3.20-2.94 (m, 2H), 2.41 (s, 3H), 2.28-2.23 (m, 2H), 1.92-1.80 (m, 2H), 1.64 (d, J = 7.0 Hz, 3H); ESI-MS: m/z = 422 $[M + H]^+$. |
| 9a | (R)-4-(2-oxopyrrolidin-1-yl)-3-(4-methylphenyl)-N-((R)-1-(5-methoxypyridin-2-yl)ethyl)-4,5-dihydro-1H-pyrazol-1-carboxamide 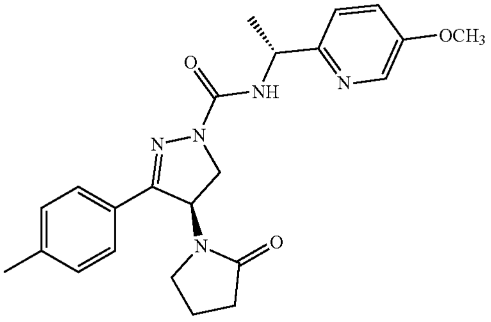 [SMILES: COc1ccc([C@@H](C)NC(=O)N2C[C@@H](N3CCCC3=O)C(c3ccc(C)cc3)=N2)nc1] | $^1$HNMR (400 MHz, $CDCl_3$) δ 8.56 (s, 1H), 7.66 (d, J = 7.8 Hz, 2H), 7.63 (d, J = 8.0 Hz, 1H), 7.34 (d, J = 7.8 Hz, 1H), 7.22 (d, J = 7.6 Hz, 2H), 6.60 (dd, J = 11.0, 3.6 Hz, 1H), 6.35 (brs, 1H), 5.15 (m, 1H), 4.00 (dd, J = 12.0, 3.6 Hz, 1H), 3.86 (m, 1H), 3.83 (s, 3H), 3.21-3.09 (m, 2H), 2.37 (s, 3H), 2.26-2.16 (m, 2H), 1.90-1.80 (m, 2H), 1.62 (d, J = 7.2 Hz, 3H); ESI-MS: m/z = 422 $[M + H]^+$. |

TABLE 2-continued

Nuclear Magnetic and Mass Spectrometric Data of Title Compounds 5 to 44

| Serial numbers of preparation embodiments | Names and structures of title compounds | Nuclear magnetic and mass spectrometric data |
|---|---|---|
| 10 | (S)-4-(2-oxopyrrolidin-1-yl)-3-(4-methylphenyl)-N-((R)-1-(5-(trifluoromethyl)pyridin-2-yl)ethyl)-4,5-dihydro-1H-pyrazol-1-carboxamide 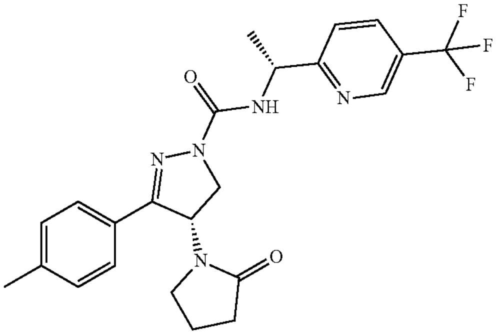 [SMILES: Cc1ccc(C2=NN(C(=O)N[C@H](C)c3ccc(C(F)(F)F)cn3)C[C@@H]2N2CCCC2=O)cc1] | $^1$HNMR (400 MHz, $CDCl_3$) δ 8.72 (s, 1H), 7.70 (d, J = 8.1 Hz, 1H), 7.65 (d, J = 8.0 Hz, 2H), 7.46 (d, J = 8.0 Hz, 1H), 7.24 (d, J = 8.0 Hz, 2H), 6.66 (dd, J = 11, 3.8 Hz, 1H), 6.33 (d, J = 7.0 Hz, 1H), 5.18-5.14 (m, 1H), 4.00 (dd, J = 12.0, 11.0 Hz, 1H), 3.87 (dd, J = 12.0, 3.8 Hz, 1H), 3.21-2.93 (m, 2H), 2.39 (s, 3H), 2.29-2.24 (m, 2H), 1.90-1.78 (m, 2H), 1.66 (d, J = 7.0 Hz, 3H); ESI-MS: m/z = 460[M + H]$^+$. |
| 10a | (R)-4-(2-oxopyrrolidin-1-yl)-3-(4-methylphenyl)-N-((R)-1-(5-(trifluoromethyl)pyridin-2-yl)ethyl)-4,5-dihydro-1H-pyrazol-1-carboxamide 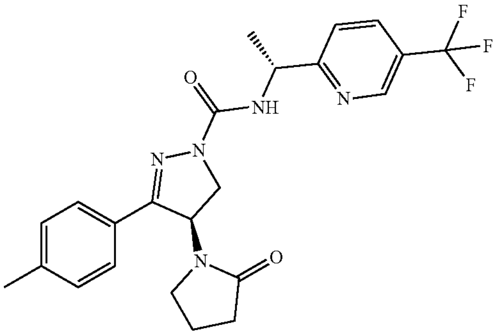 [SMILES: Cc1ccc(C2=NN(C(=O)N[C@H](C)c3ccc(C(F)(F)F)cn3)C[C@H]2N2CCCC2=O)cc1] | $^1$HNMR (400 MHz, $CDCl_3$) δ 8.68 (s, 1H), 7.72 (d, J = 8.0 Hz, 1H), 7.69 (d, J = 8.1 Hz, 2H),7.50 (d, J = 8.2 Hz, 1H), 7.22 (d, J = 7.8 Hz, 2H), 6.62 (dd, J =12, 4.0 Hz, 1H), 6.23 (d, J = 7.2 Hz, 1H), 5.16-5.13 (m, 1H), 3.98 (dd, J = 12.0, 11.0 Hz, 1H), 3.83 (dd, J = 12.2, 4.0 Hz, 1H), 3.25-3.00 (m, 2H), 2.35 (s, 3H), 2.25-2.14 (m, 2H), 1.95-1.98 (m, 2H), 1.63 (d, J = 7.2 Hz, 3H); ESI-MS: m/z = 460 [M + H]$^+$. |
| 11 | (S)-4-(N-methylacetamido)-3-(4-methylphenyl)-N-((R)-1-(6-chloropyridin-3-yl) ethyl)-4,5-dihydro-1H-pyrazol-1-carboxamide 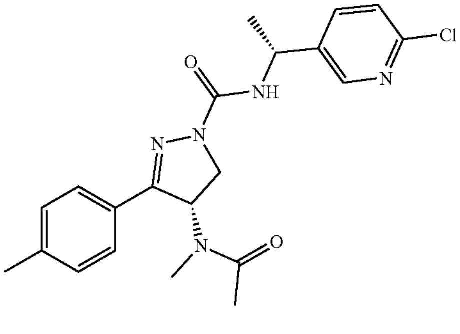 [SMILES: CC(=O)N(C)[C@H]1CN(C(=O)N[C@H](C)c2ccc(Cl)nc2)N=C1c1ccc(C)cc1] | $^1$HNMR (500 MHz, $CDCl_3$) δ 8.71 (s, 1H), 8.05 (d, J = 8.1 Hz, 1H), 7.72 (d, J = 7.6 Hz, 2H), 7.35 (d, J = 8.0 Hz, 1H), 7.28 (d, J = 7.5 Hz, 2H), 6.64 (dd, J = 12, 4.0 Hz, 1H), 6.34 (brs, 1H), 5.15-5.08 (m, 1H), 3.99 (dd, J = 12.0, 11.0 Hz, 1H), 3.85 (dd, J = 12.0, 4.0 Hz, 1H), 2.70 (s, 3H), 2.37 (s, 3H), 2.07 (s, 3H), 1.66 (d, J = 7.0 Hz, 3H); ESI-MS: m/z = 414 [M + H]$^+$. |

TABLE 2-continued

| Nuclear Magnetic and Mass Spectrometric Data of Title Compounds 5 to 44 | | |
|---|---|---|
| Serial numbers of preparation embodiments | Names and structures of title compounds | Nuclear magnetic and mass spectrometric data |
| 11a | (R)-4-(N-methylacetamido)-3-(4-methylphenyl)-N-((R)-1-(6-chloropyridin-3-yl)ethyl)-4,5-dihydro-1H-pyrazol-1-carboxamide 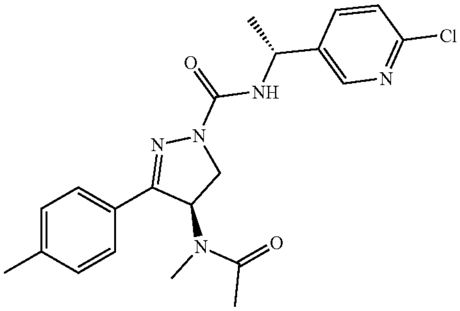 [SMILES: CC(=O)N(C)[C@@H]1CN(C(=O)N[C@H](C)c2ccc(Cl)nc2)N=C1c1ccc(C)cc1] | $^1$HNMR (400 MHz, $CDCl_3$) δ 8.73 (s, 1H), 8.07 (d, J = 8.0 Hz, 1H), 7.70 (d, J = 7.8 Hz, 2H), 7.33 (d, J = 8.0 Hz, 1H), 7.26 (d, J = 7.8 Hz, 2H), 6.61 (dd, J = 12.0, 3.8 Hz, 1H), 6.36 (brs, 1H), 5.13-5.08 (m, 1H), 4.01 (dd, J = 12.2, 11.0 Hz, 1H), 3.85 (m, 1H), 2.68 (s, 3H), 2.35 (s, 3H), 2.23 (s, 3H), 1.63 (d, J = 7.2 Hz, 3H); ESI-MS: m/z = 414 $[M + H]^+$. |
| 12 | (S)-4-(2-oxooxazolidin-3-yl)-3-(4-methylphenyl)-N-((R)-1-(5,6-difluoropyridin-3-yl)ethyl)-4,5-dihydro-1H-pyrazol-1-carboxamide 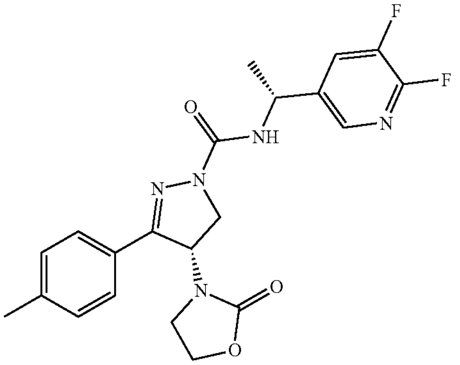 [SMILES: Cc1ccc(C2=NN(C(=O)N[C@H](C)c3cnc(F)c(F)c3)C[C@@H]2N2CCOC2=O)cc1] | $^1$HNMR (500 MHz, $CDCl_3$) δ 8.17 (s, 1H), 7.99 (m, 1H), 7.72 (d, J = 7.5 Hz, 2H), 7.26 (d, J = 7.5 Hz, 2H), 6.56 (dd, J = 11.0, 4.0 Hz, 1H), 6.36 (brs, 1H), 5.14-5.11 (m, 1H), 4.34 (m, 2H), 4.01 (dd, J = 12.0, 11.0 Hz, 1H), 3.82 (dd, J = 11.0, 4.0 Hz, 1H), 3.28 (m, 2H), 2.36 (s, 3H), 1.68 (d, J = 7.0 Hz, 3H); ESI-MS: m/z = 430 $[M + H]^+$. |
| 12a | (R)-4-(2-oxooxazolidin-3-yl)-3-(4-methylphenyl)-N-((R)-1-(5,6-difluoropyridin-3-yl)ethyl)-4,5-dihydro-1H-pyrazol-1-carboxamide 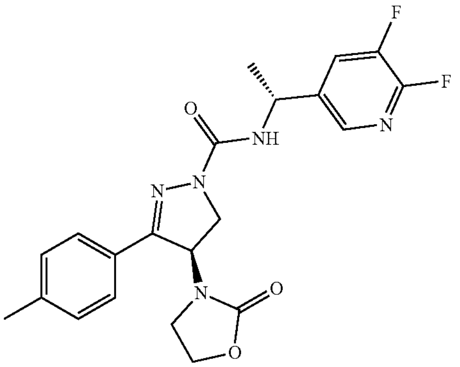 [SMILES: Cc1ccc(C2=NN(C(=O)N[C@H](C)c3cnc(F)c(F)c3)C[C@H]2N2CCOC2=O)cc1] | $^1$HNMR (400 MHz, $CDCl_3$) δ 8.15(s, 1H), 7.96 (m, 1H), 7.70 (d, J = 7.8 Hz, 2H), 7.23 (d, J = 7.8 Hz, 2H), 6.60 (dd, J = 11.2, 4.2 Hz, 1H), 6.40 (brs, 1H), 5.12-5.08 (m, 1H), 4.35-4.20 (m, 2H), 4.01 (m, 1H), 3.80 (dd, J = 11.0, 4.0 Hz, 1H), 3.28-3.21 (m, 2H), 2.34 (s, 3H), 1.67 (d, J = 7.2 Hz, 3H); ESI-MS: m/z = 430 $[M + H]^+$. |

TABLE 2-continued

Nuclear Magnetic and Mass Spectrometric Data of Title Compounds 5 to 44

| Serial numbers of preparation embodiments | Names and structures of title compounds | Nuclear magnetic and mass spectrometric data |
|---|---|---|
| 13 | (S)-4-(2-oxopyrrolidin-1-yl)-3-(4-methylphenyl)-N-((R)-1-(6-(trifluoromethoxy)pyridin)-3-yl)ethyl)-4,5-dihydro-1H-pyrazol-1-carboxamide<br>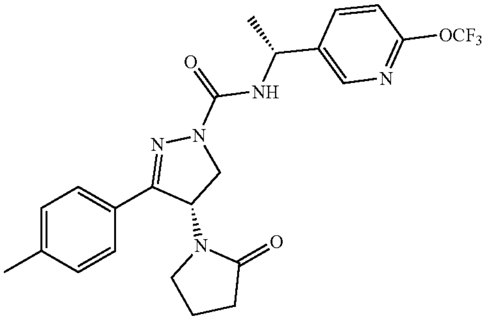 [SMILES: Cc1ccc(C2=NN(C(=O)N[C@H](C)c3ccc(OC(F)(F)F)nc3)C[C@@H]2N2CCCC2=O)cc1] | $^1$HNMR (400 MHz, $CDCl_3$) δ 7.76 (d, J = 7.6 Hz, 1H), 7.70 (d, J = 7.5 Hz, 2H), 7.61 (s,1H), 7.28 (d, J = 7.5 Hz, 2H), 6.78 (d, J = 7.6 Hz, 1H), 6.36 (dd, J = 11.0, 4.0 Hz, 1H), 6.07 (brs, 1H), 5.17-5.15 (m, 1H), 4.03 (dd, J = 12.0, 11.0 Hz, 1H), 3.84 (dd, J = 11.0, 4.0 Hz, 1H), 3.30-2.90 (m, 2H), 2.38 (s, 3H), 2.30-2.02 (m, 2H), 1.98-1.86 (m, 2H), 1.67 (d, J = 7.2 Hz, 3H); ESI-MS: m/z = 476 $[M + H]^+$. |
| 13a | (R)-4-(2-oxopyrrolidin-1-yl)-3-(4-methylphenyl)-N-((R)-1-(6-(trifluoromethoxy)pyridin)-3-yl)ethyl)-4,5-dihydro-1H-pyrazol-1-carboxamide<br>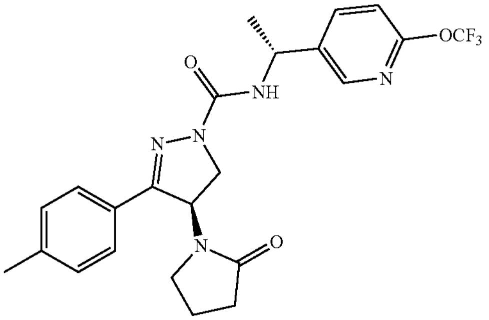 [SMILES: Cc1ccc(C2=NN(C(=O)N[C@H](C)c3ccc(OC(F)(F)F)nc3)C[C@H]2N2CCCC2=O)cc1] | $^1$HNMR (400 MHz, $CDCl_3$) δ 7.78 (d, J = 8.0 Hz, 1H), 7.72 (d, J = 7.6 Hz, 2H), 7.62 (s, 1H), 7.28 (d, J = 7.8 Hz, 2H), 6.68 (d, J = 8.0 Hz, 1H), 6.56 (dd, J = 11.2, 4.0 Hz, 1H), 6.10 (brs, 1H), 5.15-5.13 (m, 1H), 4.01 (dd, J = 12.0, 11.0 Hz, 1H), 3.84 (m, 1H), 3.30-2.92 (m, 2H), 2.38 (s, 3H), 2.32-2.00 (m, 2H), 1.95-1.84 (m, 2H), 1.66 (d, J = 7.1 Hz, 3H); ESI-MS: m/z = 476 $[M + H]^+$. |
| 14 | (S)-4-(morpholin-4-yl)-3-(4-fluorophenyl)-N-((R)-1-(6-methoxypyridin-3-yl)ethyl)-4,5-dihydro-1H-pyrazol-1-carboxamide<br>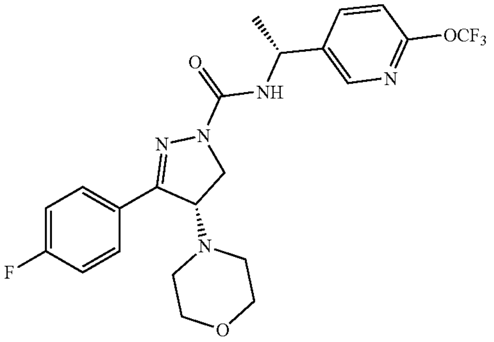 | $^1$HNMR (500 MHz, $CDCl_3$) δ 7.79-7.76 (m, 3H), 7.61 (s, 1H), 7.36 (m, 2H), 6.62 (dd, J = 11.0, 4.0 Hz, 1H), 6.58 (d, J = 7.6 Hz, 1H), 6.46 (brs, 1H), 5.15 (m, 1H), 4.00 (d, J = 12.0 Hz, 1H), 3.78 (dd, J = 12.0, 4.0 Hz, 1H), 3.73 (s, 3H), 3.60-3.37 (m, 4H), 2.66-2.55 (m, 4H), 1.59 (d, J = 7.1 Hz, 3H); ESI-MS: m/z = 428 $[M + H]^+$. |

TABLE 2-continued

Nuclear Magnetic and Mass Spectrometric Data of Title Compounds 5 to 44

| Serial numbers of preparation embodiments | Names and structures of title compounds | Nuclear magnetic and mass spectrometric data |
|---|---|---|
| 14a | (R)-4-(morpholin-4-yl)-3-(4-fluorophenyl)-N-((R)-1-(6-methoxypyridin-3-yl)ethyl)-4,5-dihydro-1H-pyrazol-1-carboxamide 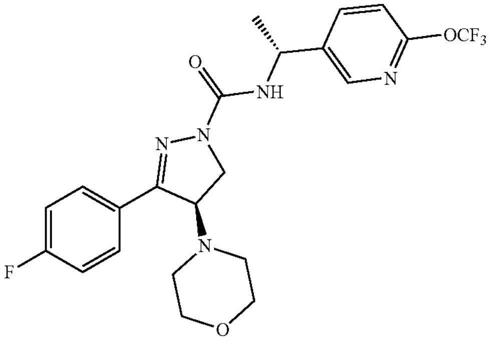 | $^1$HNMR (400 MHz, $CDCl_3$) δ 7.81-7.76 (m, 3H), 7.60 (s, 1H), 7.36 (m, 2H), 6.61 (dd, J = 11.0, 3.6 Hz, 1H), 6.58 (d, J = 7.5 Hz, 1H), 6.46 (brs, 1H), 5.14 (m, 1H), 4.01 (d, J = 12.0 Hz, 1H), 3.76 (dd, J = 11.6, 4.0 Hz, 1H), 3.80 (s, 3H), 3.59-3.35 (m, 4H), 2.67-2.56 (m, 4H), 1.61 (d, J = 7.2 Hz, 3H); ESI-MS: m/z = 428 $[M + H]^+$. |
| 15 | (S)-4-(2-(dimethylamino)-N-methylacet amido)-3-(4-methylphenyl)-N-((R)-1-(6-(trifluoromethyl)pyridin-3-yl)ethyl)-4,5-dihydro-1H-pyrazol-1-carboxamide 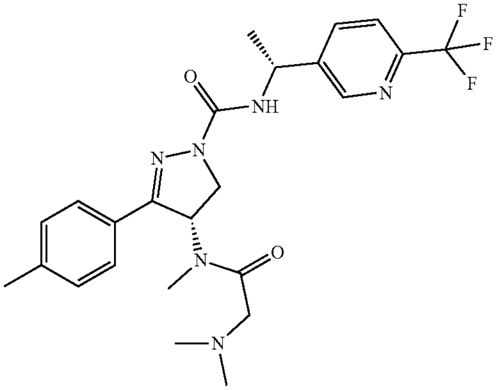 [SMILES: Cc1ccc(C2=NN(C(=O)N[C@H](C)c3ccc(C(F)(F)F)nc3)C[C@@H]2N(C)C(=O)CN(C)C)cc1] | $^1$HNMR (400 MHz, $CDCl_3$) δ 8.79(s, 1H), 7.90 (d, J = 8.0 Hz, 1H), 7.66 (d, J = 7.8 Hz, 1H), 7.61 (d, J= 8.0 Hz, 2H), 7.20 (d, J = 8.0 Hz, 2H), 6.62 (dd, J = 11.0, 4.0 Hz, 1H), 6.34 (d, J = 7.0 Hz, 1H), 5.17-5.15 (m, 1H), 4.10 (m, 1H), 3.86 (dd, J = 12.5, 4.0 Hz, 1H), 3.27 (s, 3H), 3.25 (s, 2H), 2.89 (s, 6H), 2.38 (s, 3H), 1.64 (d, J = 7.0 Hz, 3H); ESI-MS: m/z = 491 $[M + H]^+$. |
| 15a | (R)-4-(2-(dimethylamino)-N-methylacetamido)-3-(4-methylphenyl])-N-((R)-1-(6-(trifluoromethyl)pyridin-3-yl)ethyl)-4,5-dihydro-1H-pyrazol-1-carboxamide 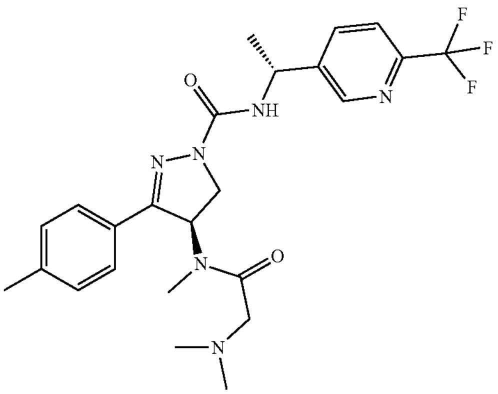 [SMILES: Cc1ccc(C2=NN(C(=O)N[C@H](C)c3ccc(C(F)(F)F)nc3)C[C@H]2N(C)C(=O)CN(C)C)cc1] | $^1$HNMR (400 MHz, $CDCl_3$) δ 8.70 (s, 1H), 7.82 (d, J = 8.0 Hz, 1H), 7.64 (d, J = 8.0 Hz, 1H), 7.60 (d, J = 8.0 Hz, 2H), 7.23 (d, J = 8.0 Hz, 2H), 6.60 (dd, J = 11.0, 3.7 Hz, 1H), 6.32 (d, J = 7.2 Hz, 1H), 5.16-5.13 (m, 1H), 4.13 (m, 1H), 3.86 (dd, J = 12.0, 3.8 Hz, 1H), 3.27 (s, 3H), 3.26 (s, 2H), 2.75 (s, 6H), 2.36 (s, 3H), 1.62 (d, J = 7.2 Hz, 3H); ESI-MS: m/z = 491 $[M + H]^+$. |

TABLE 2-continued

Nuclear Magnetic and Mass Spectrometric Data of Title Compounds 5 to 44

| Serial numbers of preparation embodiments | Names and structures of title compounds | Nuclear magnetic and mass spectrometric data |
|---|---|---|
| 16 | (S)-4-(N-methyl-N-methoxycarbonylamino)-3-(4-methoxyphenyl)-N-((R)-1-(6-(trifluoromethyl)pyridin-3-yl)ethyl)-4,5-dihydro-1H-pyrazol-1-carboxamide 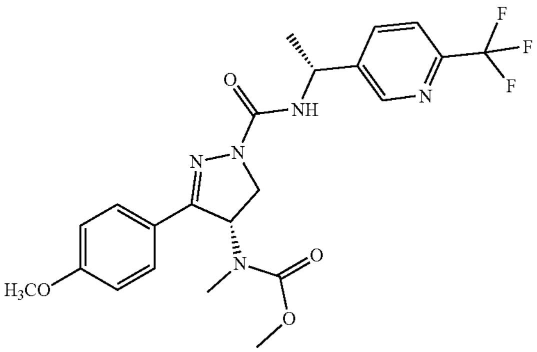 [SMILES: COC(=O)N(C)[C@H]1CN(C(=O)N[C@H](C)c2ccc(C(F)(F)F)nc2)N=C1c1ccc(OC)cc1] | $^1$HNMR (400 MHz, $CDCl_3$) δ 8.75(s, 1H), 7.91 (d, J = 7.8 Hz, 2H), 7.77 (d, J = 8.0 Hz, 1H), 7.34 (d, J = 8.0 Hz, 1H), 7.07 (d, J = 7.5 Hz, 2H), 6.60 (dd, J = 11.5, 4.0 Hz, 1H), 6.35 (d, J = 7.0 Hz, 1H), 5.17-5.15 (m, 1H), 4.0 (d, J = 12.0 Hz, 1H), 3.87 (dd, J=12.0, 4.0 Hz, 1H), 3.81 (s, 3H), 3.76 (s, 3H), 3.27 (s, 3H), 1.67 (d, J = 7.0 Hz, 3H); ESI-MS: m/z = 480 $[M + H]^+$. |
| 16a | (R)-4-(N-methyl-N-methoxycarbonylamino)-3-(4-methoxyphenyl)-N-((R)-1-(6-(trifluoromethyl)pyridin-3-yl)ethyl)-4,5-dihydro-1H-pyrazol-1-carboxamide 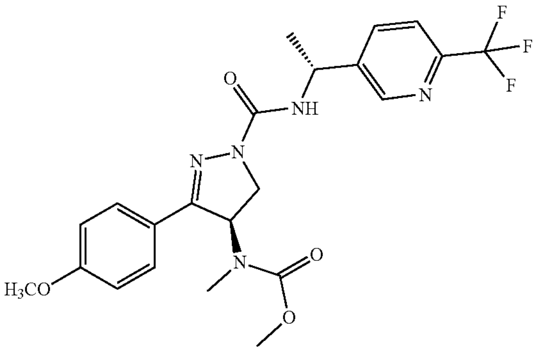 [SMILES: COC(=O)N(C)[C@@H]1CN(C(=O)N[C@H](C)c2ccc(C(F)(F)F)nc2)N=C1c1ccc(OC)cc1] | $^1$HNMR (400 MHz, $CDCl_3$) δ 8.75(s, 1H), 7.91 (d, J = 7.8 Hz, 2H), 7.76 (d, J = 8.0 Hz, 1H), 7.33 (d, J = 8.1 Hz, 1H), 7.06 (d, J = 7.5 Hz, 2H), 6.62 (dd, J = 11.0, 4.0 Hz, 1H), 6.34 (d, J = 7.0 Hz, 1H), 5.15-5.13 (m, 1H), 4.0 (d, J = 12.0 Hz, 1H), 3.90 (dd, J = 12.0, 4.0 Hz, 1H), 3.83 (s, 3H), 3.68 (s, 3H), 3.47 (s, 3H), 1.65 (d, J = 7.2 Hz, 3H); ESI-MS: m/z = 480 $[M + H]^+$. |
| 17 | (S)-4-(4-methyl-2-oxopiperazin-1-yl)-3-(4-methylphenyl)-N-((R)-1-(6-(trifluoro methyl)pyridin-3-yl)ethyl)-4,5-dihydro-1H-pyrazol-1-carboxamide 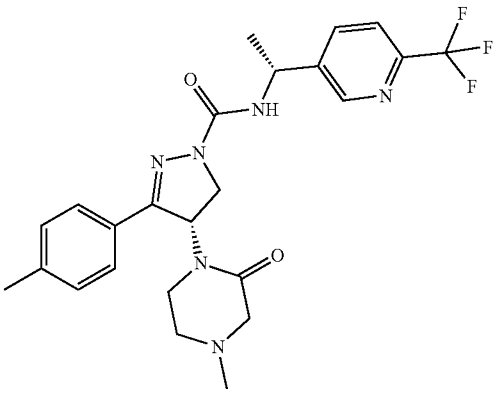 [SMILES: Cc1ccc(C2=NN(C(=O)N[C@H](C)c3ccc(C(F)(F)F)nc3)C[C@@H]2N2CCN(C)CC2=O)cc1] | $^1$HNMR (500 MHz, $CDCl_3$) δ 8.73 (s, 1H), 7.84 (d, J = 7.5 Hz, 1H), 7.64-7.60 (m, 3H), 7.22 (d, J = 7.5 Hz, 2H), 6.60 (dd, J = 11.0, 4.0 Hz, 1H), 6.34 (d, J = 7.4 Hz, 1H), 5.25-5.14 (m, 1H), 4.03-3.79 (m, 2H), 3.35 (m, 2H), 3.26 (m, 2H), 2.87 (m, 2H), 2.38 (s, 3H), 2.26 (s, 3H), 1.62 (d, J =7.0 Hz, 3H); ESI-MS: m/z = 489 $[M + H]^+$. |

TABLE 2-continued

| Nuclear Magnetic and Mass Spectrometric Data of Title Compounds 5 to 44 | | |
|---|---|---|
| Serial numbers of preparation embodiments | Names and structures of title compounds | Nuclear magnetic and mass spectrometric data |
| 17a | (R)-4-(4-methyl-2-oxopiperazin-1-yl)-3-(4-methylphenyl])-N-((R)-1-(6-(trifluoromethyl) pyridin-3-yl)ethyl)-4,5-dihydro-1H-pyrazol-1-carboxamide 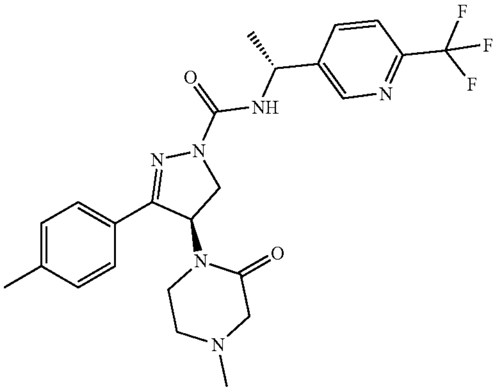 [SMILES: Cc1ccc(C2=NN(C(=O)N[C@H](C)c3ccc(C(F)(F)F)nc3)C[C@H]2N2CCN(C)CC2=O)cc1] | $^1$HNMR (400 MHz, $CDCl_3$) δ 8.70(s, 1H), 7.84 (d, J = 8.0 Hz, 1H), 7.66-7.63 (m, 3H), 7.21(d, J = 7.5 Hz, 2H), 6.59 (d, J = 11.0 Hz, 1H), 6.36 (d, J = 7.2 Hz, 1H), 5.21-5.14 (m, 1H), 4.00-3.79 (m, 2H), 3.33 (m, 2H), 3.24 (m, 2H), 2.85 (m, 2H), 2.35 (s, 3H), 2.27 (s, 3H), 1.620 (d, J = 7.2 Hz, 3H); ESI-MS: m/z = 489 $[M + H]^+$. |
| 18 | (S)-4-(3-acetyl-2-oxoimidazolidin-1-yl)-3-(4-methylphenyl])-N-((R)-1-(6-(trifluoromethyl) pyridin-3-yl)ethyl)-4,5-dihydro-1H-pyrazol-1-carboxamide 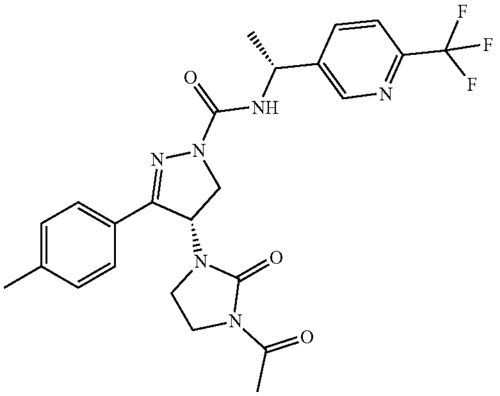 [SMILES: CC(=O)N1CCN([C@H]2CN(C(=O)N[C@H](C)c3ccc(C(F)(F)F)nc3)N=C2c2ccc(C)cc2)C1=O] | $^1$HNMR (500 MHz, $CDCl_3$) δ 8.60 (s, 1H), 7.73 (d, J = 7.5 Hz, 1H), 7.68 (d, J = 8.0 Hz, 2H), 7.29 (d, J = 7.5 Hz, 1H), 7.25 (d, J = 8.0 Hz, 2H), 6.54 (brs, 1H), 6.25 (dd, J = 11.0, 4.0 Hz, 1H), 5.16-5.08 (m, 1H), 4.02 (dd, J = 12.0, 11.0 Hz, 1H), 3.83 (dd, J = 12.0, 4.0 Hz, 1H), 3.44 (m, 4H), 2.38 (s, 3H), 2.29 (s, 3H), 1.61 (d, J = 7.0 Hz, 3H); ESI-MS: m/z = 503 $[M + H]^+$. |
| 18a | (R)-4-(3-acetyl-2-oxoimidazolidin-1-yl)-3-(4-methylphenyl])-N-((R)-1-(6-(trifluoromethyl) pyridin-3-yl)ethyl)-4,5-dihydro-1H-pyrazol-1-carboxamide 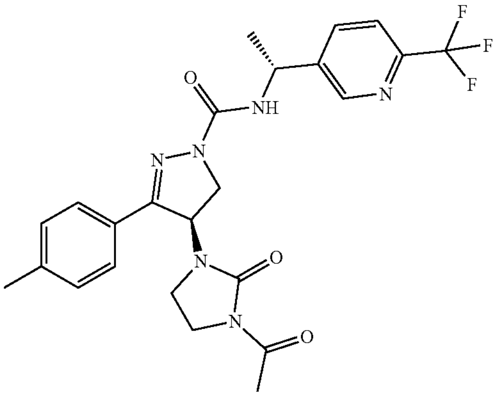 [SMILES: CC(=O)N1CCN([C@@H]2CN(C(=O)N[C@H](C)c3ccc(C(F)(F)F)nc3)N=C2c2ccc(C)cc2)C1=O] | $^1$HNMR (400 MHz, $CDCl_3$) δ 8.58 (s, 1H), 7.76 (d, J = 8.0 Hz, 1H), 7.70 (d, J = 7.8 Hz, 2H), 7.33 (d, J = 8.0 Hz, 1H), 7.28 (d, J = 7.8 Hz, 2H), 6.54 (m, 1H), 6.31 (dd, J = 11.0, 3.8 Hz, 1H), 5.14 (m, 1H), 4.01 (m, 1H), 3.84 (dd, J = 12.0, 4.0 Hz, 1H), 3.42 (m, 4H), 2.34 (s, 3H), 2.30 (s, 3H), 1.63 (d, J = 7.2 Hz, 3H); ESI-MS: m/z = 503 $[M + H]^+$. |

TABLE 2-continued

Nuclear Magnetic and Mass Spectrometric Data of Title Compounds 5 to 44

| Serial numbers of preparation embodiments | Names and structures of title compounds | Nuclear magnetic and mass spectrometric data |
|---|---|---|
| 19 | (S)-4-(4-acetylpiperazin-1-yl)-3-(4-methylphenyl)-N-((R)-1-(6-(trifluoromethyl)pyridin-3-yl)ethyl)-4,5-dihydro-1H-pyrazol-1-carboxamide 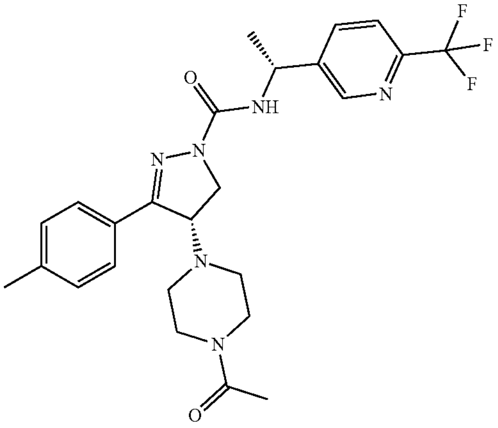 [SMILES: CC(=O)N1CCN([C@H]2CN(C(=O)N[C@H](C)c3ccc(C(F)(F)F)nc3)N=C2c2ccc(C)cc2)CC1] | $^1$HNMR (400 MHz, $CDCl_3$) δ 8.61(s, 1H), 7.77(d, J = 8.0 Hz, 1H), 7.72 (d, J = 8.0 Hz, 2H), 7.32 (d, J = 8.0 Hz, 1H), 7.26 (d, J = 8.0 Hz, 2H), 6.46 (brs, 1H), 6.35 (dd, J = 12.0, 4.0 Hz, 1H), 5.10-5.06 (m, 1H), 3.94 (dd, J = 12.5, 3.8 Hz, 1H), 3.75 (dd, J = 12.0, 4.0 Hz, 1H), 3.32 (m, 4H), 2.88 (m, 4H), 2.40 (s, 3H), 2.11 (s, 3H), 1.60 (d, J = 7.2 Hz, 3H); ESI-MS: m/z = 503 $[M + H]^+$. |
| 19a | (R)-4-(4-acetylpiperazin-1-yl)-3-(4-methylphenyl)-N-((R)-1-(6-(trifluoromethyl)pyridin-3-yl)ethyl)-4,5-dihydro-1H-pyrazol-1-carboxamide 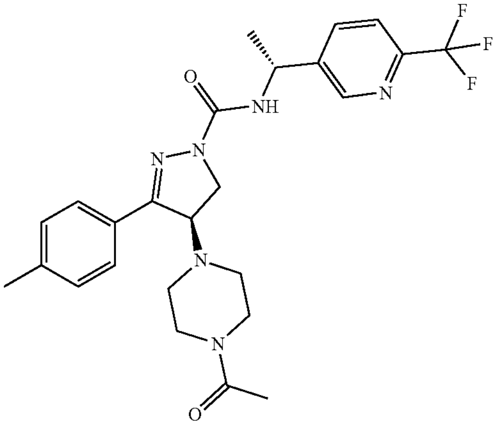 [SMILES: CC(=O)N1CCN([C@@H]2CN(C(=O)N[C@H](C)c3ccc(C(F)(F)F)nc3)N=C2c2ccc(C)cc2)CC1] | $^1$HNMR (400 MHz, $CDCl_3$) δ 8.71(s, 1H), 7.78 (d, J = 8.0 Hz, 1H), 7.68 (d, J = 7.8 Hz, 2H), 7.32 (d, J = 8.0 Hz, 1H), 7.26 (d, J = 7.8 Hz, 2H), 6.46 (brs, 1H), 6.30 (dd, J = 12.0, 4.0 Hz, 1H), 5.14 (m, 1H), 3.94 (dd, J = 12.5, 4.0 Hz, 1H), 3.75 (m, 1H), 3.34 (m, 4H), 2.86 (m, 4H), 2.35 (s, 3H), 2.21 (s, 3H), 1.64 (d, J = 7.0 Hz, 3H); ESI-MS: m/z = 503 $[M + H]^+$. |
| 20 | (S)-4-(3-oxomorpholin-4-yl)-3-(4-methylphenyl)-N-((R)-1-(4-(trifluoromethyl)phenyl)ethyl)-4,5-dihydro-1H-pyrazol-1-carboxamide 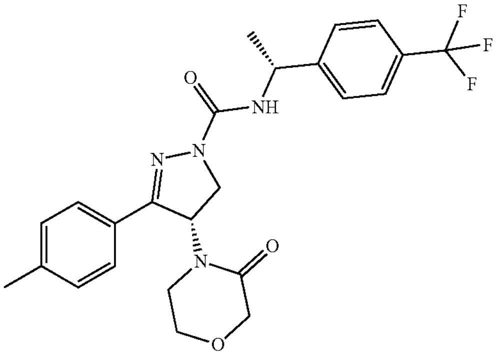 [SMILES: Cc1ccc(C2=NN(C(=O)N[C@H](C)c3ccc(C(F)(F)F)cc3)C[C@@H]2N2CCOCC2=O)cc1] | $^1$HNMR (500 MHz, $CDCl_3$) δ 7.72 (d, J = 7.5 Hz, 2H), 7.55 (d, J = 7.5 Hz, 2H), 7.27 (d, J = 7.5 Hz, 2H), 7.21 (d, J = 7.5 Hz, 2H), 6.55 (dd, J = 11.0, 4.0 Hz, 1H), 6.33 (d, J = 7.1 Hz, 1H), 5.16-5.11 (m, 1H), 4.31-4.20 (m, 2H), 4.04 (dd, J = 12.0, 11.0 Hz, 1H), 3.85 (dd, J = 12.0, 4.0 Hz, 1H), 3.81-3.74 (m, 1H), 3.69-3.57 (m, 1H), 3.25-3.09 (m, 1H), 2.95-2.84 (m, 1H), 2.40 (s, 3H), 1.63 (d, J = 7.2 Hz, 3H); ESI-MS: m/z = 475 $[M + H]^+$. |

TABLE 2-continued

| Nuclear Magnetic and Mass Spectrometric Data of Title Compounds 5 to 44 | | |
|---|---|---|
| Serial numbers of preparation embodiments | Names and structures of title compounds | Nuclear magnetic and mass spectrometric data |
| 20a | (R)-4-(3-oxomorpholin-4-yl)-3-(4-methylphenyl)-N-((R)-1-(4-(trifluoromethyl)phenyl)ethyl)-4,5-dihydro-1H-pyrazol-1-carboxamide 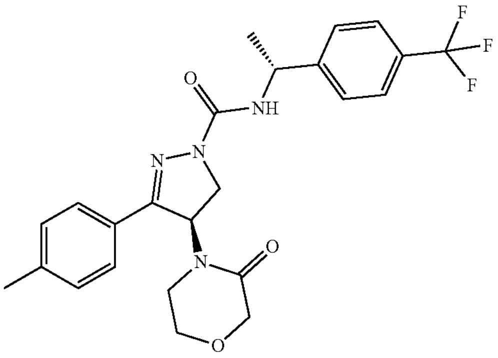 [SMILES: Cc1ccc(C2=NN(C(=O)N[C@H](C)c3ccc(C(F)(F)F)cc3)C[C@H]2N2CCOCC2=O)cc1] | $^1$HNMR (400 MHz, $CDCl_3$) δ 7.71 (d, J = 7.6 Hz, 2H), 7.57 (d, J = 7.6 Hz, 2H), 7.28 (d, J = 7.5 Hz, 2H), 7.22 (d, J = 7.5 Hz, 2H), 6.59 (dd, J = 11.0, 3.8 Hz, 1H), 6.35 (d, J = 7.2 Hz, 1H), 5.15-5.09 (m, 1H), 4.28-4.20 (m, 2H), 4.02 (m, 1H), 3.89 (dd, J = 12.0, 4.0 Hz, 1H), 3.80-3.76 (m, 1H), 3.66-3.54 (m, 1H), 3.26-3.08 (m, 1H), 2.96-2.84 (m, 1H), 2.42 (s, 3H), 1.61 (d, J = 7.0 Hz, 3H); ESI-MS: m/z = 47 5[M + H]$^+$. |
| 21 | (S)-4-(2-oxopyrrolidin-1-yl)-3-(4-methylphenyl)-N-((R)-1-(6-(trifluoromethyl)pyridin-3-yl)ethyl)-4,5-dihydro-1H-pyrazol-1-carboxamide 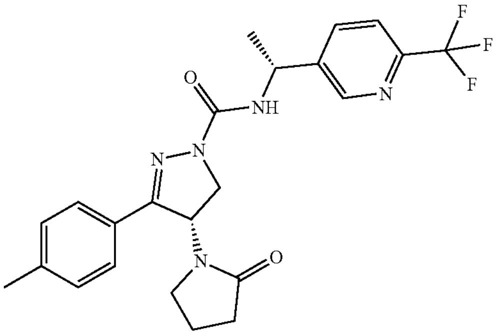 [SMILES: Cc1ccc(C2=NN(C(=O)N[C@H](C)c3ccc(C(F)(F)F)nc3)C[C@@H]2N2CCCC2=O)cc1] | $^1$HNMR (500 MHz, $CDCl_3$) δ 8.61 (s, 1H), 7.77 (d, J = 8.0 Hz, 1H), 7.70 (d, J = 8.0 Hz, 2H), 7.30 (d, J = 8.0 Hz, 1H), 7.27 (d, J = 8.0 Hz, 2H), 6.46 (brs, 1H), 6.07 (dd, J = 11.0, 4.0 Hz, 1H), 5.13 (m, 1H), 4.01 (dd, J = 12.0, 11.0 Hz, 1H), 3.86 (dd, J = 12.0, 4.0 Hz, 1H), 3.29 (m, 2H), 2.40 (s, 3H), 2.35 (m, 2H), 1.97-1.91 (m, 2H), 1.64 (d, J = 7.2 Hz, 3H); ESI-MS: m/z = 460[ M + H]$^+$. |
| 21a | (R)-4-(2-oxopyrrolidin-1-yl)-3-(4-methylphenyl)-N-((R)-1-(6-(trifluoromethyl)pyridin-3-yl)ethyl)-4,5-dihydro-1H-pyrazol-1-carboxamide 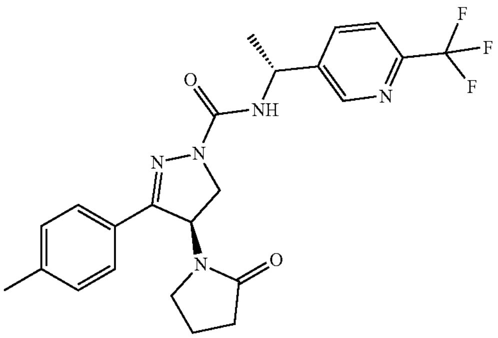 [SMILES: Cc1ccc(C2=NN(C(=O)N[C@H](C)c3ccc(C(F)(F)F)nc3)C[C@H]2N2CCCC2=O)cc1] | $^1$HNMR (500 MHz, $CDCl_3$) δ 8.64(s, 1H), 7.76 (d, J = 8.0 Hz, 1H), 7.71 (d, J = 7.8 Hz, 2H), 7.40 (d, J = 8.0 Hz, 1H), 7.25 (d, J = 7.6 Hz, 2H), 6.45 (brs, 1H), 6.10 (dd, J = 11.2, 3.5 Hz, 1H), 5.11 (m, 1H), 4.00 (dd, J = 12.2, 11.0 Hz, 1H), 3.84 (dd, J = 12.0, 4.0 Hz, 1H), 3.30 (m, 2H), 2.41 (s, 3H), 2.35-2.30 (m, 2H), 1.95-1.91 (m, 2H), 1.62 (d, J = 7.5 Hz, 3H); ESI-MS: m/z = 460 [M + H]$^+$. |

TABLE 2-continued

| Nuclear Magnetic and Mass Spectrometric Data of Title Compounds 5 to 44 | | |
|---|---|---|
| Serial numbers of preparation embodiments | Names and structures of title compounds | Nuclear magnetic and mass spectrometric data |
| 22 | (S)-4-(2-oxooxazolidin-3-yl)-3-(4-methylphenyl)-N-((R)-1-(6-(trifluoromethyl)pyridin-3-yl)ethyl)-4,5-dihydro-1H-pyrazol-1-carboxamide 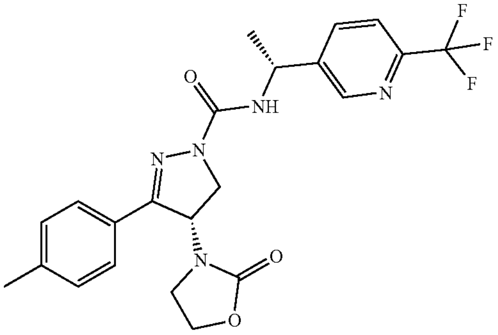 [SMILES: Cc1ccc(C2=NN(C(=O)N[C@H](C)c3ccc(C(F)(F)F)nc3)C[C@@H]2N2CCOC2=O)cc1] | $^1$HNMR (500 MHz, $CDCl_3$) δ 8.63(s, 1H), 7.75 (d, J = 8.0 Hz, 1H), 7.69 (d, J = 8.0 Hz, 2H), 7.31 (d, J = 8.0 Hz, 1H), 7.28 (d, J = 8.0 Hz, 2H), 6.44 (brs, 1H), 6.05 (dd, J = 12.0, 4.0 Hz, 1H), 5.12-5.08 (m, 1H), 4.34( m, 2H), 4.00 (dd, J = 12.5, 11.0 Hz, 1H), 3.85 (dd, J = 12.0, 4.0 Hz, 1H), 3.24 (m, 2H), 2.41 (s, 3H), 1.62 (d, J = 7.1 Hz, 3H); ESI-MS: m/z = 462 $[M + H]^+$. |
| 22a | (R)-4-(2-oxooxazolidin-3-yl)-3-(4-methylphenyl)-N-((R)-1-(6-(trifluoromethyl)pyridin-3-yl)ethyl)-4,5-dihydro-1H-pyrazol-1-carboxamide 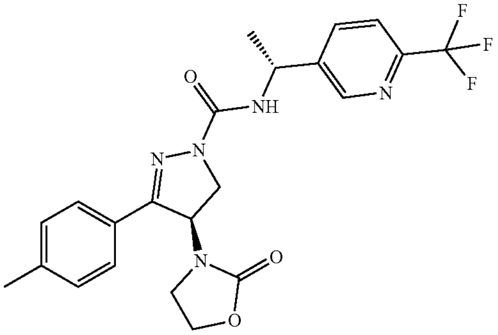 [SMILES: Cc1ccc(C2=NN(C(=O)N[C@H](C)c3ccc(C(F)(F)F)nc3)C[C@H]2N2CCOC2=O)cc1] | $^1$HNMR (400 MHz, $CDCl_3$) δ 8.60 (s, 1H), 7.76 (d, J = 8.1 Hz, 1H), 7.70 (d, J = 7.8 Hz, 2H), 7.33 (d, J = 8.0 Hz, 1H), 7.27 (d, J = 7.6 Hz, 2H), 6.54 (brs, 1H), 6.10 (dd, J = 12.2, 3.8 Hz, 1H), 5.10-5.05 (m, 1H), 4.36 (m, 2H), 3.98 (dd, J = 12.2, 11.0 Hz, 1H), 3.84 (dd, J = 12.2, 4.0 Hz, 1H), 3.23 (m, 2H), 2.42 (s, 3H), 1.60 (d, J = 7.2 Hz, 3H); ESI-MS: m/z = 462 $[M + H]^+$. |
| 23 | (S)-4-(2-oxooxazolidin-3-yl)-3-(5-methylpyridin-2-yl)-N-((R)-1-(6-(trifluoromethyl)pyridin-3-yl)ethyl)-4,5-dihydro-1H-pyrazol-1-carboxamide 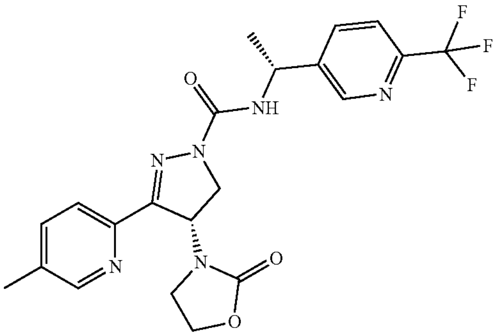 [SMILES: Cc1ccc(C2=NN(C(=O)N[C@H](C)c3ccc(C(F)(F)F)nc3)C[C@@H]2N2CCOC2=O)nc1] | $^1$HNMR (500 MHz, $CDCl_3$) δ 8.68 (s, 1H), 8.61 (s, 1H), 7.87 (d, J = 7.6 Hz,1H), 7.81 (d, J = 7.6 Hz, 1H), 7.76 (d, J = 8.0 Hz, 1H), 7.32 (d, J = 8.0 Hz, 1H), 6.47 (brs, 1H), 6.06 (dd, J = 11.5, 4.0 Hz, 1H), 5.11-5.07 (m, 1H), 4.34 (m, 2H), 4.01 (dd, J = 12.0, 11.0 Hz, 1H), 3.86 (dd, J = 12.0, 4.0 Hz, 1H), 3.22 (m, 2H), 2.16 (s, 3H), 1.61 (d, J = 7.2 Hz, 3H); ESI-MS: m/z = 463 $[M + H]^+$. |

TABLE 2-continued

| Serial numbers of preparation embodiments | Names and structures of title compounds | Nuclear magnetic and mass spectrometric data |
|---|---|---|
| | Nuclear Magnetic and Mass Spectrometric Data of Title Compounds 5 to 44 | |
| 23a | (R)-4-(2-oxooxazolidin-3-yl)-3-(5-methylpyridin-2-yl)-N-((R)-1-(6-(trifluoromethyl)pyridin-3-yl)ethyl)-4,5-dihydro-1H-pyrazol-1-carboxamide 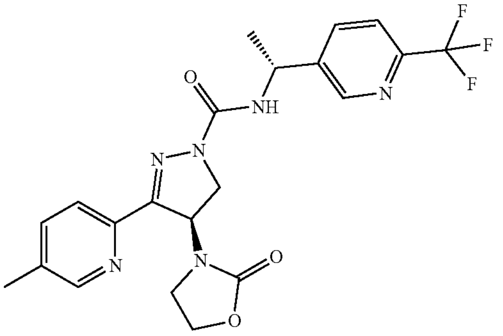 [SMILES: Cc1ccc(C2=NN(C(=O)N[C@H](C)c3ccc(C(F)(F)F)nc3)C[C@H]2N2CCOC2=O)nc1] | $^1$HNMR (400 MHz, $CDCl_3$) δ 8.64 (s, 1H), 8.60 (s, 1H), 7.88 (d, J = 8.0 Hz,1H), 7.82 (d, J = 8.0 Hz, 1H), 7.75 (d, J = 8.0 Hz, 1H), 7.34 (d, J = 8.0 Hz, 1H), 6.50 (brs, 1H), 6.04 (dd, J = 11.2, 3.8 Hz, 1H), 5.13-5.09 (m, 1H), 4.34 (m, 2H), 4.01 (dd, J = 12.0, 11.0 Hz, 1H), 3.86 (dd, J = 11.6, 4.0 Hz, 1H), 3.23 (m, 2H), 2.20 (s, 3H), 1.63 (d, J = 7.5 Hz, 3H); ESI-MS: m/z = 463 $[M + H]^+$. |
| 24 | (S)-4-(3-oxomorpholin-4-yl)-3-(4-fluorophenyl)-N-((R)-1-(2-(6-(trifluoromethyl)pyridin-3-yl)ethyl)-4,5-dihydro-1H-pyrazol-1-carboxamide 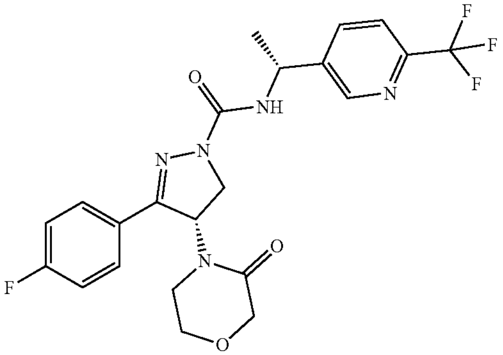 [SMILES: C[C@@H](NC(=O)N1C[C@H](N2CCOCC2=O)C(c2ccc(F)cc2)=N1)c1ccc(C(F)(F)F)nc1] | $^1$HNMR (500 MHz, $CDCl_3$) δ 8.76 (s, 1H), 7.79-7.76 (m, 3H), 7.36 (m, 2H), 7.30 (d, J = 7.8 Hz, 1H), 6.60 (dd, J = 11, 4.0 Hz, 1H), 6.48 (brs, 1H), 5.12 (m, 1H), 4.22 (m, 2H), 4.05-3.96 (m, 2H), 3.86-3.75 (m, 1H), 3.70 (m, 1H), 3.25-2.92 (m, 2H), 1.70 (d, J = 7.1 Hz, 3H); ESI-MS: m/z = 480 $[M + H]^+$. |
| 24a | (R)-4-(3-oxomorpholin-4-yl)-3-(4-fluorophenyl)-N-((R)-1-(2-(6-(trifluoromethyl)pyridin-3-yl)ethyl)-4,5-dihydro-1H-pyrazol-1-carboxamide 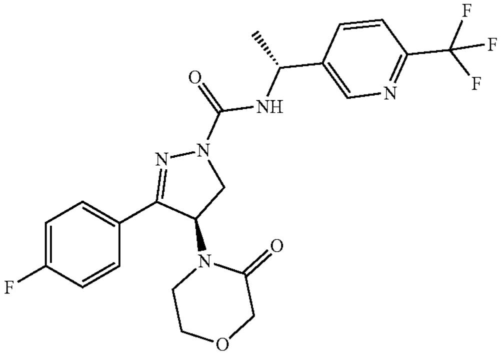 [SMILES: C[C@@H](NC(=O)N1C[C@@H](N2CCOCC2=O)C(c2ccc(F)cc2)=N1)c1ccc(C(F)(F)F)nc1] | $^1$HNMR (400 MHz, $CDCl_3$) δ 8.74 (s, 1H), 7.81-7.78 (m, 3H), 7.36 (m, 2H), 7.31 (d, J = 8.0 Hz, 1H), 6.61 (dd, J = 11, 3.8 Hz, 1H), 6.50 (brs, 1H), 5.14 (m, 1H), 4.26 (m, 2H), 4.02-3.95 (m, 2H), 3.85-3.75 (m, 1H), 3.70 (m, 1H), 3.25-2.92 (m, 2H), 1.62 (d, J = 7.2 Hz, 3H); ESI-MS: m/z = 480 $[M + H]^+$. |

TABLE 2-continued

| Nuclear Magnetic and Mass Spectrometric Data of Title Compounds 5 to 44 | | |
|---|---|---|
| Serial numbers of preparation embodiments | Names and structures of title compounds | Nuclear magnetic and mass spectrometric data |
| 25 | (S)-4-(N-methylacetamido)-3-(4-methylphenyl)-N-((R)-1-(6-(trifluoromethyl)pyridin-3-yl)ethyl)-4,5-dihydro-1H-pyrazol-1-carboxamide 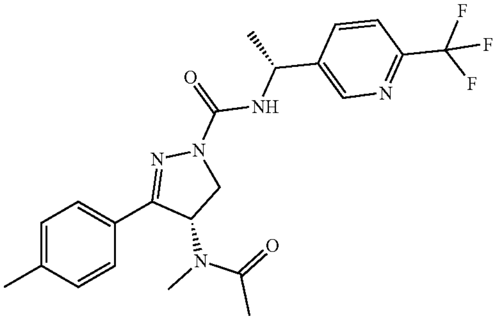 [SMILES: CC(=O)N(C)[C@H]1CN(C(=O)N[C@H](C)c2ccc(C(F)(F)F)nc2)N=C1c1ccc(C)cc1] | $^1$HNMR (400 MHz, $CDCl_3$) δ 8.75 (d, J = 1.6 Hz, 1H), 7.86 (dd, J = 8.1, 1.8 Hz, 1H), 7.72 (d, J = 7.8 Hz, 2H), 7.63 (dd, J = 11.7, 8.2 Hz, 1H), 7.21 (d, J = 8.0 Hz, 2H), 6.61 (dd, J = 11.4, 4.3 Hz, 1H), 6.34 (d, J = 7.4 Hz, 1H), 5.20-5.11 (m, 1H), 4.02 (dd, J = 12.7, 11.5 Hz, 1H), 3.87 (dd, J = 12.8, 4.4 Hz, 1H), 3.43 (s, 3H), 2.39 (s, 3H), 2.08 (s, 3H), 1.64 (d, J = 7.1 Hz, 3H); ESI-MS: m/z = 448 [M + H]$^+$. |
| 25a | (R)-4-(N-methylacetamido)-3-(4-methylphenyl)-N-((R)-1-(6-(trifluoromethyl)pyridin-3-yl)ethyl)-4,5-dihydro-1H-pyrazol-1-carboxamide 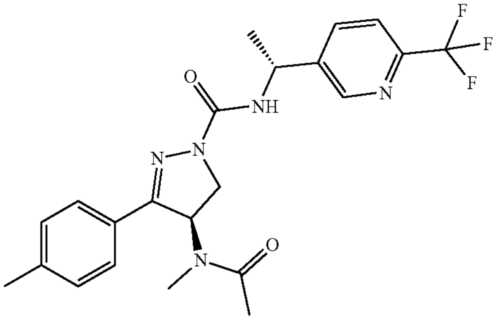 | $^1$HNMR (400 MHz, $CDCl_3$) δ 8.70 (d, J = 1.4 Hz, 1H), 7.84 (dd, J = 8.0, 1.6 Hz, 1H), 7.71 (d, J = 7.8 Hz, 2H), 7.63 (dd, J = 12.0, 8.2 Hz, 1H), 7.22 (d, J = 7.8 Hz, 2H), 6.61 (dd, J = 11.2, 4.0 Hz, 1H), 6.36 (d, J = 7.2 Hz, 1H), 5.18-5.10 (m, 1H), 4.01 (d, J = 12.2 Hz, 1H), 3.85 (dd, J = 12.5, 4.2 Hz, 1H), 3.45 (s, 3H), 2.41 (s, 3H), 2.10 (s, 3H), 1.62 (d, J = 7.2 Hz, 3H); ESI-MS: m/z = 448 [M + H]$^+$. |
| 26 | (S)-4-(3-oxomorpholin-4-yl)-3-(4-methylphenyl)-N-((R)-1-(5-(trifluoromethyl)pyrazin)-2-yl)ethyl)-4,5-dihydro-1H-pyrazol-1-carboxamide 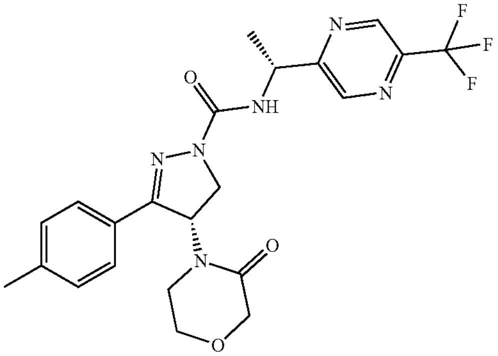 [SMILES: Cc1ccc(C2=NN(C(=O)N[C@H](C)c3cnc(C(F)(F)F)cn3)C[C@@H]2N2CCOCC2=O)cc1] | $^1$HNMR (500 MHz, $CDCl_3$) δ 8.78 (s, 2H), 7.65 (d, J = 8.0 Hz, 2H), 7.26 (d, J = 8.0 Hz, 2H), 6.66 (dd, J = 11.0, 4.0 Hz, 1H), 6.46 (d, J = 7.0 Hz, 1H), 5.15-5.03 (m, 1H), 4.26-4.09 (m, 2H), 4.02 (dd, J = 12.0, 11.0 Hz, 1H), 3.86 (dd, J = 12.0, 4.0 Hz, 1H), 3.83-3.79 (m, 1H), 3.68-3.59 (m, 1H), 3.21-3.09 (m, 1H), 2.94-2.86 (m, 1H), 2.38 (s, 3H), 1.69 (d, J = 7.2 Hz, 3H); ESI-MS: m/z = 477 [M + H]$^+$. |

TABLE 2-continued

Nuclear Magnetic and Mass Spectrometric Data of Title Compounds 5 to 44

| Serial numbers of preparation embodiments | Names and structures of title compounds | Nuclear magnetic and mass spectrometric data |
|---|---|---|
| 26a | (R)-4-(3-oxomorpholin-4-yl)-3-(4-meth ylphenyl)-N-((R)-1-(5-(trifluoromethyl) pyrazin)-2-yl)ethyl)-4,5-dihydro-1H-pyr azol-1-carboxamide 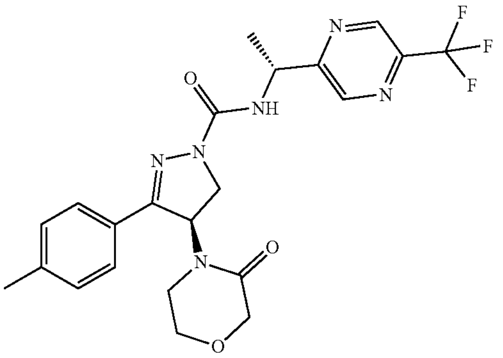 [SMILES: Cc1ccc(C2=NN(C(=O)N[C@H](C)c3cnc(C(F)(F)F)cn3)C[C@H]2N2CCOCC2=O)cc1] | $^1$HNMR (400 MHz, $CDCl_3$) δ 8.76 (s, 2H), 7.70 (d, J = 7.6 Hz, 2H), 7.28 (d, J = 7.8 Hz, 2H), 6.64 (dd, J = 11.2, 4.0 Hz, 1H), 6.44 (d, J = 7.2 Hz, 1H), 5.14-5.01 (m, 1H), 4.24-4.07 (m, 2H), 3.98 (m, 1H), 3.84 (dd, J = 12.0, 3.8 Hz, 1H), 3.82-3.77 (m, 1H), 3.65-3.52 (m, 1H), 3.22-3.07 (m, 1H), 2.98-2.89 (m, 1H), 2.38 (s, 3H), 1.65 (d, J = 7.6 Hz, 3H); ESI-MS: m/z = 477 $[M + H]^+$. |
| 27 | (S)-4-(2-oxooxazolidin-3-yl)-3-(4-methylphenyl)-N-((R)-1-(5-methylpyrazin-2-yl)ethyl)-4,5-dihydro-1H-pyrazol-1-carboxamide 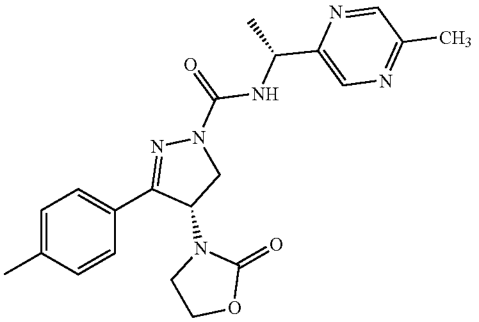 | $^1$HNMR (500 MHz, $CDCl_3$) δ 8.74 (s, 2H), 7.62 (d, J = 7.5 Hz, 2H), 7.21 (d, J = 7.5 Hz, 2H), 6.56 (dd, J = 11.0, 3.8 Hz, 1H), 6.38 (brs, 1H), 5.10-4.95 (m, 1H), 4.36-4.25 (m, 2H), 4.01 (d, J = 12.0 Hz, 1H), 3.84 (dd, J = 12.0, 3.8 Hz, 1H), 3.26-3.15 (m, 2H), 2.42 (s, 3H), 2.37 (s, 3H), 1.62 (d, J = 7.1 Hz, 3H); ESI-MS: m/z = 409 $[M + H]^+$. |
| 27a | (R)-4-(2-oxooxazolidin-3-yl)-3-(4-methylphenyl)-N-((R)-1-(5-methylpyrazin-2-yl)ethyl)-4,5-dihydro-1H-pyrazol-1-carboxamide 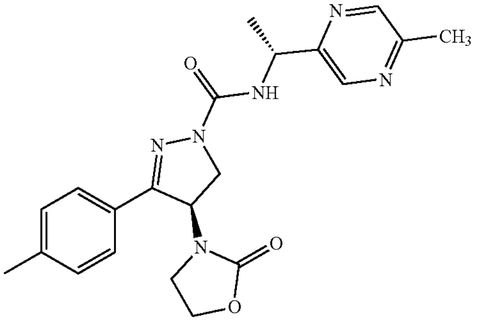 | $^1$HNMR (400 MHz, $CDCl_3$) δ 8.59 (s, 2H), 7.72 (d, J = 7.8 Hz, 2H), 7.24 (d, J = 7.8 Hz, 2H), 6.56 (dd, J = 11.0, 4.0 Hz, 1H), 6.33 (d, J = 7.2 Hz, 1H), 5.13 (m, 1H), 4.32-4.24 (m, 2H), 4.01 (dd, J = 12.0, 3.7 Hz, 1H), 3.80 (m, 1H), 3.23-3.12 (m, 2H), 2.39 (s, 3H), 2.36 (s, 3H), 1.64 (d, J = 7.0 Hz, 3H); ESI-MS: m/z = 409 $[M + H]^+$. |

TABLE 2-continued

Nuclear Magnetic and Mass Spectrometric Data of Title Compounds 5 to 44

| Serial numbers of preparation embodiments | Names and structures of title compounds | Nuclear magnetic and mass spectrometric data |
|---|---|---|
| 28 | (S)-4-(2-oxopyrrolidin-1-yl)-3-(4-fluorophenyl)-N-((R)-1-(5-methylpyrazin-2-y])ethyl)-4,5-dihydro-1H-pyrazol-1-carboxamide 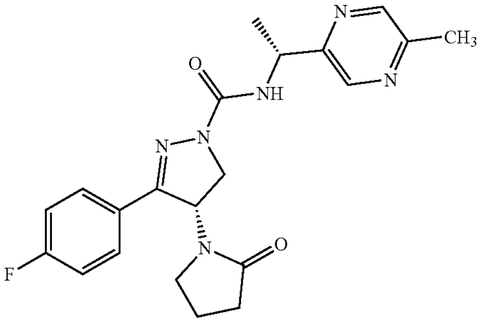 [SMILES: Cc1cnc([C@@H](C)NC(=O)N2C[C@H](N3CCCC3=O)C(c3ccc(F)cc3)=N2)cn1] | $^1$HNMR (400 MHz, $CDCl_3$) δ 8.78 (s, 1H), 8.70 (s, 1H), 7.76 (dd, J = 7.8, 5.0 Hz, 2H), 7.27 (m, 2H), 6.58 (dd, J = 11.0, 4.0 Hz, 1H), 6.43 (brs, 1H), 5.15 (m, 1H), 4.01 (d, J = 12.0 Hz, 1H), 3.96 (dd, J = 12.0, 3.8 Hz, 1H), 3.22-3.13 (m, 1H), 3.03-2.87 (m, 1H), 2.53 (s, 3H), 2.36-2.25 (m, 1H), 1.98-1.910 (m, 1H), 1.90-1.75 (m, 2H), 1.64 (d, J = 7.2 Hz, 3H); ESI-MS: m/z = 411 $[M + H]^+$. |
| 28a | (R)-4-(2-oxopyrrolidin-1-yl)-3-(4-fluorophenyl)-N-((R)-1-(5-methylpyrazin-2-y])ethyl)-4,5-dihydro-1H-pyrazol-1-carboxamide 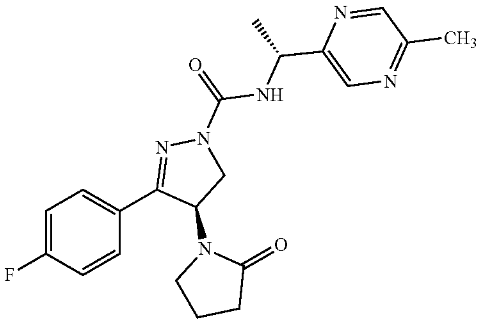 [SMILES: Cc1cnc([C@@H](C)NC(=O)N2C[C@@H](N3CCCC3=O)C(c3ccc(F)cc3)=N2)cn1] | $^1$HNMR (400 MHz, $CDCl_3$) δ 8.76 (s, 1H), 8.71 (s, 1H), 7.81 (dd, J = 7.8, 5.0 Hz, 2H), 7.35 (m, 2H), 6.60 (dd, J = 11.2, 4.0 Hz, 1H), 6.35 (brs, 1H), 5.13 (m, 1H), 4.00 (d, J = 12.0 Hz, 1H), 3.94 (dd, J = 12.0, 4.0 Hz, 1H), 3.29 (m, 1H), 2.87 (m, 1H), 2.53 (s, 3H), 2.36 (m, 1H), 1.98 (m, 1H), 1.86 (m, 2H),1.61 (d, J = 7.0 Hz, 3H); ESI-MS: m/z = 411 $[M + H]^+$. |
| 29 | (S)-4-(2-oxooxazolidin-3-yl)-3-(4-chlorophenyl)-N-((R)-1-(6-(methoxy)pyridazin-3-yl)ethyl)-4,5-dihydro-1H-pyrazol-1-carboxamide 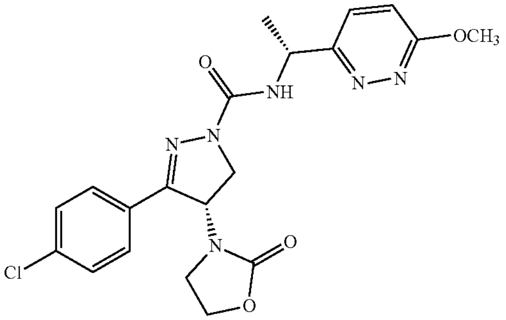 [SMILES: COc1ccc([C@@H](C)NC(=O)N2C[C@H](N3CCOC3=O)C(c3ccc(Cl)cc3)=N2)nn1] | $^1$HNMR (500 MHz, $CDCl_3$) δ 7.89 (d, J = 7.5 Hz, 2H), 7.62 (d, J = 7.5 Hz, 2H), 6.95 (d, J = 7.5 Hz, 1H), 6.87 (d, J = 7.5 Hz, 1H), 6.36 (d, J = 7.1 Hz, 1H), 6.08 (dd, J = 11.0, 3.8 Hz, 1H), 5.15-5.12 (m, 1H), 4.37-4.25 (m, 2H), 3.99 (dd, J = 12.0, 11.0 Hz, 1H), 3.86 (s, 3H), 3.81 (dd, J = 12.0, 4.0 Hz, 1H), 3.24-3.13 (m, 2H), 1.62 (d, J = 7.1 Hz, 3H); ESI-MS: m/z = 445 $[M + H]^+$. |

TABLE 2-continued

Nuclear Magnetic and Mass Spectrometric Data of Title Compounds 5 to 44

| Serial numbers of preparation embodiments | Names and structures of title compounds | Nuclear magnetic and mass spectrometric data |
|---|---|---|
| 29a | (R)-4-(2-oxooxazolidin-3-yl)-3-(4-chlorophenyl)-N-((R)-1-(6-(methoxy)pyridazin-3-yl)ethyl)-4,5-dihydro-1H-pyrazol-1-carboxamide 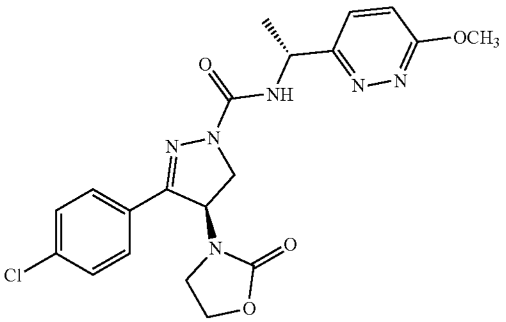 [SMILES: COc1ccc([C@@H](C)NC(=O)N2C[C@@H](N3CCOC3=O)C(c3ccc(Cl)cc3)=N2)nn1] | $^1$HNMR (400 MHz, $CDCl_3$) δ 7.96 (d, J = 7.8 Hz, 2H), 7.58 (d, J = 7.8 Hz, 2H), 6.93 (d, J = 8.0 Hz, 1H), 6.86 (d, J = 7.8 Hz, 1H), 6.56 (dd, J = 11.2, 4.0 Hz, 1H 6.29 (brs, 1H), 5.14 (m, 1H), 4.27-4.16 (m, 2H), 3.96 (dd, J = 12.0, 4.0 Hz, 1H), 3.88 (s, 3H), 3.81 (m, 1H), 3.23-3.11 (m, 2H), 1.60 (d, J = 7.0 Hz, 3H); ESI-MS: m/z = 445 $[M + H]^+$. |
| 30 | (S)-4-(3-oxomorpholin-4-yl)-3-(4-methylphenyl)-N-((R)-1-(6-(trifluoromethyl)pyridazin-3-yl)ethyl)-4,5-dihydro-1H-pyrazol-1-carboxamide 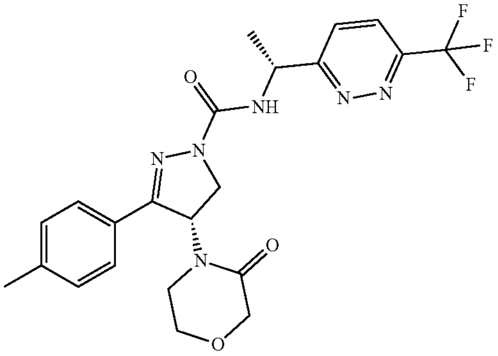 [SMILES: Cc1ccc(C2=NN(C(=O)N[C@H](C)c3ccc(C(F)(F)F)nn3)C[C@@H]2N2CCOCC2=O)cc1] | $^1$HNMR (400 MHz, $CDCl_3$) δ 7.76 (d, J = 8.0 Hz, 2H), 7.29 (d, J = 8.0 Hz, 2H), 6.88 (d, J = 7.6 Hz, 1H), 6.80 (d, J = 7.6 Hz, 1H), 6.63 (dd, J = 11.0, 3.8 Hz, 1H), 6.35 (d, J = 7.0 Hz, 1H), 5.17-5.14 (m, 1H), 4.26-4.15 (m, 2H), 4.08 (dd, J = 12.0, 11.0 Hz, 1H), 3.83 (dd, J = 12.0, 4.0 Hz, 1H), 3.80-3.72 (m, 1H), 3.67-3.58 (m, 1H), 3.21-3.09 (m, 1H), 2.94-2.86 (m, 1H), 2.39 (s, 3H), 1.65 (d, J = 7.1 Hz, 3H); ESI-MS: m/z = 477 $[M + H]^+$. |
| 30a | (R)-4-(3-oxomorpholin-4-yl)-3-(4-methylphenyl)-N-((R)-1-(6-(trifluoromethyl)pyridazin-3-yl)ethyl)-4,5-dihydro-1H-pyrazol-1-carboxamide 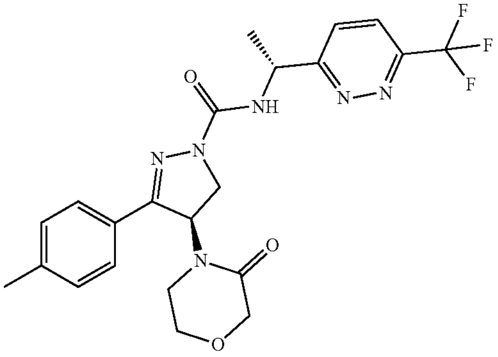 [SMILES: Cc1ccc(C2=NN(C(=O)N[C@H](C)c3ccc(C(F)(F)F)nn3)C[C@H]2N2CCOCC2=O)cc1] | $^1$HNMR (400 MHz, $CDCl_3$) δ 7.71 (d, J = 7.8 Hz, 2H), 7.27 (d, J = 7.8 Hz, 2H), 6.86 (d, J = 8.0 Hz, 1H), 6.83 (d, J = 8.0 Hz, 1H), 6.61 (dd, J = 11.0, 4.0 Hz, 1H), 6.33 (brs, 1H), 5.15 (m, 1H), 4.27-4.13 (m, 2H), 4.05 (m, 1H), 3.82 (dd, J = 12.0, 3.8 Hz, 1H), 3.76 (m, 1H), 3.60 (m, 1H), 3.20 (m, 1H), 2.90 (m, 1H), 2.35 (s, 3H), 1.62 (d, J = 7.2 Hz, 3H); ESI-MS: m/z = 477 $[M + H]^+$. |

TABLE 2-continued

Nuclear Magnetic and Mass Spectrometric Data of Title Compounds 5 to 44

| Serial numbers of preparation embodiments | Names and structures of title compounds | Nuclear magnetic and mass spectrometric data |
|---|---|---|
| 31 | (S)-4-(2-oxooxazolidin-3-yl)-3-(4-methylphenyl)-N-((R)-1-(6-chloropyridazin-3-yl)ethyl)-4,5-dihydro-1H-pyrazol-1-carboxamide 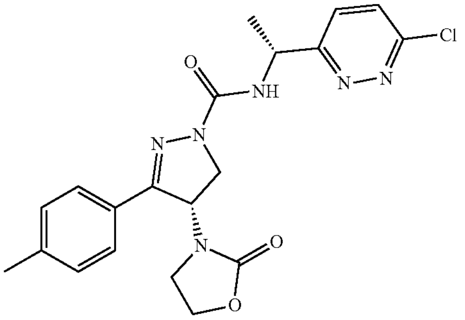 [SMILES: Cc1ccc(C2=NN(C(=O)N[C@H](C)c3ccc(Cl)nn3)C[C@@H]2N2CCOC2=O)cc1] | $^1$HNMR (400 MHz, $CDCl_3$) δ 7.72 (d, J = 7.5 Hz, 2H), 7.28 (d, J = 7.5 Hz, 2H), 7.19 (d, J = 7.6 Hz, 1H), 7.01 (d, J = 7.6 Hz, 1H), 6.38 (d, J = 7.2 Hz, 1H), 6.12 (dd, J = 11.0, 4.0 Hz, 1H), 5.16-5.13 (m, 1H), 4.38-4.27 (m, 2H), 3.97 (dd, J = 12.0, 11.0 Hz, 1H), 3.88 (dd, J = 12.0, 3.8 Hz, 1H), 3.25-3.15 (m, 2H), 2.38 (s, 3H), 1.60 (d, J = 7.0 Hz, 3H); ESI-MS: m/z = 429 $[M + H]^+$. |
| 31a | (R)-4-(2-oxooxazolidin-3-yl)-3-(4-methylphenyl)-N-((R)-1-(6-chloropyridazin-3-yl)ethyl)-4,5-dihydro-1H-pyrazol-1-carboxamide 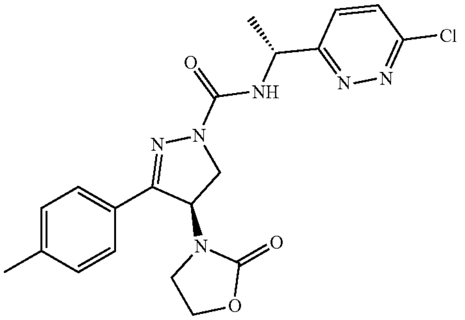 [SMILES: Cc1ccc(C2=NN(C(=O)N[C@H](C)c3ccc(Cl)nn3)C[C@H]2N2CCOC2=O)cc1] | $^1$HNMR (400 MHz, $CDCl_3$) δ 7.75 (d, J = 7.8 Hz, 2H), 7.30 (d, J = 7.8 Hz, 2H), 7.21 (d, J = 8.0 Hz, 1H), 7.04 (d, J = 8.0 Hz, 1H), 6.45 (brs, 1H), 6.32 (dd, J = 11.2, 3.8 Hz, 1H), 5.15 (m, 1H), 4.34-4.25 (m, 2H), 4.00 (dd, J = 11.6, 11.0 Hz, 1H), 3.88 (m, 1H), 3.24-3.12 (m, 2H), 2.35 (s, 3H), 1.62 (d, J = 7.2 Hz, 3H); ESI-MS: m/z = 429 $[M + H]^+$. |
| 32 | (S)-4-(2-oxopyrrolidin-1-yl)-3-(4-methylphenyl)-N-((R)-1-(2-(trifluoromethyl)pyrimidin-5-yl)ethyl)-4,5-dihydro-1H-pyrazol-1-carboxamide 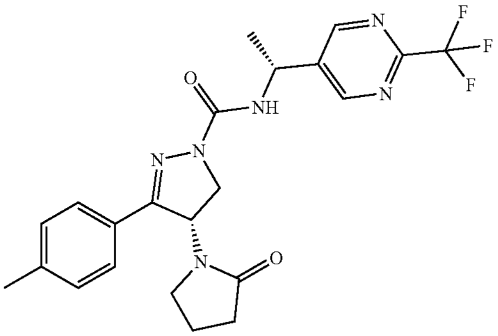 [SMILES: Cc1ccc(C2=NN(C(=O)N[C@H](C)c3cnc(C(F)(F)F)nc3)C[C@@H]2N2CCCC2=O)cc1] | $^1$HNMR (400 MHz, $CDCl_3$) δ 8.94 (s, 2H), 7.62 (d, J = 8.2 Hz, 2H), 7.21 (d, J = 8.0 Hz, 2H), 6.56 (dd, J = 11.23.7 Hz, 1H), 6.37 (d, J = 7.0 Hz, 1H), 5.15-5.06 (m, 1H), 4.00 (dd, J = 12.6, 4.0 Hz, 1H), 3.87 (dd, J = 12.6, 3.8 Hz, 1H), 3.23-2.89 (m, 2H), 2.37 (s, 3H), 2.29 (m, 1H), 1.98-1.91 (m, 1H), 1.90-1.78 (m, 2H), 1.66 (d, J = 7.1 Hz, 3H); ESI-MS: m/z = 461 $[M + H]^+$. |

TABLE 2-continued

| Nuclear Magnetic and Mass Spectrometric Data of Title Compounds 5 to 44 | | |
|---|---|---|
| Serial numbers of preparation embodiments | Names and structures of title compounds | Nuclear magnetic and mass spectrometric data |
| 32a | (R)-4-(2-oxopyrrolidin-1-yl)-3-(4-methylphenyl)-N-((R)-1-(2-(trifluoromethyl)pyrimidin-5-yl)ethyl)-4,5-dihydro-1H-pyrazol-1-carboxamide 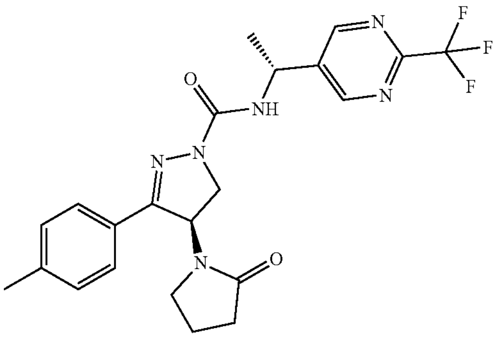 | $^1$HNMR (400 MHz, $CDCl_3$) δ 8.87 (s, 2H), 7.68 (d, J = 8.0 Hz, 2H), 7.25 (d, J = 7.8 Hz, 2H), 6.60 (d, J = 6.8 Hz, 1H), 6.36 (brs, 1H), 5.12 (m, 1H), 4.03 (dd, J = 12.1, 3.8 Hz, 1H), 3.85(dd, J = 12.0, 4.0 Hz, 1H), 3.29-2.95 (m, 2H), 2.40 (s, 3H), 2.30 (m, 1H), 2.00 (m, 1H), 1.92-1.80 (m, 2H), 1.63 (d, J = 7.2 Hz, 3H); ESI-MS: m/z =461 $[M + H]^+$. |
| 33 | (S)-4-(3-oxomorpholin-4-yl)-3-(4-fluorophenyl)-N-((R)-1-(2-(trifluoromethyl)pyrimidin-5-yl)ethyl)-4,5-dihydro-1H-pyrazol-1-carboxamide 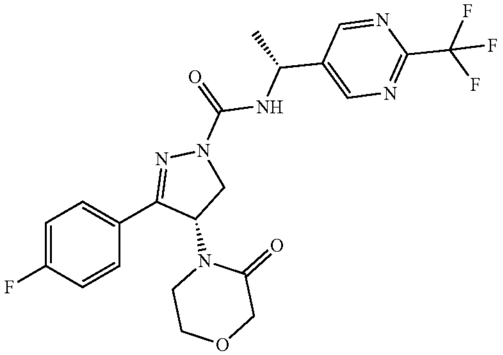 [SMILES: C[C@@H](NC(=O)N1C[C@H](N2CCOCC2=O)C(c2ccc(F)cc2)=N1)c1cnc(C(F)(F)F)nc1] | $^1$HNMR (500 MHz, $CDCl_3$) δ 8.90 (s, 2H), 7.78-7.71 (m, 2H), 7.12 (t, J = 8.6 Hz, 2H), 6.62 (dd, J = 11.0, 4.2 Hz, 1H), 6.32 (d, J = 7.0 Hz, 1H), 5.15 (t, J = 7.1 Hz, 1H), 4.20 (m, 2H), 4.05 (dd, J = 13.0, 11.0 Hz, 1H), 3.99 (dd, J = 13.1, 4.2 Hz, 1H), 3.86-3.77 (m, 1H), 3.69 (m, 1H), 3.25 (m, 1H), 2.92 (m, 1H), 1.69 (d, J = 7.1 Hz, 3H); ESI-MS: m/z = 481 $[M + H]^+$. |
| 33a | (R)-4-(3-oxomorpholin-4-yl)-3-(4-fluorophenyl)-N-((R)-1-(2-(trifluoromethyl)pyrimidin-5-yl)ethyl)-4,5-dihydro-1H-pyrazol-1-carboxamide 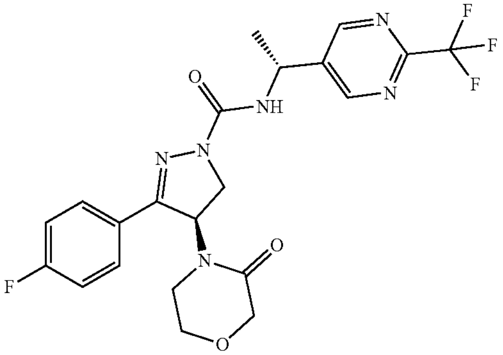 [SMILES: C[C@@H](NC(=O)N1C[C@@H](N2CCOCC2=O)C(c2ccc(F)cc2)=N1)c1cnc(C(F)(F)F)nc1] | $^1$HNMR (400 MHz, $CDCl_3$) δ 8.86 (s, 2H), 7.80-7.73 (m, 2H), 7.12 (m,2H), 6.59(dd, J = 11.0, 4.0Hz, 1H), 6.32 (brs, 1H), 5.13 (m, 1H), 4.23-4.12 (m, 2H), 4.05 (t, J = 13.0 Hz, 1H), 3.96 (dd, J = 12.1, 4.0 Hz, 1H), 3.84 (m, 1H), 3.65 (m, 1H), 3.23 (m, 1H), 2.94 (m, 1H), 1.64 (d, J = 7.0 Hz, 3H); ESI-MS: m/z = 481 $[M + H]^+$. |

TABLE 2-continued

| Nuclear Magnetic and Mass Spectrometric Data of Title Compounds 5 to 44 | | |
|---|---|---|
| Serial numbers of preparation embodiments | Names and structures of title compounds | Nuclear magnetic and mass spectrometric data |
| 34 | (S)-4-(N-methylacetamido)-3-(4-methyl phenyl)-N-((R)-1-(2-(trifluoromethyl)pyrimidin-5-yl)ethyl)-4,5-dihydro-1H-pyrazol-1-carboxamide 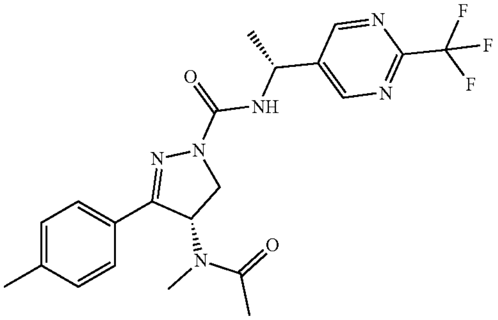 [SMILES: CC(=O)N(C)[C@H]1CN(C(=O)N[C@H](C)c2cnc(C(F)(F)F)nc2)N=C1c1ccc(C)cc1] | $^1$HNMR (500 MHz, $CDCl_3$) δ 8.90 (s, 2H), 7.61 (d, J = 8.2 Hz, 2H), 7.20 (d, J = 8.0 Hz, 2H), 6.61 (dd, J = 11.3, 4.1 Hz, 1H), 6.37 (d, J = 6.9 Hz, 1H), 5.15 (t, J = 7.0 Hz, 1H), 4.01 (dd, J = 12.5, 11.5 Hz, 1H), 3.85 (dd, J = 12.8, 4.4 Hz, 1H), 2.70 (s, 3H), 2.38 (d, J = 4.5 Hz, 3H), 2.07 (d, J = 3.1 Hz, 3H), 1.68 (d, J = 7.1 Hz, 3H); ESI-MS: m/z = 449 $[M + H]^+$. |
| 34a | (R)-4-(N-methylacetamido)-3-(4-methylphenyl)-N-((R)-1-(2-(trifluoromethyl)pyrimidin-5-yl)ethyl)-4,5-dihydro-1H-pyrazol-1-carboxamide 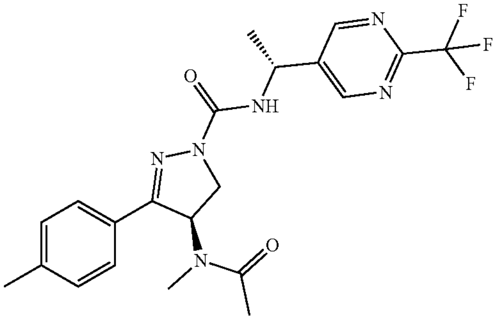 [SMILES: CC(=O)N(C)[C@@H]1CN(C(=O)N[C@H](C)c2cnc(C(F)(F)F)nc2)N=C1c1ccc(C)cc1] | $^1$HNMR (400 MHz, $CDCl_3$) δ 8.85 (s, 2H), 7.68 (d, J = 7.8 Hz, 2H), 7.25 (d, J = 7.8 Hz, 2H), 6.01 (dd, J = 11.0, 4.0 Hz, 1H), 6.41 (d, J = 7.2 Hz, 1H), 5.15 (m, 1H), 4.03 (dd, J = 12.2, 11.0 Hz, 1H), 3.90 (m, 1H), 3.25 (s, 3H), 2.38 (s, 3H), 2.21 (s, 3H), 1.63 (d, J = 7.2 Hz, 3H); ESI-MS: m/z = 449 $[M + H]^+$. |
| 35 | (S)-4-(3-oxomorpholin-4-yl)-3-(4-chlorophenyl)-N-((R)-1-(2-(trifluoromethyl)pyrimidin-5-yl)ethyl)-4,5-dihydro-1H-pyrazol-1-carboxamide 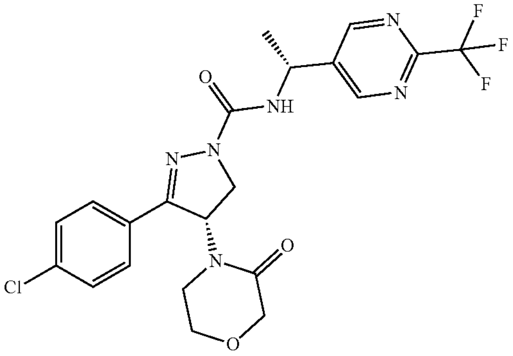 [SMILES: C[C@@H](NC(=O)N1C[C@H](N2CCOCC2=O)C(c2ccc(Cl)cc2)=N1)c1cnc(C(F)(F)F)nc1] | $^1$HNMR (500 MHz, $CDCl_3$) δ 8.86 (s, 2H), 7.98 (d, J = 8.0 Hz, 2H), 7.62 (d, J = 7.9 Hz, 2H), 6.60 (dd, J = 11.0, 3.7 Hz, 1H), 6.35 (d, J = 7.0 Hz, 1H), 5.18-5.07 (m, 1H), 4.23-4.09 (m, 2H), 4.05 (t, J = 12.0 Hz, 1H), 3.90 (dd, J = 12.9, 3.7 Hz, 1H), 3.80-3.69 (m, 1H), 3.68-3.59 (m, 1H), 3.20-3.09 (m, 1H), 2.91-2.83 (m, 1H), 1.59 (d, J = 7.0 Hz, 3H); ESI-MS: m/z = 497 $[M + H]^+$. |

TABLE 2-continued

| Nuclear Magnetic and Mass Spectrometric Data of Title Compounds 5 to 44 | | |
|---|---|---|
| Serial numbers of preparation embodiments | Names and structures of title compounds | Nuclear magnetic and mass spectrometric data |
| 35a | (R)-4-(3-oxomorpholin-4-yl)-3-(4-chlorophenyl)-N-((R)-1-(2-(trifluoromethyl)pyrimidin-5-yl)ethyl)-4,5-dihydro-1H-pyrazol-1-carboxamide 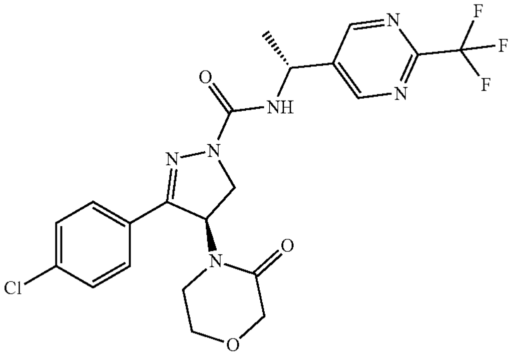 [SMILES: C[C@@H](NC(=O)N1C[C@@H](N2CCOCC2=O)C(c2ccc(Cl)cc2)=N1)c1cnc(C(F)(F)F)nc1] | $^{1}$HNMR (400 MHz, $CDCl_3$) δ 8.88 (s, 2H), 7.96 (d, J = 7.6 Hz, 2H), 7.58 (d, J = 7.5 Hz, 2H), 6.62 (dd, J = 11.0, 4.0 Hz, 1H), 6.36 (brs, 1H), 5.15 (m, 1H), 4.25-4.11 (m, 2H), 4.01 (t, J = 11.6 Hz, 1H), 3.94 (dd, J = 12.0, 3.7 Hz, 1H), 3.81-3.70 (m, 1H), 3.67 (m, 1H), 3.22 (m, 1H), 2.93 (m, 1H),1.63 (d, J = 7.2 Hz, 3H); ESI-MS: m/z = 497 $[M + H]^+$. |
| 36 | (S)-4-(3-oxomorpholin-4-yl)-3-(4-methoxyphenyl)-N-((R)-1-(2-(trifluoromethyl)pyrimidin-5-yl)ethyl)-4,5-dihydro-1H-pyrazol-1-carboxamide 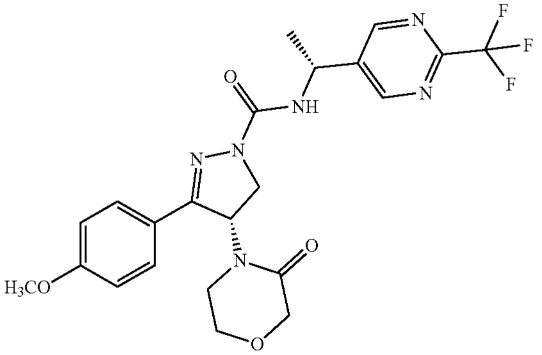 [SMILES: COc1ccc(C2=NN(C(=O)N[C@H](C)c3cnc(C(F)(F)F)nc3)C[C@@H]2N2CCOCC2=O)cc1] | $^{1}$HNMR (500 MHz, $CDCl_3$) δ 8.84 (s, 2H), 7.91 (d, J = 8.0 Hz, 2H), 7.08 (d, J = 7.8 Hz, 2H), 6.59 (dd, J = 11.0, 4.0 Hz, 1H), 6.40 (brs, 1H), 5.13 (t, J = 7.1 Hz, 1H), 4.22-4.10 (m, 2H), 4.04-3.99 (m, 2H), 3.86-3.77 (m, 1H), 3.81 (s, 3H), 3.69 (m, 1H), 3.25 (m, 1H), 2.92 (m, 1H), 1.65 (d, J = 7.1 Hz, 3H); ESI-MS: m/z = 493 $[M + H]^+$. |
| 36a | (R)-4-(3-oxomorpholin-4-yl)-3-(4-methoxyphenyl)-N-((R)-1-(2-(trifluoromethyl)pyrimidin-5-yl)ethyl)-4,5-dihydro-1H-pyrazol-1-carboxamide 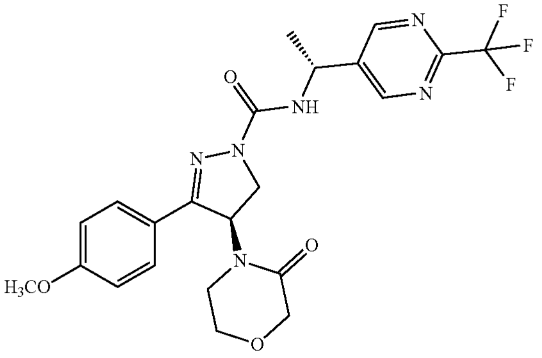 [SMILES: COc1ccc(C2=NN(C(=O)N[C@H](C)c3cnc(C(F)(F)F)nc3)C[C@H]2N2CCOCC2=O)cc1] | $^{1}$HNMR (400 MHz, $CDCl_3$) δ 8.81 (s, 2H), 7.92 (d, J = 7.6 Hz, 2H), 7.10 (d, J = 7.6 Hz, 2H), 6.61 (dd, J = 11.0, 3.7 Hz, 1H), 6.38 (brs, 1H), 5.11(m, 1H), 4.23-4.12 (m, 2H), 4.00 (m, 2H), 3.84-3.73 (m, 1H), 3.84 (s, 3H), 3.65 (m, 1H), 3.23 (m, 1H), 2.90 (m, 1H), 1.63 (d, J = 7.0 Hz, 3H); ESI-MS: m/z = 493 $[M + H]^+$. |

TABLE 2-continued

| Nuclear Magnetic and Mass Spectrometric Data of Title Compounds 5 to 44 | | |
|---|---|---|
| Serial numbers of preparation embodiments | Names and structures of title compounds | Nuclear magnetic and mass spectrometric data |
| 37 | (S)-4-(4-acetylpiperazin-1-yl)-3-(4-methylphenyl)-N-((R)-1-(2-(trifluoromethyl)pyrimidin-5-yl)ethyl)-4,5-dihydro-1H-pyrazol-1-carboxamide 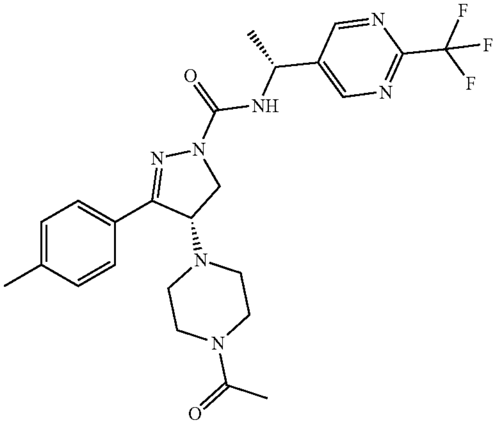 [SMILES: CC(=O)N1CCN([C@H]2CN(C(=O)N[C@H](C)c3cnc(C(F)(F)F)nc3)N=C2c2ccc(C)cc2)CC1] | $^1$HNMR (500 MHz, $CDCl_3$) δ 8.89 (s, 2H), 7.68 (d, J = 8.0 Hz, 2H), 7.25 (d, J = 8.0 Hz, 2H), 6.64 (dd, J = 11.2, 4.0 Hz, 1H), 6.36 (brs, 1H), 5.20-5.16 (m, 1H), 4.01 (t, J = 12.0 Hz, 1H), 3.89 (dd, J = 12.9, 4.0 Hz, 1H), 3.40 (m, 4H), 2.97 (m, 4H), 2.42 (s, 3H), 2.11 (m, 3H), 1.67 (d, J = 7.0 Hz, 3H); ESI-MS: m/z = 504 $[M + H]^+$. |
| 37a | (R)-4-(4-acetylpiperazin-1-yl)-3-(4-methylphenyl)-N-((R)-1-(2-(trifluoromethyl)pyrimidin-5-yl)ethyl)-4,5-dihydro-1H-pyrazol-1-carboxamide 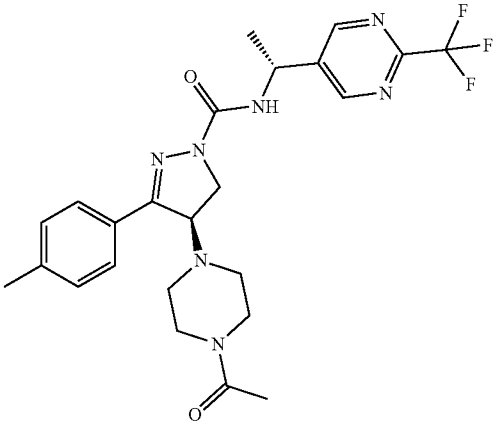 [SMILES: CC(=O)N1CCN([C@@H]2CN(C(=O)N[C@H](C)c3cnc(C(F)(F)F)nc3)N=C2c2ccc(C)cc2)CC1] | $^1$HNMR (400 MHz, $CDCl_3$) δ 8.86 (s, 2H), 7.70 (d, J = 7.6 Hz, 2H), 7.27(d, J = 7.6 Hz, 2H), 6.59 (dd, J = 11.4, 3.8 Hz, 1H), 6.16 (brs, 1H), 5.15 (m, 1H), 4.01 (m, 1H), 3.86 (dd, J = 12.2, 3.7 Hz, 1H), 3.39 (m, 4H), 2.89 (m, 4H), 2.37 (s, 3H), 2.09 (m, 3H), 1.62 (d, J = 7.2 Hz, 3H); ESI-MS: m/z = 504 $[M + H]^+$. |
| 38 | (S)-4-(4-methylpiperazin-1-yl)-3-(4-methylphenyl)-N-((R)-1-(2-(trifluoromethyl)pyrimidin-5-yl)ethyl)-4,5-dihydro-1H-pyrazol-1-carboxamide 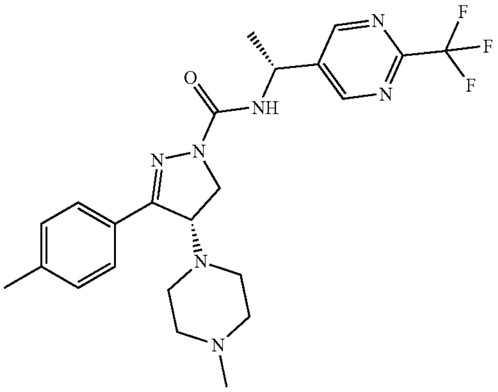 [SMILES: Cc1ccc(C2=NN(C(=O)N[C@H](C)c3cnc(C(F)(F)F)nc3)C[C@@H]2N2CCN(C)CC2)cc1] | $^1$HNMR (400 MHz, $CDCl_3$) δ 8.90 (s, 2H), 7.70 (d, J = 8.0 Hz, 2H), 7.27 (d, J = 8.0 Hz, 2H), 6.46 (d, J = 7.1 Hz, 1H), 6.05 (m, 1H), 5.18-5.12 (m, 1H), 3.78 (t, J = 12.0 Hz, 1H), 3.67 (dd, J = 12.5, 4.0 Hz, 1H), 2.97 (m, 4H), 2.88 (m, 4H), 2.41 (s, 3H), 2.14 (m, 3H), 1.66 (d, J = 7.0 Hz, 3H); ESI-MS: m/z = 476 $[M + H]^+$. |

TABLE 2-continued

Nuclear Magnetic and Mass Spectrometric Data of Title Compounds 5 to 44

| Serial numbers of preparation embodiments | Names and structures of title compounds | Nuclear magnetic and mass spectrometric data |
| --- | --- | --- |
| 38a | (R)-4-(4-methylpiperazin-1-yl)-3-(4-methylphenyl)-N-((R)-1-(2-(trifluoromethyl)pyrimidin-5-yl)ethyl)-4,5-dihydro-1H-pyrazol-1-carboxamide 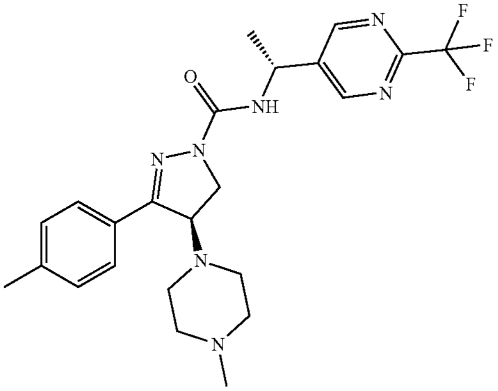 [SMILES: Cc1ccc(C2=NN(C(=O)N[C@H](C)c3cnc(C(F)(F)F)nc3)C[C@H]2N2CCN(C)CC2)cc1] | $^{1}$HNMR (400 MHz, $CDCl_3$) δ 8.86 (s, 2H), 7.73 (d, J = 7.6 Hz, 2H), 7.29 (d, J = 7.6 Hz, 2H), 6.58 (dd, J = 7.1 Hz, 1H), 6.05 (m, 1H), 5.18-5.12 (m, 1H), 3.78 (t, J = 12.0 Hz, 1H), 3.67 (dd, J = 12.5, 4.0 Hz, 1H), 2.97 (m, 4H), 2.88 (m, 4H), 2.41 (s, 3H), 2.14 (m, 3H),1.66 (d, J = 7.0 Hz, 3H); ESI-MS: m/z = 476 $[M + H]^+$. |
| 39 | (S)-4-(morpholin-4-yl)-3-(4-methylphenyl)-N-((R)-1-(2-(trifluoromethyl)pyrimidin-5-yl)ethyl)-4,5-dihydro-1H-pyrazol-1-carboxamide 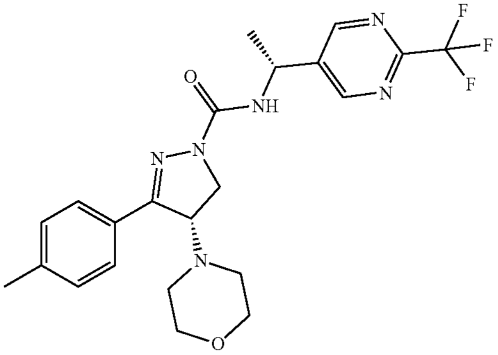 [SMILES: Cc1ccc(C2=NN(C(=O)N[C@H](C)c3cnc(C(F)(F)F)nc3)C[C@@H]2N2CCOCC2)cc1] | $^{1}$HNMR (400 MHz, $CDCl_3$) δ 8.85 (s, 2H), 7.70 (d, J = 8.0 Hz, 2H), 7.27 (d, J = 8.0 Hz, 2H), 6.59 (dd, J = 11.0, 4.0 Hz, 1H), 6.35 (brs, 1H), 5.13 (m, 1H), 3.99 (t, J = 11.2 Hz, 1H), 3.89 (dd, J = 11.0, 4.0 Hz, 1H), 3.63-3.52 (m, 4H), 2.68-2.59 (m, 4H), 2.42 (s, 3H), 1.65 (d, J = 7.2 Hz, 3H); ESI-MS: m/z = 463 $[M + H]^+$. |
| 39a | (R)-4-(morpholin-4-yl)-3-(4-methylphenyl)-N-((R)-1-(2-(trifluoromethyl)pyrimidin-5-yl)ethyl)-4,5-dihydro-1H-pyrazol-1-carboxamide 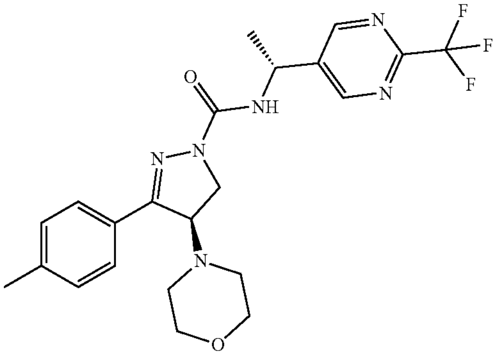 [SMILES: Cc1ccc(C2=NN(C(=O)N[C@H](C)c3cnc(C(F)(F)F)nc3)C[C@H]2N2CCOCC2)cc1] | $^{1}$HNMR (400 MHz, $CDCl_3$) δ 8.83 (s, 2H), 7.72 (d, J = 7.8 Hz, 2H), 7.25 (d, J = 7.8 Hz, 2H), 6.62 (dd, J = 11.0, 3.7 Hz, 1H), 6.45 (brs, 1H), 5.11 (m, 1H), 4.00 (t, J = 11.0 Hz, 1H), 3.91 (dd, J = 12.0, 4.0 Hz, 1H), 3.61-3.50 (m, 4H), 2.69-2.60 (m, 4H), 2.41 (s, 3H), 1.63 (d, J = 7.0 Hz, 3H); ESI-MS: m/z = 463 $[M + H]^+$. |

TABLE 2-continued

| Serial numbers of preparation embodiments | Names and structures of title compounds | Nuclear magnetic and mass spectrometric data |
|---|---|---|
| | Nuclear Magnetic and Mass Spectrometric Data of Title Compounds 5 to 44 | |
| 40 | (S)-4-(2-oxooxazolidin-3-yl)-3-(4-methylphenyl)-N-((R)-1-(2-(trifluoromethyl)pyrimidin-5-yl)ethyl)-4,5-dihydro-1H-pyrazol-1-carboxamide 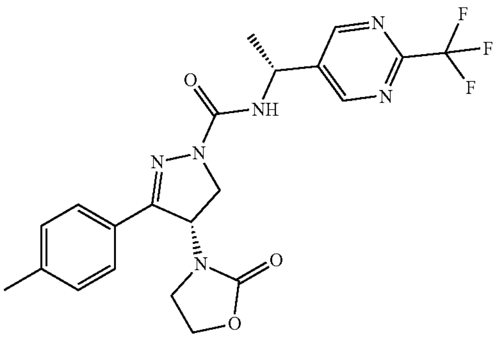 [SMILES: Cc1ccc(C2=NN(C(=O)N[C@H](C)c3cnc(C(F)(F)F)nc3)C[C@@H]2N2CCOC2=O)cc1] | $^1$HNMR (500 MHz, $CDCl_3$) δ 8.84 (s, 2H), 7.69 (d, J = 7.5 Hz, 2H), 7.2 5(d, J = 7.5 Hz, 2H), 6.57 (dd, J = 11.0, 4.0 Hz, 1H), 6.52 (d, J = 7.0 Hz, 1H), 5.17-5.11 (m, 1H), 4.44 (m, 2H), 4.00 (dd, J = 12.5, 10.9 Hz, 1H), 3.87 (dd, J = 12.4, 4.0 Hz, 1H), 3.34 (m, 2H), 2.40 (s, 3H), 1.62 (d, J = 7.2 Hz, 3H); ESI-MS: m/z = 463 $[M + H]^+$. |
| 40a | (R)-4-(2-oxooxazolidin-3-yl)-3-(4-methylphenyl)-N-((R)-1-(2-(trifluoromethyl)pyrimidin-5-yl)ethyl)-4,5-dihydro-1H-pyrazol-1-carboxamide 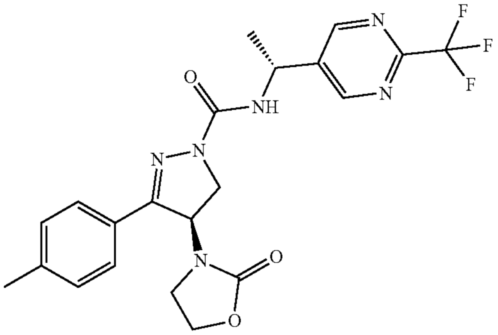 [SMILES: Cc1ccc(C2=NN(C(=O)N[C@H](C)c3cnc(C(F)(F)F)nc3)C[C@H]2N2CCOC2=O)cc1] | $^1$HNMR (400 MHz, $CDCl_3$) δ 8.80 (s, 2H), 7.72(d, J = 7.6 Hz, 2H), 7.28 (d, J = 7.6 Hz, 2H), 6.59 (dd, J = 11.3, 3.8 Hz, 1H), 6.50 (brs, 1H), 5.16-5.10 (m, 1H), 4.35 (m, 2H), 3.98 (m, 1H), 3.83 (dd, J = 12.0, 3.8 Hz, 1H), 3.26 (m, 2H), 2.43 (s, 3H), 1.65 (d, J = 7.5 Hz, 3H); ESI-MS: m/z = 463 $[M + H]^+$. |
| 41 | (S)-4-(3-methyl-2-oxoimidazolidin-1-yl)-3-(4-methylphenyl)-N-((R)-1-(2-trifluoromethyl) pyrimidin-5-yl)ethyl)-4,5-dihydro-1H-pyrazol-1-carboxamide 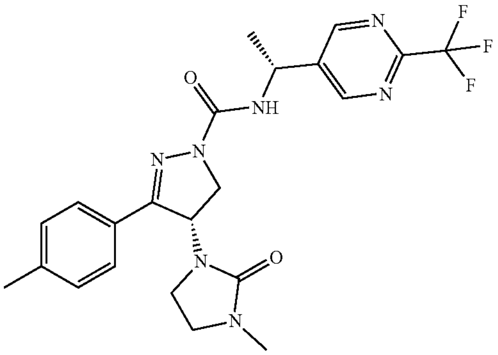 [SMILES: Cc1ccc(C2=NN(C(=O)N[C@H](C)c3cnc(C(F)(F)F)nc3)C[C@@H]2N2CCN(C)C2=O)cc1] | $^1$HNMR (400 MHz, $CDCl_3$) δ 8.86 (s, 2H), 7.71 (d, J = 8.0 Hz, 2H), 7.30 (d, J = 7.8 Hz, 2H), 6.60 (dd, J = 12.0, 4.0 Hz, 1H), 6.50 (d, J = 7.0 Hz, 1H), 5.13-5.10 (m, 1H), 3.99 (dd, J = 12.0, 3.7.0 Hz, 1H), 3.86 (dd, J=12.0, 4.0 Hz, 1H), 3.44 (m, 4H), 3.09 (s, 3H), 2.40 (s, 3H), 1.60 (d, J = 7.0 Hz, 3H); ESI-MS: m/z = 476 $[M + H]^+$. |

TABLE 2-continued

Nuclear Magnetic and Mass Spectrometric Data of Title Compounds 5 to 44

| Serial numbers of preparation embodiments | Names and structures of title compounds | Nuclear magnetic and mass spectrometric data |
|---|---|---|
| 41a | (R)-4-(3-methyl-2-oxoimidazolidin-1-yl)-3-(4-methylphenyl])-N-((R)-1-(2-trifluoromethyl) pyrimidin-5-yl)ethyl)-4,5-dihydro-1H-pyrazol-1-carboxamide 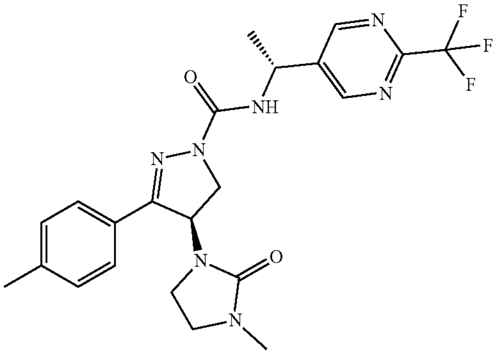 [SMILES: Cc1ccc(C2=NN(C(=O)N[C@H](C)c3cnc(C(F)(F)F)nc3)C[C@H]2N2CCN(C)C2=O)cc1] | $^1$HNMR (400 MHz, $CDCl_3$) δ 8.88 (s, 2H), 7.73(d, J = 7.6 Hz, 2H), 7.32 (d, J = 7.6 Hz, 2H), 6.59 (dd, J = 11.0, 4.0 Hz, 1H), 6.41 (brs, 1H), 5.12 (m, 1H), 4.01 (dd, J = 12.0, 4.0 Hz, 1H), 3.88 (m, 1H), 3.42 (m, 4H), 3.27 (s, 3H), 2.42 (s, 3H), 1.602 (d, J = 7.2 Hz, 3H); ESI-MS: m/z = 476 $[M + H]^+$. |
| 42 | (S)-4-(pyrazol-1-yl)-3-(4-methylphenyl])-N-((R)-1-(2-trifluoromethyl)pyrimidin-5-yl)ethyl)-4,5-dihydro-1H-pyrazol-1-carboxamide 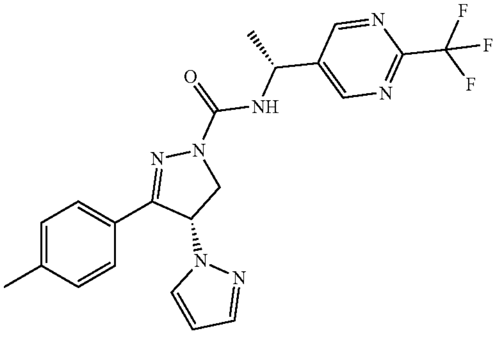 [SMILES: Cc1ccc(C2=NN(C(=O)N[C@H](C)c3cnc(C(F)(F)F)nc3)C[C@@H]2n2cccn2)cc1] | $^1$HNMR (500 MHz, $CDCl_3$) δ 8.88 (s, 2H), 7.84 (d, J = 7.5 Hz, 1H), 7.70 (d, J = 8.0 Hz, 2H), 7.29 (d, J = 7.5 Hz, 1H), 7.27 (d, J = 8.0 Hz, 2H), 6.66 (dd, J = 12.0, 4.0 Hz, 1H), 6.49 (d, J = 7.0 Hz, 1H), 6.23 (m, 1H), 5.10-5.07 (m, 1H), 4.02 (dd, J = 11.0, 3.8 Hz, 1H), 3.87 (dd, J = 12.0, 4.0 Hz, 1H), 2.38 (s, 3H), 1.61 (d, J = 7.0 Hz, 3H); ESI-MS: m/z = 444 [M + H]. |
| 42a | (R)-4-(pyrazol-1-yl)-3-(4-methylphenyl])-N-((R)-1-(2-trifluoromethyl)pyrimidin-5-yl)ethyl)-4,5-dihydro-1H-pyrazol-1-carboxamide 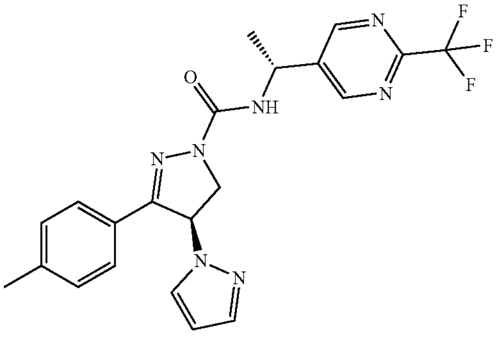 [SMILES: Cc1ccc(C2=NN(C(=O)N[C@H](C)c3cnc(C(F)(F)F)nc3)C[C@H]2n2cccn2)cc1] | $^1$HNMR (400 MHz, $CDCl_3$) δ 8.85 (s, 2H), 7.81(d, J = 7.8 Hz, 1H), 7.66 (d, J = 7.8 Hz, 2H), 7.28 (d, J = 7.8 Hz, 1H), 7.23 (d, J = 7.7 Hz, 2H), 6.63 (dd, J = 11.0, 4.0 Hz, 1H), 6.49 (brs, 1H), 6.22 (m, 1H), 5.10 (m, 1H), 4.02 (t, J = 12.0 Hz, 1H), 3.95 (dd, J = 12.6, 4.0 Hz, 1H), 2.35 (s, 3H), 1.64 (d, J = 7.2 Hz, 3H); ESI-MS: m/z = 444 [M + H]. |

TABLE 2-continued

Nuclear Magnetic and Mass Spectrometric Data of Title Compounds 5 to 44

| Serial numbers of preparation embodiments | Names and structures of title compounds | Nuclear magnetic and mass spectrometric data |
|---|---|---|
| 43 | (S)-4-(2-oxooxazolidin-3-yl)-3-(4-chlorophenyl)-N-((R)-1-(2-methylpyrimidin-5-yl)ethyl)-4,5-dihydro-1H-pyrazol-1-carboxamide 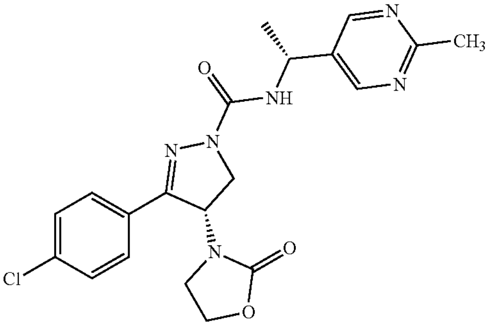 [SMILES: Cc1ncc([C@@H](C)NC(=O)N2C[C@H](N3CCOC3=O)C(c3ccc(Cl)cc3)=N2)cn1] | $^1$HNMR (500 MHz, $CDCl_3$) δ 8.82 (s, 2H), 7.98 (d, J = 8.0 Hz, 2H), 7.62 (d, J = 8.0 Hz, 2H), 6.56 (dd, J = 12.0, 4.0 Hz, 1H), 6.46 (brs, 1H), 5.11-4.97 (m, 1H), 4.34 (m, 2H), 3.98 (dd, J = 12.0, 4.0 Hz, 1H), 3.87 (dd, J = 12.5, 4.0 Hz, 1H), 3.32 (m, 2H), 2.30 (s, 3H), 1.60 (d, J = 7.2 Hz, 3H); ESI-MS: m/z = 429 $[M + H]^+$. |
| 43a | (R)-4-(2-oxooxazolidin-3-yl)-3-(4-chlorophenyl)-N-((R)-1-(2-methylpyrimidin-5-yl)ethyl)-4,5-dihydro-1H-pyrazol-1-carboxamide 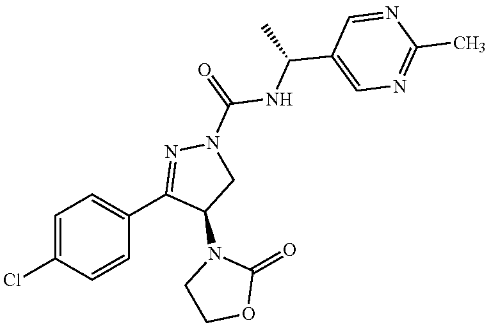 [SMILES: Cc1ncc([C@@H](C)NC(=O)N2C[C@@H](N3CCOC3=O)C(c3ccc(Cl)cc3)=N2)cn1] | $^1$HNMR (400 MHz, $CDCl_3$) δ 8.79(s, 2H), 7.95 (d, J = 7.8 Hz, 2H), 7.55 (d, J = 7.6 Hz, 2H), 6.59 (dd, J = 11.0, 4.0 Hz, 1H), 6.54 (brs, 1H), 5.12 (m, 1H), 4.32 (m, 2H), 3.98 (dd, J = 12.0, 3.7 Hz, 1H), 3.85 (dd, J = 12.0, 4.0 Hz, 1H), 3.26 (m, 2H), 2.40 (s, 3H), 1.61 (d, J = 7.0 Hz, 3H); ESI-MS: m/z = 429 $[M + H]^+$. |
| 44 | (S)-4-(2-oxopyrrolidin-1-yl)-3-(4-fluorophenyl)-N-((R)-1-(2-chloropyrimidin-5-yl)ethyl)-4,5-dihydro-1H-pyrazol-1-carboxamide 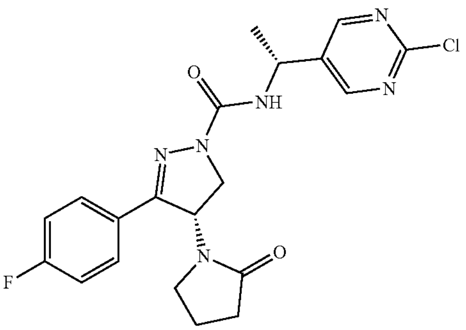 [SMILES: C[C@@H](NC(=O)N1C[C@H](N2CCCC2=O)C(c2ccc(F)cc2)=N1)c1cnc(Cl)nc1] | $^1$HNMR (500 MHz, $CDCl_3$) δ 8.68 (s, 2H), 7.79 (d, J = 8.0 Hz, 2H), 7.36 (dd, J = 8.5, 7.5 Hz, 2H), 6.46 (d, J = 7.0 Hz, 1H), 6.07 (dd, J = 11.0, 4.0 Hz, 1H), 5.15 (m, 1H), 4.02 (dd, J = 12.0, 4.0 Hz, 1H), 3.86 (dd, J = 12.0, 4.0 Hz, 1H), 3.29 (m, 2H), 2.34 (m, 2H), 1.98-1.91 (m, 2H), 1.63 (d, J = 7.2 Hz, 3H); ESI-MS: m/z = 431 $[M + H]^+$. |

TABLE 2-continued

| Nuclear Magnetic and Mass Spectrometric Data of Title Compounds 5 to 44 | | |
|---|---|---|
| Serial numbers of preparation embodiments | Names and structures of title compounds | Nuclear magnetic and mass spectrometric data |
| 44a | (R)-4-(2-oxopyrrolidin-1-yl)-3-(4-fluorophenyl)-N-((R)-1-(2-chloropyrimidin-5-yl)ethyl)-4,5-dihydro-1H-pyrazol-1-carboxamide 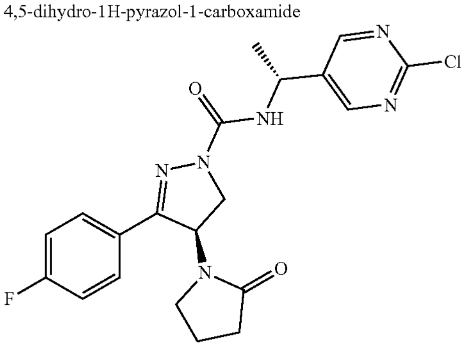 | 1HNMR (400MHZ,CDC13): 88.72 (s, 2H), 7.82(d, J=7.8Hz, 2H), 7.38(dd, J=8.8, 7.8Hz, 2H), 6.57 (dd, J=11.2, 3.8Hz, 1H), 6.46 (brs, 1H), 5.15 (m, 1H), 4.00 (dd, J = 12.0, 3.8 Hz, 1H), 3.88 (m, 1H), 3.31 (m, 2H), 2.29 (m, 2H), 1.93 (m, 2H), 1.64 (d, J = 7.0 Hz, 3H); ESI-MS: m/z = 431 [M + H]$^+$. |

Preparation Embodiment 45. Synthesis of (S)-4-(2-oxopyrrolidin-1-yl)-3-(4-methylphenyl)-N—((R)-1-(3-methyl-1,2,4-oxadiazol-5-yl)ethyl)-4,5-dihydro-1H-pyrazol-1-carboxamide (Compound 45) and Epimer 45a 1). Synthesis of (R)-1-(3-methyl-1,2,4-oxadiazol-5-yl)ethylamine (B-22)

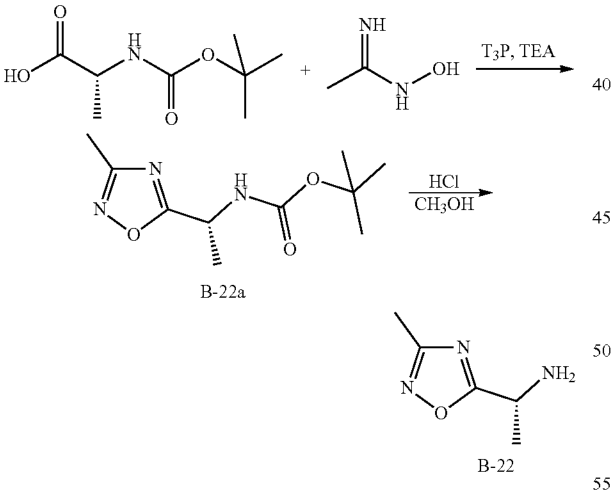

B-22a

B-22

Step 1. Synthesis of tert-butyl (R)-(1-(3-methyl-1,2,4-oxadiazol-5-yl)ethyl)carbamate (Intermediate B-22a)

N-tert-butoxycarbonyl-D-alanine (10.0 g, 53.0 mmol) was dissolved into DMF (40 mL). Then, triethylamine (22 mL), N-hydroxyacetamidine hydrochloride (4.6 g, 41.8 mmol) and 20 mL of n-propyl phosphoric anhydride (a 50% DMF solution) were added respectively. Heating was conducted to 100° C. to 110° C. under stirring for reaction for 3.5 hours. Cooling was conducted to a room temperature. Waster was added for a quenching reaction. Extracting was conducted with ethyl acetate (300 mL×3). Organic layers were combined, washed three times with saturated brine, and dried with anhydrous $Na_2SO_4$. Decompression concentration was conducted. A residue was separated by silica gel column chromatography (PE:EA=3:1, v/v) to obtain an intermediate compound B-22a with a yield of 75%; ESI-MS: m/z=228[M+1]$^+$.

Step 2. Synthesis of (R)-1-(3-methyl-1,2,4-oxadiazol-5-yl)ethylamine (B-22)

5.0 g of the compound B-22a was dissolved into ethanol (35 mL), and cooled to 0° C. A hydrochloric acid-methanol solution (50 mL) was slowly added dropwise. After addition was completed, stirring was conducted at a room temperature overnight. A reaction solution was concentrated under reduced pressure to obtain a compound B-22 hydrochloride, which was an off-white solid with a yield of 95%; ESI-MS: m/z=128[M+1]$^+$.

2). Synthesis of (S)-4-(2-oxopyrrolidin-1-yl)-3-(4-methylphenyl)-N—((R)-1-(3-methyl-1,2,4-oxadiazol-5-yl)ethyl)-4,5-dihydro-1H-pyrazol-1-carboxamide (Compound 45)

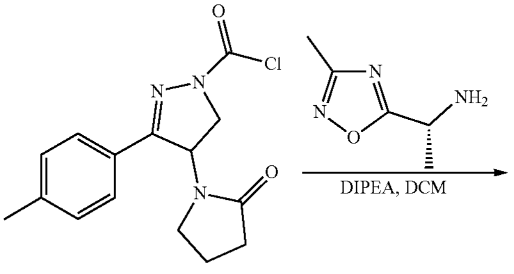

A-3

-continued

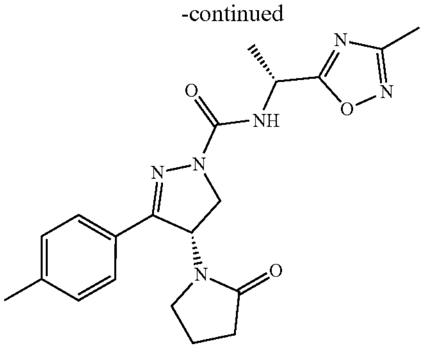

45

+

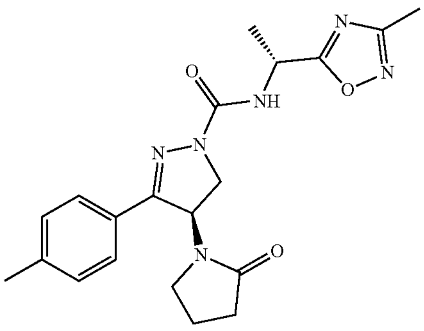

45a

A compound A-3 (1.0 g, 3.27 mmol) and the compound B-22 (0.53 g, 3.27 mmol) were added into dichloromethane (10 mL). Then, N,N-diisopropylethylamine (DIPEA, 1.27 g, 9.81 mmol) was added. Stirring was conducted at a room temperature overnight. A 0.5 N hydrochloric acid (10 mL) was added. Stirring was conducted for 10 minutes. Still standing for stratification was conducted. Organic phases were separated. An aqueous phase was extracted with dichloromethane (10 mL×3). The organic phases were combined, dried with anhydrous $Na_2SO_4$, and filtered. A filtrate was subjected to decompression concentration to dryness. A residue was subjected to gradient separation by silica gel column chromatography (PE:EA=2:1 to 1:3, v/v) to obtain a title compound 45 with a yield of 35%. $^1$HNMR (500 MHz, $CDCl_3$): δ 7.65 (d, J=8.1 Hz, 2H), 7.22 (d, J=8.0 Hz, 2H), 6.45 (d, J=7.2 Hz, 1H), 6.04 (dd, J=11.2, 4.0 Hz, 1H), 5.10 (m, 1H), 3.99 (dd, J=12.0, 11.0 Hz, 1H), 3.87 (dd, J=12.0, 3.8 Hz, 1H), 3.24-3.21 (m, 1H), 2.90-2.82 (m, 1H), 2.39 (s, 3H), 2.27 (s, 3H), 2.32-2.23 (m, 1H), 2.05-1.78 (m, 3H), 1.66 (d, J=7.1 Hz, 3H); ESI-MS: m/z=397[M+1]$^+$.

An epimer 45a with a yield of 32%. $^1$HNMR (400 MHz, $CDCl_3$): δ 7.62 (d, J=7.8 Hz, 2H), 7.21 (d, J=7.6 Hz, 2H), 6.59 (dd, J=11.0, 4.0 Hz, 1H), 6.48 (brs, 1H), 5.12 (m, 1H), 3.99 (dd, J=11.0, 4.0 Hz, 1H), 3.86 (dd, J=11.0, 3.8 Hz, 1H), 3.36-3.29 (m, 2H), 2.43 (s, 3H), 2.34 (s, 3H), 2.32-2.23 (m, 2H), 2.05-1.78 (m, 2H), 1.65 (d, J=7.2 Hz, 3H); ESI-MS: m/z=397[M+1]$^+$.

Preparation Embodiment 46. Synthesis of (S)-4-(3-oxomorpholinyl)-3-(4-methylphenyl)-N—((R)-1-(3-methyl-1,2,4-oxadiazol-5-yl)ethyl)-4,5-dihydro-1H-pyrazol-1-carboxamide (Compound 46) and Epimer 46a

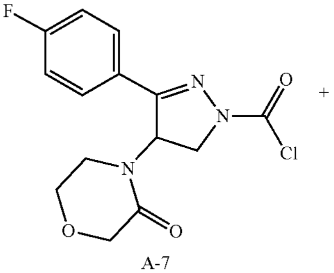

A-7

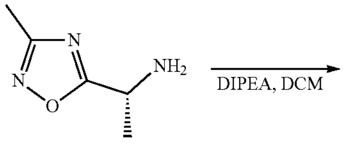

B-22

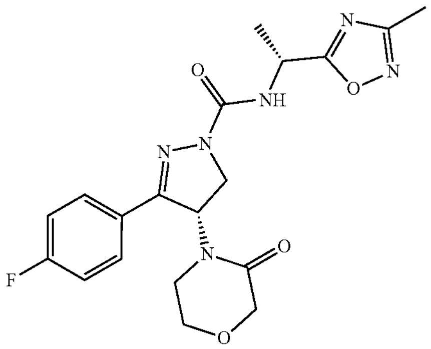

46

+

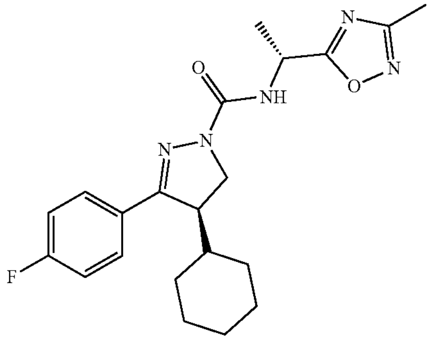

46a

For synthesis steps, refer to Preparation Embodiment 45. Step 3. Is only to prepare the title compound 46 by reacting a compound A-7 with the compound B-22; $^1$HNMR (500 MHz, $CDCl_3$): δ7.78 (m, 2H), 7.35 (m, 2H), 6.62 (dd, J=11.0, 3.8 Hz, 1H), 6.55 (d, J=7.2 Hz, 1H), 5.13-5.08 (m, 1H), 4.24-4.10 (m, 2H), 4.06 (t, J=12.0 Hz, 1H), 3.89 (dd, J=12.5, 3.8 Hz, 1H), 3.80-3.70 (m, 1H), 3.67-3.58 (m, 1H), 3.20-3.10 (m, 1H), 2.90-2.82 (m, 1H), 2.35 (s, 3H), 1.58 (d, J=7.2 Hz, 3H); ESI-MS: m/z=417[M+1]$^+$.

An epimer 46a; $^1$HNMR (400 MHz, $CDCl_3$): δ7.80 (m, 2H), 7.37 (m, 2H), 6.65 (m, 1H), 6.60 (dd, J=11.0, 4.0 Hz, 1H), 5.12 (m, 1H), 4.23-4.13 (m, 2H), 4.02 (t, J=11.0 Hz, 1H), 3.92 (dd, J=11.6, 3.6 Hz, 1H), 3.79 (m, 1H), 3.65 (m, 1H), 3.22-3.13 (m, 1H), 2.93 (m, 1H), 2.37 (s, 3H), 1.63 (d, J=7.0 Hz, 3H); ESI-MS: m/z=417[M+1]$^+$.

Preparation Embodiment 47. Synthesis of (S)-4-(N-methylacetamido)-3-(4-methylphenyl)-N—((S)-1-(6-(trifluoromethyl)pyridin-3-yl))ethyl)-4,5-dihydro-1H-pyrazol-1-carboxamide (Compound 47) and Epimer 47a

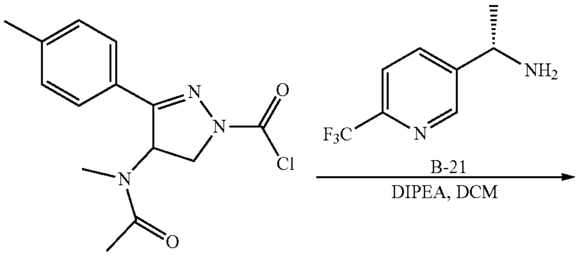

A-1

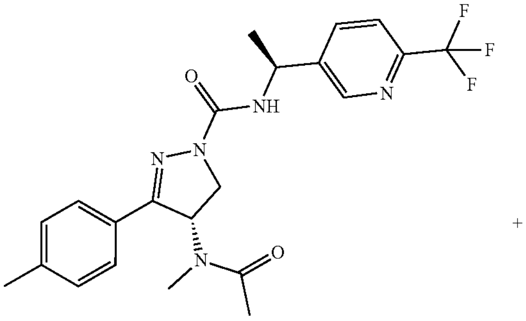

+

S,S
47

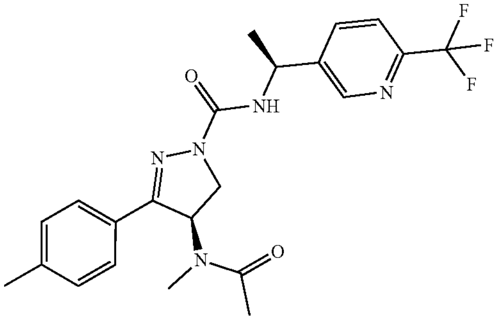

R,S
47a

Synthesis steps: A compound A-1 (1.5 g, 5.1 mmol) and a compound B-21 (0.95 g, 5 mmol) were added into dichloromethane (10 mL). Then, N,N-diisopropylethylamine (DIPEA, 2.0 g, 12.2 mmol) was added. Stirring was conducted at a room temperature overnight. A hydrochloric acid (0.5 N, 10 mL) was added for a quenching reaction. Stirring was conducted for 10 minutes. Still standing for stratification was conducted. An aqueous phase was extracted three times with dichloromethane (10 mL). Organic phases were combined, dried with anhydrous sodium sulfate, and filtered. A filtrate was subjected to decompression concentration to dryness. A residue was subjected to gradient separation by silica gel column chromatography (PE:EA=2:1 to 1:3, v/v) to obtain a crude product, which was separated by preparative chromatography on a silica gel plate to obtain a title compound 47 with a yield of 25%, and an R,R-epimer 47a thereof with a yield of 22%.

Title compound 47: $^1$H NMR (400 MHz, $CDCl_3$): δ 8.79 (s, 1H), 7.90 (d, J=7.0 Hz, 1H), 7.68 (d, J=8.2 Hz, 1H), 7.62 (d, J=8.0 Hz, 2H), 7.21 (d, J=8.0 Hz, 2H), 6.62 (dd, J=11.2, 4.0 Hz, 1H), 6.34 (d, J=6.9 Hz, 1H), 5.20-5.10 (m, 1H), 4.05 (t, J=12.2 Hz, 1H), 3.83 (dd, J=12.8, 4.2 Hz, 1H), 2.67 (s, 3H), 2.38 (s, 3H), 2.07 (s, 3H), 1.63 (d, J=6.8 Hz, 3H); ESI-MS: m/z=448[M+1]$^+$.

Epimer 47a: $^1$H NMR (400 MHz, $CDCl_3$): δ 8.75 (s, 1H), 7.87 (d, J=8.1 Hz, 1H), 7.66-7.60 (m, 3H), 7.21 (d, J=8.0 Hz, 2H), 6.61 (dd, J=11.3, 4.3 Hz, 1H), 6.34 (d, J=7.4 Hz, 1H), 5.16 (t, J=7.2 Hz, 1H), 4.06-3.98 (m, 1H), 3.86 (dd, J=12.8, 4.4 Hz, 1H), 2.71 (s, 3H), 2.38 (s, 3H), 2.08 (s, 3H), 1.64 (d, J=7.1 Hz, 3H).

III. Biological Assessment

1. Determination of Inhibitory Activity of Title Compounds Against P2X by an Electrophysiological Method $IC_{50}$ detection experiments of compounds on P2X receptors were completed by a perforated patch clamp [Wang et al. (2018) Proc Natl Acad Sci USA 115 (19): 4939-4944]. All compounds required to prepare solutions were purchased from sigma Company.

1) Cell Culture

An HEK293 cell line was used as cells. HEK293 cells were placed in a 37° C. incubator with 5% $CO_2$ for culture. Passage was conducted when the cells grew to a density of 80% to 90%. A culture medium in an original 60 mm culture dish was discarded. After the cells were washed 3 times with a sterilized PBS solution, and the solution was blotted up. 1 mL of 0.25% trypsin (Gibco) was added for digestion for 10 seconds. After the trypsin was blotted up, 3 mL of a cell culture medium was added to resuspend the cells. 0.5 mL of a resuspension solution was taken to be added into a new culture dish, and an total culture solution was supplemented to 5 mL. The culture dish was gently shaken to distribute the cells evenly, and then placed in a 37° C. incubator with 5% $CO_2$ for culture.

2) Plasmid Transfection

First, treated slides were spread in a small 35 mm culture dish. 100 μL of resuspended cells were added, and then a total amount of a culture medium was supplemented to 2 mL. Target genes were transferred into the HEK293 cell line by adopting a calcium transfection method. Small dishes to be transfected were subjected to medium change 1 hour before transfection. 2 mL of a fresh cell culture solution was added. A 1.5 mL EP tube was taken, 200 μL of a 0.25 M $CaCl_2$) solution was added, and 3 μg of plasmids to be transfected were added, and even mixing was conducted to form a DNA-$CaCl_2$ solution. Then the mixed solution was slowly added into an equal volume of 2×HBS solutions (NaCl of 140 mM, $Na_2HPO_4$ of 1.5 mM, HEPES of 50 mM, adjusting pH to 6.96). A pipette tip was used for mixing while adding. After adding all, gentle blowing and beating were conducted 8 to 10 times. After still standing for 5 minutes, they were added into small dishes. The small dishes were shaken slightly to mix the solution evenly, and the placed in a cell incubator. Culture mediums were replaced after 8 to 10 hours. Electrophysiological experiments were performed 24 to 48 hours after transfection.

3) Electrophysiological Experiment

Electrophysiological recording electrodes were obtained by two-step pulling by using an electrode puller (PP-10, Narishige). After an internal solution is injected into the electrodes, a water inlet resistance is 3 to 5 MΩ. During the experiment, a high potassium salt internal solution containing nystatin ($K_2SO_4$ of 75 mM, KCl of 120 mM, $MgSO_4$ of 5 mM, HEPES of 10 mM, adjusting pH to 7.2 with Tris-base, and used after filtration) was used as an electrode internal solution. After the cells were sealed by the electrodes, there was no need to further break cell membranes in a sucked manner, but the cell membranes were bored through the perforation of the nystatin to the cell membranes, to form a hole channel. This experiment used an Axon 200B amplifier and a Digidata° 1440A digital-to-analog converter, and used Clampfit in a voltage clamp mode to record data. A clamping voltage was −60 mV, a sampling frequency was 10 kHz, and filtering was conducted at 2 kHz.

A working concentration of a P2X3 receptor agonist ATP was 1 μM, and an interval time between two times of ATP administrations was 10 minutes. All test compounds, including a reference substance AF-219, were pre-administered for 2 minutes before co-administration with the ATP.

TABLE 3.1

Inhibitory activity of title compounds against human P2X3 (electrophysiological method)

| Serial numbers of compounds | hP2X3 ($IC_{50}$, μM) |
|---|---|
| 1 | 0.106 |
| 1a | 0.098 |
| 2 | 7.543 |
| 3 | 0.215 |
| 3a | 0.318 |
| 4 | 0.132 |
| 4c | 0.181 |
| 5 | 0.409 |
| 5a | 0.353 |
| 6 | 1.231 |
| 7 | 0.985 |
| 8 | 0.793 |
| 9 | 0.529 |
| 10 | 0.216 |
| 10a | 0.136 |
| 11 | 0.357 |
| 11a | 0.281 |
| 12 | 0.436 |
| 12a | 0.322 |
| 13 | 0.257 |
| 13a | 0.329 |
| 14 | 0.736 |
| 15 | 2.298 |
| 16 | 0.132 |
| 16a | 0.088 |
| 17 | 0.287 |
| 17a | 0.301 |
| 18 | 0.173 |
| 18a | 0.095 |
| 19 | 3.859 |
| 20 | 0.528 |
| 21 | 0.129 |
| 21a | 0.085 |
| 22 | 0.056 |
| 22a | 0.038 |
| 23 | 0.038 |
| 23a | 0.046 |
| 24 | 0.212 |
| 24a | 0.145 |
| 25 | 0.158 |
| 25a | 0.112 |
| 26 | 0.143 |
| 26a | 0.332 |

TABLE 3.1-continued

Inhibitory activity of title compounds against human P2X3 (electrophysiological method)

| Serial numbers of compounds | hP2X3 ($IC_{50}$, μM) |
|---|---|
| 27 | 0.389 |
| 27a | 0.257 |
| 28 | 0.218 |
| 28a | 0.165 |
| 29 | 0.152 |
| 29a | 0.105 |
| 30 | 0.102 |
| 30a | 0.087 |
| 31 | 0.103 |
| 31a | 0.092 |
| 32 | 0.127 |
| 32a | 0.082 |
| 33 | 0.254 |
| 33a | 0.365 |
| 34 | 0.169 |
| 34a | 0.231 |
| 35 | 0.215 |
| 35a | 0.451 |
| 36 | 0.283 |
| 36a | 0.422 |
| 37 | 3.728 |
| 38 | 2.673 |
| 39 | 6.102 |
| 40 | 0.094 |
| 40a | 0.135 |
| 41 | 0.115 |
| 41a | 0.109 |
| 42 | 4.912 |
| 43 | 0.331 |
| 44 | 0.233 |
| 44a | 0.421 |
| 45 | 0.178 |
| 45a | 0.206 |
| 46 | 0.151 |
| 46a | 0.256 |
| AF-219* | 0.333 |

*AF-219 was purchased from MedChemExpress (CAS No. 1015787-98-0).

TABLE 3.2

Inhibitory activity of compounds against P2X3 in rats and guinea pigs (electrophysiological method)

| Serial numbers of compounds | rP2X3 ($IC_{50}$, μM) | Serial numbers of compounds | gpP2X3 ($IC_{50}$, μM) |
|---|---|---|---|
| 4 | 0.165 | 4 | 0.421 |
| 17 | 0.140 | 17 | 0.387 |
| 22 | 0.090 | 22 | 0.297 |
| 22a | 0.057 | 22a | 0.578 |
| 23 | 0.103 | 23 | 0.359 |

TABLE 3.3

Inhibitory activity of title compounds against human P2X2/3 (electrophysiological method)

| Serial numbers of compounds | hP2X2/3 ($IC_{50}$, μM) |
|---|---|
| 4 | 8.584 |
| 17 | 8.872 |
| 22 | 2.417 |
| 23 | 1.152 |

TABLE 3.4

| Inhibitory activity of title compounds against human P2X4 (electrophysiological method) | |
|---|---|
| Serial numbers of compounds | hP2X4 ($IC_{50}$, μM) |
| 1 | >20 |
| 4 | >20 |
| 17 | >20 |
| 20 | >20 |
| 21 | >20 |
| 22 | >20 |
| 22a | >20 |
| 23 | >20 |
| 30 | >20 |
| 31 | >20 |
| 32a | >20 |
| 40 | >20 |
| 41 | >20 |
| 45 | >20 |

4) Conclusion: it could be seen from the above test results that the title compounds had stronger inhibitory activity against human and murine P2X3, and had obviously weak inhibitory activity against human P2X2/3, but had no inhibitory effect on P2X4, which shown that the compounds obtained by the present invention had good selectivity to P2X3.

2. Determination of Inhibitory Activity of Title Compounds Against PAR-1 (Platelet Protease-Activated Receptor)

The inhibitory activity of the title compounds against human PAR-1 was determined by a calcium ion flux fluorescence method (an FLIPR method). The method thereof was reported in the literature of Zhong et al. [Zhong et al. J Biomol Struct Dyn, 2017, 35(13):2853].

1) Cell Culture

An HEK293/Ga15 recombinant cell line (HD Biosciences, Shanghai, China) stably expressing human PAR-1 was cultured in a DMEM (Thermo Fisher Scientific, Shanghai) culture solution (containing 10% calf serum, 800 μg/mL G418). Incubator conditions were 37° C. and an air humidity with 5% $CO_2$.

2) Preparation of Compound Analysis Plate

On the first day, 20 μL per well of PAR-1 cells at a concentration of 4E+5 cells/mL were seeded in a 384-well analysis plate (Corning 3712). The cell analysis plate was centrifuged for 1 minute at 300 rpm, and then cultured for 24 hours in a 37° C. incubator with 5% $CO_2$. On the second day, a culture solution in each well was poured off. Then, 20 μL of 1×loading dye (2 μM Fluo-8 AM in 1×HBSS with 20 mM HEPES, 1 mM Probenecid, 0.025% Pluronic F-127 assay buffer) was added in each well. The cell analysis plate was cultured for 1 hour at a room temperature.

3) Sample Preparation

The compounds were dissolved into 100% DMSO to prepare a 10 mM stock solution, which was stored at −20° C. On the day of use, the compound stock solution was thawed at a room temperature. Each compound was subjected to 1:3 serial dilution at 11 concentration points with a DMEM culture solution with a starting concentration of 30 μM. Each compound was subjected to double dilution for testing. A positive control compound was diluted in the same way with SCH79797 with a starting concentration of 30 μM.

4) FLIPR Determination

The cell analysis plate was placed in a FLIPR instrument (Molecular Device) and 10 μL of compounds (3× of a final concentration) in a compound plate was added to corresponding wells of the cell analysis plate. After 10 minutes, 10 μL of TFLLR-NH2 (TFA) (a final concentration of 10 μM) was added to each well to stimulate generation of intracellular calcium flux signals. $Ca^{++}$-dependent fluorescence signals were continuously monitored at excitation wavelengths of 470/495 nm and emission wavelengths of 515/575 nm to analyze the inhibitory activity of the compounds.

5) Data Analysis

Data were collected and analyzed by using an FLIPR program. The inhibitory (or agonistic) activity of the compounds at each concentration was assessed by fluorescence peaks. $IC_{50}$ values of the compounds were calculated by using EXCEL and PRISM programs.

TABLE 3.5

| Inhibitory activity of title compounds against PAR-1 (electrophysiological method) | |
|---|---|
| Serial numbers of compounds | PAR-1 ($IC_{50}$, μM) |
| 1 | >30 |
| 4 | >30 |
| 17 | >30 |
| 20 | >30 |
| 21 | >30 |
| 22 | >30 |
| 23 | >30 |
| 30 | >30 |
| 31 | >30 |
| 40 | >30 |
| 41 | >30 |
| 45 | >30 |

6) Conclusion: under the above experimental conditions, the title compounds had no inhibitory effect on the PAR-1.

3. In-Vivo Pharmacokinetic Experiments of Title Compounds on Rats

1) Administration Modes

SD rats were used, half male and half female, which were administered with compounds by intravenous injection (3 mg/kg), intraperitoneal injection (10 mg/kg) or gavage (30 mg/kg) at different doses. At different time points after administration, blood was collected into EDTA blood sample collection tubes. Plasma was separated by centrifugation and stored at −20° C. pending analysis.

2) Blood Sample Processing and LC-MS/MS Analysis

Standard curve and quality control sample preparation and processing: a compound stock solution was taken and diluted with 50% methanol water to make standard working solutions containing each compound concentration of 20 to 10,000 ng/mL, and 60, 600, 6,000 ng/mL quality control working solutions. 47.5 μL of blank rat plasma was taken, respectively, in which 2.50 μL of the standard curve working solutions and quality control working solutions were added to prepare standard curve samples with each compound concentration of 1.00 to 500.00 ng/mL and quality control samples with concentrations of 3.00, 30.00 and 300.00 ng/mL. 200 μL of acetonitrile (containing 5 ng/mL internal standard verapamil) was added into each sample. After vortex oscillation for 3 minutes, centrifuging was conducted for 15 minutes at 20,000 rcf at 4° C. Supernatants were taken for LC-MS/MS analysis.

Compound blood sample processing: 5 μL of plasma samples were taken. 45 μL of Blank rat plasma was added.

200 μL of Acetonitrile (containing 5 ng/mL internal standard verapamil) was added. After vortex oscillation for 3 minutes, centrifuging was conducted for 15 minutes at 20,000 rcf at 4° C. Supernatants were taken for LC-MS/MS analysis. (Chromatographic Column: ACQUITY UPLC® BEH C18 2.1×50 mm 1.7 μm; Mobile Phase A: 0.1% formic acid water; Mobile Phase B: acetonitrile; Flow Rate: 0.35 mL/min).

TABLE 3.6

Main pharmacokinetic parameters of title compounds

| | | Compound 22 | Compound 4 |
|---|---|---|---|
| RatPK i.v | Cl (L/h/kg) | 1.59 | 2.35 |
| 3 mg/kg | $t_{1/2}$ (h) | 1.31 | 0.6 |
| | ACU (hr*kg*ng/mL/mg) | 275.63 | 427.84 |
| | Vss (L/kg) | 2.8 | 2.05 |
| | Cmax/Co (ng/mL) | 2212 | 1750 |
| Rat PK p.o | $t_{1/2}$ (h) | 2.71 | 2.23 |
| 30 mg/kg | Tmax (h) | 0.92 | 1.8 |
| | ACU (hr*kg*ng/mL/mg) | 766 | 367.68 |
| | Cmax (ng/mL) | 1449 | 4949 |
| | F % | 36 | 86 |

3) Conclusion: it could be seen from the above experimental results that the title compound had good oral pharmacokinetic properties and oral bioavailability.

4. Experiments of ATP/Citric Acid-Induced Cough in Guinea Pigs

The inhibitory effect of compounds on cough in guinea pigs by intraperitoneal injection and gavage administration was observed by adopting models of ATP/citric acid-induced cough in guinea pigs [Carceau and Chauret (2019) Pulmonary Pharmacology & Therapeutics 56: 56-62].

1) Experimental Animals

Ordinary grade SD guinea pigs were used. The weight of male animals was 244 to 320 g; the weight of female animals was 227 to 331 g. The guinea pigs were fed in plastic cages with free ingestion and free access to water. Corncob bedding was spread in the cages. The males and the females were fed in separate cages, with 10 guinea pigs per cage. A temperature was controlled to be 20° C. to 26° C., and a relative humidity was controlled to be 40% to 70%. Automatic lighting was adopted, with alternating lightness and darkness every 12 hours. Lights were turned on at 8:00 a.m. and turned off at 8:00 p.m.

2) Animal Grouping and Administration

Grouping was conducted by a stratified randomization method according to genders and the number of times of inducing coughs by citric acid during preliminary screening, with 10 guinea pigs in each group. Administration with compounds was conducted by intravenous injection or gavage at different doses. AF-219 was used as a positive control compound. A blank solvent was a 0.9% sodium chloride solution with 5% DMSO and 5% Solutol HS.

3) Experimental Methods

Guinea pig screening: the guinea pigs were placed in an organic glass box of about 25 cm×10 cm×8 cm (length, width, height), in which a 20% citric acid solution was sprayed for 1 minute. The number of times of coughs of animals within 10 minutes was recorded by using a multi-channel physiological signal collecting and processing system. According to the number of times of the coughs of the guinea pigs, the guinea pigs that did not cough were eliminated, and finally 35 male guinea pigs and 35 female guinea pigs were screened, and were grouped by the stratified randomization method for a formal test.

4) Formal test: 20 minutes after intraperitoneal injection administration of the guinea pigs in each group, or 45 minutes after gavage administration, the guinea pigs in each group were placed in an organic glass box of about 25 cm×10 cm×8 cm (length, width, height). A 10 μM ATP solution was continuously sprayed into the box with a pressure nebulizer for 2 minutes (a spraying flow rate of 0.6 mL/min). Then, a 20% citric acid solution was sprayed for 1 minute. The number of times of coughs of animals within 10 minutes was recorded by the multi-channel physiological signal collecting and processing system.

5) Data Statistics

Figure 5:
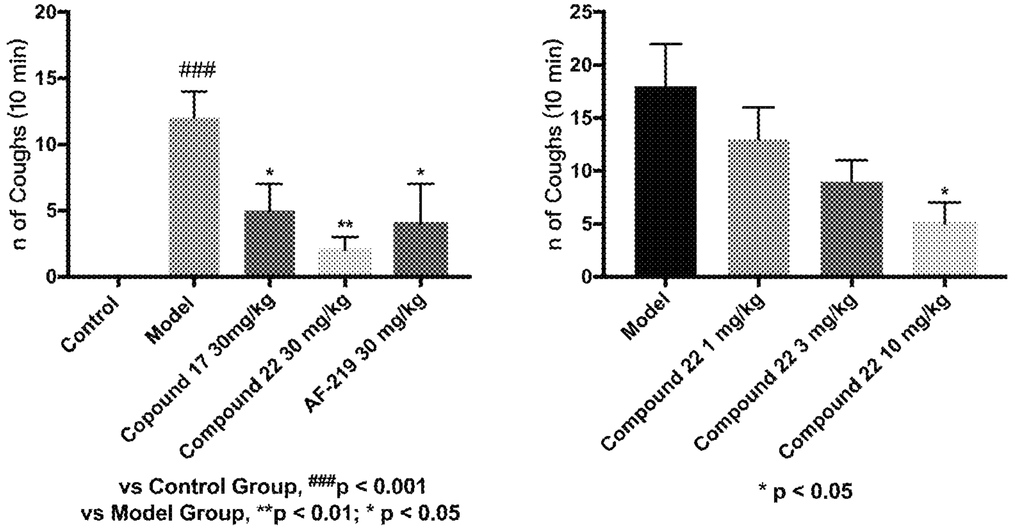
FIG. 5 shows an inhibitory effect of title compounds on ATP/citric acid-induced cough in guinea pigs (intraperitoneal injection).
Figure 6:
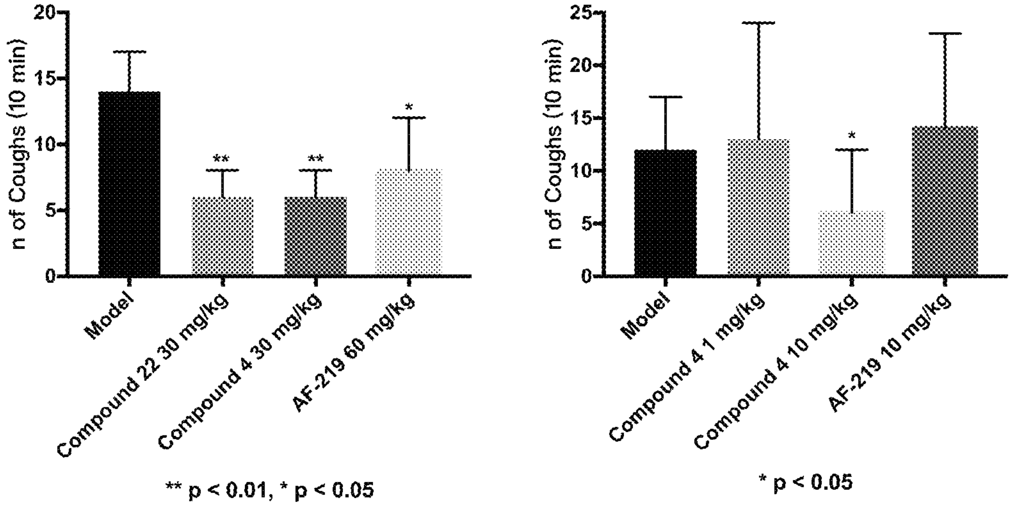
FIG. 6 shows an inhibitory effect of title compounds on ATP/citric acid-induced cough in guinea pigs (oral administration).

The number of times of the coughs was recorded with Excel software. GraphPad Prism 8 software was used for graphing, and SPSS 18 software was used for statistical analysis. Results were shown in FIGS. 5 and 6. The number of times of coughs and time of an incubation period in each group were subjected to a homogeneity test for variance, respectively. If the variance was homogeneous ($P>0.05$), one-way analysis of variance would be conducted. If there was a significant difference ($P\leq0.05$), Dunnett test would be conducted between each dose group and the control group; otherwise, the test ended. If the variance was heterogeneous ($P\leq0.05$), a nonparametric test (a Kruskal-Wallis H test, i.e., a K-W H test) would be conducted. If there was a statistic difference ($P\leq0.05$) in the K-W H test, a Mann-Whitney U test would be conducted between each dose group and the control group; otherwise the test ended.

6) Conclusion: under the above experimental conditions, the title compounds could significantly reduce the cough frequency of experimental animals by intraperitoneal injection or gavage administration.

5. Rat Taste Test

Experimental purpose: to observe an effect of title compounds on taste of SD rats.

1) Experimental Methods 1.1) Animals and grouping: 40 male SD rats, with about 300 grams per rat. The animals were randomly divided into 4 groups with 10 animals in each group, the weights of each group were similar, and they were fed in single cages.

1.2) Training of drinking habits: the animals in each group were given normal drinking water for 30 minutes at 8.30 a.m. and 16.30 p.m. every day, and forbidden from drinking water for the rest of the time for 5 days.

1.3) Administration: water was forbidden the night before the experiment, and the following drugs were given by intraperitoneal injection at the following doses the next morning:

(1) a solvent (5% DMSO/5% Solutol HS/a 0.9% sodium chloride solution) 10 mL/kg (2) a compound 22 10 mg/kg (volume 10 mL/kg)

(3) a compound 4 10 mg/kg (volume 10 mL/kg)

(4) AF-21910 mg/kg (volume 10 mL/kg)

1.4) Measurement of water intakes: after injection, the animals were put back into the original cages. The injection time of the solvents, the compound 22, the compound 4, and the AF-219 was within a Tmax interval of each drug, respectively. A bottle of normal drinking water and a bottle of drinking water containing 0.3 mM quinine hydrochloride were placed in each cage at the same time, and left and right positions where the two bottles of water were placed in all animal feeding cages were the same. After the animals were allowed to freely drink water for 15 minutes, drinking amounts of the two bottles of water were measured respectively to the nearest 0.1 mL.

1.5) Data statistics: drinking amounts of quinine bitter water and tap water and a total water drinking amount thereof as well as a percentage of quinine water in the total water drinking amount were counted respectively. Water drinking amounts of the bitter water of animals in each group were compared. Whether differences between groups were significant was compared by analysis of variance.

2) Experimental Results

Figure 7:
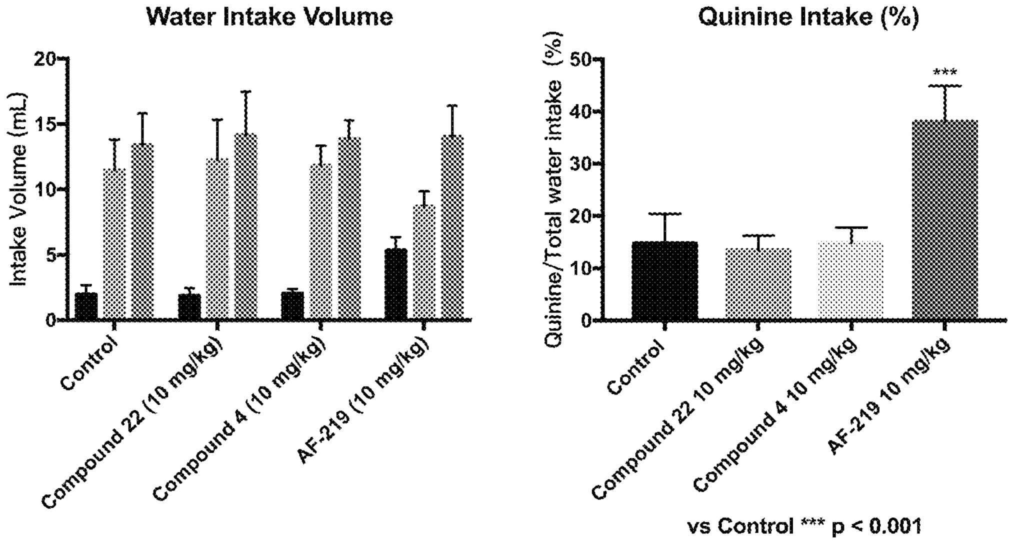
FIG. 7 shows percentages of drinking water and quinine water after administration of experimental animals in each title group.

Compared with a solvent control group, there was no significant difference (P>0.05) in the total water drinking amount of SD rats in each administration group, while the drinking amount of bitter water of SD rats in the positive control AF-219 group increased significantly, indicating that under this experimental conditions, the tested compounds had no significant effect on rat taste (FIG. 7 and Table 3.7).

TABLE 3.7

Water drinking amounts of experimental animals in each group

| Serial numbers of compounds | Administration amount | Water drinking amount | | |
|---|---|---|---|---|
| | | Tap water | Quinine | Sum |
| 22 | 10 mg/kg | 12.26 | 1.87 | 14.13 |
| 4 | 10 mg/kg | 11.84 | 2.03 | 13.87 |
| AF-219 | 10 mg/kg | 8.69 | 5.33 | 14.02 |
| Solvent | 10 mL/kg | 11.45 | 1.96 | 13.41 |

6. Liver Microsomal Enzyme Stability Test

1) Detection Method

An LC-MS/MS method, wherein A liquid phase method adopts a gradient elution method. Chromatographic Column: ACQUITY UPLC® BEH C18 (2.1 mm×50 mm, 1.7 μm); Flow Rate: 0.35 mL/min; Injection Volume: 1 μL (YS001), 3 μL (testosterone); Column Temperature: 40° C.; Automatic Sampler Temperature: 4° C.; Mobile Phase Compositions: mobile phase A: 0.1% formic acid water, and mobile phase B: acetonitrile. Mass spectrometry conditions adopt an ESI source, and positive ion and multiple reaction monitoring (MRM) modes were used for mass spectrometry analysis.

2) Sample Processing

Liver microsome incubation samples were taken, in which 400 μL of an acetonitrile solution containing an internal standard (1 ng/mL loratadine) was added for a termination reaction. Even vortex mixing was conducted at 2,500 rpm. Centrifuging was conducted for 10 minutes at 20,000 rcf at 4° C. Supernatants were taken into clean lined tubes. Contents of prototype drugs were detected by LC-MS/MS.

3) Solution Preparation

Preparation of Stock Solutions

Administration group stock solution: appropriate amounts of compound 4 and compound 22 powder were weighed respectively, and dissolved with dimethyl sulfoxide (DMSO), to prepare a 10 mM administration group stock solution, which was stored in a −20° C. refrigerator;

Testosterone stock solution: an appropriate amount of testosterone was weighed, and dissolved with dimethyl sulfoxide (DMSO), to prepare a 10 mM testosterone stock solution, which was stored in a −20° C. refrigerator; and Internal standard stock solution: an appropriate amount of loratadine was weighed, and dissolved with methanol, to prepare a 1.0 mg/mL loratadine stock solution, which was stored in a −20° C. refrigerator.

Preparation of Working Solutions

Administration group working solution: appropriate amounts of the compound 4 and compound 22 administration group stock solutions were pipetted, to prepare a 500 μM working solution with methanol; and Testosterone working solution: an appropriate amount of the testosterone stock solution was pipetted, to prepare a 500 μM working solution with methanol.

4) Test Content

Metabolic rate test: human liver microsomes were taken, unfrozen and thawed on ice, and gently shaken evenly. The liver microsomes were pipetted and added into a 100 mM phosphate buffer solution, and then the compound 4 (or compound 22) administration group working solution was added respectively, so that a concentration of the microsomes was 0.625 mg/mL, and a concentration of a compound 4 or a compound 22 was 1.25 μM. 80 μL of the above solution was pipetted, and pre-incubated for 5 minutes in a 37° C. water bath, then, 20 μL of a 5 mM NADPH solution was added, and incubating was conducted in a 37° C. water bath. A total sample volume of each metabolic incubation system is 100 μL, and the incubation system includes liver microsomal protein with a final concentration of 0.5 mg/mL, 1 μM the compound 4 (or compound 22) and 1 mM NADPH. After reaction for 0, 10, 30, 60, and 90 minutes, the reaction was terminated with 4 times the volume of acetonitrile (containing 1 ng/mL internal standard loratadine). Even vortex mixing was conducted. High-speed centrifuging was conducted for 10 minutes at 20,000 rcf at 4° C. Supernatants were taken for LC-MS/MS detection. Each incubation sample was subjected to a parallel test in triplicate. Positive control was metabolic samples of microsomes of corresponding species to a positive drug testosterone (1 μM). The reaction was terminated with 4 times the volume of acetonitrile (containing 1 ng/mL internal standard loratadine). Incubation time points were 0, 30, 60 minutes.

5) Data Processing

Analyst 1.6.3 software was used for data collecting. After integration parameters were optimized, target chromatographic peaks were automatically integrated, individual chromatographic peaks were not allowed to be integrated separately or manually, and retention time and a peak area were calculated. Data was collected by Analyst 1.6.3, and subjected to integration processing to obtain the retention time and the peak area, and a peak area ratio of an analyte to an internal standard was calculated. Then, Microsoft Office Excel was used for secondary processing to calculate a half-life period $t_{1/2}$ and a clearance rate CLint thereof. A residual percentage (% Control) of tested compounds was calculated from a ratio of a concentration of a non-zero time point sample to a concentration of a zero-time sample. Ln (% Control) was plotted against incubation time and subjected to linear fitting. An elimination constant (ke, 1/min), an elimination half-life period ($t_{1/2}$, min) and an in-vitro intrinsic clearance rate (CLint, μL/(mg·min)) of the tested compounds were calculated. $T_{1/2}$=0.693/ke, CLint=ke/Cprotein (Note: ke is a slope, and Cprotein is a protein concentration.)

| Serial numbers of compounds | Species | ke (=−slope, $min^{-1}$) | $t_{1/2}$ (=0.693/k, min) | $Cl_{int, microsome}$ (=k/$C_{protein}$, μL × $min^{-1}$ × $mg^{-1}$ proteins) |
|---|---|---|---|---|
| 4 | Human | 0.0019 | 363.8 | 3.8 |
| 22 | Human | 0.0107 | 64.8 | 21.4 |

6) Conclusion: under the above experimental conditions, the title compounds had good stability to liver microsomal enzymes.

7. Stability Experiments of Simulated Gastric Fluids and Simulated Intestinal Fluids 1) Detection Method An LC-MS/MS method, wherein A liquid phase method adopts a gradient elution method. Chromatographic Column: ACQUITY UPLC® BEH C18 (2.1 mm×50 mm, 1.7 μm); Flow Rate: 0.35 mL/min; Injection Volume: 1 μL; Column Temperature: 40° C.; Automatic Sampler Temperature: 10° C.; Mobile Phase Compositions: mobile phase A: 0.1% formic acid water, and mobile phase B: acetonitrile. Mass spectrometry conditions adopt an ESI source, and positive ion and multiple reaction monitoring (MRM) modes were used for mass spectrometry analysis.

2) Sample Processing

Simulated gastric fluid and simulated intestinal fluid samples were taken, in which 1,200 μL of an acetonitrile solution containing an internal standard (5 ng/mL loratadine) was added. Even vortex mixing was conducted at 2,500 rpm. Centrifuging was conducted for 10 minutes at 20,000 rcf at 4° C. Supernatants were taken into clean lined tubes. Contents of prototype drugs were detected by LC-MS/MS.

3) Solution Preparation

Preparation of Working Solutions

Administration group working solution: appropriate amounts of the compound 4 and compound 22 administration group stock solutions were pipetted, to prepare a 50 μM working solution with methanol; and Internal standard working solution: an appropriate amount of a loratadine stock solution was pipetted, to prepare a 5 ng/mL loratadine working solution with acetonitrile.

Preparation of Simulated Gastric Fluids and Simulated Intestinal Fluids

Blank artificial gastric fluid: 3.28 mL of a diluted hydrochloric acid was taken. 160 mL of water was added. After even shaking was conducted to make full dissolving, a pH value was adjusted to 1.3. Water was added for diluting and a constant volume to 200 mL, to obtain a blank artificial gastric fluid.

Artificial gastric fluid: 3.28 mL of a diluted hydrochloric acid was taken. 160 mL of water and 2 g of pepsin were added. After even shaking was conducted to make full dissolving, a pH value was adjusted to 1.3. Water was added for diluting and a constant volume to 200 mL, to obtain an artificial gastric fluid.

Blank artificial intestinal fluid: 1.36 g of potassium dihydrogen phosphate was weighed. 100 mL of water was added to dissolve the potassium dihydrogen phosphate. A pH value was adjusted to 6.8 with a 0.1 mol/L sodium hydroxide solution. Water was added for a constant volume to 200 mL, to obtain a blank artificial intestinal fluid.

Artificial intestinal fluid: 1.36 g of potassium dihydrogen phosphate was weighed. 100 mL of water was added to dissolve the potassium dihydrogen phosphate. A pH value was adjusted to 6.8 with a 0.1 mol/L sodium hydroxide solution. In addition, 2 g of trypsin was weighed. An appropriate amount of water was added to dissolve the trypsin. After the two solutions were mixed, water was added for a constant volume to 200 mL, to obtain an empty artificial intestinal fluid.

4) Test Content

The simulated gastric fluids and the simulated intestinal fluids were taken to be gently shaken evenly. The simulated gastric fluids and the simulated intestinal fluids were pipetted, in which the compound 4 (or compound 22) working solution was added respectively, and a concentration of a compound 4 (or a compound 22) was 1.25 μM. 300 μL of the above solutions were pipetted, and pre-incubated in a 37° C. water bath. Samples were taken at 0, 0.5, 1, 1.5, 2, 3, and 5 hours. A reaction was terminated with 4 times the volume of acetonitrile (containing 5 ng/mL internal standard loratadine). Even vortex mixing was conducted. High-speed centrifuging was conducted for 10 minutes at 20,000 rcf at 4° C. Supernatants were taken for LC-MS/MS detection. Each incubation sample was subjected to a parallel test in triplicate.

5) Data Processing

MassLynx V4.2 software was used for data collecting. After integration parameters were optimized, target chromatographic peaks were automatically integrated, individual chromatographic peaks were not allowed to be integrated separately or manually, and retention time and a peak area were calculated. Data was collected by MassLynx V4.2, and subjected to integration processing to obtain the retention time and the peak area, and a peak area ratio of an analyte to an internal standard was calculated. Then, Microsoft Office Excel was used for secondary processing to calculate an average residual percentage.

6) Experimental Results

Figure 8:
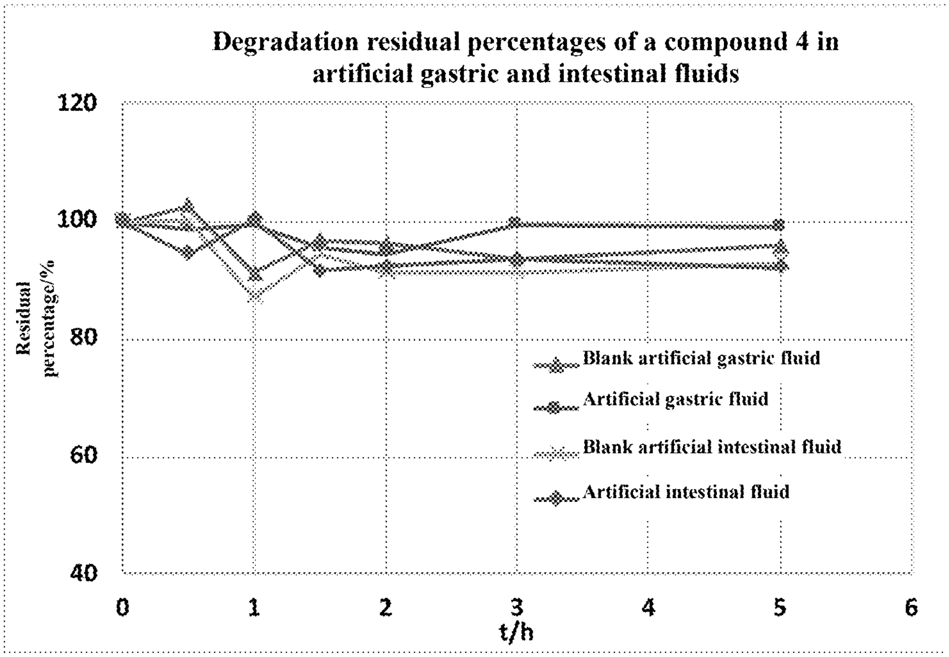
FIG. 8 shows degradation residual percentages of a title compound 4 in artificial gastric and intestinal fluids.
Figure 9:
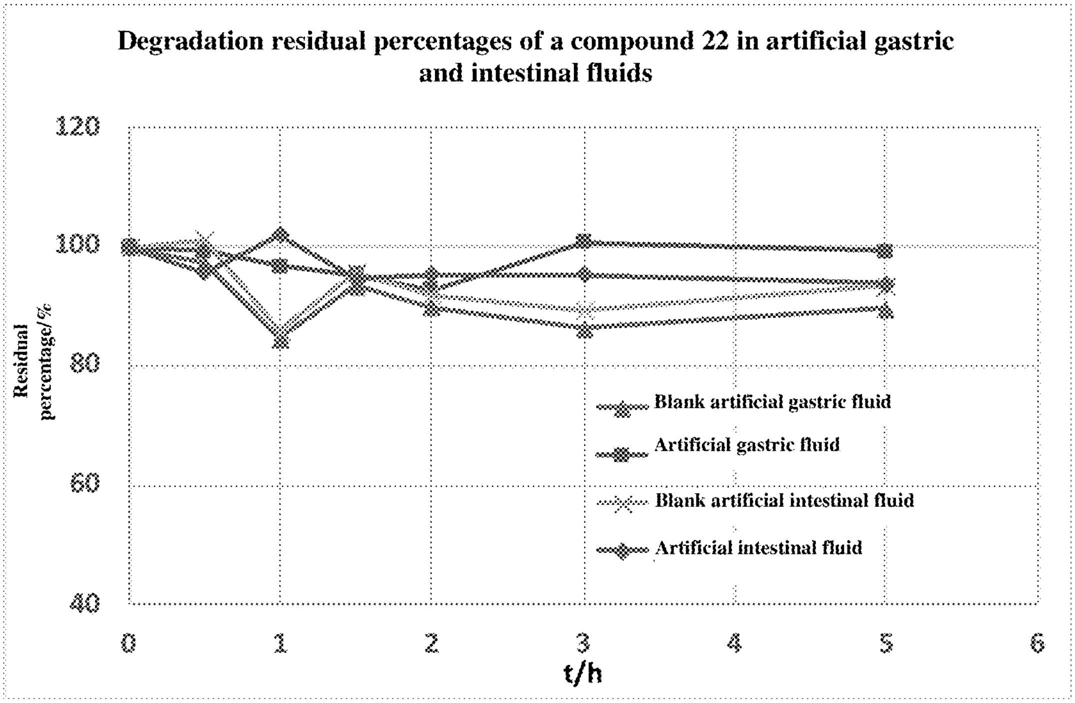
FIG. 9 shows degradation residual percentages of a title compound 22 in artificial gastric and intestinal fluids.

Under the above experimental conditions, the compound 4 and the compound 22 were relatively stable in artificial gastric and intestinal fluids (FIGS. 8 and 9).

The invention claimed is:

1. An N-formamidopyrazoline compound of General Formula (I), or an enantiomer, a diastereomer, a racemate thereof, or a pharmaceutically acceptable salt thereof:

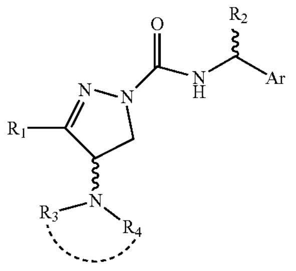

(I)

wherein

Ar is selected from 1,3-benzodioxole; or Ar is selected from the following substituted phenyls, substitute five-membered or six-membered heteroaromatic ring groups:

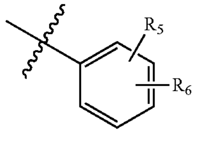

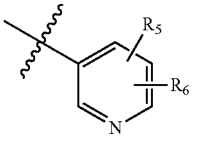

-continued

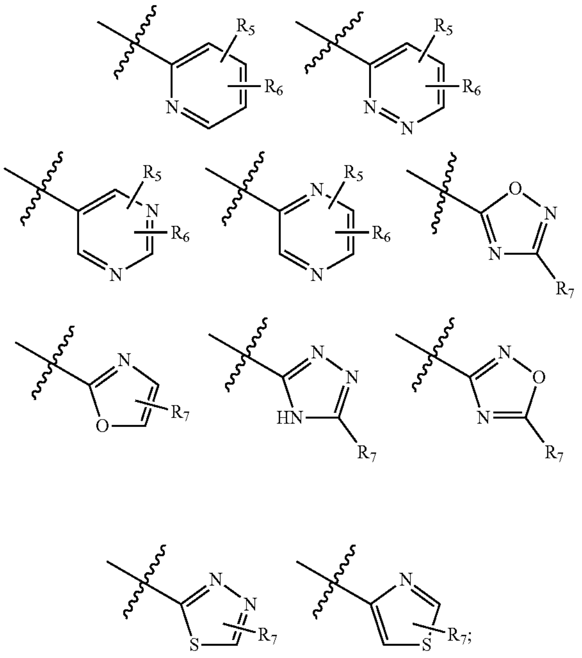

$R_5$ and $R_6$ are independently selected from the group consisting of H, halogen, nitryl, cyano group, methyl, trifluoromethyl, trifluoromethoxy, and C1 to C3 straight or branched chain alkoxy; and $R_7$ is selected from methyl, ethyl, isopropyl, and cyclopropyl;

$R_1$ is selected from substituted or unsubstituted phenyl or substituted or unsubstituted pyridyl, wherein $R_1$ is substituted with a group selected from halogen, C1 to C3 straight or branched chain alkyl, C1 to C3 straight or branched chain alkoxy, trifluoromethyl and trifluoromethoxy; and $R_2$ is selected from a methyl, an ethyl, an isopropyl and a cyclopropyl; and wherein the $R_3$ and the $R_4$ are each independently selected from H, methyl, ethyl, methoxycarbonyl, ethoxycarbonyl, propoxycarbonyl, isopropoxycarbonyl, tert-butoxycarbonyl, formyl, acetyl, and N,N-dialkylaminoacetyl; or the $R_3$ and the $R_4$ together with the N to which they both are connected form substituted or unsubstituted morpholinone, substituted or unsubstituted morpholinyl, substituted or unsubstituted piperidinyl, substituted or unsubstituted piperazinyl, substituted or unsubstituted piperazinone, substituted or unsubstituted pyrrolidone, substituted or unsubstituted oxazolidinone, substituted or unsubstituted imidazolidinone, substituted or unsubstituted imidazolyl, substituted or unsubstituted pyrazolyl, 1,2,3-triazolyl, and 1,2,4-triazolyl; and wherein substituted groups on morpholinone, morpholinyl, piperidinyl, piperazinyl, piperazinone, pyrrolidone, oxazolidinone, imidazolidinone, imidazolyl and pyrazolyl are selected from C1 to C3 straight or branched chain alkyl, formyl, acetyl, and C1 to C5 straight or branched chain alkoxy.

2. The N-formamidopyrazoline compound according to claim 1 having General Formulas (Ia), (Ib), (Ic) and (Id):

(Ia)

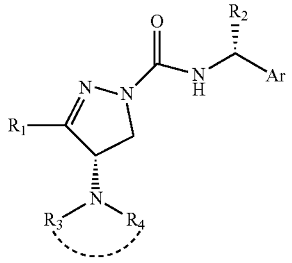

(S,R)

(Ib)

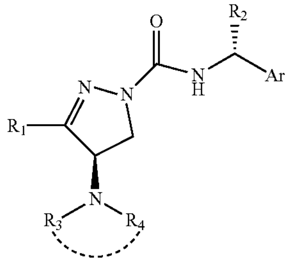

(R,R)

(Ic)

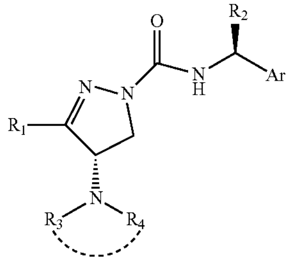

(S,S)

(Id)

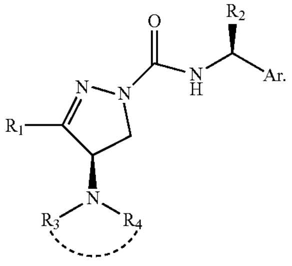

(R,A)

3. The N-formamidopyrazoline compound according to claim 2, wherein the Ar is selected from phenyl, p-trifluoromethylphenyl, dimethoxyphenyl, dioxolane phenyl, p-cyanophenyl, chlorophenyl, methoxypyridyl, trifluoromethyl pyridyl, chloropyridyl, difluoropyridyl, trifluoromethyloxypyridyl, trifluoromethylpyrazinyl, methylpyrazinyl, chloropyrazinyl, methoxypyridazinyl, trifluoromethylpyridazinyl, chloropyridazinyl, trifluoromethylpyrimidinyl, methylpyrimidinyl, chloropyrimidinyl, and methyl-1,2,4-oxadiazolyl;

the $R_1$ is selected from p-methylphenyl, p-methoxyphenyl, p-fluorophenyl, p-chlorophenyl, and methylpyridyl; and the $R_2$ is selected from methyl; and the $R_3$ and the $R_4$ are each independently selected from H, methyl, ethyl, methoxycarbonyl, ethoxycarbonyl, acetyl, and N,N-dialkylaminoacetyl; or the $R_3$ and the $R_4$ together with the N to which they both are connected form morpholinone, piperazinone, methylpiperazinone, pyrrolidone, oxazolidinone, imidazolidinone, acetyl imidazolidinone, morpholinyl, piperazinyl, N-acetylpiperazinyl, and pyrazolyl.

4. The N-formamidopyrazoline compound according to claim 1, wherein the compound in General Formula (I) is one of the following compounds:

(S)-4-(3-oxomorpholin-4-yl)-3-(4-methylphenyl)-N—((R)-1-(6-(trifluoromethyl) pyridin-3-yl)ethyl)-4,5-dihydro-1H-pyrazol-1-carboxamide (1)

(R)-4-(3-oxomorpholin-4-yl)-3-(4-methylphenyl)-N—((R)-1-(6-(trifluoromethyl) pyridin-3-yl)ethyl)-4,5-dihydro-1H-pyrazol-1-carboxamide (1a) (S)-4-(4-methyl-2-oxopiperazin-1-yl)-3-(4-methylphenyl)-N—((R)-1-(4-chlorophenyl)ethyl)-4,5-dihydro-1H-pyrazol-1-carboxamide (2)

(R)-4-(4-methyl-2-oxopiperazin-1-yl)-3-(4-methylphenyl)-N—((R)-1-(4-chlorophenyl))ethyl)-4,5-dihydro-1H-pyrazol-1-carboxamide (2a)

(S)-4-(3-oxomorpholin-4-yl)-3-(4-methylphenyl)-N—((R)-1-(2-(trifluoromethyl)pyrimidin-5-yl)ethyl)-4,5-dihydro-1H-pyrazol-1-carboxamide (3)

(R)-4-(3-oxomorpholin-4-yl)-3-(4-methylphenyl)-N—((R)-1-(2-(trifluoromethyl)pyrimidin-5-yl)ethyl)-4,5-dihydro-1H-pyrazol-1-carboxamide (3a)

(S)-4-(N-methyl-N-ethoxycarbonylamino)-3-(4-methylphenyl)-N—((R)-1-(2-(trifluoromethyl)pyrimidin-5-yl)ethyl)-4,5-dihydro-1H-pyrazol-1-carboxamide (4)

(R)-4-(N-methyl-N-ethoxycarbonylamino)-3-(4-methylphenyl)-N—((R)-1-(2-(trifluoromethyl)pyrimidin-5-yl)ethyl)-4,5-dihydro-1H-pyrazol-1-carboxamide (4c)

(S)-4-(N-methylacetamido)-3-(4-methylphenyl)-N—((R)-1-(4-(trifluoromethyl)phenyl)ethyl)-4,5-dihydro-1H-pyrazol-1-carboxamide (5)

(R)-4-(N-methylacetamido)-3-(4-methylphenyl)-N—((R)-1-(4-(trifluoromethyl)phenyl)ethyl)-4,5-dihydro-1H-pyrazol-1-carboxamide (5a)

(S)-4-(2-oxooxazolidin-3-yl)-3-(4-methylphenyl)-N—((R)-1-(3,4-dimethoxyphenyl)ethyl)-4,5-dihydro-1H-pyrazol-1-carboxamide (6)

(R)-4-(2-oxooxazolidin-3-yl)-3-(4-methylphenyl)-N—((R)-1-(3,4-dimethoxyphenyl)ethyl)-4,5-dihydro-1H-pyrazol-1-carboxamide (6a)

(S)-4-(2-oxopyrrolidin-1-yl)-3-(4-methylphenyl)-N—((R)-1-(3,4-(methylenedioxy)phenyl)ethyl)-4,5-dihydro-1H-pyrazol-1-carboxamide (7)

(R)-4-(2-oxopyrrolidin-1-yl)-3-(4-methylphenyl)-N—((R)-1-(3,4-(methylenedioxy)phenyl)ethyl)-4,5-dihydro-1H-pyrazol-1-carboxamide (7a)

(S)-4-(3-acetyl-2-oxoimidazolidin-1-yl)-3-(4-methylphenyl)-N—((R)-1-(4-cyanophenyl)ethyl)-4,5-dihydro-1H-pyrazol-1-carboxamide (8)

(R)-4-(3-acetyl-2-oxoimidazolidin-1-yl)-3-(4-methylphenyl)-N—((R)-1-(4-cyanophenyl)ethyl)-4,5-dihydro-1H-pyrazol-1-carboxamide (8a)

(S)-4-(2-oxopyrrolidin-1-yl)-3-(4-methylphenyl)-N—((R)-1-(5-methoxypyridin-2-yl)ethyl)-4,5-dihydro-1H-pyrazol-1-carboxamide (9)

(R)-4-(2-oxopyrrolidin-1-yl)-3-(4-methylphenyl)-N—((R)-1-(5-methoxypyridin-2-yl)ethyl)-4,5-dihydro-1H-pyrazol-1-carboxamide (9a)

(S)-4-(2-oxopyrrolidin-1-yl)-3-(4-methylphenyl)-N—((R)-1-(5-(trifluoromethyl) pyridin-2-yl)ethyl)-4,5-dihydro-1H-pyrazol-1-carboxamide (10)

(R)-4-(2-oxopyrrolidin-1-yl)-3-(4-methylphenyl)-N—((R)-1-(5-(trifluoromethyl) pyridin-2-yl)ethyl)-4,5-dihydro-1H-pyrazol-1-carboxamide (10a)

(S)-4-(N-methylacetamido)-3-(4-methylphenyl)-N—((R)-1-(6-chloropyridin-3-yl)ethyl)-4,5-dihydro-1H-pyrazol-1-carboxamide (11)

(R)-4-(N-methylacetamido)-3-(4-methylphenyl)-N—((R)-1-(6-chloropyridin-3-yl)ethyl)-4,5-dihydro-1H-pyrazol-1-carboxamide (11a)

(S)-4-(2-oxooxazolidin-3-yl)-3-(4-methylphenyl)-N—((R)-1-(5,6-difluoropyridin-3-yl)ethyl)-4,5-dihydro-1H-pyrazol-1-carboxamide (12)

(R)-4-(2-oxooxazolidin-3-yl)-3-(4-methylphenyl)-N—((R)-1-(5,6-difluoropyridin-3-yl)ethyl)-4,5-dihydro-1H-pyrazol-1-carboxamide (12a) (S)-4-(2-oxopyrrolidin-1-yl)-3-(4-methylphenyl)-N—((R)-1-(6-(trifluoromethoxy)pyridin)-3-yl)ethyl)-4,5-dihydro-1H-pyrazol-1-carboxamide (13)

(R)-4-(2-oxopyrrolidin-1-yl)-3-(4-methylphenyl)-N—((R)-1-(6-(trifluoromethoxy)pyridin)-3-yl)ethyl)-4,5-dihydro-1H-pyrazol-1-carboxamide (13a)

(S)-4-(morpholin-4-yl)-3-(4-fluorophenyl)-N—((R)-1-(6-methoxypyridin-3-yl)ethyl)-4,5-dihydro-1H-pyrazol-1-carboxamide (14)

(R)-4-(morpholin-4-yl)-3-(4-fluorophenyl)-N—((R)-1-(6-methoxypyridin-3-yl)ethyl)-4,5-dihydro-1H-pyrazol-1-carboxamide (14a)

(S)-4-(2-(dimethylamino)-N-methylacetamido)-3-(4-methylphenyl)-N—((R)-1-(6-(trifluoromethyl) pyridin-3-yl)ethyl)-4,5-dihydro-1H-pyrazol-1-carboxamide (15)

(R)-4-(2-(dimethylamino)-N-methylacetamido)-3-(4-methylphenyl)-N—((R)-1-(6-(trifluoromethyl) pyridin-3-yl)ethyl)-4,5-dihydro-1H-pyrazol-1-carboxamide (15a)

(S)-4-(N-methyl-N-methoxycarbonylamino)-3-(4-methoxyphenyl)-N—((R)-1-(6-(trifluoromethyl) pyridin-3-yl)ethyl)-4,5-dihydro-1H-pyrazol-1-carboxamide (16)

(R)-4-(N-methyl-N-methoxycarbonylamino)-3-(4-methoxyphenyl)-N—((R)-1-(6-(trifluoromethyl) pyridin-3-yl)ethyl)-4,5-dihydro-1H-pyrazol-1-carboxamide (16a)

(S)-4-(4-methyl-2-oxopiperazin-1-yl)-3-(4-methylphenyl)-N—((R)-1-(6-(trifluoromethyl) pyridin-3-yl) ethyl)-4,5-dihydro-1H-pyrazol-1-carboxamide (17)

(R)-4-(4-methyl-2-oxopiperazin-1-yl)-3-(4-methylphenyl)-N—((R)-1-(6-(trifluoromethyl) pyridin-3-yl) ethyl)-4,5-dihydro-1H-pyrazol-1-carboxamide (17a)

(S)-4-(3-acetyl-2-oxoimidazolidin-1-yl)-3-(4-methylphenyl)-N—((R)-1-(6-(trifluoromethyl) pyridin-3-yl) ethyl)-4,5-dihydro-1H-pyrazol-1-carboxamide (18)

(R)-4-(3-acetyl-2-oxoimidazolidin-1-yl)-3-(4-methylphenyl)-N—((R)-1-(6-(trifluoromethyl) pyridin-3-yl) ethyl)-4,5-dihydro-1H-pyrazol-1-carboxamide (18a)

(S)-4-(4-acetylpiperazin-1-yl)-3-(4-methylphenyl)-N—((R)-1-(6-(trifluoromethyl) pyridin-3-yl)ethyl)-4,5-dihydro-1H-pyrazol-1-carboxamide (19)

(R)-4-(4-acetylpiperazin-1-yl)-3-(4-methylphenyl)-N—((R)-1-(6-(trifluoromethyl) pyridin-3-yl)ethyl)-4,5-dihydro-1H-pyrazol-1-carboxamide (19a)

(S)-4-(3-oxomorpholin-4-yl)-3-(4-methylphenyl)-N—((R)-1-(4-(trifluoromethyl)phenyl)ethyl)-4,5-dihydro-1H-pyrazol-1-carboxamide (20)

(R)-4-(3-oxomorpholin-4-yl)-3-(4-methylphenyl)-N—((R)-1-(4-(trifluoromethyl)phenyl)ethyl)-4,5-dihydro-1H-pyrazol-1-carboxamide (20a)

(S)-4-(2-oxopyrrolidin-1-yl)-3-(4-methylphenyl)-N—((R)-1-(6-(trifluoromethyl) pyridin-3-yl)ethyl)-4,5-dihydro-1H-pyrazol-1-carboxamide (21)

(R)-4-(2-oxopyrrolidin-1-yl)-3-(4-methylphenyl)-N—((R)-1-(6-(trifluoromethyl) pyridin-3-yl)ethyl)-4,5-dihydro-1H-pyrazol-1-carboxamide (21a)

(S)-4-(2-oxooxazolidin-3-yl)-3-(4-methylphenyl)-N—((R)-1-(6-(trifluoromethyl) pyridin-3-yl)ethyl)-4,5-dihydro-1H-pyrazol-1-carboxamide (22)

(R)-4-(2-oxooxazolidin-3-yl)-3-(4-methylphenyl)-N—((R)-1-(6-(trifluoromethyl) pyridin-3-yl)ethyl)-4,5-dihydro-1H-pyrazol-1-carboxamide (22a)

(S)-4-(2-oxooxazolidin-3-yl)-3-(5-methylpyridin-2-yl)-N—((R)-1-(6-(trifluoromethyl) pyridin-3-yl)ethyl)-4,5-dihydro-1H-pyrazol-1-carboxamide (23)

(R)-4-(2-oxooxazolidin-3-yl)-3-(5-methylpyridin-2-yl)-N—((R)-1-(6-(trifluoromethyl) pyridin-3-yl)ethyl)-4,5-dihydro-1H-pyrazol-1-carboxamide (23a)

(S)-4-(3-oxomorpholin-4-yl)-3-(4-fluorophenyl)-N—((R)-1-(2-(6-(trifluoromethyl) pyridin-3-yl)ethyl)-4,5-dihydro-1H-pyrazol-1-carboxamide (24)

(R)-4-(3-oxomorpholin-4-yl)-3-(4-fluorophenyl)-N—((R)-1-(2-(6-(trifluoromethyl) pyridin-3-yl)ethyl)-4,5-dihydro-1H-pyrazol-1-carboxamide (24a)

(S)-4-(N-methylacetamido)-3-(4-methylphenyl)-N—((R)-1-(6-(trifluoromethyl) pyridin-3-yl)ethyl)-4,5-dihydro-1H-pyrazol-1-carboxamide (25)

(R)-4-(N-methylacetamido)-3-(4-methylphenyl)-N—((R)-1-(6-(trifluoromethyl) pyridin-3-yl)ethyl)-4,5-dihydro-1H-pyrazol-1-carboxamide (25a)

(S)-4-(3-oxomorpholin-4-yl)-3-(4-methylphenyl)-N—((R)-1-(5-(trifluoromethyl) pyrazin)-2-yl)ethyl)-4,5-dihydro-1H-pyrazol-1-carboxamide (26)

(R)-4-(3-oxomorpholin-4-yl)-3-(4-methylphenyl)-N—((R)-1-(5-(trifluoromethyl) pyrazin)-2-yl)ethyl)-4,5-dihydro-1H-pyrazol-1-carboxamide (26a)

(S)-4-(2-oxooxazolidin-3-yl)-3-(4-methylphenyl)-N—((R)-1-(5-methylpyrazin-2-yl)ethyl)-4,5-dihydro-1H-pyrazol-1-carboxamide (27)

(R)-4-(2-oxooxazolidin-3-yl)-3-(4-methylphenyl)-N—((R)-1-(5-methylpyrazin-2-yl)ethyl)-4,5-dihydro-1H-pyrazol-1-carboxamide (27a)

(S)-4-(2-oxopyrrolidin-1-yl)-3-(4-fluorophenyl)-N—((R)-1-(5-methylpyrazin-2-yl)ethyl)-4,5-dihydro-1H-pyrazol-1-carboxamide (28)

(R)-4-(2-oxopyrrolidin-1-yl)-3-(4-fluorophenyl)-N—((R)-1-(5-methylpyrazin-2-yl)ethyl)-4,5-dihydro-1H-pyrazol-1-carboxamide (28a)

(S)-4-(2-oxooxazolidin-3-yl)-3-(4-chlorophenyl)-N—((R)-1-(6-(methoxy)pyridazin-3-yl)ethyl)-4,5-dihydro-1H-pyrazol-1-carboxamide (29)

(R)-4-(2-oxooxazolidin-3-yl)-3-(4-chlorophenyl)-N—((R)-1-(6-(methoxy)pyridazin-3-yl)ethyl)-4,5-dihydro-1H-pyrazol-1-carboxamide (29a)

(S)-4-(3-oxomorpholin-4-yl)-3-(4-methylphenyl)-N—((R)-1-(6-(trifluoromethyl)pyridazin-3-yl)ethyl)-4,5-dihydro-1H-pyrazol-1-carboxamide (30)

(R)-4-(3-oxomorpholin-4-yl)-3-(4-methylphenyl)-N—((R)-1-(6-(trifluoromethyl)pyridazin-3-yl)ethyl)-4,5-dihydro-1H-pyrazol-1-carboxamide (30a)

(S)-4-(2-oxooxazolidin-3-yl)-3-(4-methylphenyl)-N—((R)-1-(6-chloropyridazin-3-yl)ethyl)-4,5-dihydro-1H-pyrazol-1-carboxamide (31)

(R)-4-(2-oxooxazolidin-3-yl)-3-(4-methylphenyl)-N—((R)-1-(6-chloropyridazin-3-yl)ethyl)-4,5-dihydro-1H-pyrazol-1-carboxamide (31a)

(S)-4-(2-oxopyrrolidin-1-yl)-3-(4-methylphenyl)-N—((R)-1-(2-(trifluoromethyl)pyrimidin-5-yl)ethyl)-4,5-dihydro-1H-pyrazol-1-carboxamide (32)

(R)-4-(2-oxopyrrolidin-1-yl)-3-(4-methylphenyl)-N—((R)-1-(2-(trifluoromethyl)pyrimidin-5-yl)ethyl)-4,5-dihydro-1H-pyrazol-1-carboxamide (32a)

(S)-4-(3-oxomorpholin-4-yl)-3-(4-fluorophenyl)-N—((R)-1-(2-(trifluoromethyl)pyrimidin-5-yl)ethyl)-4,5-dihydro-1H-pyrazol-1-carboxamide (33)

(R)-4-(3-oxomorpholin-4-yl)-3-(4-fluorophenyl)-N—((R)-1-(2-(trifluoromethyl)pyrimidin-5-yl)ethyl)-4,5-dihydro-1H-pyrazol-1-carboxamide (33a)

(S)-4-(N-methylacetamido)-3-(4-methylphenyl)-N—((R)-1-(2-(trifluoromethyl)pyrimidin-5-yl)ethyl)-4,5-dihydro-1H-pyrazol-1-carboxamide (34)

(R)-4-(N-methylacetamido)-3-(4-methylphenyl)-N—((R)-1-(2-(trifluoromethyl)pyrimidin-5-yl)ethyl)-4,5-dihydro-1H-pyrazol-1-carboxamide (34a)

(S)-4-(3-oxomorpholin-4-yl)-3-(4-chlorophenyl)-N—((R)-1-(2-(trifluoromethyl)pyrimidin-5-yl)ethyl)-4,5-dihydro-1H-pyrazol-1-carboxamide (35)

(R)-4-(3-oxomorpholin-4-yl)-3-(4-chlorophenyl)-N—((R)-1-(2-(trifluoromethyl)pyrimidin-5-yl)ethyl)-4,5-dihydro-1H-pyrazol-1-carboxamide (35a)

(S)-4-(3-oxomorpholin-4-yl)-3-(4-methoxyphenyl)-N—((R)-1-(2-(trifluoromethyl)pyrimidin-5-yl)ethyl)-4,5-dihydro-1H-pyrazol-1-carboxamide (36)

(R)-4-(3-oxomorpholin-4-yl)-3-(4-methoxyphenyl)-N—((R)-1-(2-(trifluoromethyl)pyrimidin-5-yl)ethyl)-4,5-dihydro-1H-pyrazol-1-carboxamide (36a)

(S)-4-(4-acetylpiperazin-1-yl)-3-(4-methylphenyl)-N—((R)-1-(2-(trifluoromethyl)pyrimidin-5-yl)ethyl)-4,5-dihydro-1H-pyrazol-1-carboxamide (37)

(R)-4-(4-acetylpiperazin-1-yl)-3-(4-methylphenyl)-N—((R)-1-(2-(trifluoromethyl)pyrimidin-5-yl)ethyl)-4,5-dihydro-1H-pyrazol-1-carboxamide (37a)

(S)-4-(4-methylpiperazin-1-yl)-3-(4-methylphenyl)-N—((R)-1-(2-(trifluoromethyl)pyrimidin-5-yl)ethyl)-4,5-dihydro-1H-pyrazol-1-carboxamide (38)

(R)-4-(4-methylpiperazin-1-yl)-3-(4-methylphenyl)-N—((R)-1-(2-(trifluoromethyl)pyrimidin-5-yl)ethyl)-4,5-dihydro-1H-pyrazol-1-carboxamide (38a)

(S)-4-(morpholin-4-yl)-3-(4-methylphenyl)-N—((R)-1-(2-(trifluoromethyl)pyrimidin-5-yl)ethyl)-4,5-dihydro-1H-pyrazol-1-carboxamide (39)

(R)-4-(morpholin-4-yl)-3-(4-methylphenyl)-N—((R)-1-(2-(trifluoromethyl)pyrimidin-5-yl)ethyl)-4,5-dihydro-1H-pyrazol-1-carboxamide (39a)

(S)-4-(2-oxooxazolidin-3-yl)-3-(4-methylphenyl)-N—((R)-1-(2-(trifluoromethyl)pyrimidin-5-yl)ethyl)-4,5-dihydro-1H-pyrazol-1-carboxamide (40)

(R)-4-(2-oxooxazolidin-3-yl)-3-(4-methylphenyl)-N—((R)-1-(2-(trifluoromethyl)pyrimidin-5-yl)ethyl)-4,5-dihydro-1H-pyrazol-1-carboxamide (40a)

(S)-4-(3-methyl-2-oxoimidazolidin-1-yl)-3-(4-methylphenyl)-N—((R)-1-(2-trifluoromethyl)pyrimidin-5-yl)ethyl)-4,5-dihydro-1H-pyrazol-1-carboxamide (41)

(R)-4-(3-methyl-2-oxoimidazolidin-1-yl)-3-(4-methylphenyl)-N—((R)-1-(2-trifluoromethyl)pyrimidin-5-yl)ethyl)-4,5-dihydro-1H-pyrazol-1-carboxamide (41a)

(S)-4-(pyrazol-1-yl)-3-(4-methylphenyl)-N—((R)-1-(2-trifluoromethyl)pyrimidin-5-yl)ethyl)-4,5-dihydro-1H-pyrazol-1-carboxamide (42)

(R)-4-(pyrazol-1-yl)-3-(4-methylphenyl)-N—((R)-1-(2-trifluoromethyl)pyrimidin-5-yl)ethyl)-4,5-dihydro-1H-pyrazol-1-carboxamide (42a)

(S)-4-(2-oxooxazolidin-3-yl)-3-(4-chlorophenyl)-N—((R)-1-(2-methylpyrimidin-5-yl)ethyl)-4,5-dihydro-1H-pyrazol-1-carboxamide (43)

(R)-4-(2-oxooxazolidin-3-yl)-3-(4-chlorophenyl)-N—((R)-1-(2-methylpyrimidin-5-yl)ethyl)-4,5-dihydro-1H-pyrazol-1-carboxamide (43a)

(S)-4-(2-oxopyrrolidin-1-yl)-3-(4-fluorophenyl)-N—((R)-1-(2-chloropyrimidin-5-yl)ethyl)-4,5-dihydro-1H-pyrazol-1-carboxamide (44)

(R)-4-(2-oxopyrrolidin-1-yl)-3-(4-fluorophenyl)-N—((R)-1-(2-chloropyrimidin-5-yl)ethyl)-4,5-dihydro-1H-pyrazol-1-carboxamide (44a)

(S)-4-(2-oxopyrrolidin-1-yl)-3-(4-methylphenyl)-N—((R)-1-(3-methyl-1,2,4-oxadiazol-5-yl)ethyl)-4,5-dihydro-1H-pyrazol-1-carboxamide (45)

(R)-4-(2-oxopyrrolidin-1-yl)-3-(4-methylphenyl)-N—((R)-1-(3-methyl-1,2,4-oxadiazol-5-yl)ethyl)-4,5-dihydro-1H-pyrazol-1-carboxamide (45a)

(S)-4-(3-oxomorpholin-4-yl)-3-(4-methylphenyl)-N—((R)-1-(3-methyl-1,2,4-oxadiazol-5-yl)ethyl)-4,5-dihydro-1H-pyrazol-1-carboxamide (46)

(R)-4-(3-oxomorpholin-4-yl)-3-(4-methylphenyl)-N—((R)-1-(3-methyl-1,2,4-oxadiazol-5-yl)ethyl)-4,5-dihydro-1H-pyrazol-1-carboxamide (46a) (S)-4-(N-methylacetamido)-3-(4-methylphenyl)-N—((S)-1-(6-(trifluoromethyl) pyridin-3-yl)ethyl)-4,5-dihydro-1H-pyrazol-1-carboxamide (47)

(R)-4-(N-methylacetamido)-3-(4-methylphenyl)-N—((S)-1-(6-(trifluoromethyl) pyridin-3-yl)ethyl)-4,5-dihydro-1H-pyrazol-1-carboxamide (47a).

5. The N-formamidopyrazoline compound according to claim 1, wherein the pharmaceutically acceptable salt is selected from pharmaceutically acceptable inorganic acid salts and organic acid salts; the inorganic acid salts comprise salts formed with haloid acid, nitric acid, carbonic acid, sulfuric acid or phosphoric acid; and the organic acid salts comprise salts formed with malic acid, citric acid, fumaric acid, oxalic acid, lactic acid, camphorsulfonic acid, p-toluenesulfonic acid, methanesulfonic acid and benzoic acid.

6. A method of treating diseases comprising administering a compound of claim 1, wherein the diseases comprise cough.

7. A pharmaceutical composition comprising the N-formamidopyrazoline compound of claim 1 and one or more pharmaceutically acceptable carriers or excipients.

8. The pharmaceutical composition according to claim 7, wherein the carriers or excipients comprise one or more of filler, diluent, wetting agent, lubricant, binder, disintegrant, absorption enhancer, surfactant, adsorption carrier, antioxidant, metal chelating agent, pH conditioning agent, flavouring agent, and sweetening agent.

9. The pharmaceutical composition of claim 7 wherein the composition is in the form of tablets, capsules, inhalants, emulsions, suspensions, gels, powders, granules, oral liquids and injections.

10. A method of treating cough mediated by P2X3 comprising the step of administering the N-formamidopyrazoline compound of claim 1 to a subject.

* * * * *